US 7,429,604 B2

(12) United States Patent
Corte et al.

(10) Patent No.: US 7,429,604 B2
(45) Date of Patent: Sep. 30, 2008

(54) SIX-MEMBERED HETEROCYCLES USEFUL AS SERINE PROTEASE INHIBITORS

(75) Inventors: James R. Corte, Lawrenceville, NJ (US); Jon J. Hangeland, Morrisville, PA (US); Miml L. Quan, Yardley, PA (US); Joanne M. Smallheer, Yardley, PA (US); Tianan Fang, Levittown, PA (US)

(73) Assignee: Bristol Myers Squibb Company, Princeton, NJ (US)

( * ) Notice: Subject to any disclaimer, the term of this patent is extended or adjusted under 35 U.S.C. 154(b) by 431 days.

(21) Appl. No.: 11/151,627

(22) Filed: Jun. 13, 2005

(65) Prior Publication Data

US 2006/0009455 A1 Jan. 12, 2006

Related U.S. Application Data

(60) Provisional application No. 60/683,838, filed on May 24, 2005, provisional application No. 60/579,637, filed on Jun. 15, 2004.

(51) Int. Cl.
 A61K 31/44 (2006.01)
 C07D 211/82 (2006.01)
 C07D 401/02 (2006.01)

(52) U.S. Cl. .................... 514/336; 514/357; 546/268.1; 546/336

(58) Field of Classification Search .............. 546/268.1, 546/336; 514/357, 336
See application file for complete search history.

(56) References Cited

U.S. PATENT DOCUMENTS

| 5,622,982 | A  | 4/1997  | Schuster et al.  |
|-----------|-----|---------|------------------|
| 6,448,281 | B1 | 9/2002  | Beaulieu et al.  |
| 6,465,493 | B1 | 10/2002 | Burgess et al.   |
| 6,503,933 | B1 | 1/2003  | Maloney et al.   |
| 2003/0153604 | A1 | 8/2003 | Dankulich et al. |
| 2003/0225131 | A1 | 12/2003 | Burgey et al.   |
| 2004/0214888 | A1 | 10/2004 | Matsuura et al. |
| 2004/0220206 | A1 | 11/2004 | Smallheer et al. |
| 2004/0235847 | A1 | 11/2004 | Quan et al.     |
| 2005/0228000 | A1 | 10/2005 | Smallheer et al. |
| 2005/0282805 | A1 | 12/2005 | Hangeland et al. |
| 2006/0154915 | A1 | 7/2006  | Corte et al.    |

FOREIGN PATENT DOCUMENTS

| WO | WO 92/02513    | 2/1992  |
| WO | WO 200071512   | 11/2000 |
| WO | WO 200127079   | 4/2001  |
| WO | WO 02/44273    | 5/2002  |
| WO | WO 02/064559   | 8/2002  |
| WO | WO 03/035076 A1 * | 5/2003 |
| WO | WO 2003062222  | 7/2003  |
| WO | WO 2004/014844 | 2/2004  |
| WO | WO 2004/019868 | 3/2004  |
| WO | WO 2005/007627 | 1/2005  |
| WO | WO 2005/063690 | 7/2005  |
| WO | WO 2005/085198 | 9/2005  |

OTHER PUBLICATIONS

U.S. Appl. No. 11/610,027, Pinto et al.
U.S. Appl. No. 11/151,667, filed Jun. 13, 2005, Hangeland et al.
Desai et al., "Synthesis and biological activity of cyanopyridine, isoxazole and pyrazoline derivatives having thymol moiety," Indian Journal of Chemistry, Section B: Organic Chemistry Including Medicinal Chemistry, vol. 42B(2), pp. 382-385, 2003.
Artis et al., "Structure-Based Design of Six Novel Classes of Nonpeptide Antagonists of the Bradykinin $B_2$ Receptor," Bioorganic & Medicinal Chemistry Letters, vol. 10, pp. 2421-2425, 2000.
Galiani, D., "Activation of Factor IX by Factor XIa", Trends in Cardiovascular Medicine, vol. 10, No. 5, 2000. pp. 198-204.
Bouma, B.N. et al., "Thrombin-Activatable Fibrinolysis Inhibitor (TAFI, Plasma Procarboxypeptidase B, Procarboxypeptidase R, Procarboxypeptidase U)", Thrombosis. Research, 2001, 101, pp. 329-354.
Gailani, D., "Gene Targeting in Hemostasis. Factor XI", Frontiers in Bioscience, 2001, 6, pp. d201-d207.
Gailani, D., et al., "A murine model of factor XI deficiency", Blood Coagulation and Fibrinolysis, 1997, vol. 8, pp. 134-144.
Minnema, M.C., et al., "Activation of Clotting Factors XI and IX in Patients with Acute Myocardial Infarction", Arterioscler. Thromb. Vasc. Biol., 2000, 20, pp. 2489-2493.
Murakami, T., et al., "Evaluation of Factor XIa-$\alpha_1$ -Antitrypsin in Plasma, a Contact Phase-Activated Coagulation Factor-Inhibitor Complex, in Patients With Coronary Artery Disease", Arterioscler. Thromb. Vasc. Biol., 1995, 15, pp. 1107-1113.
Meijers, J.C.M., et al., "High Levels of Coagulation Factor XI as a Risk Factor for Venous Thrombosis", N. Engl. J. Med., 2000, vol. 342, No. 10, pp. 696-701.
Walsh, P.N., "Platelets and Factor XI Bypass the Contact System of Blood Coagulation", Thromb. Haemostasis. 82(2), pp. 234-242, 1999.
Colman, R. Contact Activation Pathway: Inflammatory, Fibrinolytic, Anticoagulant, Antiadhesive, and Antiangiogenic Activities, Hemostasis and thrombosis: basic principles and clinical practice, Lippincott Williams & Wilkins, 2001, pp. 103-122.
Schmaier, A.H., "Contact Activation", Thrombosis and Hemorrhage, Williams & Wilkins, 1998, pp. 105-128.
* cited by examiner Primary Examiner—Zinna N Davis
(74) Attorney, Agent, or Firm—Jing G. Sun

(57) ABSTRACT

The present invention provides compounds of Formula (I):

$$A \diagdown_L Z \diagdown \begin{matrix} X^1 \\ X^2 \\ X^5 \diagup X^3 \\ X^4 \end{matrix} \quad (I)$$

or a stereoisomer or pharmaceutically acceptable salt or solvate form thereof, wherein the variables A, L, Z, $X^1$, $X^2$, $X^3$, $X^4$, and $X^5$ are as defined herein. The compounds of Formula (I) are useful as selective inhibitors of serine protease enzymes of the coagulation cascade and/or contact activation system; for example thrombin, factor Xa, factor XIa, factor IXa, factor VIIa and/or plasma kallikrein. In particular, it relates to compounds that are selective factor XIa inhibitors. This invention also relates to pharmaceutical compositions comprising these compounds and methods of treating thromboembolic and/or inflammatory disorders using the same.

20 Claims, No Drawings

SIX-MEMBERED HETEROCYCLES USEFUL AS SERINE PROTEASE INHIBITORS

CROSS-REFERENCE TO RELATED APPLICATIONS

The present application claims the priority benefit of U.S. Provisional Application No. 60/579,637, filed Jun. 11, 2004 and the priority benefit of U.S. Provisional Application No. 60/683,838, filed May 24, 2005, all of which are expressly incorporated fully herein by reference.

FIELD OF THE INVENTION

The present invention relates generally to compounds that inhibit serine proteases. In particular it is directed to novel six-membered heterocycle derivatives of Formula (I):

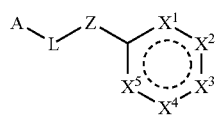

or a stereoisomer or pharmaceutically acceptable salt or solvate form thereof, wherein the variables A, L, Z, $X^1$, $X^2$, $X^3$, $X^4$, and $X^5$ are as defined herein. The compounds of Formula (I) are useful as selective inhibitors of serine protease enzymes of the coagulation cascade and/or contact activation system; for example thrombin, factor XIa, factor Xa, factor IXa, factor VIIa, and/or plasma kallikrein. In particular, it relates to compounds that are selective factor XIa inhibitors or dual inhibitors of fXIa and plasma kallikrein. This invention also relates to pharmaceutical compositions comprising these compounds and methods of using the same.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood coagulation is initiated in vivo by the binding of tissue factor (TF) to Factor VII (FVII) to generate Factor VIIa (FVIIa). The resulting TF:FVIIa complex activates Factor IX (FIX) and Factor X (FX) which leads to the production of Factor Xa (FXa). The FXa that is generated catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Walsh, P. N. *Thromb. Haemostasis.* 1999, 82, 234-242.) Factor XIa plays a key role in propagating this amplification loop and is thus an attractive target for anti-thrombotic therapy.

An alternative way of initiation of coagulation is operative when blood is exposed to artificial surfaces (e.g., during hemodialysis, 'on-pump' cardiovascular surgery, vessel grafts, bacterial sepsis). This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Contact activation is a surface mediated process responsible in part for the regulation of thrombosis and inflammation, and is mediated, at least in part, by fibrinolytic-, complement-, kininogen/ kinin-, and other humoral and cellular pathways (for review, Coleman, R. *Contact Activation Pathway*, pages 103-122 in Hemostasis and Thrombosis, Lippincott Williams & Wilkins 2001; Schmaier A. H. *Contact Activation*, pages 105-128 in *Thrombosis and Hemorrhage*, 1998).

Factor XI is a zymogen of a trypsin-like serine protease and is present in plasma at a relatively low concentration. Proteolytic activation at an internal R369-1370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor 1x as its normal macromolecular substrate. (Galiani, D. *Trends Cardiovasc. Med.* 2000, 10, 198-204.)

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al. *Thromb. Res.* 2001, 101, 329-354.) Thus, inhibitors of factor XIa are expected to be anticoagulant and profibrinolytic.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or posttraumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of APTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The APTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailiani, D. *Frontiers in Bioscience* 2001, 6, 201-207; Gailiani, D. et al. *Blood Coagulation and Fibrinolysis* 1997, 8, 134-144.) Taken together, these observations suggest that high levels of inhibition of factor XIa should be well tolerated. This is in contrast to gene targeting experiments with other coagulation factors.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al. *Arterioscler. Thromb. Vasc. Biol.* 2000, 20, 2489-2493). A second study establishes a positive correlation between the extent of coronary arteriosclerosis and factor XIa in complex with alpha 1 antitrypsin (Murakami, T. et al. *Arterioscler Thromb Vasc Biol* 1995, 15, 1107-1113.). In another study, Factor XI levels above the 90th percentile in patients were associated with a 2.2-fold increased risk for venous thrombosis (Meijers, J. C. M. et al. *N. Engl. J. Med.* 2000, 342, 696-701.).

Plasma kallikrein is a zymogen of a trypsin-like serine protease and is present in plasma at 35 to 50 μg/mL. The gene structure is similar to that of factor XI, overall, the amino acid sequence of plasma kallikrein has 58% homology to factor XI. Proteolytic activation by factor XIIa at an internal 1389R390 bond yields a heavy chain (371 amino acids) and a light chain (248 amino acids). The active site of kallikrein is contained in the light chain. The light chain of plasma kallikrein reacts with protease inhibitors, including alpha 2 macroglobulin and $C_1$-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Kallikrein cleaves HMWK to liberate bradykinin. Bradykinin release results in increase of vascular permeability and vasodilation (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage*, 1998).

Proteins or peptides that reportedly inhibit Factor XIa are disclosed in WO 01/27079. There are advantages in using small organic compounds, however, in preparing pharmaceuticals, e.g., small compounds generally have better oral bioavailability and compatibility in making formulations to aid in delivery of the drug as compared with large proteins or peptides. Small molecule inhibitors of Factor XIa are disclosed in U.S. Patent Application Publication U.S. 20040235847A1 and US Patent Application Publication U.S. 20040220206A1.

Moreover, it is also desirable to find new compounds with improved pharmacological characteristics compared with known serine protease inhibitors. For example, it is preferred to find new compounds with improved factor XIa inhibitory activity and selectivity for factor XIa versus other serine proteases. Also, it is preferred to find new compounds with improved plasma kallikrein inhibitory activity and selectivity for plasma kallikrein versus other serine proteases. It is also desirable and preferable to find compounds with advantageous and improved characteristics in one or more of the following categories, but are not limited to: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and (g) factors that improve manufacturing costs or feasibility.

SUMMARY OF THE INVENTION

The present invention provides novel six-membered heterocycle derivatives, and analogues thereof, which are useful as selective inhibitors of serine protease enzymes, especially factor XIa and/or plasma kallikrein, or stereoisomers or pharmaceutically acceptable salts, solvates, or prodrugs thereof.

The present invention also provides processes and intermediates for making the compounds of the present invention or a stereoisomer or a pharmaceutically acceptable salt, solvate, or prodrug form thereof.

The present invention also provides pharmaceutical compositions comprising a pharmaceutically acceptable carrier and a therapeutically effective amount of at least one of the compounds of the present invention or a pharmaceutically acceptable salt, solvate or prodrug form thereof.

The present invention also provides a method for modulation of the coagulation cascade and/or the contact activation system comprising administering to a host in need of such treatment a therapeutically effective amount of at least one of the compounds of the present invention or a pharmaceutically acceptable salt, solvate, or prodrug form thereof.

The present invention also provides a method for treating thromboembolic disorders comprising administering to a host in need of such treatment a therapeutically effective amount of at least one of the compounds of the present invention or a pharmaceutically acceptable salt, solvate, or prodrug form thereof.

The present invention also provides a method for treating inflammatory diseases disorders comprising administering to a host in need of such treatment a therapeutically effective amount of at least one of the compounds of the present invention or a pharmaceutically acceptable salt, solvate, or prodrug form thereof.

The present invention also provides novel six-membered heterocycle derivatives, and analogues thereof, for use in therapy.

The present invention also provides the use of six-membered heterocycle derivatives, and analogues thereof, for the manufacture of a medicament for the treatment of a thromboembolic disorder.

The present invention also provides the use of six-membered heterocycle derivatives, and analogues thereof, for the manufacture of a medicament for the treatment of an inflammatory disorder.

These and other embodiments, which will become apparent during the following detailed description, have been achieved by the inventors' discovery that the presently claimed novel compounds of the present invention, or pharmaceutically acceptable salt or prodrug forms thereof, are effective factor XIa inhibitors and/or plasma kallikrein inhibitors.

DETAILED DESCRIPTION OF THE INVENTION

In a first aspect, the present invention provides, inter alia, a compound of Formula (I):

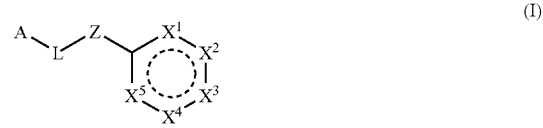

or a stereoisomer or pharmaceutically acceptable salt, solvate, or prodrug thereof, wherein:

A is $C_{3-7}$ cycloalkyl substituted with 0-1 $R^1$ and 0-2 $R^2$, $C_{3-7}$ cycloalkenyl substituted with 0-1 $R^1$ and 0-2 $R^2$, phenyl substituted with 0-1 $R^1$ and 0-3 $R^2$, naphthyl substituted with 0-1 $R^1$ and 0-3 $R^2$, or a 5- to 12-membered heterocycle comprising: carbon atoms and 1-4 heteroatoms selected from N, O, and $S(O)_p$, wherein said heterocycle is substituted 0-1 $R^1$ and 0-3 $R^2$;

$X^1$, $X^2$, $X^3$, and $X^4$, are independently $CR^3$, $CR^4$, N, $NR^6$, N→O, or C(O); provided that at least one of $X^1$, $X^2$, $X^3$, and $X^4$ is $CR^3$;

$X^5$ is N, $NR^6$ or N→O;

Z is —CH($R^{11}$) or $NR^{13}$;

L is —C(O)$NR^{10}$—, —$NR^{10}$C(O)—, —$CH_2$C(O)$NR^{10}$—, —$CH_2NR^{10}$C(O)—, —C(O)$NR^{10}CH_2$—, or —$NR^{10}$C(O)$CH_2$—;

$R^1$ is, independently at each occurrence, —$NH_2$, —NH($C_{1-3}$ alkyl), —N($C_{1-3}$ alkyl)$_2$, —C(=NH)$NH_2$, —C(O)$NH_2$, —$CH_2NH_2$, —(CH$_2$)$_r$$NR^7R^8$, —$CH_2$NH($C_{1-3}$ alkyl), —$CH_2$N($C_{1-3}$ alkyl)$_2$, —$CH_2CH_2NH_2$, —$CH_2CH_2$NH($C_{1-3}$ alkyl), —$CH_2CH_2$N($C_{1-3}$ alkyl)$_2$, —CH($C_{1-4}$ alkyl)$NH_2$, —C($C_{1-4}$ alkyl)$_2NH_2$, —C(=$NR^{8a}$)$NR^7R^8$, —$NR^8CR^8$(=$NR^{8a}$), —NHC(=$NR^{8a}$)$NR^7R^8$, —$NR^8$, —C(O)$NR^8R^9$, —S(O)$_pNR^8R^9$, —(CH$_2$)$_rNR^7$C(O)O$R^a$, F, Cl, Br, I, OCF$_3$, CF$_3$, OR$^a$, SR$^a$, CN, —NH$_2$-1-cyclopropyl, or $C_{1-6}$ alkyl substituted with 0-1 $R^{1a}$;

$R^{1a}$ is H, —C(=$NR^{8a}$)$NR^7R^8$, —NHC(=$NR^{8a}$)$NR^7R^8$, —$NR^8CR^8$(=$NR^{8a}$), —$NR^7R^8$, —C(O)$NR^8R^9$, F, OCF$_3$, CF$_3$, OR$^a$, SR$^a$, CN, —$NR^8SO_2NR^8R^9$, —$NR^8SO_2R^c$, —S(O)$_p$—$C_{1-4}$ alkyl, —S(O)$_p$-phenyl, or —(CF$_2$)$_r$CF$_3$;

$R^2$ is, independently at each occurrence, H, =O, F, Cl, Br, I, OCF$_3$, CF$_3$, CHF$_2$, CN, NO$_2$, OR$^a$, SR$^a$, —C(O)$R^a$, —C(O)OR$^a$, —OC(O)R$^a$, —$NR^7R^8$, —C(O)$NR^7R^8$, —$NR^7$C(O)$R^b$, —S(O)$_pNR^8R^9$, —$NR^8S(O)_2R^c$, —S(O)$R^c$, —S(O)$_2R^c$, $C_{1-6}$ alkyl substituted with 0-2 $R^{2a}$, $C_{2-6}$ alkenyl substituted with 0-2 $R^{2a}$, $C_{2-6}$ alkynyl substituted with 0-2 $R^{2a}$, —(CH$_2$)$_r$—$C_{3-10}$ carbocycle substituted with 0-3 $R^{2b}$, or —(CH$_2$)$_r$-5- to 10-membered heterocycle comprising: carbon atoms and 1-4 heteroatoms selected from N, O, and $S(O)_p$, wherein said heterocycle is substituted with 0-3 $R^{2b}$;

$R^{2a}$ is, independently at each occurrence, H, F, Cl, Br, I, =O, =$NR^8$, CN, OCF$_3$, CF$_3$, OR$^a$, SR$^a$, —$NR^7R^8$, —C(O)$NR^8R^9$, —$NR^7$C(O)$R^b$, —S(O)$_pNR^8R^9$, —$NR^8SO_2R^c$, —S(O)$R^c$, or —S(O)$_2R^c$;

$R^{2b}$ is, independently at each occurrence, H, F, Cl, Br, I, =O, =$NR^8$, CN, NO$_2$, OR$^a$, SR$^a$, —C(O)$R^a$, —C(O)OR$^a$, —OC(O)R$^a$, —$NR^7R^8$, —C(O)$NR^7R^8$, —$NR^7$C(O)$R^b$, —S(O)$_pNR^8R^9$, —SO$_2R^c$, —$NR^8SO_2NR^8R^9$, —$NR^8SO_2R^c$, —(CF$_2$)$_r$CF$_3$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$ haloalkyloxy-;

alternately, when $R^1$ and $R^2$ are substituted on adjacent ring atoms, they can be taken together with the ring atoms to which they are attached to form a 5- to 7-membered carbocycle or heterocycle comprising: carbon atoms and 0-4 heteroatoms selected from N, O, and $S(O)_p$, wherein said carbocycle or heterocycle is substituted with 0-2 $R^{2b}$;

$R^3$ is, independently at each occurrence, —(CH$_2$)$_r$C(O)$NR^8R^9$, —(CH$_2$)$_r$C(O)$NR^8$(CH$_2$)$_sCO_2R^{3b}$, —(CH$_2$)$_r$CO$_2R^{3b}$, —(CH$_2$)$_r$-phenyl substituted with 0-3 $R^{3a}$ and 0-1 $R^{3d}$, or —(CH$_2$)$_r$-5- to 10-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^{3a}$ is, independently at each occurrence, =O, F, Cl, Br, I, OCF$_3$, CF$_3$, CN, NO$_2$, —(CH$_2$)$_r$OR$^{3b}$, —(CH$_2$)$_r$SR$^{3b}$, —(CH$_2$)$_rNR^7R^8$, —C(=$NR^{8a}$)$NR^8R^9$, —NHC(=$NR^{8a}$)$NR^7R^8$, —$NR^8CR^8$(=$NR^{8a}$), —(CH$_2$)$_rNR^8$C(O)$R^{3b}$, =$NR^8$, —(CH$_2$)$_rNR^8$C(O)$R^{3b}$, —(CH$_2$)$_rNR^8$C(O)$_2R^{3b}$, —(CH$_2$)$_rS(O)_pNR^8R^9$, —(CH$_2$)$_rNR^8S(O)_pR^{3c}$, —S(O)$R^{3c}$, —S(O)$_2R^{3c}$, —C(O)—$C_{1-4}$ alkyl, —(CH$_2$)$_rCO_2R^{3b}$, —(CH$_2$)$_r$C(O)$NR^8R^9$, —(CH$_2$)$_r$OC(O)$NR^8R^9$, —NHCOCF$_3$, —NHSO$_2$CF$_3$, —SO$_2$NHR$^{3b}$, —SO$_2$NHCOR$^{3c}$, —SO$_2$NHCO$_2R^{3c}$, —CONHSO$_2R^{3c}$, —NHSO$_2R^{3c}$, —CONHOR$^{3b}$, $C_{1-4}$ haloalkyl, $C_{1-4}$ haloalkyloxy-, $C_{1-6}$ alkyl substituted by $R^{3d}$, $C_{2-6}$ alkenyl substituted by $R^{3d}$, $C_{1-6}$ alkynyl substituted by $R^{3d}$, $C_{3-6}$ cycloalkyl substituted by 0-1 $R^{3d}$, —(CH$_2$)$_r$—$C_{3-10}$ carbocycle substituted with 0-3 $R^{3d}$, or —(CH$_2$)$_r$-5- to 10-membered heterocycle comprising: carbon atoms and 1-4 heteroatoms selected from N, O, and $S(O)_p$, wherein said heterocycle is substituted with 0-3 $R^{3d}$;

alternately, when two $R^{3a}$ groups are substituted on adjacent atoms, they can be taken together with the atoms to which they are attached to form a $C_{3-10}$ carbocycle substituted with 0-2 $R^{3d}$, or a 5- to 10-membered heterocycle comprising: carbon atoms and 1-4 heteroatoms selected from N, O, and $S(O)_p$, wherein said heterocycle is substituted with 0-2 $R^{3d}$;

$R^{3b}$ is, independently at each occurrence, H, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, —(CH$_2$)$_r$—$C_{3-10}$ carbocycle substituted with 0-3 $R^{3d}$, or —(CH$_2$)$_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3c}$ is, independently at each occurrence, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, —(CH$_2$)$_r$—$C_{3-10}$ carbocycle substituted with 0-3 $R^{3d}$, or —(CH$_2$)$_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3d}$ is, independently at each occurrence, H, =O, —(CH$_2$)$_r$OR$^a$, F, Cl, Br, CN, NO$_2$, —(CH$_2$)$_rNR^7R^8$, —C(O)$R^a$, —C(O)OR$^a$, —OC(O)R$^a$, —$NR^7$C(O)$R^b$, —C(O)$NR^8R^9$, —S(O)$_pNR^8R^9$, —$NR^8S(O)_2NR^8R^9$, —$NR^8S(O)_2R^c$, —S(O)$_pR^c$, —(CF$_2$)$_r$CF$_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —(CH$_2$)$_r$—$C_{3-10}$ carbocycle substituted with 0-3 $R^d$, or —(CH$_2$)$_r$-5- to 10-membered heterocycle comprising: carbon atoms and 1-4 heteroatoms selected from N, O, and $S(O)_p$, wherein said heterocycle is substituted with 0-3 $R^d$;

$R^4$ is, independently at each occurrence, H, =O, F, Cl, Br, I, OCF$_3$, CF$_3$, CN, NO$_2$, OR$^a$, SR$^a$, —C(O)$R^a$, —C(O)OR$^a$, —OC(O)R$^a$, —$NR^7R^8$, —C(O)$NR^8R^9$, —$NR^7$C(O)$R^b$, —S(O)$_pNR^8R^9$, —$NR^8S(O)_pR^c$, —S(O)$_2R^c$, $C_{1-6}$ alkyl substituted with 0-2 $R^{4a}$, $C_{2-6}$ alkenyl substituted with 0-2 $R^{4a}$, $C_{2-6}$ alkynyl substituted with 0-2 $R^{4a}$, —(CH$_2$)$_r$—$C_{3-10}$ carbocycle substituted with 0-3 $R^{4b}$, or —(CH$_2$)$_r$-5- to 10-membered heterocycle comprising: carbon atoms and 1-4 heteroatoms selected from N, O, and $S(O)_p$, wherein said heterocycle is substituted with 0-3 $R^{4b}$;

$R^{4a}$ is, independently at each occurrence, H, F, =O, $C_{1-4}$ alkyl, OR$^a$, SR$^a$, CF$_3$, CN, NO$_2$, —C(O)$R^a$, —C(O)OR$^a$, —$NR^7R^8$, —C(O)$NR^8R^9$, —$NR^7$C(O)$R^b$, —S(O)$_pNR^8R^9$, —$NR^8S(O)_pR^c$, —S(O)$R^c$, or —S(O)$_2R^c$;

$R^{4b}$ is, independently at each occurrence, H, =O, =$NR^8$, F, Cl, Br, I, OR$^a$, SR$^a$, CN, NO$_2$, —$NR^7R^8$, —C(O)$R^a$, —C(O)OR$^a$, —$NR^7$C(O)$R^b$, —C(O)$NR^8R^9$, —SO$_2NR^8R^9$, —S(O)$_2R^c$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$ haloalkyloxy-;

alternately, $R^3$ and $R^4$ groups when located on adjacent atoms, can be taken together to form a $C_{3-10}$ carbocycle substituted with 0-2 $R^{3d}$ or a 5- to 10-membered heterocycle comprising: carbon atoms and 1-4 heteroatoms selected from N, O, and $S(O)_p$, wherein said heterocycle is substituted with 0-2 $R^{3d}$;

$R^6$ is, independently at each occurrence, H, $C_{1-6}$ alkyl, $C_{1-4}$ haloalkyl, —$CH_2OR^a$, —$C(O)R^c$, —$C(O)_2R^c$, —$S(O)_2R^c$, or —$(CH_2)_r$-phenyl substituted with 0-3 $R^d$;

$R^7$ is, independently at each occurrence, H, $C_{1-6}$ alkyl, —$(CH_2)_n$—$C_{3-10}$ carbocycle, —$(CH_2)_n$-(5-10 membered heteroaryl), —$C(O)R^c$, —CHO, —$C(O)_2R^c$, —$S(O)_2R^c$, —$CONR^8R^c$, —$OCONHR^c$, —$C(O)O$—$(C_{1-4}$ alkyl)OC(O)—$(C_{1-4}$ alkyl), or —$C(O)O$—$(C_{1-4}$ alkyl)OC(O)—$(C_{6-10}$ aryl); wherein said alkyl, carbocycle, heteroaryl, and aryl are optionally substituted with 0-2 $R^f$;

$R^8$ is, independently at each occurrence, H, $C_{1-6}$ alkyl, —$(CH_2)_n$-phenyl, or —$(CH_2)_n$-5-10 membered heterocycle comprising: carbon atoms and 1-4 heteroatoms selected from N, O, and $S(O)_p$; wherein said alkyl, phenyl and heterocycle are optionally substituted with 0-2 $R^f$;

alternatively, $R^7$ and $R^8$, when attached to the same nitrogen, combine to form a 5- to 10-membered heterocycle comprising: carbon atoms and 0-2 additional heteroatoms selected from N, O, and $S(O)_p$, wherein said heterocycle is substituted with 0-2 $R^d$;

$R^{8a}$ is, independently at each occurrence, $R^7$, OH, $C_{1-6}$ alkyl, $C_{1-4}$ alkoxy, ($C_{6-10}$ aryl)-$C_{1-4}$ alkoxy, —$(CH_2)_n$-phenyl, —$(CH_2)_n$-(5-10 membered heteroaryl); wherein said phenyl, aryl and heteroaryl are optionally substituted with 0-2 $R^f$;

$R^9$ is, independently at each occurrence, H, $C_{1-6}$ alkyl, or —$(CH_2)_n$-phenyl; wherein said alkyl and phenyl are optionally substituted with 0-2 $R^f$;

$R^{9a}$ is, independently at each occurrence, H, $C_{1-6}$ alkyl, or —$(CH_2)_n$-phenyl;

alternatively, $R^8$ and $R^9$, when attached to the same nitrogen, combine to form a 5- to 10-membered heterocycle comprising: carbon atoms and 0-2 additional heteroatoms selected from N, O, and $S(O)_p$, wherein said heterocycle is substituted with 0-2 $R^d$;

$R^{10}$ is, independently at each occurrence, H, $C_{1-6}$ alkyl substituted with 0-2 $R^{10a}$, $C_{2-6}$ alkenyl substituted with 0-3 $R^{10a}$, $C_{2-6}$ alkynyl substituted with 0-3 $R^{10a}$, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, wherein said heterocycle is substituted with 0-3 $R^d$;

$R^{10a}$ is, independently at each occurrence, H, =O, $C_{1-4}$ alkyl, $OR^a$, $SR^a$, F, $CF_3$, CN, $NO_2$, —$C(O)R^a$, —$C(O)OR^a$, —$C(O)NR^7R^8$, —$NR^7C(O)R^b$, —$S(O)_pNR^8R^9$, —$NR^8S(O)_pR^c$, —$S(O)R^c$, or —$S(O)_2R^c$;

$R^{11}$ is $C_{1-4}$ haloalkyl, —$(CH_2)_r$—$C(O)NR^8R^9$, $C_{1-6}$ alkyl substituted with 0-3 $R^{11a}$, $C_{2-6}$ alkenyl substituted with 0-3 $R^{11a}$, $C_{2-6}$ alkynyl substituted with 0-3 $R^{11a}$, —$(CR_{14}R^{15})_r$—$C_{3-10}$ carbocycle substituted with 0-3 $R^{11b}$, or —$(CR^{14}R^{15})_r$-5- to 10-membered heterocycle comprising: carbon atoms and 1-4 heteroatoms selected from N, O, and $S(O)_p$, wherein said heterocycle is substituted with 0-3 $R^{11b}$;

$R^{11a}$ is, independently at each occurrence, H, =O, $C_{1-4}$ alkyl, $OR^a$, $SR^a$, F, $CF_3$, CN, $NO_2$, —$NR^7R^8$, —$C(O)R^a$, —$C(O)OR^a$, —$C(O)NR^7R^8$, —$NR^7C(O)R^b$, —$S(O)_pNR^8R^9$, —$NR^8S(O)_pR^c$, —$S(O)_pR^c$, $C_{3-6}$ cycloalkyl, $C_{1-4}$ haloalkyl, $C_{1-4}$ haloalkyloxy-, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

$R^{11b}$ is, independently at each occurrence, H, =O, =$NR^8$, $OR^a$, F, Cl, Br, CN, $NO_2$, $CF_3$, $OCF_3$, $OCHF_2$, —$NR^7R^8$, —$C(O)R^a$, —$C(O)OR^a$, —$C(O)NR^7R^8$, —$NR^7C(O)R^b$, —$NR^8C(O)_2R^c$, —$S(O)_pNR^8R^9$, —$NR^8S(O)_pR^c$, —$S(O)_pR^c$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

alternately, when two $R^{11b}$ groups are substituents on adjacent atoms they may be taken together with the atoms to which they are attached to form a 5- to 7-membered heterocycle comprising carbon atoms and 1-4 heteroatoms selected from N, O, and $S(O)_p$ and substituted with 0-2 $R^g$;

$R^{13}$ is H, $C_{1-6}$ alkyl, —$C(O)R^c$, —$C(O)OR^c$, —$CONR^8R^c$, —$OCONR^8R^c$, —$S(O)_2R^c$, —$(CH_2)_n$-phenyl, —$(CH_2)_n$-(5-10 membered heteroaryl), —$C(O)O$—$(C_{1-4}$ alkyl)-OC(O)—$(C_{1-4}$ alkyl), or —$C(O)O$—$(C_{1-4}$ alkyl)-OC(O)—$(C_{6-10}$ aryl); wherein said alkyl, phenyl, aryl, and heteroaryl are optionally substituted with 0-2 $R^f$;

$R^{14}$ and $R^{15}$ are, independently at each occurrence, H, F, or $C_{1-4}$ alkyl;

alternatively, $R^{14}$ combines with $R^{15}$ to form =O;

$R^a$ is, independently at each occurrence, H, $CF_3$, $C_{1-6}$ alkyl, —$(CH_2)_r$—$C_{3-7}$ cycloalkyl, —$(CH_2)_r$—$C_{6-10}$ aryl, or —$(CH_2)_r$-5- to 10-membered heterocycle comprising: carbon atoms and 1-4 heteroatoms selected from N, O, and $S(O)_p$; wherein said cycloalkyl, aryl and heterocycle groups are optionally substituted with 0-2 $R^f$;

$R^b$ is, independently at each occurrence, $CF_3$, OH, $C_{1-4}$ alkoxy, $C_{1-6}$ alkyl, —$(CH_2)_r$—$C_{3-10}$ carbocycle substituted with 0-3 $R^d$, or —$(CH_2)_r$-5- to 10-membered heterocycle comprising: carbon atoms and 1-4 heteroatoms selected from N, O, and $S(O)_p$ and substituted with 0-2 $R^d$;

$R^c$ is, independently at each occurrence, $CF_3$, $C_{1-6}$ alkyl substituted with 0-2 $R^f$, $C_{3-6}$ cycloalkyl substituted with 0-2 $R^f$, $C_{6-10}$ aryl, 5- to 10-membered heteroaryl, ($C_{6-10}$ aryl)-$C_{1-4}$ alkyl, or (5- to 10-membered heteroaryl)-$C_{1-4}$ alkyl, wherein said aryl and heteroaryl groups are substituted with 0-3 $R^f$;

$R^d$ is, independently at each occurrence, H, =O, =$NR^8$, $OR^a$, F, Cl, Br, I, CN, $NO_2$, —$NR^7R^8$, —$C(O)R^a$, —$C(O)OR^a$, —$OC(O)R^a$, —$NR^8C(O)R^a$, —$C(O)NR^7R^8$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

$R^e$ is, independently at each occurrence, =O, $OR^a$, F, Cl, Br, I, CN, $NO_2$, —$NR^8R^9$, —$C(O)R^a$, —$C(O)OR^a$, —$NR^8C(O)R^a$, —$C(O)NR^7R^8$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, or —$(CF_2)_rCF_3$;

$R^f$ is, independently at each occurrence, H, =O, —$(CH_2)_rOR^9$, F, Cl, Br, I, CN, $NO_2$, —$NR^{9a}R^{9a}$, —$C(O)R^9$, —$C(O)OR^g$, —$NR^{9a}C(O)R^9$, —$C(O)NR^{9a}R^{9a}$, —$SO_2NR^{9a}R^{9a}$, —$NR^{9a}SO_2NR^{9a}R^{9a}$, —$NR^{9a}SO_2$—$C_{1-4}$ alkyl, —$NR^{9a}SO_2CF_3$, —$NR^{9a}SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, $C_{2-6}$ alkynyl, or —$(CH_2)_n$-phenyl;

$R^g$ is, independently at each occurrence, H, $C_{1-6}$ alkyl, or —$(CH_2)_n$-phenyl;

n, at each occurrence, is selected from 0, 1, 2, 3, and 4;

p, at each occurrence, is selected from 0, 1, and 2; and r, at each occurrence, is selected from 0, 1, 2, 3, and 4; and s, at each occurrence, is selected from 1, 2, 3, and 4.

In a second aspect, the present invention includes a compound of Formula (I), within the scope of the first aspect wherein:

the group

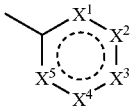

is selected from:

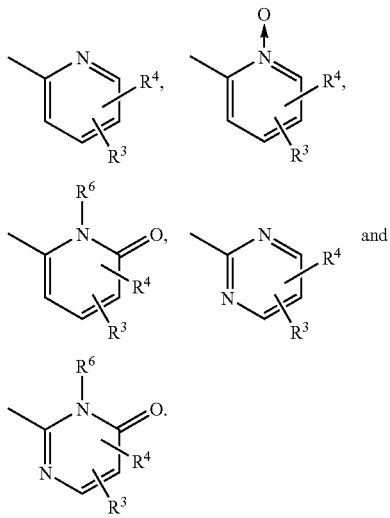

In a third aspect, the present invention includes a compound of Formula (I), within the scope of the first aspect wherein:

A is substituted with 0-1 $R^1$ and 0-2 $R^2$ and selected from; $C_{3-7}$ cycloalkyl, phenyl, naphthyl, pyridyl, 1,2,3,4-tetrahydronaphthyl, indazolyl, benzimidazolyl, benzisoxazolyl, isoquinolinyl, 5,6,7,8-tetrahydroisoquinolinyl, 1,2,3,4-tetrahydroisoquinolinyl, quinazolinyl, 1H-quinazolin-4-onyl, 2H-isoquinolin-1-onyl, 3H-quinazolin-4-onyl, 3,4-dihydro-2H-isoquinolin-1-onyl, 2,3-dihydroisoindolinonyl, and phthalazinyl;

the group

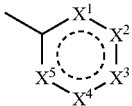

is selected from:

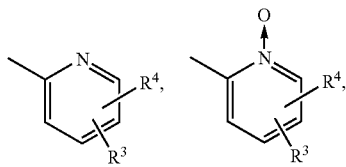

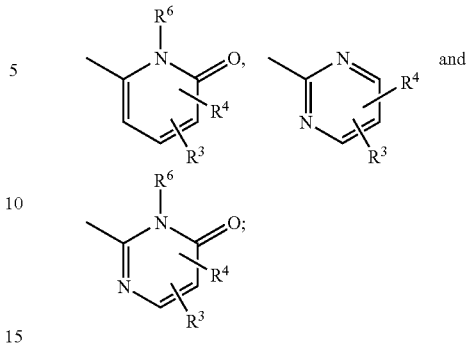

L is —C(O)NR$^{10}$—, or —NR$^{10}$C(O)—;

Z is CHR$^{11}$;

$R^4$ is, independently at each occurrence, H, F, Cl, Br, I, OCF$_3$, CF$_3$, CN, NO$_2$, OR$^a$, SR$^a$, —C(O)R$^a$, —C(O)OR$^a$, —NR$^7$R$^8$, —C(O)NR$^8$R$^9$, —NR$^7$C(O)R$^b$, —S(O)$_p$NR$^8$R$^9$, —NR$^8$S(O)$_p$R$^c$, —S(O)R$^c$, —S(O)$_2$R$^c$, C$_{1-6}$ alkyl substituted with 0-2 R$^{4a}$, C$_{2-6}$ alkenyl substituted with 0-2 R$^{4a}$, C$_{2-6}$ alkynyl substituted with 0-2 R$^{4a}$, phenyl substituted with 0-2 R$^{4b}$, or a 5-10 membered heterocycle comprising: carbon atoms and 1-4 heteroatoms selected from N, O, and S(O)$_p$, wherein said heterocycle is substituted with 0-3 R$^{4b}$;

$R^6$ is H, or C$_{1-4}$ alkyl;

$R^{10}$ is, independently at each occurrence, H, C$_{1-6}$ alkyl substituted with 0-2 R$^{10a}$, —(CH$_2$)$_r$-phenyl substituted with 0-2 R$^d$, or —(CH$_2$)$_r$-5-10 membered heterocycle comprising carbon atoms and 1-4 heteroatoms selected from N, O, and S(O)$_p$, wherein said heterocycle is substituted with 0-2 R$^d$; and $R^{11}$ is C$_{1-4}$ haloalkyl, —(CH$_2$)$_r$—CONR$^8$R$^9$, C$_{1-6}$ alkyl substituted with 0-2 R$^{11a}$, C$_{2-6}$ alkenyl substituted with 0-2 R$^{11a}$, C$_{2-6}$ alkynyl substituted with 0-2 R$^{11a}$, —(CH$_2$)$_r$—C$_{3-0}$ carbocycle substituted with 0-3 R$^{11b}$, or —(CH$_2$)$_r$-5- to 10-membered heterocycle comprising carbon atoms and 1-4 heteroatoms selected from N, O, and S(O)$_p$, wherein said heterocycle is substituted with 0-3 R$^{11b}$.

In a fourth aspect, the present invention includes a compound of Formula (I), within the scope of the third aspect wherein:

$R^1$ is, independently at each occurrence, F, Cl, Me, Et, —NH$_2$, —C(=NH)NH$_2$, —C(O)NH$_2$, —CH$_2$NH$_2$, —CH$_2$CH$_2$NH$_2$, —CH$_2$NHCO$_2$Bn, —CH$_2$NHCO$_2$(t-Bu), —CH(Me)NH$_2$, —CMe$_2$NH$_2$, —NHEt, —NHCO$_2$(t-Bu), —NHCO$_2$Bn, —SO$_2$NH$_2$, OR$^a$, or —CH$_2$R$^{1a}$;

$R^3$ is —CO$_2$H, —CO$_2$Me, —C(O)NHCH$_2$CO$_2$H, —C(O)NHCH$_2$CO$_2$Et, —C(O)NH$_2$, —C(O)NHMe, —C(O)NHBn, —(CH$_2$)$_r$-phenyl substituted with 0-2 R$^{3a}$ and 0-1 R$^{3d}$, naphthyl substituted with 0-2 R$^{3a}$ and 0-1 R$^{3d}$, indanyl substituted with 0-2 R$^{3a}$ and 0-1 R$^{3d}$, or a 5- to 10-membered heterocycle selected from N, O, and S(O)$_p$, wherein said heterocycle is substituted with 0-2 R$^{3a}$ and 0-1 R$^{3d}$;

$R^4$ is H, F, Cl, Br, OMe, NH$_2$, CF$_3$, CO$_2$H, CO$_2$Me, CO$_2$Et, —CONR$^8$R$^9$, C$_{1-6}$ alkyl substituted with 0-2 R$^{4a}$, phenyl substituted with 0-2 R$^{4b}$, or a 5-10 membered heterocycle comprising: carbon atoms and 1-4 heteroatoms selected from N, O, and S(O)$_p$, wherein said heterocycle is substituted with 0-3 R$^{4b}$;

$R^6$ is H;

$R^{10}$ is H; and $R^{11}$ is C$_{1-6}$ alkyl, —(CH$_2$)$_r$—C(O)NR$^8$R$^9$, —CH$_2$OBn, —CH$_2$SBn, —(CH$_2$)$_s$—cyclohexyl substituted with 0-2 R$^{11b}$, —(CH$_2$)$_s$-phenyl substituted with 0-2 R$^{11b}$, —(CH$_2$)$_s$- naphthyl substituted with 0-2 $R^{11b}$, —$(CH_2)_s$-5- to 10-membered heteroaryl substituted with 0-1 $R^{11b}$; wherein said heteroaryl selected from thiazolyl, imidazolyl, pyridyl, indolyl benzimidazolyl, and benzothiazolyl.

In a fifth aspect, the present invention includes a compound of Formula (I), within the scope of the fourth aspect wherein:

L is —C(O)NH—; and $R^{11}$ is phenylmethyl, 4-imidazolylmethyl, 4-thiazolylmethyl, 2-benzthiazolylmethyl, 2-pyridylmethyl, 3-pyridylmethyl, 4-pyridylmethyl, 3-indolylmethyl, 2-benzimidazolylmethyl, 1-naphthylmethyl, 2-naphthylmethyl, cyclohexylmethyl, —$CH_2C(O)NHCH_2$-pyridin-2-yl or —$(CH_2)_2C(O)NHCH_2$-pyridin-2-yl, wherein each phenyl, naphthyl, imidazolyl, thiazolyl, benzthiazolyl, pyridinyl, or cyclohexyl group is substituted with 0-2 $R^{11b}$;

$R^{11b}$ is, independently at each occurrence, H, F, Cl, Br, $CF_3$, OMe, $OCF_3$, $OCHF_2$, OPh, OBn, $NO_2$, —$NH_2$, —C(O)Ph, —NHC(O)Bn, —$NHC(O)CH_2CH_2Ph$, —$NHS(O)_2Ph$, —$C(O)NR^7R^8$, —$NR^7C(O)R^b$, —$S(O)_pNR^8R^9$, —$NR^8S(O)_pR^c$, Ph, or Bn;

alternately, when two $R^{11b}$ groups are substituents on adjacent atoms they may be taken together with the atoms to which they are attached to form a 5- to 7-membered heterocycle comprising carbon atoms and 1-4 heteroatoms selected from N, O, and $S(O)_p$ and substituted with 0-2 $R^g$.

In a sixth aspect, the present invention includes a compound of Formula (I), within the scope of the fifth aspect wherein:

$R^3$ is phenyl substituted with 0-2 $R^{3a}$, naphthyl substituted with 0-2 $R^{3a}$, indanone substituted with 0-2 $R^{3a}$, or a 5- to 10-membered heterocycle substituted with 0-2 $R^{3a}$ and selected from: pyridine, pyridinone, pyrimidine, pyrrole, pyrazole, indole, 2-oxoindole, indazole, benzofuran, benzothiophene, benzimidazole, benzisoxazole, benzoxazole, quinazoline, 3H-quinazolin-4-one, phthalazine, 2H-phthalazin-1-one, 1H-quinolin-4-one, isoquinoline, and 2H-3,4-dihydroisoquinolin-1-one.

In a seventh aspect, the present invention includes a compound of Formula (I), within the scope of the sixth aspect wherein:

A is 4-aminomethyl-cyclohexyl, 4-carbamoyl-cyclohexyl, 4-amidino-phenyl, 4-benzyloxycarbonylamino-cyclohexyl, phenyl, 1,2,3,4-tetrahydronaphth-2-yl, 4-aminomethyl-phenyl, 4-carbamoyl-phenyl, 4 aminomethyl-2-fluoro-phenyl, 2-F-5-OMe-phenyl, 2-F-4-Me-phenyl, 2-F-4-Cl-phenyl, 2-F-4-carbamoyl-phenyl, 2-OMe-4-carbamoyl-phenyl, 3-OMe-4-carbamoyl-phenyl, 2-Et-4-aminomethyl-phenyl, 2-$NH_2$-pyridin-4-yl, 2-ethylamino-4-aminomethyl-phenyl, 1-aminoisoquinolin-6-yl, 1-$NH_2$-5,6,7,8-tetrahydroisoquinolin-6-yl, 1-$NH_2$-1,2,3,4-tetrahydroisoquinolin-6-yl, 3-$NH_2$-benzisoxazol-5-yl, 3-$NH_2$-benzisoxazol-6-yl, 3-$NH_2$-indazol-6-yl, 3-$NH_2$-indazol-5-yl, I-Me-3-$NH_2$-indazoly-6-yl, 1,2,3,4-tetrahydroisoquinolin-3-yl, 1,2,3,4-tetrahydroisoquinolin-1-on-6-yl, isoquinolin-6-yl, 1-$NH_2$-isoquinolin-6-yl, 1-$NH_2$-5,6,7,8-tetrahydroisoquinolin-6-yl, 1,2,3,4-tetrahydroisoquinolin-6-yl, 1H-quinazolin-4-onyl, 2H-isoquinolin-1-onyl, 3H-quinazolin-4-onyl, 3,4-dihydro-2H-isoquinolin-1-onyl, 2,3-dihydroisoindolinonyl, or 1-$NH_2$-phthalazin-6-yl; and $R^3$ is phenyl, 3-OH-phenyl, 3,4-methylenedioxyphenyl, 2-naphthyl, 1-naphthyl, 3-$NMe_2$-phenyl, 4-benzyloxyphenyl, 4-t-butoxyphenyl, 4-methylsulfonylphenyl, 4-Cl-phenyl, 2-OMe-phenyl, 3-OMe-phenyl, 4-OMe-phenyl, 2-F-phenyl, 3-F-phenyl, 4-F-phenyl, 4-Br-phenyl, 3-$CF_3$-phenyl, 3-$NH_2$-phenyl, 4-$NH_2$-phenyl, 3-CN-phenyl, 4-CN-phenyl, 3-$CO_2H$-phenyl, 4-$CO_2H$-phenyl, 3-$CO_2Me$-phenyl, 4-$CO_2Me$-phenyl, 3-OH-phenyl, 3-$CH_2CO_2H$-phenyl, 3-$CH_2CO_2Me$-phenyl, 3-$CH_2CO_2Et$-phenyl, 3-$CONH_2$-phenyl, 4-$CONH_2$-phenyl, 4-$CH_2CO_2Et$-phenyl, 3-$CH_2C(O)NH_2$-phenyl, 4-C(O)NHMe-phenyl, 3-NHCOMe-phenyl, 4-$NHCO_2Me$-phenyl, 2,4-diF-phenyl, 3-F-4-CN-phenyl, 3-CN-4-F-phenyl, 3-OMe-4-$CONH_2$-phenyl, 3-OH-4-$CONH_2$-phenyl, 3-$NH_2$-4-$CONH_2$-phenyl, 3-$CO_2Me$-4-$NH_2$-phenyl, 3-$CO_2H$-4-$NH_2$-phenyl, 3-$CONH_2$-4-$NH_2$-phenyl, 3-$CO_2H$-4-F-phenyl, pyrrol-3-yl, pyrazol-3-yl, pyrazol-4-yl, 3-$NH_2$-pyrazol-5-yl, pyridyl-2-yl, pyrid-3-yl, pyrid-4-yl, 2-F-pyrid-4-yl, 2-F-pyrid-5-yl, 2-OMe-pyrid-4-yl, 2-OMe-pyrid-5-yl, 2-$NH_2$-pyrid-3-yl, 2-$NH_2$-pyrid-4-yl, 2-$NH_2$-pyrid-5-yl, 2-$NH_2$-pyrid-6-yl, 2-NHMe-pyrid-4-yl, 2-$NMe_2$-pyrid-4-yl, 2-$CONH_2$-pyrid-4-yl, 2-$CO_2H$-pyrid-4-yl, 2-$CONH_2$-pyrid-5-yl, 2-OMe-6-$NH_2$-pyridyl-4-yl, 4-$NH_2$-pyrimidin-6-yl, 4-$NH_2$-pyrimidin-2-yl, 2-$NH_2$-pyrimidin-4-yl, 2-$NH_2$-pyrimidin-5-yl, indol-5-yl, indol-6-yl, indazol-5-yl, indazol-6-yl, 3-OH-indazol-5-yl, 3-OH-indazol-6-yl, 3-OMe-indazol-5-yl, 3-OMe-indazol-6-yl, 3-$NH_2$-indazol-5-yl, 3-$NH_2$-indazol-6-yl, benzisoxalol-6-yl, benzisoxazol-5-yl, 3-$NH_2$-benzoisoxazol-5-yl, 3-$NH_2$-benzoisoxazol-6-yl, 4-OMe-quinolin-6-yl, 1-$NH_2$-phthalazin-6-yl, 1-$NH_2$-phthalazin-7-yl, 4-$NH_2$-quinazolin-6-yl, 2-Me-4-amino-quinazolin-6-yl, 4-$NH_2$-quinazolin-7-yl, 2-Me-4-$NH_2$-quinazolin-7-yl, 2,4-di-$NH_2$-quinazolin-7-yl,

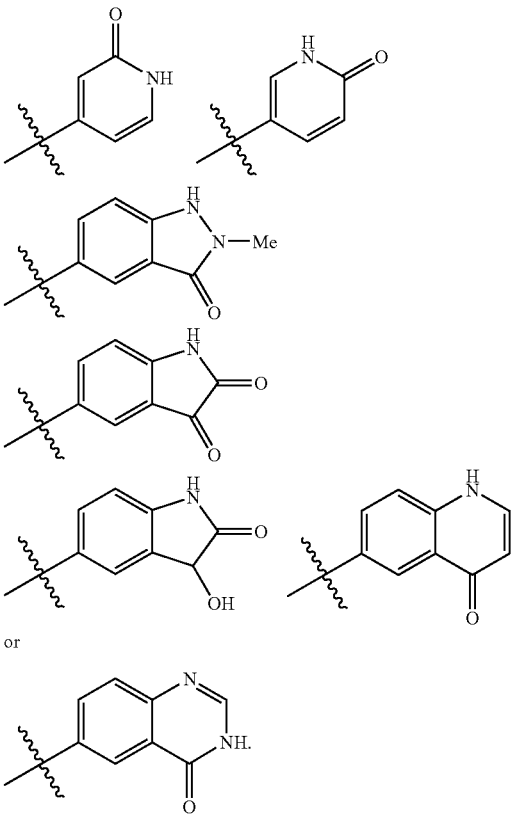

or

In an eighth aspect, the present invention provides a compound of Formula (Ia):

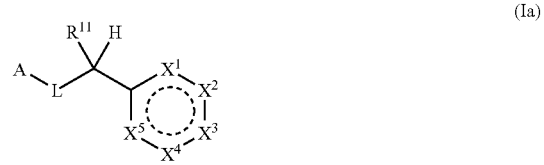

(Ia)

or a stereoisomer or pharmaceutically acceptable salt, solvate, or prodrug thereof, wherein:

A is $C_{3-7}$ cycloalkyl substituted with 0-1 $R^1$ and 0-2 $R^2$, $C_{3-7}$ cycloalkenyl substituted with 0-1 $R^1$ and 0-2 $R^2$, phenyl substituted with 0-1 $R^1$ and 0-3 $R^2$, naphthyl substituted with 0-1 $R^1$ and 0-3 $R^2$, or a 5- to 10-membered heterocycle comprising: carbon atoms and 1-4 heteroatoms selected from N, O, and $S(O)_p$, wherein said heterocycle is substituted 0-1 $R^1$ and 0-3 $R^2$;

the group

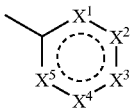

is selected from:

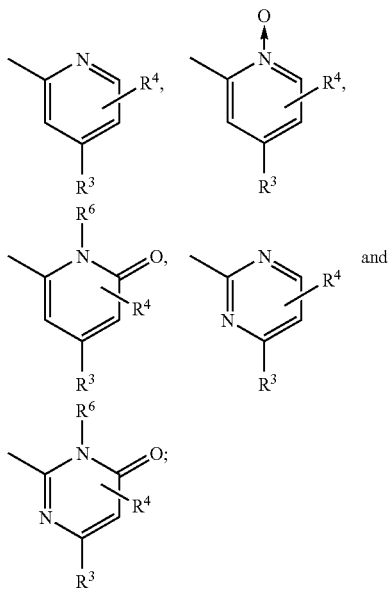

L is $-C(O)NR^{10}-$, $-NR^{10}C(O)-$, $-CH_2C(O)NR^{10}-$, $-CH_2NR^{10}C(O)-$, $-C(O)NR^{11}CH_2-$, or $-NR^{10}C(O)CH_2-$;

$R^1$ is, independently at each occurrence, $-NH_2$, $-NH(C_{1-3}\text{ alkyl})$, $-N(C_{1-3}\text{ alkyl})_2$, $-C(=NH)NH_2$, $-C(O)NH_2$, $-CH_2NH_2$, $-(CH_2)_rNR^7R^8$, $-CH_2NH(C_{1-3}\text{ alkyl})$, $-CH_2N(C_{1-3}\text{ alkyl})_2$, $-CH_2CH_2NH_2$, $-CH_2CH_2NH(C_{1-3}\text{ alkyl})$, $-CH_2CH_2N(C_{1-3}\text{ alkyl})_2$, $-CH(C_{1-4}\text{ alkyl})NH_2$, $-C(C_{1-4}\text{ alkyl})_2NH_2$, $C(=NR^{8a})NR^7R^8$, $-NR^8CR^8(=NR^{8a})$, $-NHC(=NR^{8a})NR^7R^8$, $=NR^8$, $-C(O)NR^8R^9$, $-S(O)_pNR^8R^9$, $-(CH_2)_rNR^7C(O)OR^a$, F, Cl, Br, I, $OCF_3$, $CF_3$, $OR^a$, $SR^a$, CN, 1-$NH_2$-1-cyclopropyl, or $C_{1-6}$ alkyl substituted with 0-1 $R^{1a}$;

$R^{1a}$ is H, $-C(=NR^{8a})NR^7R^8$, $-NHC(=NR^{8a})NR^7R^8$, $-NR^8CR^8(=NR^{8a})$, $-NR^7R^8$, $-C(O)NR^8R^9$, F, $OCF_3$, $CF_3$, $OR^a$, $SR^a$, CN, $-NR^8SO_2NR^8R^9$, $NR^8SO_2R^c$, $-S(O)_p-C_4$ alkyl, $-S(O)_p$-phenyl, or $-(CF_2)_rCF_3$;

$R^2$ is at each occurrence, H, =O, F, Cl, Br, I, $OCF_3$, $CF_3$, $CHF_2$, CN, $NO_2$, $OR^a$, $SR^a$, $-C(O)OR^a$, $-OC(O)R^a$, $-NR^7R^8$, $-C(O)NR^7R^8$, $-NR^7C(O)R^b$, $-S(O)_pNR^8R^9$, $-NR^8S(O)_2R^c$, $-S(O)R^c$, $-S(O)_2R^c$, $C_{1-6}$ alkyl, $C_{2-6}$ alkenyl, $C_{2-6}$ alkynyl, $-(CH_2)_r$-phenyl substituted with 0-2 $R^{2b}$, or $-(CH_2)_r$-5- to 6-membered heterocycle comprising: carbon atoms and 1-4 heteroatoms selected from N, O, and $S(O)_p$, wherein said heterocycle is substituted with 0-3 $R^{2b}$;

$R^{2b}$ is, independently at each occurrence, H, F, Cl, Br, I, =O, =$NR^8$, CN, $NO_2$, $CF_3$, $OR^a$, $SR^a$, $-C(O)R^a$, $-C(O)OR^a$, $-OC(O)R^a$, $-NR^7R^8$, $-C(O)NR^7R^8$, $-NR^7C(O)R^b$, $-S(O)_pNR^8R^9$, $-SO_2R^c$, $-NR^8SO_2NR^8R^9$, $-NR^8SO_2R^c$, $-(CF_2)_rCF_3$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$ haloalkyloxy-;

alternately, when $R^1$ and $R^2$ are substituted on adjacent ring atoms, they can be taken together with the ring atoms to which they are attached to form a 5- to 7-membered carbocycle or heterocycle comprising: carbon atoms and 0-4 heteroatoms selected from N, O, and $S(O)_p$, wherein said carbocycle or heterocycle is substituted with 0-2 $R^{2b}$;

$R^3$ is, independently at each occurrence, $-(CH_2)_rC(O)NR^8R^9$, $-(CH_2)_rC(O)NR^8(CH_2)_sCO_2R^{3b}$, $-(CH_2)_rCO_2R^{3b}$, $-(CH_2)_r$-phenyl substituted with 0-3 $R^{3a}$ and 0-1 $R^{3d}$, or $-(CH_2)_r$-5- to 10-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^{3a}$ is, independently at each occurrence, =O, F, Cl, Br, I, $OCF_3$, $CF_3$, CN, $NO_2$, $-(CH_2)_rOR^{3b}$, $SR^{3b}$, $-(CH_2)_rNR^7R^8$, $-C(=NR^{8a})NR^8R^9$, $-NHC(=NR^{8a})NR^7R^8$, $-NR^8CR^8(=NR^{8a})$, $-(CH_2)_rNR^8C(O)R^{3b}$, =$NR^8$, $-(CH_2)_rNR^8C(O)R^{3b}$, $-(CH_2)_rNR^8C(O)_2R^{3b}$, $-(CH_2)_rS(O)_pNR^8R^9$, $-(CH_2)_rNR^8S(O)_pR^{3c}$, $-S(O)R^{3c}$, $-S(O)_2R^{3c}$, $-C(O)-C_{1-4}$ alkyl, $-(CH_2)_rCO_2R^{3b}$, $-(CH_2)_rC(O)NR^8R^9$, $-(CH_2)_rOC(O)NR^8R^9$, $-NHCOCF_3$, $-NHSO_2CF_3$, $-SO_2NHR^{3b}$, $-SO_2NHCOR^{3c}$, $-SO_2NHCO_2R^{3c}$, $-CONHSO_2R^{3c}$, $-NHSO_2R^{3c}$, $-CONHOR^{3b}$, $C_{1-4}$ haloalkyl, $C_{1-4}$ haloalkyloxy-, $C_{1-6}$ alkyl substituted by $R^{3d}$, $C_{2-6}$ alkenyl substituted by $R^{3d}$, $C_{1-6}$ alkynyl substituted by $R^{3d}$, $C_{3-6}$ cycloalkyl substituted by 0-1 $R^{3d}$, $-(CH_2)_r-C_{3-10}$ carbocycle substituted with 0-3 $R^{3d}$, or $-(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

alternately, when two $R^{3a}$ groups are substituted on adjacent atoms, they can be taken together with the atoms to which they are attached to form a $C_{3-10}$ carbocycle substituted with 0-2 $R^{3d}$, or a 5- to 10-membered heterocycle comprising: carbon atoms and 1-4 heteroatoms selected from N, O, and $S(O)_p$, wherein said heterocycle is substituted with 0-2 $R^{3d}$;

$R^{3b}$ is, independently at each occurrence, H, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, $-(CH_2)_r-C_{3-10}$ carbocycle substituted with 0-3 $R^{3d}$, or $-(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3c}$ is, independently at each occurrence, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, $-(CH_2)_r-C_{3-10}$ carbocycle substituted with 0-3 $R^{3d}$, or $-(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3d}$ is, independently at each occurrence, H, =O, $-(CH_2)_rOR^a$, F, Cl, Br, CN, $NO_2$, $-(CH_2)_rNR^7R^8$, $-C(O)R^a$, $-C(O)OR^a$, $-OC(O)R^a$, $-NR^7C(O)R^b$, $-C(O)NR^8R^9$, $-S(O)_2NR^8R^9$, $-NR^8S(O)_2NR^8R^9$, $-NR^8S(O)_2R^c$, $-S(O)_pR^c$, $-(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_r C_{3-10}$ carbocycle substituted with 0-3 $R^d$, or —$(CH_2)_r$-5- to 10-membered heterocycle comprising: carbon atoms and 1-4 heteroatoms selected from N, O, and $S(O)_p$, wherein said heterocycle is substituted with 0-3 $R^d$;

$R^4$ is, independently at each occurrence, H, =O, F, Cl, Br, I, $OCF_3$, $CF_3$, CN, $NO_2$, $OR^a$, $SR^a$, —$C(O)R^a$, —$C(O)OR^a$, —$OC(O)R^a$, —$NR^7R^8$, —$C(O)NR^8R^9$, —$NR^7C(O)R^b$, —$S(O)_pNR^8R^9$, —$NR^8S(O)_pR^c$, —$S(O)_2R^c$, $C_{1-6}$ alkyl substituted with 0-2 $R^{4a}$, $C_{2-6}$ alkenyl substituted with 0-2 $R^{4a}$, $C_{2-6}$ alkynyl substituted with 0-2 $R^{4a}$, —$(CH_2)_r$—$C_{3-10}$ carbocycle substituted with 0-3 $R^{4b}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{4b}$;

$R^{4a}$ is, independently at each occurrence, H, F, =O, $C_{1-4}$ alkyl, $OR^a$, $SR^a$, $CF_3$, CN, $NO_2$, —$C(O)R^a$, —$C(O)OR^a$, —$NR^7R^8$, —$C(O)NR^8R^9$, —$NR^7C(O)R^b$, —$S(O)_pNR^8R^9$, —$NR^8S(O)_pR^c$, —$S(O)R^c$, or —$S(O)_2R^c$;

$R^{4b}$ is, independently at each occurrence, H, =O, =$NR^8$, F, Cl, Br, I, $OR^a$, $SR^a$, CN, $NO_2$, —$NR^7R^8$, —$C(O)R^a$, —$C(O)OR^a$, —$NR^7C(O)R^b$, —$C(O)NR^8R^9$, —$SO_2NR^8R^9$, —$S(O)_2R^c$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$ haloalkyloxy-;

alternately, $R^3$ and $R^4$ groups when located on adjacent atoms, can be taken together to form a $C_{3-10}$ carbocycle substituted with 0-2 $R^{3d}$ or a 5- to 10-membered heterocycle comprising: carbon atoms and 1-4 heteroatoms selected from N, O, and $S(O)_p$, wherein said heterocycle is substituted with 0-2 $R^{3d}$;

$R^6$ is, independently at each occurrence, H, $C_{1-6}$ alkyl, $C_{1-4}$ haloalkyl, —$CH_2OR^a$, —$C(O)R^c$, —$C(O)_2R^c$, —$S(O)_2R^c$, or —$(CH_2)_r$-phenyl substituted with 0-3 $R^d$;

$R^7$ is, independently at each occurrence, H, $C_{1-6}$ alkyl, —$(CH_2)_n$—$C_{3-10}$ carbocycle, —$(CH_2)_n$-(5-10 membered heteroaryl), —$C(O)R^c$, —CHO, —$C(O)_2R^c$, —$S(O)_2R^c$, —$CONR^8R^c$, —$OCONHR^c$, —$C(O)O$—$(C_{1-4}$ alkyl)OC(O)—$(C_{1-4}$ alkyl), or —$C(O)O$—$(C_{1-4}$ alkyl)OC(O)—$(C_{6-10}$ aryl); wherein said alkyl, carbocycle, heteroaryl, and aryl are optionally substituted with 0-2 $R^f$;

$R^8$ is, independently at each occurrence, H, $C_{1-6}$ alkyl, —$(CH_2)_n$-phenyl, or —$(CH_2)_n$-5-10 membered heterocycle comprising: carbon atoms and 1-4 heteroatoms selected from N, O, and $S(O)_p$; wherein said alkyl, phenyl and heterocycle are optionally substituted with 0-2 $R^f$;

alternatively, $R^7$ and $R^8$, when attached to the same nitrogen, combine to form a 5- to 10-membered heterocycle comprising: carbon atoms and 0-2 additional heteroatoms selected from N, O, and $S(O)_p$, wherein said heterocycle is substituted with 0-2 $R^d$;

$R^{8a}$ is, independently at each occurrence, $R^7$, OH, $C_{1-6}$alkyl, $C_{1-4}$ alkoxy, $(C_{6-10}$ aryl)-$C_{1-4}$ alkoxy; wherein said aryl is optionally substituted with 0-2 $R^f$;

$R^9$ is, independently at each occurrence, H, $C_{1-6}$ alkyl, or —$(CH_2)_n$-phenyl; wherein said alkyl and phenyl are optionally substituted with 0-2 $R^f$;

$R^{9a}$ is, independently at each occurrence, H, $C_{1-6}$ alkyl, or —$(CH_2)_n$-phenyl;

alternatively, $R^8$ and $R^9$, when attached to the same nitrogen, combine to form a 5- to 10-membered heterocycle comprising: carbon atoms and 0-2 additional heteroatoms selected from N, O, and $S(O)_p$, wherein said heterocycle is substituted with 0-2 $R^d$;

$R^{10}$ is, independently at each occurrence, H, $C_{1-6}$ alkyl substituted with 0-2 $R^{10a}$, —$(CH_2)_r$-phenyl substituted with 0-3 $R^d$, or —$(CH_2)_r$-5- to 10-membered heterocycle comprising carbon atoms and 1-4 heteroatoms selected from N, O, and $S(O)_p$, wherein said heterocycle is substituted with 0-3 $R^d$;

$R^{10a}$ is, independently at each occurrence, H, —O, $C_{1-4}$ alkyl, $OR^a$, $SR^a$, F, $CF_3$, CN, $NO_2$, —$C(O)R^a$, —$C(O)OR^a$, —$C(O)NR^7R^8$, —$NR^7C(O)R^b$, —$S(O)_pNR^8R^9$, —$NR^8S(O)_pR^c$, —$S(O)R^c$, or —$S(O)_2R^c$;

$R^{11}$ is $C_{1-4}$ haloalkyl, —$(CH_2)_r$—$C(O)NR^8R^9$, $C_{1-6}$ alkyl substituted with 0-3 $R^{11a}$, $C_{2-4}$ alkenyl substituted with 0-3 $R^{11a}$, $C_{2-4}$ alkynyl substituted with 0-3 $R^{11a}$, —$(CH_2)_s$—$C_{3-7}$ cycloalkyl substituted with 0-3 $R^{11b}$, —$(CH_2)_s$-phenyl substituted with 0-3 $R^{11b}$, or —$(CH_2)_s$-5- to 10-membered heterocycle comprising: carbon atoms and 1-4 heteroatoms selected from N, O, and $S(O)_p$, wherein said heterocycle is substituted with 0-3 $R^{11b}$;

$R^{11a}$ is, independently at each occurrence, H, =O, $C_{1-4}$ alkyl, $OR^a$, $SR^a$, F, $CF_3$, CN, $NO_2$, —$NR^7R^8$, —$C(O)R^a$, —$C(O)OR^a$, —$C(O)NR^7R^8$, —$NR^7C(O)R^b$, —$S(O)_pNR^8R^9$, —$NR^8S(O)_pR^c$, or —$S(O)_pR^c$, $C_{3-6}$ cycloalkyl, $C_{1-4}$ haloalkyl, $C_{1-4}$ haloalkyloxy-, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

$R^{11b}$ is, independently at each occurrence, H, =O, =$NR^8$, $OR^a$, F, Cl, Br, CN, $NO_2$, $CF_3$, $OCF_3$, $OCHF_2$, —$NR^7R^8$, —$C(O)R^a$, —$C(O)OR^a$, —$C(O)NR^7R^8$, —$NR^7C(O)R^b$, —$NR^8C(O)_2R^c$, —$S(O)_pNR^8R^9$, —$NR^8S(O)_pR^c$, —$S(O)_pR^c$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

alternately, when two $R^{11b}$ groups are substituents on adjacent atoms they may be taken together with the atoms to which they are attached to form a 5- to 7-membered heterocycle comprising carbon atoms and 1-4 heteroatoms selected from N, O, and $S(O)_p$ and substituted with 0-2 $R^g$;

$R^{13}$ is H, $C_{1-6}$ alkyl, —$C(O)R^c$, —$C(O)OR^c$, —$CONR^8R^c$, —$OCONR^8R^c$, —$S(O)_2R^c$, —$(CH_2)_n$-phenyl, —$(CH_2)_n$-(5-10 membered heteroaryl), —$C(O)O$—$(C_{1-4}$ alkyl)-OC(O)—$(C_{1-4}$ alkyl), or —$C(O)O$—$(C_{1-4}$ alkyl)-OC(O)—$(C_{6-10}$ aryl); wherein said alkyl, phenyl, aryl, and heteroaryl are optionally substituted with 0-2 $R^f$;

$R^a$ is, independently at each occurrence, H, $CF_3$, $C_{1-6}$ alkyl, —$(CH_2)_r$—$C_{3-7}$ cycloalkyl, —$(CH_2)_r$—$C_{6-10}$ aryl, or —$(CH_2)_r$-5- to 10-membered heterocycle comprising: carbon atoms and 1-4 heteroatoms selected from N, O, and $S(O)_p$; wherein said cycloalkyl, aryl and heterocycle groups are optionally substituted with 0-2 $R^f$;

$R^b$ is, independently at each occurrence, $CF_3$, OH, $C_{1-4}$ alkoxy, $C_{1-6}$ alkyl, —$(CH_2)_r C_{3-10}$ carbocycle substituted with 0-3 $R^d$, or —$(CH_2)_r$-5- to 10-membered heterocycle comprising: carbon atoms and 1-4 heteroatoms selected from N, O, and $S(O)_p$ and substituted with 0-2 $R^d$;

$R^c$ is, independently at each occurrence, $CF_3$, $C_{1-6}$ alkyl substituted with 0-2 $R^f$, $C_{3-6}$ cycloalkyl substituted with 0-2 $R^f$, $C_{6-10}$ aryl, 5- to 10-membered heteroaryl, $(C_{6-10}$ aryl)-$C_{1-4}$ alkyl, or (5- to 10-membered heteroaryl)-$C_{1-4}$ alkyl, wherein said aryl and heteroaryl groups are substituted with 0-3 $R^f$;

$R^d$ is, independently at each occurrence, H, =O, =$NR^8$, $OR^a$, F, Cl, Br, I, CN, $NO_2$, —$NR^7R^8$, —$C(O)R^a$, —$C(O)OR^a$, —$OC(O)R^a$, —$NR^8C(O)R^a$, —$C(O)NR^7R^8$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

$R^e$ is, independently at each occurrence, =O, $OR^a$, F, Cl, Br, I, CN, $NO_2$, —$NR^8R^9$, —$C(O)R^a$, —$C(O)OR^a$, —$NR^8C(O)R^a$, —$C(O)NR^7R^8$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, or —$(CF_2)_rCF_3$;

$R^f$ is, independently at each occurrence, H, =O, —(CH$_2$)$_r$OR$^g$, F, Cl, Br, I, CN, $NO_2$, —$NR^{9a}R^{9a}$, —$C(O)R^9$, —$C(O)OR^g$, —$NR^{9a}C(O)R^9$, —$C(O)NR^{9a}R^{9a}$, —$SO_2NR^{9a}R^{9a}$, —$NR^{9a}SO_2NR^{9a}R^{9a}$, —$NR^{9a}SO_2C_{1-4}$ alkyl, —$NR^{9a}SO_2CF_3$, —$NR^{9a}SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, $C_{2-6}$ alkynyl, or —$(CH_2)_n$-phenyl;

$R^g$ is, independently at each occurrence, H, $C_{1-6}$ alkyl, or —$(CH_2)_n$-phenyl;

n, at each occurrence, is selected from 0, 1, 2, 3, and 4;

p, at each occurrence, is selected from 0, 1, and 2; and r, at each occurrence, is selected from 0, 1, 2, 3, and 4; and s, at each occurrence, is selected from 1, 2, 3, and 4.

In a ninth aspect, the present invention includes compounds of Formula (Ia), within the scope of the eighth aspect wherein:

A is substituted with 0-1 $R^1$ and 0-2 $R^2$ and selected from: $C_{3-7}$ cycloalkyl, phenyl, naphthyl, pyridyl, 1,2,3,4-tetrahydronaphthyl, indazolyl, benzimidazolyl, benzisoxazolyl, isoquinolinyl, 5,6,7,8-tetrahydroisoquinolinyl, 1,2,3,4-tetrahydroisoquinolinyl, quinazolinyl, 1H-quinazolin-4-onyl, 2H-isoquinolin-1-onyl, 3H-quinazolin-4-onyl, 3,4-dihydro-2H-isoquinolin-1-onyl, 2,3-dihydroisoindolinonyl, and phthalazinyl;

L is —C(O)NR$^{10}$—, or —NR$^{10}$C(O)—;

$R^4$ is, independently at each occurrence, H, F, Cl, Br, I, $CF_3$, CN, $NO_2$, $OR^a$, $SR^a$, —$C(O)R^a$, —$C(O)OR^a$, —$NR^7R^8$, —$C(O)NR^8R^9$, —$NR^7C(O)R^b$, —$S(O)_pNR^8R^9$, —$NR^8S(O)_pR^c$, —$S(O)_2R^c$, $C_{1-6}$ alkyl substituted with 0-2 $R^{4a}$, $C_{2-6}$ alkenyl substituted with 0-2 $R^{4a}$, $C_{2-6}$ alkynyl substituted with 0-2 $R^{4a}$; and $R^6$ is H, or $C_{1-4}$ alkyl.

In a tenth aspect, the present invention includes compounds of Formula (Ia), within the scope of the ninth aspect wherein:

$R^1$ is, independently at each occurrence, F, Cl, Me, Et, —$NH_2$, —C(=NH)NH$_2$, —C(O)NH$_2$, —CH$_2$NH$_2$, —CH$_2$NHCO$_2$Bn, —CH$_2$NHCO$_2$(t-Bu), —CH(Me)NH$_2$, —CMe$_2$NH$_2$, —NHEt, —NHCO$_2$(t-Bu), —NHCO$_2$Bn, —SO$_2$NH$_2$, $OR^a$, or —CH$_2R^{1a}$;

$R^2$ is, independently at each occurrence, F, Cl, Me, OMe, OEt, Bn, —CH$_2$OMe, —CH$_2$OEt, or —CH$_2$OPh;

$R^3$ is —CO$_2$H, —CO$_2$Me, —C(O)NHCH$_2$CO$_2$H, —C(O)NHCH$_2$CO$_2$Et, —C(O)NH$_2$, —C(O)NHMe, —C(O)NHBn, phenyl substituted with 0-2 $R^{3a}$, naphthyl substituted with 0-2 $R^{3a}$, indane substituted with 0-2 $R^{3a}$, or a 5- to 10-membered heterocycle selected from N, O, and S(O)$_p$, wherein said heterocycle is substituted with 0-2 $R^3$a;

$R^{3a}$ is, independently at each occurrence, =O, F, Cl, Br, Me, CN, OH, NH$_2$, OMe, O(t-Bu), OBn, $CF_3$, CO$_2$H, CO$_2$Me, —CH$_2$CO$_2$H, —CH$_2$CO$_2$Me, —CH$_2$CO$_2$Et, —NHCOMe, —CONH$_2$, —CH$_2$CONH$_2$, —CONHMe, —CONMe$_2$, —C(=NH)NH$_2$, —NR$^7$R$^8$, SO$_2$Me, —SO$_2$NH$_2$, Ph, or 2-oxo-piperidin-1-yl; wherein two of the $R^{3a}$ groups located on adjacent atoms can be taken together to form 5- to 10-membered heterocycle with 0-2 $R^{3d}$;

$R^4$ is H, F, Cl, Br, OMe, or NH$_2$;

$R^6$ is H;

$R^{10}$ is H; and $R^{11}$ is —(CH$_2$)$_r$—C(O)NR$^8$R$^9$, —CH$_2$OBn, —CH$_2$SBn, —(CH$_2$)$_s$-cyclohexyl substituted with 0-2 $R^{11b}$, —(CH$_2$)$_s$-phenyl substituted with 0-2 $R^{11b}$, —(CH$_2$)$_s$-naphthyl substituted with 0-2 $R^{11b}$, —(CH$_2$)$_s$-5- to 10-membered heteroaryl substituted with 0-1 $R^{11b}$; wherein said heteroaryl selected from thiazolyl, imidazolyl, pyridyl, indolyl benzimidazolyl, and benzothiazolyl.

In an eleventh aspect, the present invention includes compounds of Formula (Ia), within the scope of the tenth aspect wherein:

L is —C(O)NH—; and $R^{11}$ is phenylmethyl, 4-imidazolylmethyl, 4-thiazolylmethyl, 2-benzthiazolylmethyl, 2-pyridylmethyl, 3-pyridylmethyl, 4-pyridylmethyl, 3-indolylmethyl, 2-benzimidazolylmethyl, 1-naphthylmethyl, 2-naphthylmethyl, cyclohexylmethyl, —CH$_2$C(O)NHCH$_2$-pyridin-2-yl or —(CH$_2$)$_2$C(O)NHCH$_2$-pyridin-2-yl, wherein each phenyl, naphthyl, imidazolyl, thiazolyl, benzthiazolyl, pyridinyl, or cyclohexyl group is substituted with 0-2 $R^{11b}$;

$R^{11b}$ is, independently at each occurrence, H, F, Cl, Br, $CF_3$, OMe, OCF$_3$, OCHF$_2$, OPh, OBn, NO$_2$, —NH$_2$, —C(O)Ph, —NHC(O)Bn, —NHC(O)CH$_2$CH$_2$Ph, —NHS(O)$_2$Ph, —C(O)NR$^7$R$^8$, —NR$^7$C(O)R$^b$, —S(O)$_p$NR$^8$R$^9$, —NR$^8$S(O)$_p$R$^c$, Ph, or Bn;

alternately, when two $R^{11b}$ groups are substituents on adjacent atoms they may be taken together with the atoms to which they are attached to form a 5- to 7-membered heterocycle comprising carbon atoms and 1-4 heteroatoms selected from N, O, and S(O)$_p$ and substituted with 0-2 $R^g$.

In a twelfth aspect, the present invention includes compounds of Formula (Ia), within the scope of the eleventh aspect wherein:

$R^3$ is phenyl substituted with 0-2 $R^{3a}$, naphthyl substituted with 0-2 $R^{3a}$, indanone substituted with 0-2 $R^{3a}$, or a 5- to 10-membered heterocycle substituted with 0-2 $R^{3a}$ and selected from: pyridine, pyridinone, pyrimidine, pyrrole, pyrazole, indole, 2-oxoindole, indazole, benzofuran, benzothiophene, benzimidazole, benzisoxazole, benzoxazole, quinazoline, 3H-quinazolin-4-one, phthalazine, 2H-phthalazin-1-one, 1H-quinolin-4-one, isoquinoline, and 2H-3,4-dihydroisoquinolin-1-one.

In a thirteenth aspect, the present invention includes compounds of Formula (Ia), within the scope of the twelfth aspect wherein:

A is 4-aminomethyl-cyclohexyl; 4-carbamoyl-cyclohexyl, 4-amidino-phenyl, 4-benzyloxycarbonylamino-cyclohexyl, phenyl, 1,2,3,4-tetrahydronaphth-2-yl, 4-aminomethyl-phenyl, 4-carbamoyl-phenyl, 4 aminomethyl-2-fluoro-phenyl, 2-F-5-OMe-phenyl, 2-F-4-Me-phenyl, 2-F-4-Cl-phenyl, 2-F-4-carbamoyl-phenyl, 2-OMe-4-carbamoyl-phenyl, 3-OMe-4-carbamoyl-phenyl, 2-Et-4-aminomethyl-phenyl, 2-NH$_2$-pyridin-4-yl, 2-ethylamino-4-aminomethyl-phenyl, 1-aminoisoquinolin-6-yl, 1-NH$_2$-5,6,7,8-tetrahydroisoquinolin-6-yl, 1-NH$_2$-1,2,3,4-tetrahydroisoquinolin-6-yl, 3-NH$_2$-benzisoxazol-5-yl, 3-NH$_2$-benzisoxazol-6-yl, 3-NH$_2$-indazol-6-yl, 3-NH$_2$-indazol-5-yl, 1-Me-3-NH$_2$-indazoly-6-yl, 1,2,3,4-tetrahydroisoquinolin-3-yl, 1,2,3,4-tetrahydroisoquinolin-1-on-6-yl, isoquinolin-6-yl, 1-NH$_2$-isoquinolin-6-yl, 1-NH$_2$-5,6,7,8-tetrahydroisoquinolin-6-yl, 1,2,3,4-tetrahydroisoquinolin-6-yl, 1H-quinazolin-4-onyl, 2H-isoquinolin-1-onyl, 3H-quinazolin-4-onyl, 3,4-dihydro-2H-isoquinolin-1-onyl, 2,3-dihydroisoindolinonyl, or 1-NH$_2$-phthalazin-6-yl; and $R^3$ is phenyl, 3-OH-phenyl, 3,4-methylenedioxyphenyl, 2-naphthyl, 1-naphthyl, 3-NMe$_2$-phenyl, 4-benzyloxyphenyl, 4-t-butoxyphenyl, 4-methylsulfonylphenyl, 4-Cl-phenyl, 2-OMe-phenyl, 3-OMe-phenyl, 4-OMe-phenyl, 2-F- phenyl, 3-F-phenyl, 4-F-phenyl, 4-Br-phenyl, 3-CF$_3$-phenyl, 3-NH$_2$-phenyl, 4-NH$_2$-phenyl, 3-CN-phenyl, 4-CN-phenyl, 3-CO$_2$H-phenyl, 4-CO$_2$H-phenyl, 3-CO$_2$Me-phenyl, 4-CO$_2$Me-phenyl, 3-OH-phenyl, 3-CH$_2$CO$_2$H-phenyl, 3-CH$_2$CO$_2$Me-phenyl, 3-CH$_2$CO$_2$Et-phenyl, 3-CONH$_2$-phenyl, 4-CONH$_2$-phenyl, 4-CH$_2$CO$_2$Et-phenyl, 3-CH$_2$C(O)NH$_2$-phenyl, 4-C(O)NHMe-phenyl, 3-NHCOMe-phenyl, 4-NHCO$_2$Me-phenyl, 2,4-diF-phenyl, 3-F-4-CN-phenyl, 3-CN-4-F-phenyl, 3-OMe-4-CONH$_2$-phenyl, 3-OH-4-CONH$_2$-phenyl, 3-NH$_2$-4-CONH$_2$-phenyl, 3-CO$_2$Me-4-NH$_2$-phenyl, 3-CO$_2$H-4-NH$_2$-phenyl, 3-CONH$_2$-4-NH$_2$-phenyl, 3-CO$_2$H-4-F-phenyl, pyrrol-3-yl, pyrazol-3-yl, pyrazol-4-yl, 3-NH$_2$-pyrazol-5-yl, pyridyl-2-yl, pyrid-3-yl, pyrid-4-yl, 2-F-pyrid-4-yl, 2-F-pyrid-5-yl, 2-OMe-pyrid-4-yl, 2-OMe-pyrid-5-yl, 2-NH$_2$-pyrid-3-yl, 2-NH$_2$-pyrid-4-yl, 2-NH$_2$-pyrid-5-yl, 2-NH$_2$-pyrid-6-yl, 2-NHMe-pyrid-4-yl, 2-NMe$_2$-pyrid-4-yl, 2-CONH$_2$-pyrid-4-yl, 2-CO$_2$H-pyrid-4-yl, 2-CONH$_2$-pyrid-5-yl, 2-OMe-6-NH$_2$-pyridyl-4-yl, 4-NH$_2$-pyrimidin-6-yl, 4-NH$_2$-pyrimidin-2-yl, 2-NH$_2$-pyrimidin-4-yl, 2-NH$_2$-pyrimidin-5-yl, indol-5-yl, indol-6-yl, indazol-5-yl, indazol-6-yl, 3-OH-indazol-5-yl, 3-OH-indazol-6-yl, 3-OMe-indazol-5-yl, 3-OMe-indazol-6-yl, 3-NH$_2$-indazol-5-yl, 3-NH$_2$-indazol-6-yl, benzisoxalol-6-yl, benzisoxazol-5-yl, 3-NH$_2$-benzoisoxazol-5-yl, 3-NH$_2$-benzoisoxazol-6-yl, 4-OMe-quinolin-6-yl, 1-NH$_2$-phthalazin-6-yl, 1-NH$_2$-phthalazin-7-yl, 4-NH$_2$-quinazolin-6-yl, 2-Me-4-amino-quinazolin-6-yl, 4-NH$_2$-quinazolin-7-yl, 2-Me-4-NH$_2$-quinazolin-7-yl, 2,4-di-NH$_2$-quinazolin-7-yl, In a fourteenth aspect, the present invention includes compounds of Formula (Ia), within the scope of the thirteenth aspect wherein:

A is 4-aminomethyl-cyclohexyl; and
the group

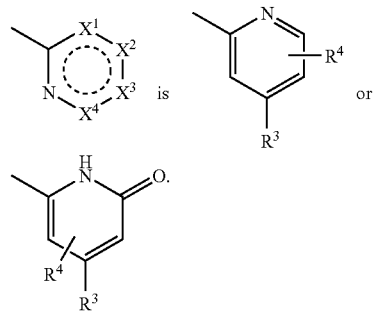

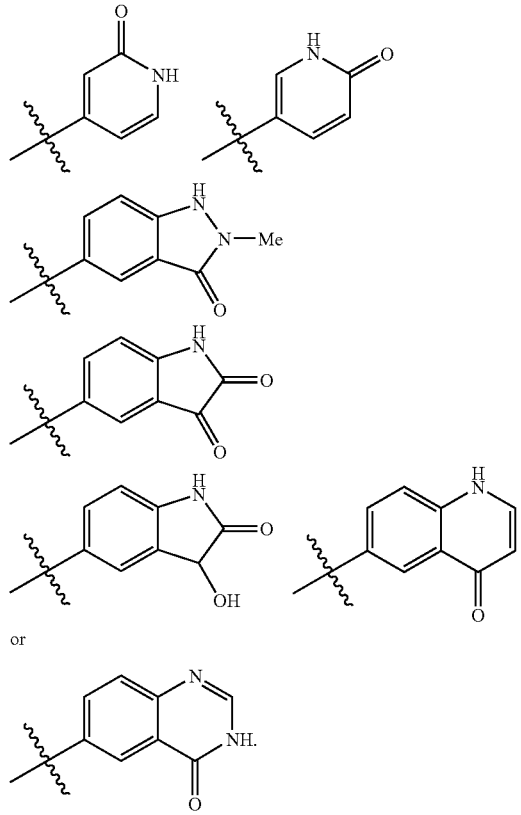

In a fifteenth aspect, the present invention provides a compound selected from the exemplified examples or stereoisomers or pharmaceutically acceptable salts, solvates, or prodrugs thereof.

In another aspect, the present invention includes, inter alia, compounds of Formula (III):

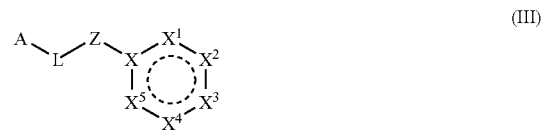

or a stereoisomer or pharmaceutically acceptable salts, solvates, or prodrugs thereof, wherein:

A is $C_{3-10}$ carbocycle substituted with 0-1 $R^1$ and 0-3 $R^2$, or a 5- to 10-membered heterocycle comprising: carbon atoms and 1-4 heteroatoms selected from N, O, and $S(O)_p$, wherein said heterocycle is substituted 0-1 $R^1$ and 0-3 $R^2$;

X is C, CH, or N;

$X^1$, $X^2$, $X^3$, $X^4$, and $X^5$ are independently $CR^3$, $CR^4$, $CR^5$, $CR^4R^5$, O, $S(O)_p$, N, $NR^3$, $NR^6$, N→O, or C(O); provided that at least one of $X^1$, $X^2$, $X^3$, $X^4$, and $X^5$ is $CR^3$; no S—S, S—O, or O—O bond is present in the ring; and when X is C or CH, at least one of $X^1$, $X^2$, $X^3$, $X^4$, and $X^5$ is selected from N, $NR^3$, $NR^6$, and N→O;

Z is —C($R^{11}$)($R^{12}$)— or —$NR^{13}$—;

L is —C(O)$NR^{10}$—, —$NR^{10}$C(O)—, —CH$_2$C(O)$NR^{10}$—, —CH$_2NR^{10}$C(O)—, —C(O)$NR^{10}$CH$_2$—, —$NR^{10}$C(O)CH$_2$—, —S(O)$_2$NR O—, —$NR^{10}$S(O)$_2$—, —CH$_2$S(O)$_2NR^{10}$—, —CH$_2NR^{10}$S(O)$_2$—, —S(O)$_2$$NR^{10}$CH$_2$—, —$NR^{10}$S(O)$_2$CH$_2$—, —CH$_2$CH$_2$—, —CH$_2$CH$_2$CH$_2$—, —CH$_2NR^7$—, —$NR^7$CH$_2$—, —CH$_2$CH$_2NR^7$—, —$NR^7$CH$_2$CH$_2$—, —CH$_2NR^7$CH$_2$—, —CH$_2$O—, —OCH$_2$—, —CH$_2$CH$_2$O—, —OCH$_2$CH$_2$—, —CH$_2$OCH$_2$—, —CH$_2$S(O)$_p$—, —S(O)$_p$CH$_2$—, —CH$_2$CH$_2$S(O)$_p$—, —S(O)$_p$CH$_2$CH$_2$—, —CH$_2$S(O)$_p$CH$_2$—, —CH$_2$C(O), —C(O)CH$_2$—, —CH$_2$CH$_2$C(O)—, —C(O)CH$_2$CH$_2$—, or —CH$_2$C(O)CH$_2$—;

$R^1$ is, independently at each occurrence, —NH$_2$, —NH(C$_{1-3}$ alkyl), —N(C$_{1-3}$ alkyl)$_2$, —C(=NH)NH$_2$, —C(O)NH$_2$, —CH$_2$NH$_2$, —(CH$_2$)$_r$NR$^7$R$^8$, —CH$_2$NH(C$_{1-3}$ alkyl), —CH$_2$N(C$_{1-3}$ alkyl)$_2$, —CH$_2$CH$_2$NH$_2$, —CH$_2$CH$_2$NH(C$_{1-3}$ alkyl), —CH$_2$CH$_2$N(C$_{1-3}$ alkyl)$_2$, —CH(C$_{1-4}$ alkyl)NH$_2$, —C(C$_{1-4}$ alkyl)$_2$NH$_2$, —C(=NR$^{8a}$)NR$^7$R$^8$, —NR$^8$CR$^8$(=NR$^{8a}$), —NHC(=NR$^{8a}$)NR$^7$R$^8$, =NR$^8$, —C(O)NR$^8$R$^9$, —S(O)$_p$NR$^8$R$^9$, —(CH$_2$)$_r$NR$^7$C(O)OR$^a$, F, Cl, Br, I, OCF$_3$, CF$_3$, OR$^a$, SR$^a$, CN, 1-NH$_2$-1-cyclopropyl, or C$_{1-6}$ alkyl substituted with 0-1 R$^{1a}$;

R$^{1a}$ is H, —C(=NR$^{8a}$)NR$^8$R$^9$, —NHC(=NR$^{8a}$)NR$^8$R$^9$, —NR$^8$CR$^8$(=NR$^{8a}$), —NR$^7$R$^8$, —C(O)NR$^7$R$^8$, F, OCF$_3$, CF$_3$, OR$^a$, SR$^a$, CN, —NR$^8$SO$_2$NR$^8$R$^9$, —NR$^8$SO$_2$R$^c$, —S(O)$_p$—C$_{1-4}$ alkyl, —S(O)$_p$-phenyl, or —(CF$_2$)$_r$CF$_3$;

R$^2$ is, independently at each occurrence, H, =O, F, Cl, Br, I, OCF$_3$, CF$_3$, CHF$_2$, CN, NO$_2$, OR$^a$, SR$^a$, —C(O)R$^a$, —C(O)OR$^a$, —OC(O)R$^a$, —NR$^7$R$^8$, —C(O)NR$^7$R$^8$, —NR$^7$C(O)R$^b$, —S(O)$_p$NR$^8$R$^9$, —NR$^8$S(O)$_2$R$^c$, —S(O)R$^c$, —S(O)$_2$R$^c$, C$_{1-6}$ alkyl substituted with 0-2 R$^{2a}$, C$_{2-6}$ alkenyl substituted with 0-2 R$^{2a}$, C$_{2-6}$ alkynyl substituted with 0-2 R$^{2a}$, —(CH$_2$)$_r$—C$_{3-10}$ carbocycle substituted with 0-3 R$^{2b}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{2b}$;

R$^{2a}$ is, independently at each occurrence, H, F, Cl, Br, I, =O, =NR$^8$, CN, OCF$_3$, CF$_3$, OR$^a$, SR$^a$, —NR$^7$R$^8$, —C(O)NR$^8$R$^9$, —NR$^7$C(O)R$^b$, —S(O)$_p$NR$^8$R$^9$, —NR$^8$SO$_2$R$^c$, —S(O)R$^c$, or —S(O)$_2$R$^c$;

R$^{2b}$ is, independently at each occurrence, H, F, Cl, Br, I, =O, =NR$^8$, CN, NO$_2$, CF$_3$, OR$^a$, SR$^a$, —C(O)R$^a$, —C(O)OR$^a$, —OC(O)R$^a$, —NR$^7$R$^8$, —C(O)NR$^7$R$^8$, —NR$^7$C(O)R$^b$, —S(O)$_p$NR$^8$R$^9$, —SO$_2$R$^c$, —NR$^8$SO$_2$NR$^8$R$^9$, —NR$^8$SO$_2$R$^c$, —(CF$_2$)$_r$CF$_3$, C$_{1-6}$ alkyl, C$_{2-6}$ alkenyl, C$_{2-6}$ alkynyl, C$_{3-6}$ cycloalkyl, C$_{1-4}$ haloalkyl, or C$_{1-4}$ haloalkyloxy-;

alternately, when R$^1$ and R$^2$ are substituted on adjacent ring atoms, they can be taken together with the ring atoms to which they are attached to form a 5- to 7-membered carbocycle or heterocycle comprising: carbon atoms and 0-4 heteroatoms selected from N, O, and S(O)$_p$, wherein said carbocycle or heterocycle is substituted with 0-2 R$^{2b}$;

R$^3$ is, independently at each occurrence, —(CH$_2$)$_r$C(O)NR$^8$R$^9$, —(CH$_2$)$_r$C(O)NR$^8$(CH$_2$)$_s$CO$_2$R$^{3b}$, —(CH$_2$)$_r$CO$_2$R$^{3b}$, —(CH$_2$)$_r$—C$_{3-10}$ carbocycle substituted with 0-3 R$^{3a}$ and 0-1 R$^{3d}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{3a}$ and 0-1 R$^{3d}$;

R$^{3a}$ is, independently at each occurrence, =O, F, Cl, Br, I, OCF$_3$, CF$_3$, CN, NO$_2$, —(CH$_2$)$_r$OR$^{3b}$, SR$^{3b}$, —(CH$_2$)$_r$NR$^7$R$^8$, —C(=NR$^9$)NR$^8$R$^9$, —NHC(=NR$^{8a}$)NR$^8$R$^9$, —NR$^8$CR$^8$(=NR$^{8a}$), —(CH$_2$)$_r$NR$^8$C(O)R$^{3b}$, =NR$^8$, —(CH$_2$)$_r$NR$^8$C(O)$_2$R$^{3b}$, —(CH$_2$)$_r$S(O)$_p$NR$^8$R$^9$, —(CH$_2$)$_r$NR$^8$S(O)$_2$R$^{3c}$, —S(O)R$^{3c}$, —S(O)$_2$R$^{3c}$, C$_{1-6}$ alkyl substituted by R$^{3e}$, C$_{2-6}$ alkenyl substituted by R$^{3e}$, C$_{1-6}$ alkynyl substituted by R$^{3e}$, C$_{3-6}$ cycloalkyl substituted by 0-1 R$^{3d}$, C$_{1-4}$ haloalkyl, C$_{1-4}$ haloalkyloxy-, —(CH$_2$)$_r$CO$_2$R$^{3b}$, —(CH$_2$)$_r$C(O)NR$^8$R$^9$, —(CH$_2$)$_r$OC(O)NR$^8$R$^9$, —(CH$_2$)$_r$SO$_3$H, —OSO$_3$H, —(CH$_2$)$_r$PO$_3$H, —OPO$_3$H$_2$, —PO$_3$H$_2$, —NHCOCF$_3$, —NHSO$_2$CF$_3$, —CONHNHSO$_2$CF$_3$, —C(CF$_3$)$_2$OH, —SO$_2$NHR$^{3b}$, —CONHSO$_2$NHR$^{3b}$, —SO$_2$NHCOR$^{3c}$, —SO$_2$NHCO$_2$R$^{3c}$, —CONHSO$_2$R$^{3c}$, —NHSO$_2$R$^{3c}$, —CONHOR$^{3b}$,

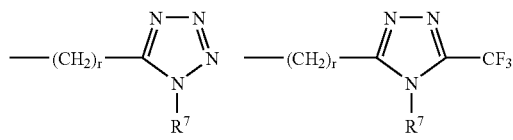

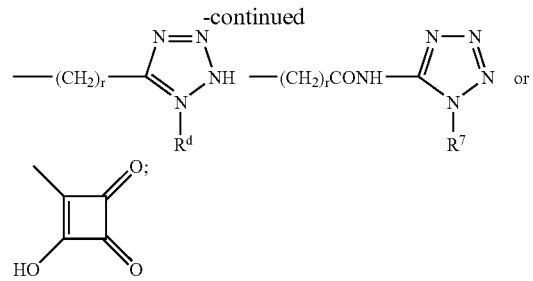

alternately, when two R$^{3a}$ groups are substituted on adjacent atoms, they can be taken together with the atoms to which they are attached to form a C$_{3-10}$ carbocycle substituted with 0-2 R$^{3d}$, or a 5- to 10-membered heterocycle comprising: carbon atoms and 1-4 heteroatoms selected from N, O, and S(O)$_p$, wherein said heterocycle is substituted with 0-2 R$^{3d}$;

R$^{3b}$ is, independently at each occurrence, H, C$_{1-6}$ alkyl substituted with 0-2 R$^{3d}$, C$_{2-6}$ alkenyl substituted with 0-2 R$^{3d}$, C$_{2-6}$ alkynyl substituted with 0-2 R$^{3d}$, —(CH$_2$)$_r$—C$_{3-10}$ carbocycle substituted with 0-3 R$^{3d}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{3d}$;

R$^{3c}$ is, independently at each occurrence, C$_{1-6}$ alkyl substituted with 0-2 R$^{3d}$, C$_{2-6}$ alkenyl substituted with 0-2 R$^{3d}$, C$_{2-6}$ alkynyl substituted with 0-2 R$^{3d}$, —(CH$_2$)$_r$—C$_{3-10}$ carbocycle substituted with 0-3 R$^{3d}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{3d}$;

R$^{3d}$ is, independently at each occurrence, H, =O, —(CH$_2$)$_r$OR$^a$, F, Cl, Br, CN, NO$_2$, —(CH$_2$)$_r$NR$^7$R$^8$, —C(O)R$^a$, —C(O)OR$^a$, —OC(O)R$^a$, —NR$^7$C(O)R$^b$, —C(O)NR$^8$R$^9$, —S(O)$_2$NR$^8$R$^9$, —NR$^8$S(O)$_2$NR$^8$R$^9$, —NR$^8$S(O)$_2$R$^c$, —S(O)$_p$R$^c$, —(CF$_2$)$_r$CF$_3$, C$_{1-6}$ alkyl substituted with 0-2 R$^e$, C$_{2-6}$ alkenyl substituted with 0-2 R$^e$, C$_{2-6}$ alkynyl substituted with 0-2 R$^e$, —(CH$_2$)$_r$—C$_{3-10}$ carbocycle substituted with 0-3 R$^d$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^d$;

R$^{3e}$ is, independently at each occurrence, H, —(CH$_2$)$_r$OR$^a$, F, Cl, Br, I, CN, NO$_2$, —(CH$_2$)$_r$NR$^7$R$^8$, —C(O)R$^a$, —C(O)OR$^a$, —OC(O)R$^a$, —NR$^7$C(O)R$^b$, —C(O)NR$^8$R$^9$, —S(O)$_2$NR$^8$R$^9$, —NR$^8$S(O)$_2$NR$^8$R$^9$, —NR$^8$S(O)$_2$R$^c$, —S(O)$_p$R$^c$, —(CF$_2$)$_r$CF$_3$, C$_{1-6}$ alkyl substituted with 0-2 R$^e$, C$_{2-6}$ alkenyl substituted with 0-2 R$^e$, C$_{2-6}$ alkynyl substituted with 0-2 R$^e$, —(CH$_2$)$_r$—C$_{3-10}$ carbocycle substituted with 0-3 R$^d$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^d$;

R$^4$ is, independently at each occurrence, H, =O, F, Cl, Br, I, OCF$_3$, CF$_3$, CN, NO$_2$, OR$^a$, SR$^a$, —C(O)R$^a$, —C(O)OR$^a$, —OC(O)R$^a$, —NR$^7$R$^8$, —C(O)NR$^8$R$^9$, —NR$^7$C(O)R$^b$, —S(O)$_p$NR$^8$R$^9$, —NR$^8$S(O)$_p$R$^c$, —S(O)$_2$R$^c$, C$_{1-6}$ alkyl substituted with 0-2 R$^{4a}$, C$_{2-6}$ alkenyl substituted with 0-2 R$^{4a}$, C$_{2-6}$ alkynyl substituted with 0-2 R$^{4a}$, —(CH$_2$)$_r$—C$_{3-10}$ carbocycle substituted with 0-3 R$^{4b}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{4b}$;

R$^{4a}$ is, independently at each occurrence, H, F, =O, C$_{1-4}$ alkyl, OR$^a$, SR$^a$, CF$_3$, CN, NO$_2$, —C(O)R$^a$, —C(O)OR$^a$, —NR$^7$R$^8$, —C(O)NR$^8$R$^9$, —NR$^7$C(O)R$^b$, —S(O)$_p$NR$^8$R$^9$, —NR$^8$S(O)$_p$R$^c$, —S(O)R$^c$, or —S(O)$_2$R$^c$;

$R^{4b}$ is, independently at each occurrence, H, =O, =NR$^8$, OR$^a$, F, Cl, Br, I, CN, NO$_2$, —NR$^7$R$^8$, —C(O)R$^a$, —C(O)OR$^a$, —NR$^7$C(O)R$^b$, —C(O)NR$^8$R$^9$, —SO$_2$NR$^8$R$^9$, —S(O)$_2$R$^c$, C$_{1-6}$ alkyl, C$_{2-6}$ alkenyl, C$_{2-6}$ alkynyl, C$_{3-6}$ cycloalkyl, C$_{1-4}$ haloalkyl, or C$_{1-4}$ haloalkyloxy-;

alternately, R$^3$ and R$^4$ groups when located on adjacent atoms, can be taken together to form a C$_{3-10}$ carbocycle substituted with 0-2 R$^{3d}$ or a 5- to 10-membered heterocycle comprising: carbon atoms and 1-4 heteroatoms selected from N, O, and S(O)$_p$, wherein said heterocycle is substituted with 0-2 R$^{3d}$;

R$^5$ is, independently at each occurrence, H, F, Cl, Br, I, OCF$_3$, CF$_3$, OR$^a$, SR$^a$, CN, NO$_2$, —C(O)R$^a$, —C(O)OR$^a$, —OC(O)R$^a$, —NR$^7$R$^8$, —C(O)NR$^7$R$^8$, —NR$^7$C(O)R$^b$, —S(O)$_p$NR$^8$R$^9$, —NR$^8$S(O)$_p$R$^c$, —S(O)R$^c$, —S(O)$_2$R$^c$, C$_{1-6}$ alkyl substituted with 0-2 R$^{5a}$, C$_{2-6}$ alkenyl substituted with 0-2 R$^{5a}$, C$_{2-6}$ alkynyl substituted with 0-2 R$^{5a}$, —(CH$_2$)$_r$—C$_{3-10}$ carbocycle substituted with 0-3 R$^{5b}$, or —(CH$_2$)$_r$-5- to 10-membered heterocycle comprising: carbon atoms and 1-4 heteroatoms selected from N, O, and S(O)$_p$, and substituted with 0-3 R$^{5b}$;

R$^{5a}$ is, independently at each occurrence, H, =O, F, Cl, Br, I, OCF$_3$, CF$_3$, OR$^a$, SR$^a$, CN, NO$_2$, —NR$^7$R$^8$, —C(O)NR$^7$R$^8$, —NR$^7$C(O)R$^b$, —S(O)$_p$NR$^8$R$^9$, NR$^8$S(O)$_p$R$^c$, —S(O)R$^c$, or —S(O)$_2$R$^c$;

R$^{5b}$ is, independently at each occurrence, H, =O, OR$^a$, F, Cl, Br, I, CN, NO$_2$, —NR$^7$R$^8$, —C(O)R$^a$, —C(O)OR$^a$, —NR$^7$C(O)R$^b$, —C(O)NR$^8$R$^9$, —SO$_2$NR$^8$R$^9$, —S(O)$_2$R$^c$, C$_{1-6}$ alkyl, C$_{2-6}$ alkenyl, C$_{2-6}$ alkynyl, C$_{3-6}$ cycloalkyl, C$_{1-4}$ haloalkyl, C$_{1-4}$ haloalkyloxy-, C$_{1-4}$ alkyloxy-, C$_{1-4}$ alkylthio-, C$_{1-4}$ alkyl-C(O)—, or C$_{1-4}$ alkyl-C(O)NH—;

alternately, when R$^3$, R$^4$, or R$^5$ are substituted on adjacent atoms, two of them can be taken together with the carbon atoms to which they are attached to form a 5- to 7-membered carbocycle or heterocycle substituted with 0-3 R$^{3a}$ and 0-1 R$^{3d}$;

R$^6$ is, independently at each occurrence, H, C$_{1-6}$ alkyl substituted with 0-2 R$^{6a}$, C$_{2-6}$ alkenyl substituted with 0-2 R$^{6a}$, C$_{2-6}$ alkynyl substituted with 0-2 R$^{6a}$, —C(O)R$^c$, —S(O)$_2$R$^c$, —CO$_2$R$^c$, —C(O)NHR$^c$, —OC(O)NHR$^c$, —C(O)N(C$_{1-6}$ alkyl)R$^c$, —(CH$_2$)$_r$—C$_{3-10}$ carbocycle substituted with 0-3 R$^d$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^d$;

R$^{6a}$ is, independently at each occurrence, H, =O, F, OCF$_3$, CF$_3$, OR$^a$, SR$^a$, CN, NO$_2$, —NR$^7$R$^8$, —C(O)NR$^7$R$^8$, —NR$^7$C(O)R$^b$, —S(O)$_p$NR$^8$R$^9$, —NR$^8$S(O)$_p$R$^c$, —S(O)R$^c$, or —S(O)$_2$R$^c$;

R$^7$ is, independently at each occurrence, H, C$_{1-6}$ alkyl, —(CH$_2$)$_n$—C$_{3-10}$ carbocycle, —(CH$_2$)$_n$-(5-10 membered heteroaryl), —CHO, —C(O)R$^c$, —C(O)OR$^c$, —CONR$^8$R$^c$, —OC(O)NHR$^c$, —S(O)$_2$R$^c$, —C(O)O—(C$_{1-4}$ alkyl)-OC(O)—(C$_{1-4}$ alkyl), or —C(O)O—(C$_{1-4}$ alkyl)-OC(O)—(C$_{6-10}$ aryl); wherein said alkyl, carbocycle, aryl, and heteroaryl are optionally substituted with 0-2 R$^f$;

R$^8$ is, independently at each occurrence, H, C$_{1-6}$ alkyl, or —(CH$_2$)$_n$-phenyl, or —(CH$_2$)$_n$-5-10 membered heterocycle comprising: carbon atoms and 1-4 heteroatoms selected from N, O, and S(O)$_p$; wherein said alkyl, phenyl and heterocycle are optionally substituted with 0-2 R$^f$, alternatively, R$^7$ and R$^8$, when attached to the same nitrogen, combine to form a 5- to 10-membered heterocycle comprising: carbon atoms and 0-2 additional heteroatoms selected from N, O, and S(O)$_p$, wherein said heterocycle is substituted with 0-2 R$^d$;

R$^{8a}$ is, independently at each occurrence, R$^7$, OH, C$_{1-4}$ alkoxy, (C$_{6-10}$ aryl)-C$_{1-4}$ alkoxy, —(CH$_2$)$_n$-phenyl, —(CH$_2$)$_n$-(5-10 membered heteroaryl); wherein said aryl, and heteroaryl is optionally substituted with 0-2 R$^f$;

R$^9$ is, independently at each occurrence, H, C$_{1-6}$ alkyl, or —(CH$_2$)$_n$-phenyl; wherein said alkyl and phenyl are optionally substituted with 0-2 R$^f$;

R$^{9a}$ is, independently at each occurrence, H, C$_{1-6}$ alkyl, or —(CH$_2$)$_n$-phenyl;

alternatively, R$^8$ and R$^9$, when attached to the same nitrogen, combine to form a 5- to 10-membered heterocycle comprising: carbon atoms and 0-2 additional heteroatoms selected from N, O, and S(O)$_p$, wherein said heterocycle is substituted with 0-2 R$^d$;

R$^{10}$ is, independently at each occurrence, H, C$_{1-6}$ alkyl substituted with 0-3 R$^{10a}$, C$_{2-6}$ alkenyl substituted with 0-3 R$^{10a}$, C$_{2-6}$ alkynyl substituted with 0-3 R$^{10a}$, —(CH$_2$)$_r$—C$_{3-10}$ carbocycle substituted with 0-3 R$^d$, or —(CH$_2$)$_r$-5- to 10-membered heterocycle comprising carbon atoms and 1-4 heteroatoms selected from N, O, and S(O)$_p$, wherein said heterocycle is substituted with 0-3 R$^d$;

R$^{10a}$ is, independently at each occurrence, H, =O, C$_{1-4}$ alkyl, OR$^a$, SR$^a$, F, CF$_3$, CN, NO$_2$, —C(O)R$^a$, —C(O)OR$^a$, —C(O)NR$^7$R$^8$, —NR$^7$C(O)R$^b$, —S(O)$_p$NR$^8$R$^9$, —NR$^8$S(O)$_p$R$^c$, —S(O)R$^c$, or —S(O)$_2$R$^c$;

R$^{11}$ is C$_{1-4}$ haloalkyl, —(CH$_2$)$_r$—C(O)NR$^7$R$^8$, C$_{1-6}$ alkyl substituted with 0-3 R$^{11a}$, C$_{2-6}$ alkenyl substituted with 0-3 R$^{11a}$, C$_{2-6}$ alkynyl substituted with 0-3 R$^{11a}$, —(CR$^{14}$R$^{15}$)$_r$—C$_{3-10}$ carbocycle substituted with 0-3 R$^{11b}$, or —(CR$^{14}$R$^{15}$)$_r$-5- to 10-membered heterocycle comprising: carbon atoms and 1-4 heteroatoms selected from N, O, and S(O)$_p$, wherein said heterocycle is substituted with 0-3 R$^{11b}$;

R$^{11a}$ is, independently at each occurrence, H, =O, C$_{1-4}$ alkyl, OR$^a$, F, CN, NO$_2$, —NR$^7$R$^8$, —C(O)R$^a$, —C(O)OR$^a$, —C(O)NR$^7$R$^8$, —NR$^7$C(O)R$^b$, —S(O)$_p$NR$^8$R$^9$, —NR$^8$S(O)$_p$R$^c$, —S(O)$_p$R$^c$, C$_{3-6}$ cycloalkyl, C$_{1-4}$ haloalkyl, C$_{1-4}$ haloalkyloxy-, —(CH$_2$)$_r$—C$_{3-10}$ carbocycle substituted with 0-3 R$^d$, or —(CH$_2$)$_r$-5- to 10-membered heterocycle comprising carbon atoms and 1-4 heteroatoms selected from N, O, and S(O)$_p$, and substituted with 0-3 R$^d$;

R$^{11b}$ is, independently at each occurrence, H, =O, =NR$^8$, OR$^a$, F, Cl, Br, CN, NO$_2$, CF$_3$, OCF$_3$, OCHF$_2$, —NR$^7$R$^8$, —C(O)R$^a$, —C(O)OR$^a$, —C(O)NR$^7$R$^8$, —NR$^7$C(O)R$^b$, —S(O)$_p$NR$^8$R$^9$, —NR$^8$S(O)$_p$R$^c$, —S(O)$_p$R$^c$, C$_{1-6}$ alkyl, C$_{2-6}$ alkenyl, C$_{2-6}$ alkynyl, C$_{3-6}$ cycloalkyl, C$_{1-4}$ haloalkyl, C$_{1-4}$ haloalkyloxy-, —(CH$_2$)$_r$—C$_{3-10}$ carbocycle substituted with 0-3 R$^d$, or —(CH$_2$)$_r$-5- to 10-membered heterocycle comprising carbon atoms and 1-4 heteroatoms selected from N, O, and S(O)$_p$, and substituted with 0-3 R$^d$;

alternatively, when two R$^{11b}$ groups are substituents on adjacent atoms they may be taken together with the atoms to which they are attached to form a 5- to 7-membered carbocycle or heterocycle comprising carbon atoms and 0-4 heteroatoms selected from N, O, and S(O)$_p$ and substituted with 0-2 R$^g$;

R$^{12}$ is H, F, C$_{1-4}$ haloalkyl, C$_{1-6}$ alkyl substituted with 0-3 R$^{12a}$, C$_{2-6}$ alkenyl substituted with 0-3 R$^{12a}$, C$_{2-6}$ alkynyl substituted with 0-3 R$^{12a}$, —(CH$_2$)$_r$—C$_{3-10}$ carbocycle substituted with 0-3 R$^{12b}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{12b}$;

R$^{12a}$ is, independently at each occurrence, H, =O, C$_{1-4}$ alkyl, OR$^a$, F, Cl, Br, CN, NO$_2$, —NR$^7$R$^8$, —C(O)R$^a$, —C(O)OR$^a$, —C(O)NR$^7$R$^8$, —NR$^7$C(O)R$^b$, —S(O)$_p$NR$^8$R$^9$, —NR$^8$S(O)$_p$R$^c$, or —S(O)$_p$R$^c$;

R$^{12b}$ is, independently at each occurrence, H, =O, OR$^a$, F, Cl, Br, CN, NO$_2$, —NR$^7$R$^8$, —C(O)OR$^a$, —C(O)NR$^7$R$^8$, —S(O)$_2$R$^c$, C$_{1-6}$ alkyl, C$_{2-6}$ alkenyl, C$_{2-6}$ alkynyl, C$_{3-6}$ cycloalkyl, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, or $C_{1-4}$ alkyl-C(O)NH—;

alternately, $R^{11}$ and $R^{12}$ can be taken together to form a $C_{3-10}$ carbocycle substituted with 0-2 $R^{12b}$, or a 5- to 10-membered heterocycle comprising: carbon atoms and 1-4 heteroatoms selected from N, O, and $S(O)_p$, wherein said heterocycle is substituted with 0-2 $R^{12b}$;

alternately, $R^{11}$ or $R^{12}$ can be taken together with $R^{10}$ to form a 5- to 10-membered heterocycle comprising: carbon atoms and 1-4 heteroatoms selected from N, O, and $S(O)_p$, wherein said heterocycle is substituted with 0-2 $R^{12b}$;

alternately, $R^{11}$ or $R^{12}$ can be taken together with $R^7$, when $R^7$ is a substituent on L, to form a 5- to 10-membered heterocycle comprising: carbon atoms and 1-4 heteroatoms selected from N, O, and $S(O)_p$, wherein said heterocycle is substituted with 0-2 $R^{12b}$;

$R^{13}$ is H, $C_{1-6}$ alkyl, —C(O)$R^c$, —C(O)O$R^c$, —CONR$^8R^c$, —OCONR$^8R^c$, —S(O)$_2R^c$, —(CH$_2$)$_n$-phenyl, —(CH$_2$)$_n$-(5-10 membered heteroaryl), —C(O)O—($C_{1-4}$ alkyl)-OC(O)—($C_{1-4}$ alkyl), or —C(O)O—($C_{1-4}$ alkyl)-OC(O)—($C_{6-10}$ aryl); wherein said alkyl, phenyl, aryl, and heteroaryl are optionally substituted with 0-2 $R^f$;

alternately, $R^{13}$ can be taken together with $R^{10}$ to form a 5- to 10-membered heterocycle comprising: carbon atoms and 1-4 heteroatoms selected from N, O, and $S(O)_p$, wherein said heterocycle is substituted with 0-2 $R^d$;

$R^{14}$ is, independently at each occurrence, H, $C_{1-4}$ alkyl, OR$^a$, F, CN, NO$_2$, —NR$^7R^8$, —C(O)$R^a$, —C(O)O$R^a$, —C(O)NR$^7R^8$, —NR$^7$C(O)$R^b$, —S(O)$_p$NR$^8R^9$, —NR$^8$S(O)$_pR^c$, or —S(O)$_pR^c$;

$R^{15}$ is, independently at each occurrence, H, F, or $C_{1-4}$ alkyl;

alternately, $R^{14}$ combines with $R^{15}$ to form =O;

$R^a$ is, independently at each occurrence, H, CF$_3$, $C_{1-6}$ alkyl, —(CH$_2$)$_r$—$C_{3-7}$ cycloalkyl, —(CH$_2$)$_r$—$C_{6-10}$ aryl, or —(CH$_2$)$_r$-5- to 10-membered heterocycle comprising: carbon atoms and 1-4 heteroatoms selected from N, O, and $S(O)_p$; wherein said cycloalkyl, aryl and heterocycle groups are optionally substituted with 0-2 $R^f$;

$R^b$ is, independently at each occurrence, CF$_3$, OH, $C_{1-4}$ alkoxy, $C_{1-6}$ alkyl, —(CH$_2$)$_r$—$C_{3-10}$ carbocycle substituted with 0-2 $R^d$, or —(CH$_2$)$_r$-5- to 10-membered heterocycle comprising: carbon atoms and 1-4 heteroatoms selected from N, O, and S(O)$_p$ and substituted with 0-2 $R^d$;

$R^c$ is, independently at each occurrence, CF$_3$, $C_{1-6}$ alkyl substituted with 0-2 $R^f$, $C_{3-6}$ cycloalkyl substituted with 0-2 $R^f$, $C_{6-10}$ aryl, 5- to 10-membered heteroaryl, ($C_{6-10}$ aryl)-$C_{1-4}$ alkyl, or (5- to 10-membered heteroaryl)-$C_{1-4}$ alkyl, wherein said aryl and heteroaryl groups are substituted with 0-3 $R^f$;

$R^d$ is, independently at each occurrence, H, =O, =NR$^8$, OR$^a$, F, Cl, Br, I, CN, NO$_2$, —NR$^7R^8$, —C(O)$R^a$, —C(O)OR$^a$, —OC(O)$R^a$, —NR$^8$C(O)$R^a$, —C(O)NR$^7R^8$, —SO$_2$NR$^8R^9$, —NR$^8$SO$_2$NR$^8R^9$, —NR$^8$SO$_2$—$C_{1-4}$ alkyl, —NR$^8$SO$_2$CF$_3$, —NR$^8$SO$_2$-phenyl, —S(O)$_2$CF$_3$, —S(O)$_p$—$C_{1-4}$ alkyl, —S(O)$_p$-phenyl, —(CF$_2$)$_r$CF$_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

$R^e$ is, independently at each occurrence, =O, OR$^a$, F, Cl, Br, I, CN, NO$_2$, —NR$^8R^9$, —C(O)$R^a$, —C(O)OR$^a$, —NR$^8$C(O)$R^a$, —C(O)NR$^7R^8$, —SO$_2$NR$^8R^9$, —NR$^8$SO$_2$NR$^8R^9$, —NR$^8$SO$_2$—$C_{1-4}$ alkyl, —NR$^8$SO$_2$CF$_3$, —NR$^8$SO$_2$-phenyl, —S(O)$_2$CF$_3$, —S(O)$_p$—$C_{1-4}$ alkyl, —S(O)$_p$-phenyl, or —(CF$_2$)$_r$CF$_3$;

$R^f$ is, independently at each occurrence, H, =O, —(CH$_2$)$_r$OR$^g$, F, Cl, Br, I, CN, NO$_2$, —NR$^{9a}R^{9a}$, —C(O)$R^g$, —C(O)OR$^g$, —NR$^{9a}$C(O)R$^9$, —C(O)NR$^{9a}R^{9a}$, —SO$_2$NR$^{9a}R^{9a}$, —NR$^{9a}$SO$_2$NR$^{9a}R^{9a}$, —NR$^{9a}$SO$_2C_{1-4}$ alkyl, —NR$^{9a}$SO$_2$CF$_3$, —NR$^{9a}$SO$_2$-phenyl, —S(O)$_2$CF$_3$, —S(O)$_p$—$C_{1-4}$ alkyl, —S(O)$_p$-phenyl, —(CF$_2$)$_r$CF$_3$, $C_{1-6}$ alkyl, $C_{2-6}$ alkenyl, $C_{2-6}$ alkynyl, or —(CH$_2$)$_n$-phenyl;

$R^g$ is, independently at each occurrence, H, $C_{1-6}$ alkyl, or —(CH$_2$)$_n$-phenyl;

n, at each occurrence, is selected from 0, 1, 2, 3, and 4;

p, at each occurrence, is selected from 0, 1, and 2; and r, at each occurrence, is selected from 0, 1, 2, 3, and 4; and s, at each occurrence, is selected from 1, 2, 3, and 4.

In another aspect, the present invention includes compounds of Formula (III) or a stereoisomer or pharmaceutically acceptable salts, solvates, or prodrugs thereof, wherein:

A is $C_{3-8}$ cycloalkyl substituted with 0-1 $R^1$ and 0-3 $R^2$, A is $C_{3-8}$ cycloalkenyl substituted with 0-1 $R^1$ and 0-3 $R^2$, phenyl substituted with 0-1 $R^1$ and 0-3 $R^2$, naphthyl substituted with 0-1 $R^1$ and 0-3 $R^2$, or a 5- to 10-membered heterocycle comprising: carbon atoms and 1-4 heteroatoms selected from N, O, and $S(O)_p$, wherein said heterocycle is substituted 0-1 $R^1$ and 0-3 $R^2$;

Z is —C($R^{11}$)($R^{12}$)—;

L is —C(O)NR$^{10}$—, —NR$^{10}$C(O)—, —CH$_2$C(O)NR$^{10}$—, —CH$_2$NR$^{10}$C(O)—, —C(O)NR$^{10}$CH$_2$—, or —NR$^{10}$C(O)CH$_2$—;

$R^3$ is, independently at each occurrence, —(CH$_2$)$_r$C(O)NR$^8R^9$, —(CH$_2$)$_r$C(O)NR$^8$(CH$_2$)$_s$CO$_2R^{3b}$, —(CH$_2$)$_r$CO$_2R^{3b}$, —(CH$_2$)$_r$—$C_{3-8}$ cycloalkyl substituted with 0-2 $R^{3a}$ and 0-1 $R^{3d}$, —(CH$_2$)$_r$-phenyl substituted with 0-3 $R^{3a}$ and 0-1 $R^{3d}$, or —(CH$_2$)$_r$-5- to 10-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^6$ is, independently at each occurrence, H, $C_{1-6}$ alkyl substituted with 0-2 $R^{6a}$, $C_{2-6}$ alkenyl substituted with 0-2 $R^{6a}$, $C_{2-6}$ alkynyl substituted with 0-2 $R^{6a}$, ($C_{1-6}$ alkyl)C(O)—, ($C_{3-6}$ cycloalkyl)$C_{1-3}$ alkyl-C(O)—, ($C_{3-6}$ cycloalkyl)C(O)—, phenyl-C(O)—, benzyl-C(O)—, benzyl-S(O)$_2$—, ($C_{1-6}$ alkyl)-S(O)$_2$—, phenyl-S(O)$_2$—, —(CH$_2$)$_r$—$C_{3-10}$ carbocycle substituted with 0-3 $R^d$, or —(CH$_2$)$_r$-5- to 10-membered heterocycle comprising: carbon atoms and 1-4 heteroatoms selected from N, O, and $S(O)_p$, wherein said heterocycle is substituted with 0-3 $R^d$;

$R^{10}$ is, independently at each occurrence, H, $C_{1-6}$ alkyl substituted with 0-3 $R^{10a}$, —(CH$_2$)$_r$—$C_{3-10}$ carbocycle substituted with 0-3 $R^d$, or —(CH$_2$)$_r$-5- to 10-membered heterocycle comprising carbon atoms and 1-4 heteroatoms selected from N, O, and $S(O)_p$, and substituted with 0-3 $R^d$; and $R^{11}$ is $C_{1-4}$ haloalkyl, $C_{1-6}$ alkyl substituted with 0-3 $R^{11a}$, $C_{2-6}$ alkenyl substituted with 0-3 $R^{11a}$, $C_{2-6}$ alkynyl substituted with 0-3 $R^{11a}$, —(CH$_2$)$_r$—$C_{3-10}$ carbocycle substituted with 0-3 $R^{11b}$, or —(CH$_2$)$_r$-5- to 10-membered heterocycle comprising: carbon atoms and 1-4 heteroatoms selected from N, O, and $S(O)_p$, wherein said heterocycle is substituted with 0-3 $R^{11b}$.

In another aspect, the present invention includes compounds of Formula (III) or a stereoisomer or pharmaceutically acceptable salts, solvates, or prodrugs thereof, wherein:

A is $C_{5-6}$ cycloalkyl substituted with 0-1 $R^1$ and 0-2 $R^2$, A is $C_{5-6}$ cycloalkenyl substituted with 0-1 $R^1$ and 0-2 $R^2$, phenyl substituted with 0-1 $R^1$ and 0-3 $R^2$, naphthyl substituted with 0-1 $R^1$ and 0-3 $R^2$, or a 5- to 10-membered heterocycle comprising: carbon atoms and 1-4 heteroatoms selected from N, O, and $S(O)_p$, wherein said heterocycle is substituted 0-1 $R^1$ and 0-3 $R^2$;

$R^3$ is, independently at each occurrence, —(CH$_2$)$_r$C(O)NR$^8R^9$, —(CH$_2$)$_r$C(O)NR$^8$(CH$_2$)$_s$CO$_2R^{3b}$, —(CH$_2$)$_r$CO$_2R^{3b}$, —(CH$_2$)$_r$-phenyl substituted with 0-3 $R^{3a}$ and 0-1 $R^{3d}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^6$ is, independently at each occurrence, H, or $C_{1-6}$ alkyl substituted with 0-2 $R^{6a}$;

$R^{10}$ is, independently at each occurrence, H, $C_{1-6}$ alkyl substituted with 0-2 $R^{10a}$, —$(CH_2)_r$-phenyl substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

$R^{11}$ is $C_{1-6}$ alkyl substituted with 0-3 $R^{11a}$, —$(CH_2)_r$-phenyl substituted with 0-3 $R^{11b}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{11b}$; and $R^{12}$ is H, F, $C_{1-4}$ haloalkyl, $C_{1-6}$ alkyl, phenyl, or benzyl.

In another embodiment, the present invention provides a novel pharmaceutical composition, comprising: a pharmaceutically acceptable carrier and a therapeutically effective amount of a compound of the present invention or a stereoisomer or a pharmaceutically acceptable salt, solvate or prodrug form thereof.

In another embodiment, the present invention provides a novel process for making a compound of the present invention or a stereoisomer or pharmaceutically acceptable salt, solvate or prodrug form thereof.

In another embodiment, the present invention provides a novel intermediate for making a compound of the present invention or a stereoisomer or pharmaceutically acceptable salt, solvate or prodrug form thereof.

In another embodiment, the present invention provides a pharmaceutical composition further comprising additional therapeutic agent(s) selected from potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an antiplatelet agent, a thrombin inhibiting agent, a thrombolytic agent, a fibrinolytic agent, a calcium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In a preferred embodiment, the present invention provides a pharmaceutical composition wherein the additional therapeutic agent is an antihypertensive agent selected from ACE inhibitors, AT-1 receptor antagonists, ET receptor antagonists, dual ET/AII receptor antagonists, and vasopepsidase inhibitors, an antiarrythmic agent selected from IKur inhibitors, or an antithrombotic agent selected from anticoagulants selected from thrombin inhibitors, other factor XIa inhibitors, other kallikrein inhibitors, factor VIIa inhibitors and factor Xa inhibitors, and antiplatelet agents selected from GPIIb/IIIa blockers, $P2Y_1$ and $P2Y_{12}$ antagonists, thromboxane receptor antagonists, and aspirin, or a combination thereof.

In a preferred embodiment, the present invention provides pharmaceutical composition, wherein the additional therapeutic agent(s) are an anti-platelet agent or a combination thereof.

In a preferred embodiment, the present invention provides a pharmaceutical composition, wherein the additional therapeutic agent is the anti-platelet agent clopidogrel.

In another embodiment the present invention provides a method for modulation of the coagulation cascade and/or contact activation system comprising administering to a patient in need of such treatment a therapeutically effective amount of at least one of the compounds of the present invention or a pharmaceutically acceptable salt, solvate or prodrug form thereof.

In another embodiment, the present invention provides a novel method for treating thromboembolic disorders comprising: administering to a patient in need of such treatment a therapeutically effective amount of at least one of the compounds of the present invention or a pharmaceutically acceptable salt, solvate or prodrug form thereof.

In another embodiment, the present invention provides a novel method, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the present invention provides a novel method, wherein the thromboembolic disorder is selected unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

In another embodiment, the present invention provides a method for treating inflammatory disorders comprising: administering to a patient in need of such treatment a therapeutically effective amount of at least one of the compounds of the present invention or a pharmaceutically acceptable salt or prodrug form thereof.

In another embodiment, the present invention provides a method, wherein the inflammatory disorder is selected from the group consisting of sepsis, acute respiratory dystress syndrome, and systemic inflammatory response syndrome.

In another embodiment, the present invention provides a novel method of treating a patient in need of thromboembolic disorder treatment, comprising: administering a compound of the present invention or a pharmaceutically acceptable salt, solvate, or prodrug form thereof in an amount effective to treat a thromboembolic disorder.

In another embodiment, the present invention provides a method of treating a patient in need of inflammatory disorder treatment, comprising: administering a compound of the present invention or a pharmaceutically acceptable salt form thereof in an amount effective to treat an inflammatory disorder.

In another embodiment, the present invention provides a novel article of manufacture, comprising:
  (a) a first container;
  (b) a pharmaceutical composition located within the first container, wherein the composition, comprises: a first therapeutic agent, comprising: a compound of the present invention or a pharmaceutically acceptable salt, solvate, or prodrug form thereof; and
  (c) a package insert stating that the pharmaceutical composition can be used for the treatment of a thromboembolic and/or inflammatory disorder.

In another preferred embodiment, the present invention provides a novel article of manufacture, further comprising:
  (d) a second container;

wherein components (a) and (b) are located within the second container and component (c) is located within or outside of the second container.

In another embodiment, the present invention provides a novel article of manufacture, comprising:
  (a) a first container;
  (b) a pharmaceutical composition located within the first container, wherein the composition, comprises: a first therapeutic agent, comprising: a compound of the present invention or a pharmaceutically acceptable salt, solvate, or prodrug form thereof; and
  (c) a package insert stating that the pharmaceutical composition can be used in combination with a second therapeutic agent to treat a thromboembolic and/or inflammatory disorder.

In another preferred embodiment, the present invention provides a novel article of manufacture, further comprising:
  (d) a second container;

wherein components (a) and (b) are located within the second container and component (c) is located within or outside of the second container.

In another embodiment, the present invention provides a novel method, comprising: administering a compound of the present invention or a pharmaceutically acceptable salt, solvate, or prodrug form thereof in an amount effective to treat a thromboembolic and/or inflammatory disorder.

In another embodiment, the present invention provides a compound of the present invention or a pharmaceutically acceptable salt, solvate, or prodrug form thereof, for use in therapy.

In another embodiment, the present invention also provides the use of a compound of the present invention or a pharmaceutically acceptable salt, solvate, or prodrug form thereof, for the manufacture of a medicament for the treatment of a thromboembolic and/or inflammatory disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

Definitions

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Accordingly, the present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. All tautomers of shown or described compounds are also considered to be part of the present invention.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

As used herein, the term "alkyl" or "alkylene" is intended to include both branched and straight-chain saturated aliphatic hydrocarbon groups having the specified number of carbon atoms. For example, "$C_1$-$C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_{1-6}$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Halo" or "halogen" includes fluoro, chloro, bromo, and iodo. "Haloalkyl" refers to branched and straight-chained, having one or more halogen substituents. Example haloalkyl groups include, but are not limited to, $CF_3$, $C_2F_5$, $CHF_2$, $CCl_3$, $CHCl_2$, $C_2C_5$, and the like.

The term "alkoxy" or "alkyloxy" refers to an O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy, and the like. Similarly, "alkylthio" or "thioalkoxy" represents an alkyl group as defined above with the indicated number of carbon atoms attached through a sulphur bridge; for example methyl-S—, ethyl-S—, and the like.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

"Aryl" groups refer to monocyclic or polycyclic aromatic hydrocarbons, including, for example, phenyl, naphthyl, phenanthranyl, and the like. Aryl moieties are well known and described, for example, in *Hawley's Condensed Chemical Dictionary* (13 ed.), R. J. Lewis, ed., J. Wiley & Sons, Inc., New York (1997). Aryl groups can be substituted or unsubstituted.

As used herein, the term "heterocycle" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a small, negatively charged species such as chloride, bromide, hydroxide, acetate, and sulfate.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

When any variable (e.g., $R^{2a}$, $R^{2b}$, etc.) occurs more than one time in any constituent or formula for a compound, its definition at each occurrence is independent of its definition at every other occurrence. Thus, for example, if a group is shown to be substituted with 0-3 $R^{2b}$, then said group may optionally be substituted with up to three $R^{2b}$ groups and $R^{2b}$ at each occurrence is selected independently from the definition of $R^{2b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

When a dotted ring is used within a ring structure, this indicates that the ring structure may be saturated, partially saturated or unsaturated.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" refers to acid or base salts of the compounds described herein. Examples of pharmaceutically acceptable salts include, but are not limited to, mineral or organic acid salts of basic residues such as amines; alkali or organic salts of acidic residues such as carboxylic acids; and the like. Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference in its entirety. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309-396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, at pp. 113-191 (1991);

c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et. al., *Chem Phar Bull.*, Vol. 32, p. 692 (1984).

Preparation of prodrugs is well known in the art and described in, for example, *Medicinal Chemistry: Principles and Practice*, ed. F. D. King, The Royal Society of Chemistry, Cambridge, UK, 1994, which is incorporated herein by reference in its entirety.

Radiolabelled compounds of the present invention, i.e., wherein one or more of the atoms described are replaced by a radioactive isotope of that atom (e.g., C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

It should further be understood that solvates (e.g., hydrates) of the compounds of the present invention are also with the scope of the present invention. Methods of solvation are generally known in the art.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor XIa and/or plasma kallikrein. "Therapeutically effective amount" is also intended to include an amount of the combination of compounds claimed that is effective to inhibit factor XIa and/or plasma kallikrein. The combination of compounds is preferably a synergistic combination. Synergy, as described, for example, by Chou and Talalay, *Adv. Enzyme Regul.* 1984, 22:27-55, occurs when the effect (in this case, inhibition of factor XIa and/or plasma kallikrein) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic and/or anti-inflammatory effect, or some other beneficial effect of the combination compared with the individual components.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., Mack Publishing Company, Easton, Pa., 1985, which is incorporated herein by reference in its entirety.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley-Interscience, 3$^{rd}$ Edition, 1999).

All references cited herein are hereby incorporated in their entirety herein by reference. Methods for synthesis of a large variety of substituted pyridine and pyridone compounds useful as starting materials for the preparation of compounds of the present invention are well known in the art and have been extensively reviewed. (For examples of methods useful for the preparation of pyridine and pyridone starting materials see: Krohnke, F. *Synthesis*, 1976, 1.; *Pyridine and Its Derivatives*. In *The Chemistry of Heterocyclic Compounds*, Abramovitch, R. A., Ed.; John Wiley and Sons: New York, 1974; Vol 14; Supplemental 1-4.; *Comprehensive Heterocyclic Chemistry*, Vol. 2, Boulton, A. J. and McKillop, A, Eds. Pergamon Press, New York, 1984, pp 165-524; *Comprehensive Heterocyclic Chemistry*, Vol. 5, McKillop, A, Ed. Pergamon Press, New York, 1996, pp 1-300). Methods for synthesis of a large variety of substituted pyrimidine and pyrimidone compounds useful as starting materials for the preparation of compounds of the present invention are well known in the art and have been extensively reviewed. (For examples of methods useful for the preparation of pyrimidine and pyrimidone starting materials see: *The Pyrimidines*. In *The Chemistry of*

Heterocyclic Compounds, Taylor, E. C., Ed.; John Wiley and Sons: New York, 1993; Vol 52).

Representative pyridine compounds of this invention can be prepared as shown in Scheme 1. Suzuki coupling between an appropriately functionalized pyridine, such as 1a and an appropriately substituted aryl or heteroaryl boronic acid or ester 1b in the presence of a base such as anhydrous potassium carbonate in a solvent such as methanol or THF using a catalyst such as PXPd2 provides the biaryl compound. Using a modification of the procedure described by Schlosser (Schlosser, M. and Cottet, F. Eur. J. Org. Chem., 2002, 24, 4181-4184), the 2-chloropyridine derivative is treated with trimethylsilyl bromide in propionitrile at elevated temperature in a microwave to give the 2-bromopyridine derivative 1c. Metal-halogen exchange with n-butyllithium and quenching the intermediate anion with a suitable formyl source such as 1-formyl piperidine or DMF provides aldehyde 1d. Using a modification of the procedure described by Hart (Hart, D. J. et al. J. Org. Chem., 1983, 48(3), 289-294), in situ generation of N-trimethylsilylaldimines from 1d and lithium bis(trimethylsilyl)amide, followed by the addition of Grignard or alkyllithium reagents give after aqueous work up the primary amine 1e. Amide coupling between 1e and appropriately substituted carboxylic acid (1f), for example, Boc-tranexamic acid, employing suitable coupling reagents, such as EDCI, HOBt, and base generates 1g (for alternative coupling reagents see: Han, S-Y; Kim, Y-A. Tetrahedron, 2004, 60, 2447). Further manipulation of functional groups on A using methods known to one skilled in the art of organic synthesis will give additional compounds of the invention. For instance, when A is a Boc-tranexamic acid moiety, the Boc group can be deprotected with TFA to give the cyclohexyl methyl amine derivative. The pyridine N-oxide derivatives 1 h can be prepared by oxidation of 1 g with a suitable oxidant such as m-chloroperbenzoic acid in chloroform. Further manipulation of functional groups on $R^3$ and $R^4$ using methods known to one skilled in the art of organic synthesis will give additional compounds of the invention.

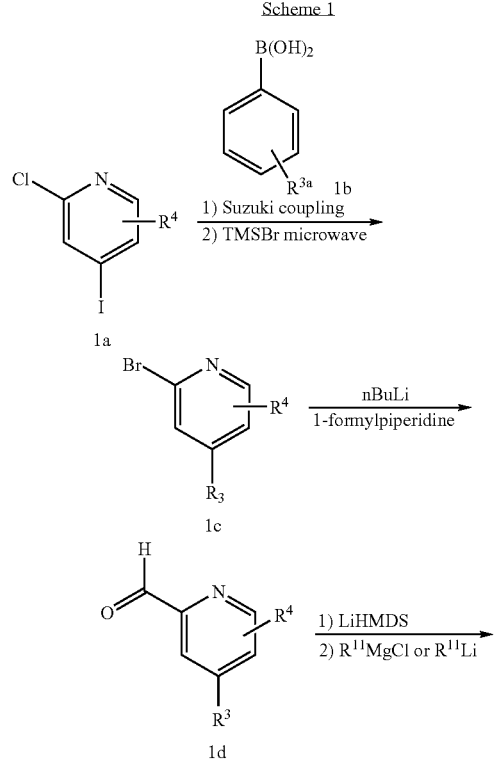

Scheme 1

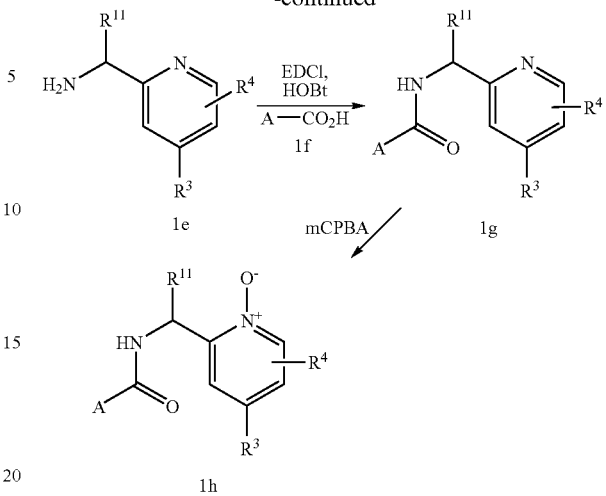

Alternately, the $R^3$ moiety can be introduced via a Suzuki coupling strategy later in the synthesis as shown in Scheme 2. Compound 2c can be prepared in three steps according to a modified procedure described by Negi (Negi, S. et al. Synthesis, 1996, 991). Addition of Grignard or lithium reagents to a suitably substituted ester or Weinreb amide 2a yields ketone 2b. Condensation of 2b with hydroxylamine hydrochloride generates the oxime which can be reduced to the primary amine 2c with zinc dust and TFA. Amide coupling between 2c and carboxylic acid 1f employing suitable coupling reagents as described in Scheme 1 gives 2d. Suzuki coupling between 4-chloropyridine 2d and an appropriately substituted aryl or heteroaryl boronic acid or ester 1b in the presence of a base such as anhydrous cesium carbonate, potassium fluoride, or potassium phosphate in a solvent, such as dioxane, dimethylsulfoxide, or dimethylformamide, using a catalyst such as tetrakis(triphenylphosphine)palladium(0), tris(dibenzylideneacetone)dipalladium(0) and tri-t-butylphosphonium tetrafluoroborate or Pd(dppf)$_2$Cl$_2$•CH$_2$Cl$_2$ complex provides the biaryl compound 1g. Further manipulation of functional groups on A, $R^3$, and $R^4$ using methods known to one skilled in the art of organic synthesis will give additional compounds of the invention.

Scheme 2

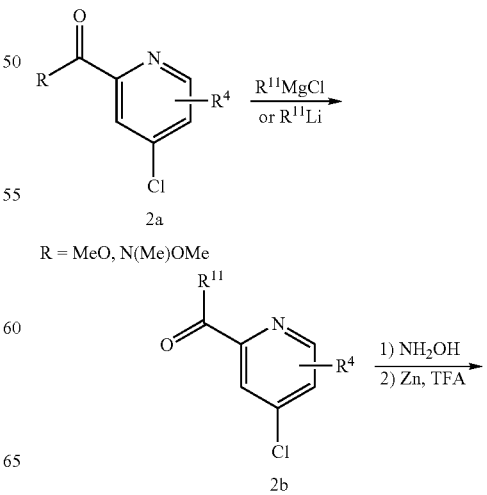

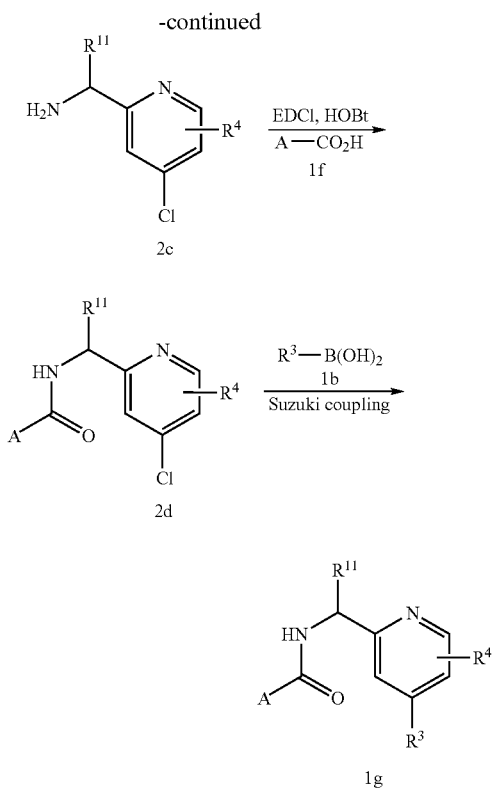

In cases where suitably substituted boronic acids are not commercially available, a modification to this approach may be adopted wherein an aryl halide is subjected to a palladium mediated coupling with a diboron species such as bis(pinacolato) diboron to provide the corresponding 4,4,5,5-tetramethyl-[1,3,2]dioxaborolane intermediate using the method of Ishiyama, T. et al. (*J. Org. Chem.* 1995, 60(23), 7508-7510). Alternately, this same intermediate can be prepared by reaction of the intermediate halide with the corresponding dialkoxyhydroborane as described by Murata et al. (*J. Org. Chem.* 1997, 62(19), 6458-6459). The boron pinacolate intermediates can be used in place of boronic acids for coupling to the aryl/heteroaryl halides or triflates or the boron pinacolate intermediate can be converted to the boronic acids. Alternately, the corresponding boronic acids can be prepared by metal-halogen exchange of the aryl/heteroaryl halide, quenching with a trialkoxyborate reagent, and aqueous workup to provide the boronic acids (Miyaura, N.; Suzuki, A. *Chem. Review*, 1995, 95, 2457).

It is also realized that the scope of intermediate synthesis can be further extended outside the use of Suzuki methodology since the precursor aryl halides or triflates described above are also precursors for Stille, Negishi, Hiyama, and Kumada-type cross coupling methodologies (Tsuji, J. *Transition Metal Reagents and Catalysts: Innovations in Organic Synthesis*, John Wiley & Sons, 2000; Tsuji, J. *Palladium Reagents and Catalysts: Innovations in Organic Synthesis*, John Wiley & Sons, 1996.)

Representative pyrimidine and pyrimidone compounds of this invention can be prepared as shown in Scheme 3. A suitably substituted amino nitrile 3a can be converted to the corresponding amidine 3b by treatment with N-acetylcysteine and ammonium acetate in the presence of dithiothreitol. Condensation of amidine 3b with an appropriately substituted aryl propynone 3 g in the presence of a base such as sodium carbonate and in a solvent such as acetonitrile provides the pyrimidine compound 3c (Bagley, C. Synlett 2003, 2, 259-261). After deprotection with TFA, the amine is coupled with carboxylic acid 1f employing suitable amide coupling conditions as described in Scheme 1 to yield 3d. The pyrimidone derivatives 3e can be prepared similarly by condensation of amidine 3b with an appropriately substituted aryl propiolate 3 h in the presence of a base such as Hunig's base and in a solvent such as ethanol (Gupta, K. A, et al. *Indian J. Chem.*, 1983, 22B, 384). After deprotection with TFA, the amine is coupled with carboxylic acid 1f as described above to yield 3f. Further manipulation of functional groups on A and $R^3$ using methods known to one skilled in the art of organic synthesis will give additional compounds of the invention.

Scheme 3

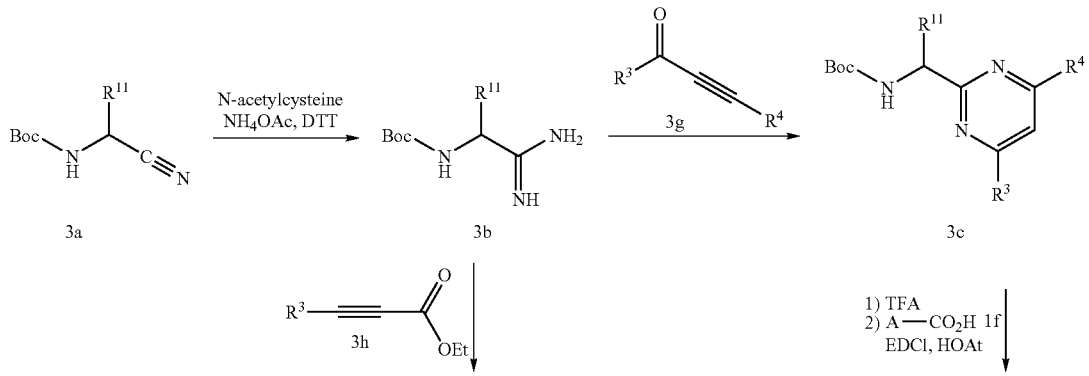

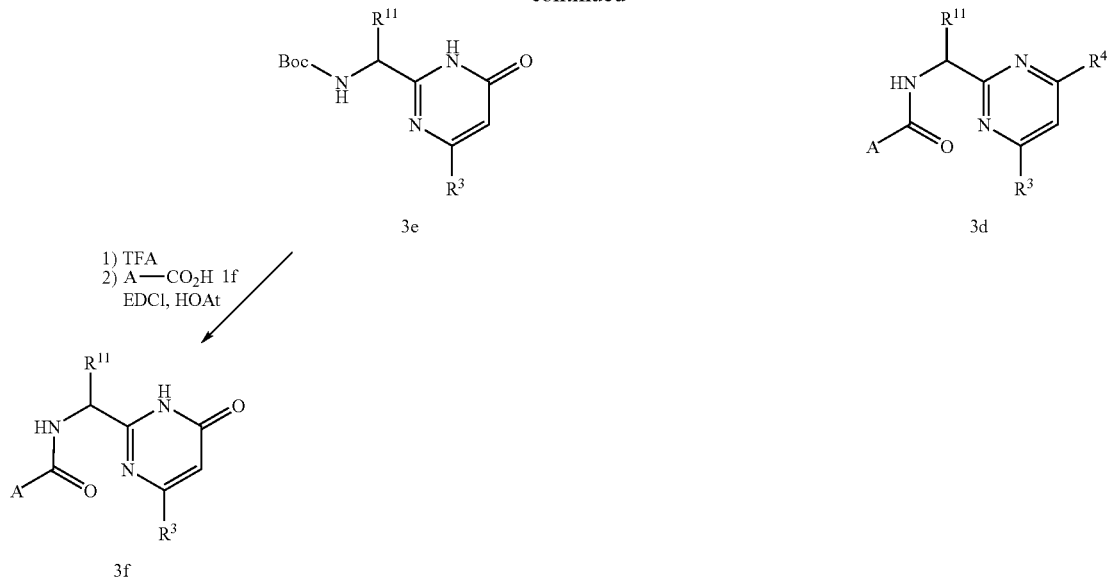

Representative pyridone compounds of this invention can be prepared as shown in Scheme 4. Compound 4d can be prepared in two steps according to a modified procedure described by Resmini (Resmini, M. et al., *Tetrahedron Asymmetry*, 2004, 15, 1847). A suitably substituted amino ester 4a can be converted to the corresponding β-ketophosphonate 4b by treatment with lithium dimethylmethylphosphonate. Homer-Wadsworth-Emmons reaction of 4b and a suitably substituted aldehyde 4c in the presence of base such as potassium carbonate in a solvent such as ethanol or tetrahydrofuran gives the α,β-unsaturated ketone 4d. Condensation of 4d with 1-(ethoxycarbonylmethyl)-pyrdinium chloride or 1-(carbamoylmethyl)-pyridinium chloride in the presence of ammonium acetate in a solvent such as ethanol or glacial acetic acid generates the pyridone 4e. After deprotection with TFA, the amine is coupled with carboxylic acid 1f employing suitable amide coupling reagents as described in Scheme 1 to yield 4f. Further manipulation of functional groups on A and $R^3$ using methods known to one skilled in the art of organic synthesis will give additional compounds of the invention.

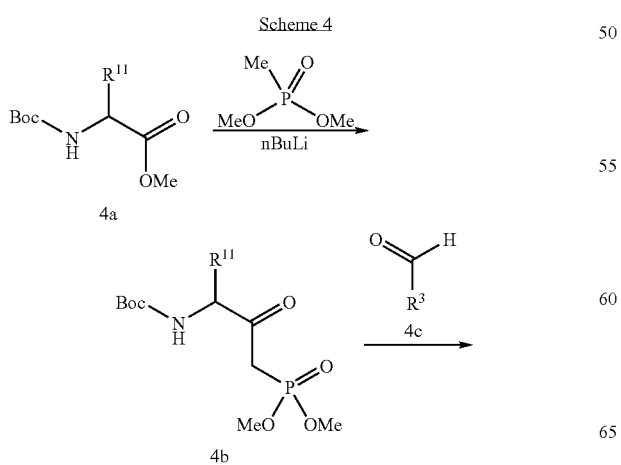

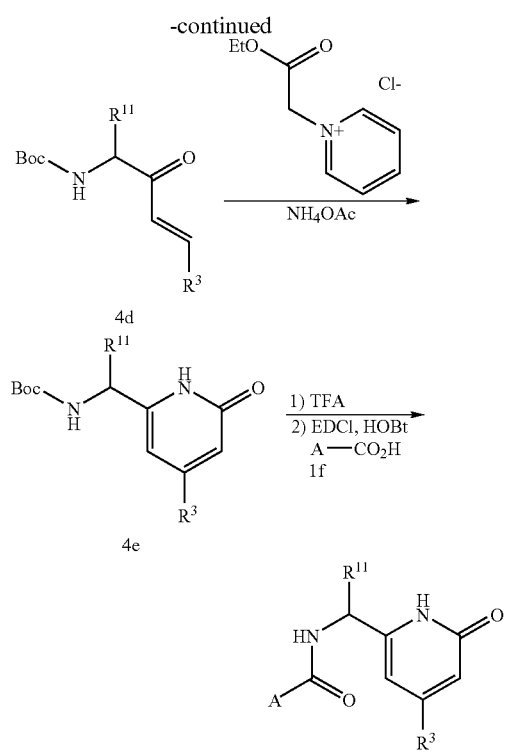

Alternately, pyridine and pyridone compounds of this invention can be prepared as shown in Scheme 5. Compound 5c can be prepared in two steps from β-ketophosphonate 5a as described Scheme 4. Selective O-alkylation as described by Rao (Rao, J. M., et al *Tetrahedron*, 1989, 45(22), 7093 and references cited there in) can be achieved with silver carbonate and an alkyl iodide, such as methyl iodide, in a solvent, such as benzene or chloroform, to give 5d. Alternatively, 5c can be treated with phosphorus oxychloride to give chloro-pyridine 5e. Dibromination of 5d/5e with NBS and subsequent reaction with morpholine at elevated temperatures followed by hydrolysis gives aldehydes 5 f and 5 g which can be converted to 5 j and 5 k, respectively, as described in Scheme 1. The chloro compound 5 k is converted to the amine 5l via a modification of the procedure described by Buchwald (Buchwald, S. L. et al, *Tetrahedron Letters*, 1997, 38(36), 6363). After demethylation of 5h with HCl or BBr$_3$, the amine is converted to the imine via transimination with benzophenone imine according to a modified procedure described by O'Donnell (O'Donnell, M. J., Polt, R. L. *J. Org Chem.*, 1982, 47, 2663). Deprotonation of the pyridone with a base such as sodium hydride in a solvent such as THF or DMF and quenching with an alkyl halide, such as methyl iodide, gives the N-alkyl derivative. Following hydrolysis of the imine with aqueous HCl, the amine is coupled with carboxylic acid 1f employing suitable amide coupling reagents as described in Scheme 1 to yield 5m. Further manipulation of functional groups on A and R$^3$ using methods known to one skilled in the art of organic synthesis will give additional compounds of the invention.

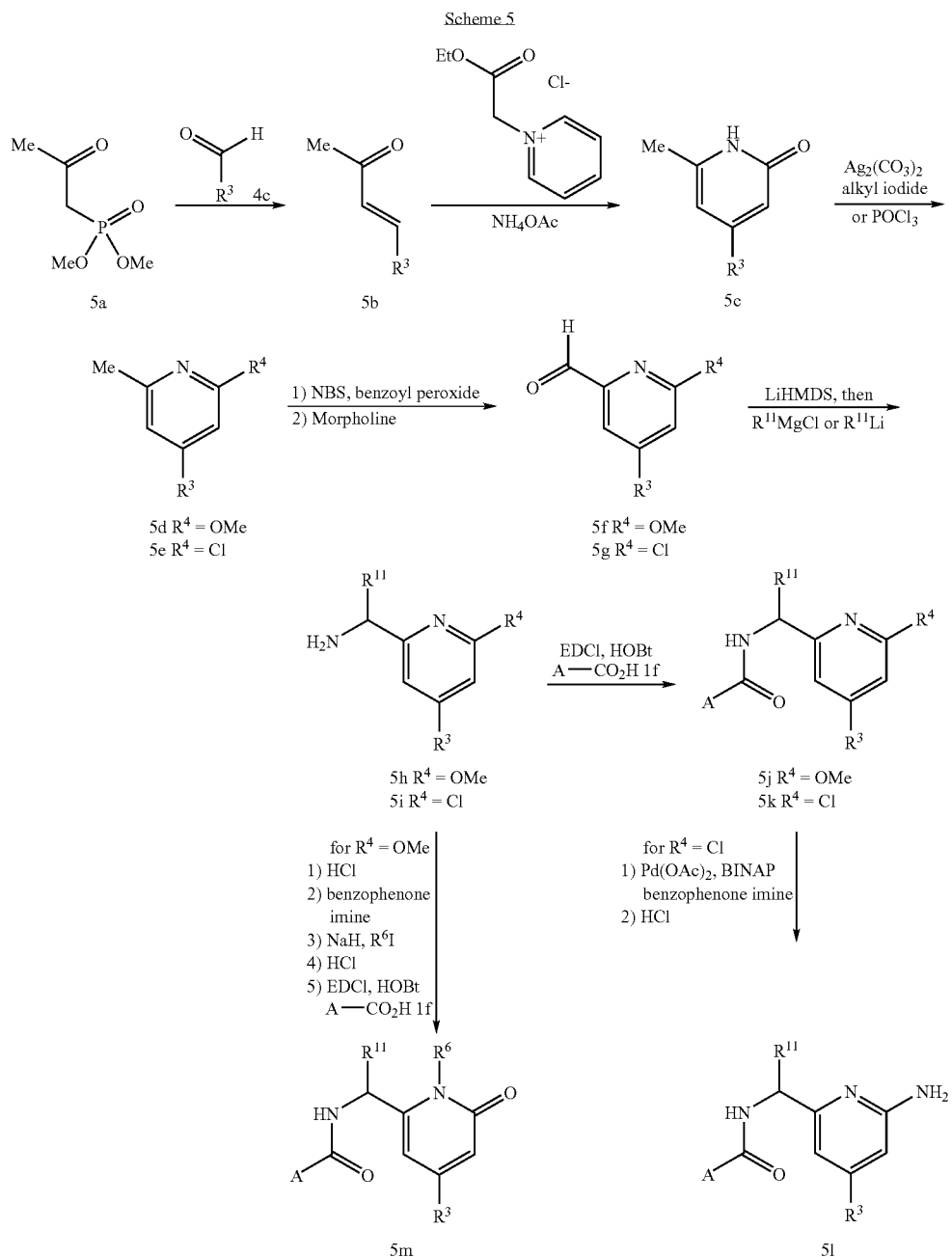

Representative examples of manipulation of functional groups on R$^3$ using methods known to one skilled in the art of organic synthesis are shown in Scheme 6. Heating 6a and 6b/6c with hydrazine monohydrate in n-butanol gives the 3-aminoindazole 6d and the 3-hydroxy indazole 6e, respectively. Reacting 6a with acetohydroxamic acid and potassium tert-butoxide in DMF according to a modified procedure described by Palermo (Palermo, M. G. *Tetrahedron Letters*, 1996, 37(17), 2885) provides 3-aminobenzisoxazole 6f. Alternately, heating 6a with formamidine acetate or acetamidine acetate in DMA, according to a modified procedure described by Lam (Lam, P. Y. S. et al, *J. Med. Chem.* 2003, 46, 4405.) gives 4-amino quinazolines 6 g and 6 h. Quinazolinone 6 k may be prepared similarly by heating the corresponding anthranilic acid derivatives 6i with formamide as described by Alexandre et al. (*Tet. Lett.* 2002 43, 3911). Alternatively, quinazolinone 6 k can be prepared by heating 6j with ammonium acetate and trimethylorthoformate according to a modified procedure from published WO patent WO2005/012264.

of this invention may be obtained through oxidation of the corresponding alcohol 7a or aldehyde 7b as taught in "*Advanced Organic Chemistry*" (Jerry March, Wiley Interscience, 4th Edition, pg 1196 and 701-703 and references therein). Alternately, oxidation of aromatic side chains in 7c gives aromatic carboxylic acids as taught in "*Advanced Organic Chemistry*" (Jerry March, Wiley Interscience, 4th Edition, pg 1183-1184 and references therein). Alternately, hydrolysis of esters 7d or nitriles 7e yields the carboxylic acid as taught in "Advanced Organic Chemistry" (Jerry March, Wiley Interscience, $4^{th}$ Edition, pg 378-383 and 887-889 and references therein). Alternately, carbonylation of bromide 7f gives the carboxylic acid as taught in "*Advanced Organic Chemistry*" (Jerry March, Wiley Interscience, $4^{th}$ Edition, pg

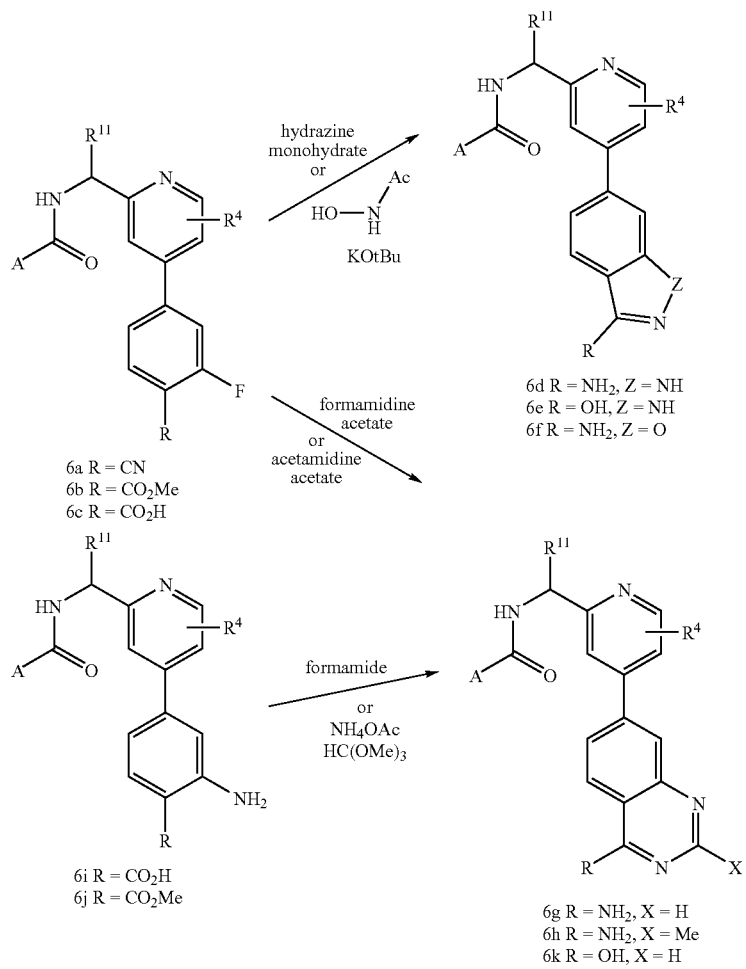

Scheme 6

It is understood that the pyridine ring system depicted in Scheme 6 can be interchanged with pyrimidine, pyrimidone, pyridone, and additional ring systems claimed in this invention.

A suitably substituted carboxylic acid (A-CO$_2$H, 1f) is used in the amide coupling shown in Scheme 1-5. Many of these carboxylic acids are commercially available. In cases where the carboxylic acids are not commercially available, they can be prepared using methods known in the art (Scheme 7). Carboxylic acids suitable for use in preparing compounds 484-486, 546-547, and 664-665 and references therein). The $R^1$ and $R^2$ groups can be further manipulated using methods known in the art to provide additional compounds of this invention. For example, when $R^1$ is a cyano group, it can be reduced to give CH$_2$NH$_2$ with a suitable reducing agent. The nitrile can also be converted to an amidine by reaction with hydroxylamine followed hydrogenolysis with a palladium catalyst under a hydrogen atmosphere or via a Pinner reaction followed by ammonolysis.

Scheme 7

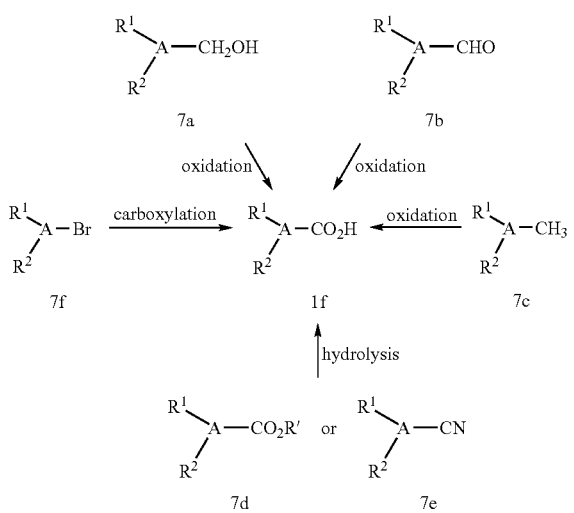

Schemes 8 and 9 describe the synthesis of additional examples of acids A-CO$_2$H (1f) useful for preparing compounds of this invention. When A is an isoquinoline moiety, a modified procedure from published US patent U.S. 2004/0077865 is followed. Heating the 2-methyl benzonitrile derivative 8a with 1-(t-butoxy)-N—N—N'—N'-tetramethyl-methanediamine in a suitable solvent such as DMF gives the enamine 8b. Condensation of enamine 8b and 2,4-dimethoxybenzylamine in DMPU at elevated temperatures gives the 1-imino-1,2-dihydroisoquinoline skeleton and subsequent hydrolysis provides 8c. Debenzylation of 8c with anisole in TFA at elevated temperatures provides 1-amino-isoquinoline 8d. When A is a 5,6,7,8-tetrahydroisoquinoline moiety, a modified procedure described by McEachern is followed (McEachern, E. J. et al. *J. Org. Chem.* 2002, 67, 7890). Acid 8c is converted to the ester 8e. Debenzylation of 8e with anisole in TFA at elevated temperatures and acetylation with acetyl chloride and triethylamine yields 8f Hydrogenation over platinum oxide in the presence of TFA provides the 1-amino-5,6,7,8-tetrahydroisoquinoline. Saponification of the ester with NaOH and hydrolysis of the amide under acidic conditions gives 8 g.

Scheme 8

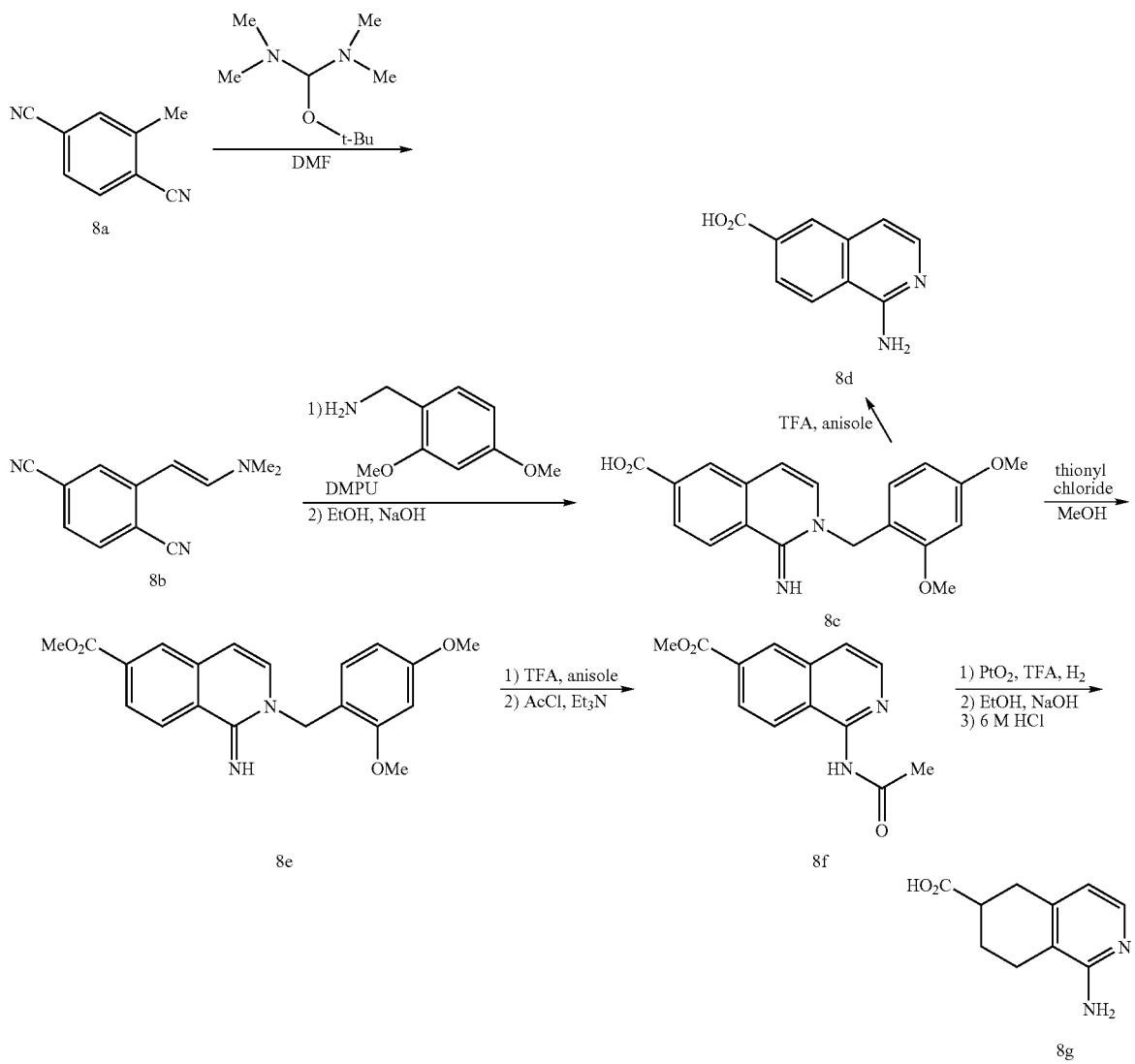

Scheme 9 describes the synthesis of specific examples of A-CO$_2$H (1f) when A is the 4-amino-quinazoline moiety. Heating an appropriately substituted ortho-fluoro benzonitrile 9a with formamidine acetate or acetamidine acetate in DMA, according to a modified procedure described by Lam (Lam, P. Y. S. et al. *J. Med. Chem.* 2003, 46, 4405.) gives 4-amino quinazoline 9b and 9c. Saponification of the ester under basic conditions provides 9d and 9e.

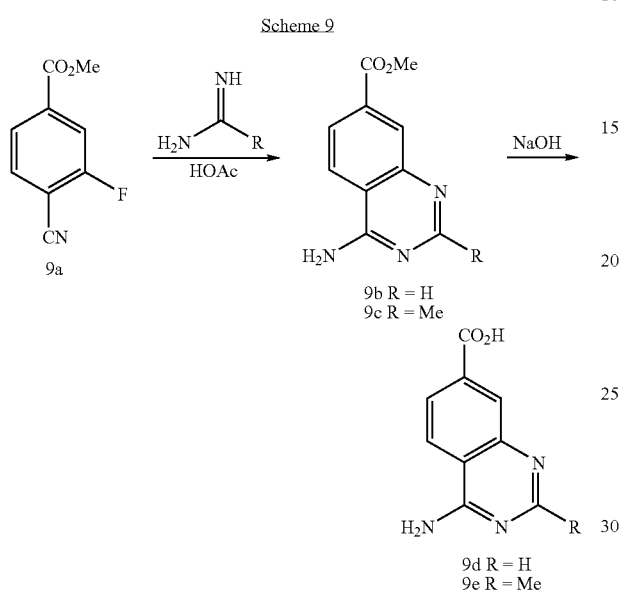

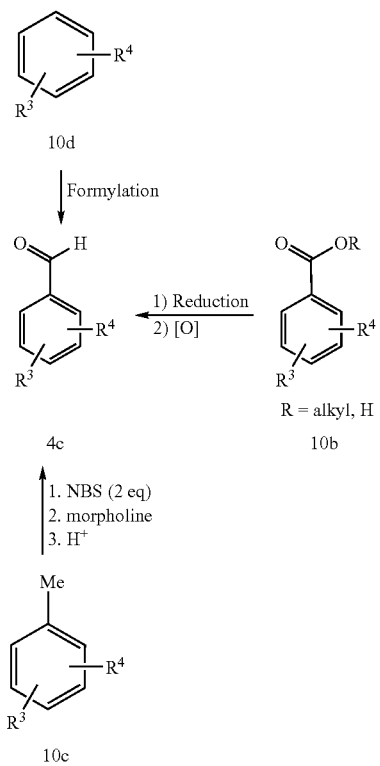

In cases where suitably substituted aldehydes 4c are not commericially available, the suitable aldehydes useful for the synthesis of compounds in Schemes 4 and 5 are accessible from a variety of straightforward chemical transformations known to one skilled in the art. As outlined in Scheme 10, aldehydes 4c (when R$^3$ is phenyl) suitable for use in preparing compounds of this invention may be obtained through oxidation of the corresponding alcohols or halides 10a as taught in "*Advanced Organic Chemistry*" (Jerry March, Wiley Interscience, 4$^{th}$ Edition, pp. 1167-1171, 1190, and 1193 and references therein). Alternatively suitable aldehydes may be prepared by hydrogenation of the corresponding carboxylic acids 10b in the presence of palladium complexes and pivalic anhydride (Nagayama et al. *Chemistry Letters* 1998, 27, 1143-1144) or by reduction of the corresponding carboxylic acid 10b with borane followed by oxidation of the intermediate alcohol with manganese dioxide or Dess-Martin periodinane. In addition, the ester (10b; R=alkyl) can be reduced with DIBAL-H (Chandrasekhar et al. *Tetrahedron Letters* 1998, 39, 909-910) to give the aldehyde 4c. Additional aryl aldehydes may be obtained from the corresponding toluene derivatives 10c by direct oxidation or by a two step procedure which involves formation of the dibromide intermediate and subsequent conversion to the aldehyde with a silver salt, hexamethylenetetramine, or morpholine (with silver: Demir, A. S.; Reis, O. *Tetrahedron*, 2004, 60, 3803; hexamethylenetetramine: Tidwell, R. R.; et al. *J. Med. Chem.*, 1978, 21(7), 613; morpholine: published WO patent WO2002/32884). Additional suitable aldehydes may be prepared through formylation of the aromatic ring 10d as taught in "*Advanced Organic Chemistry*" (Jerry March, Wiley Interscience, 4th Edition, pp. 542-546 and references therein).

A modification of Scheme 2 is shown in Scheme 11. Reacting 4-chloropyridine 2b with TMSBr or acetyl bromide at elevated temperatures as described in Scheme 1 provides 4-bromopyridine 11a. Compound 11a can be carried through the sequence described in Scheme 2 to give 1 g. Alternately, the Suzuki coupling strategy can be reversed. The 4-bromopyridine 11c can be converted to either the boronate or boronic acid derivative as described previously to yield 11d. Suzuki coupling between 4-pyridineboronic acid 11d and an appropriately substituted aryl or heteroaryl halide or pseudohalide 11e in the presence of a base such as anhydrous cesium carbonate, potassium fluoride, or potassium phosphate in a solvent, such as dioxane, dimethylsulfoxide, or dimethylformamide, using a catalyst such as tetrakis(triphenylphosphine)palladium(0), tris(dibenzylideneacetone)dipalladium(0) and tri-t-butylphosphonium tetrafluoroborate or Pd(dppf)$_2$Cl$_2$·$_{CH2}$Cl$_2$ complex provides the biaryl compound 1g. Further manipulation of functional groups on A, R$^3$, and R$^4$ using methods known to one skilled in the art of organic synthesis will give additional compounds of the invention.

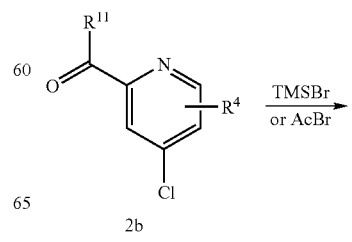

-continued

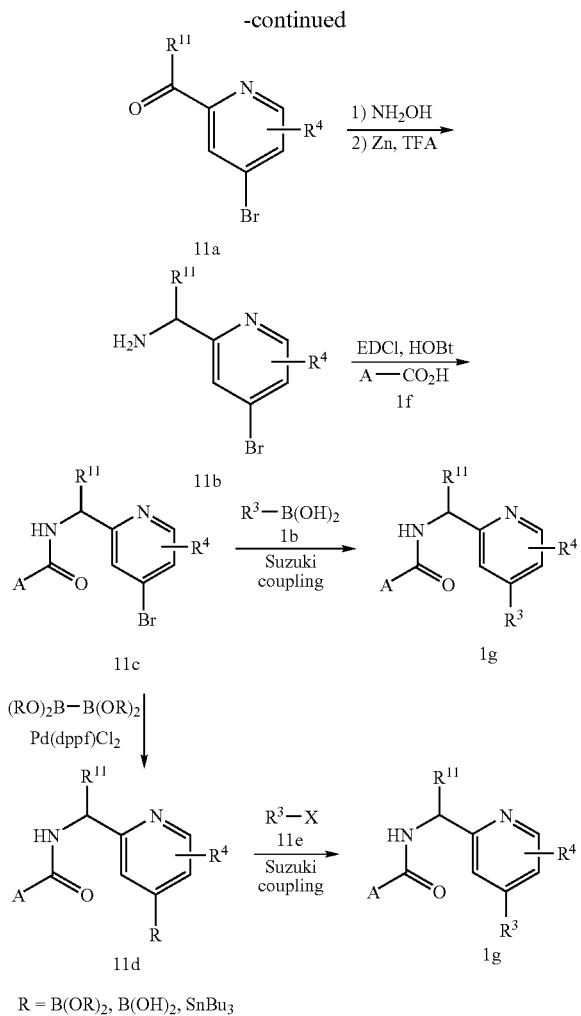

Representative examples of manipulation of functional groups on $R^3$ using methods known to one skilled in the art of organic synthesis are shown in Scheme 12. Fluoropyridine 12a can be displaced with amines, such as ammonium hydroxide, to give aminopyridine 12b, alkoxides, such as sodium methoxide, to give 12c, or sodium hydroxide to give 12d according to a modified procedures described by Queguiner (Queguiner, G. et al. *J. Org. Chem.*, 1988, 53, 2740.)

Scheme 12

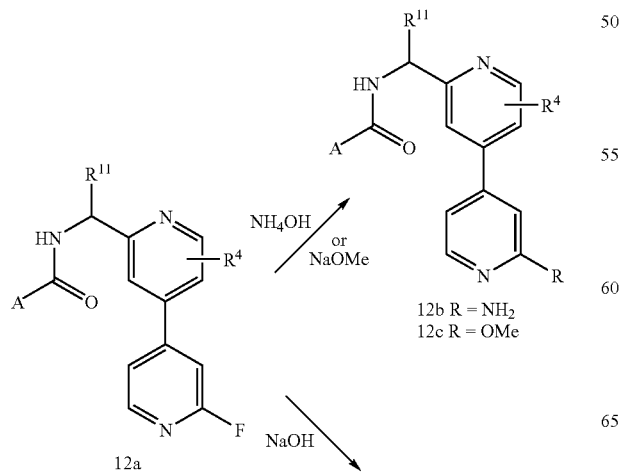

-continued

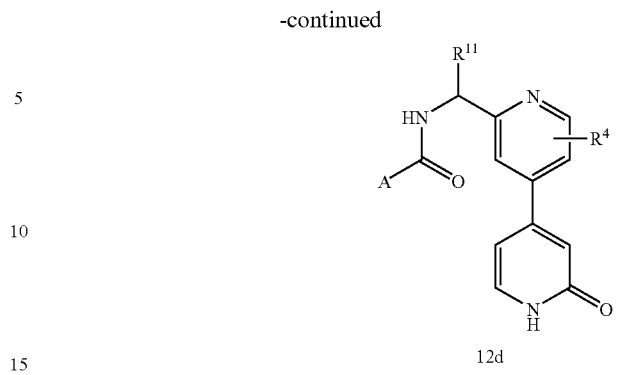

Representative examples of this invention when $R^3$ is a pyrimidine ring system are shown in Schemes 13 and 14. Condensation of amidine 13b, which can be synthesized from cyanopyridine 13a via the Pinner reaction, with an appropriately substituted propiolate can provide pyrimidone 13c. Pyrimidone 13c can be converted to the aminopyrimidine 13d in two steps. A regioisomeric pyrimidine synthesis is described in Scheme 14. The β-ketonitrile 14b can be prepared from the acid 14a according to a modified procedure described by Katritzky (Katritzky, A. R. et al. *J. Org. Chem.*, 2003, 68, 4932). Condensation of 14b with formamide and ammonia according to a modified procedure of Hirota (Hirota, T. et al. *Synthesis*, 1991, 303.) can provide aminopyrimidine 14c. The β-ketonitrile 14b can also be used to synthesize pyrazoles (Watson, S. P. et al. *Tetrahedron Letters*, 1997, 38, 9065.)

Scheme 13

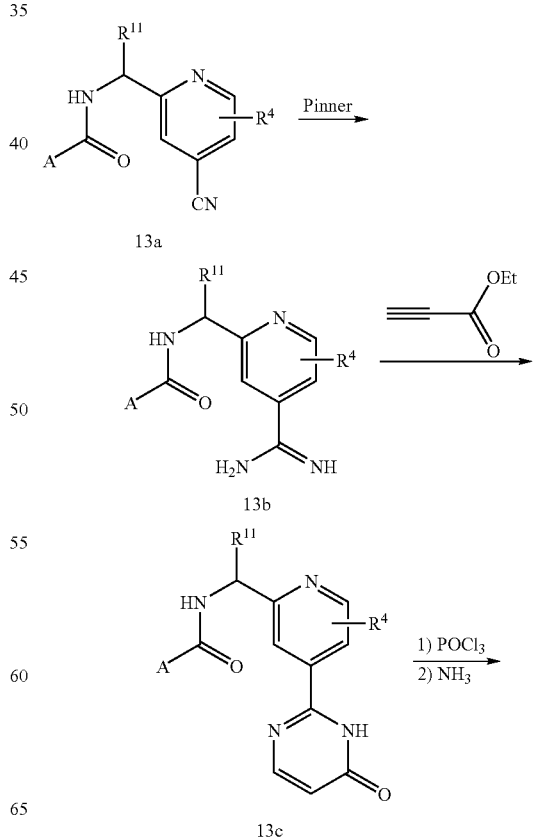

-continued

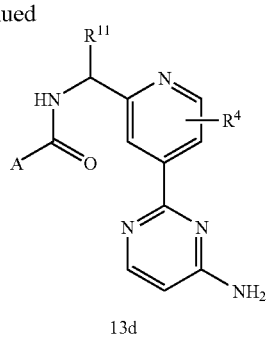

13d

Scheme 14

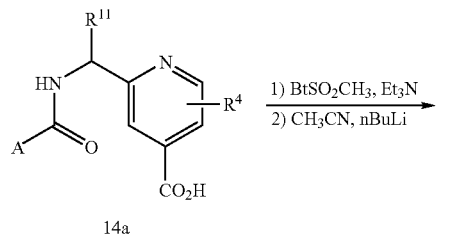

14a

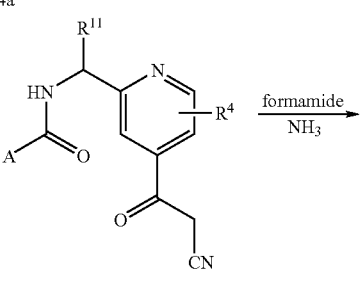

14b

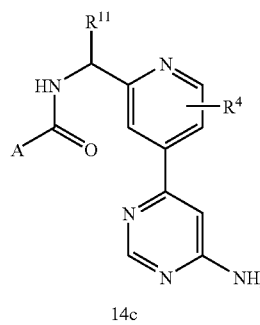

14c

Other features of the invention will become apparent in the course of the following descriptions of exemplary embodiments that are given for illustration of the invention and are not intended to be limiting thereof.

Solution ratio expresses a volume relationship, unless stated otherwise. NMR chemical shifts (δ) are reported in parts per million. Flash chromatography was carried out on silica gel according to Still's method (Still, W. C. et al. *J. Org. Chem.* 1978, 43, 2923). Preparatory HPLC was carried out on Phenomenex Luna columns with the specific conditions designated in the experimentals with the following solvent system: Solvent A: 90% water, 10% methanol, and 0.1% TFA. Solvent B: 10% water, 90% methanol, and 0.1% TFA.

As used throughout the specification, the following abbreviations for chemical reagents apply:

AcOH or HOAc=acetic acid
Bn=benzyl
Bu=butyl
t-Bu=tertiary butyl
Boc=tert-butyl oxycarbonyl
$CH_2Cl_2$=dichloromethane
DCE=1,2-dichloroethane
DMF=dimethylformamide
DMSO=dimethyl sulfoxide
DTT=dithiothreitol
EDCI=1-(3-(dimethylamine)propyl)-3-ethylcarbodiimide hydrochloride
Et=ethyl
$Et_2O$=diethyl ether
EtOH=ethanol
EtOAc=ethyl acetate
HCl=hydrochloric acid
HOAt=7-aza-1-hydroxybenzotriazole
HOBt=1-hydroxybenzotriazole
LiHMDS=Lithium hexamethyldisilazide
Me=methyl
MeOH=methanol
mCPBA=m-chloroperbenzoic acid
NaOAc=sodium actetate
$Na_2SO_4$=sodium sulfate
NMM=N-methylmorpholine
OAc=acetate
Ph=phenyl
Pr=propyl
i-Pr=isopropyl
i-PrOH=isopropanol
PXPd2=Bis[di-tert-butyl phosphinous chloride-kP]di-m-chlorodichloro dipalladium
TFA=trifluoroacetic acid
THF=tetrahydrofuran
° C.=degrees Celsius
anh.=anhydrous
atm=atmosphere
conc.=concentrated
eq=equivalent(s)
h or hr=hour(s)
g=gram(s)
mg=milligram(s)
L=liter(s)
mL=milliliter(s)
μL=microliter(s)
mmol=millimolar
M=molar
meq=milliequivalent(s)
min=minute(s)
MW=molecular weight
mp=melting point
rt or RT=room temperature
sat or sat'd=saturated
sec=second(s)
ESI=electrospray ionization mass spectroscopy
HPLC=high performance liquid chromatography
MS=mass spectrometry
LC/MS=liquid chromatography mass spectrometry
NMR=nuclear magnetic resonance spectroscopy
TLC=thin layer chromatography "α", "β", "R", "S", "E", and "Z" are stereochemical designations familiar to one skilled in the art. One stereoisomer of a compound of Formula I may display superior activity compared with the others. Thus, each stereoisomer of a compound of Formula I is considered to be a part of the present invention. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases.

The following Examples have been prepared, isolated and characterized using the methods disclosed herein. The following Examples demonstrate a partial scope of the invention and are not meant to be limiting of the scope of the invention.

EXAMPLES

Example 1

4-Aminomethyl-cyclohexanecarboxylic acid [2-phenyl-1-(4-phenyl-pyridin-2-yl)-ethyl]-amide, bistrifluoroacetic acid salt 1A. 2-Chloro-4-phenylpyridine: A flask was charged with 2-chloro-4-iodo pyridine (2.5 g, 10.4 mmol), phenylboronic acid (1.33 g, 10.96 mmol), $K_2CO_3$ (4.54 g, 32.88 mmol), PXPd2 (0.186 g, 0.261 mmol), and methanol (34.8 mL). Argon was blown through flask for 30 sec. The dark brown suspension was stirred for 3 h and then filtered, washing with methanol. The filtrate was concentrated to give 2.15 g as a brown solid. Column chromatography (120 g silica gel column; gradient elution; 0-35% ethyl acetate/hexane) afforded 1A (1.79 g, 90%) as a yellow solid. $^1$H-NMR (400 MHz, CDCl$_3$) δ: 8.43 (d, J=5.3 Hz, 1H), 7.61 (dd, J=8.2, 1.5 Hz, 2H), 7.54 (d, J=2.2 Hz, 1H), 7.52-7.47 (m, 3H), 7.43 (dd, J=5.1, 1.5 Hz, 1H).
$^{13}$C-NMR (125 MHz, CDCl$_3$) δ: 152.2, 151.5, 149.9, 136.8, 129.6, 129.2, 127.0, 122.0, 120.4. MS 190.0 (M+H)+ and 192.0 (M+2+H)$^+$.

1B. 4-Phenyl-pyridine-2-carbaldehyde: To a clear, colorless solution of 1A (0.850 g, 4.5 mmol) in propionitrile (4.5 mmol) was added trimethylsilyl bromide (2.95 mL, 22.4 mmol). The resulting orange suspension was microwaved in a sealed tube at 150° C. for 10 min. The reaction was cooled to rt and poured into 1.0 N NaOH containing ice. The aqueous layer was extracted with diethyl ether (2×). The combined organic layers were washed with sat. NaHCO$_3$, brine, dried over Na$_2$SO$_4$, filtered and concentrated to give 1.07 g of 2-bromo-4-phenyl pyridine as an off-white solid. MS 233.9 (M+H)$^+$ and 235.9 (M+2+H)$^+$.

To a cooled (−78° C.) clear, slightly yellow solution of 2-bromo-4-phenyl-pyridine (0.500 g, 2.14 mmol) in THF (8.6 mL) was added dropwise 2.5 M n-BuLi in hexane (0.86 mL, 2.14 mmol). The resulting red solution was stirred at −78° C. for 1 h, then 1-formylpiperidine (0.48 mL, 4.28 mmol) was added dropwise. The reaction was allowed to warm to 0° C. over 1 h and then stirred at 0° C. for 1 h. The reaction was quenched with 1.0 N HCl. The reaction was extracted with ethyl acetate. The combined organic layers were washed with sat. NaHCO$_3$, brine, dried over Na$_2$SO$_4$, filtered, and concentrated to give 0.555 g as a golden oil. Column chromatography (40 g silica gel; gradient elution; 0-40% ethyl acetate/hexane) provided 1B (0.194 g, 49%) as a yellow solid. $^1$H-NMR (400 MHz, CDCl$_3$) δ: 10.16 (s, 1H), 8.84 (d, J=5.3 Hz, 1H), 8.21 (d, J=1.3 Hz, 1H), 7.75 (dd, J=5.3, 1.8 Hz, 1H), 7.71-7.69 (m, 2H), 7.55-7.48 (m, 3H). MS 184.1 (M+H)$^+$.

1C. 2-Phenyl-1-(4-phenylpyridin-2-yl)-ethanamine, bistrifluoroacetic acid salt: To a cooled (0° C.), clear, yellow solution of 1B (0.184 g, 1.00 mmol) in THF (2.0 mL) was added dropwise 1.0 N lithium bis(trimethylsilyl)amide in THF (1.10 mL, 1.10 mmol). The resulting brown-yellow solution was stirred at 0° C. for 15 min. Subsequently, a 2.0 M benzylmagnesium chloride solution in THF (0.60 mL, 1.20 mmol) was added dropwise to give a red solution. The reaction was stirred at 0° C. for 20 min and then warmed to rt. After 30 min, the reaction was quenched with sat. NH$_4$Cl, diluted with water and diethyl ether. The layers were separated and the organic layer was washed with sat. NaHCO$_3$, brine, dried over Na$_2$SO$_4$, filtered, and concentrated to a thick orange residue. Prep. HPLC [21.2×100 mm; 10 min. gradient; 20-100% B; 20 mL/min.] afforded 1C (0.238 g, 47%) as an off-white foam. $^1$H-NMR (500 MHz, MeOD$_4$) δ: 8.69 (d, J=5.5 Hz, 1H); 7.64 (dd, J=5.5, 1.6 Hz, 1H), 7.56-7.51 (m, 2H), 7.47-7.42 (m, 3H), 7.29-7.23 (m, 4H), 7.11-7.09 (m, 2H), 5.25 (bs, 2H), 4.77 (dd, J=9.4, 6.0 Hz, 1H), 3.41 (dd, J=13.2, 6.0 Hz, 1H), 3.22 (dd, J=13.2, 9.4 Hz, 1H). MS 275.1 (M+H)$^+$.

1D. {4-[2-Phenyl-1-(4-phenyl-pyridin-2-yl)-ethylcarbamoyl]-cyclohexylmethyl}-carbamic acid tert-butyl ester: To a cooled (0° C.), clear, orange solution of 1C (0.138 g, 0.275 mmol) in DMF (0.9 mL) was added Hunig's base (0.11 mL, 0.605 mmol). To the resulting clear, yellow solution was added sequentially BOC-transexamic acid (0.078 g, 0.302 mmol), HOBt (0.0557 g, 0.412 mmol), and EDCI (0.079 g, 0.412 mmol). After 15 min at 0° C., the suspension was warmed to rt. After 2.5 h, the solution was diluted with water to give a suspension. The reaction was extracted with CH$_2$Cl$_2$. The combined organic layers were washed with brine, dried over MgSO$_4$, filtered and concentrated to give 1D (0.155 g) as an off-white solid. The material was carried onto the next step without further purification or characterization. MS 514.22 (M+H)$^+$.

1E. Example 1: To a clear, colorless solution of 1D (0.086 g, 0.167 mmol) in CH$_2$Cl$_2$ (3.0 mL) was added TFA (0.9 mL). After 1 h, the reaction was concentrated. CH$_2$Cl$_2$ was added and the reaction was concentrated again. The above process was repeated again to give a yellow residue. Prep. HPLC [21.2×100 mm; 10 min. gradient; 20-100% B; 20 mL/min.] afforded Example 1 (0.0484 g, 45%) as a white solid. $^1$H-NMR (500 MHz, MeOD$_4$) δ: 8.68 (d, J=6.0 Hz, 1H), 8.12-8.10 (m, 2H), 7.86-7.84 (m, 2H), 7.61-7.58 (m, 3H), 7.29-7.26 (m, 2H), 7.23-7.20 (m, 3H), 5.38 (t, J=8.1 Hz, 1H), 3.34-3.26 (m, 2H), 2.77 (d, J=7.4 Hz, 2H), 2.34-2.28 (m, 1H), 1.85-1.83 (m, 3H), 1.77-1.75 (m, 1H), 1.61-1.53 (m, 1H), 1.42-1.31 (m, 2H), 1.11-1.02 (m, 2H). HRMS m/z calc'd. for C$_{27}$H$_{32}$N$_3$O (M+H)$^+$: 414.2545. Found 414.2545.

Example 2

4-Aminomethyl-cyclohexanecarboxylic acid [1-(1-oxy-4-phenyl-pyridin-2-yl)-2-phenyl-ethyl]-amide, bistrifluoroacetic acid salt To a clear, slightly yellow solution of 1D (0.069 g, 0.134 mmol) in chloroform (0.54 mL) was added m-chloroperbenzoic acid (0.039 g, 0.174 mmol). After 2 h, the reaction was diluted with CH$_2$Cl$_2$ and washed with sat. sodium sulfite, sat. NaHCO$_3$, brine, dried over MgSO$_4$, filtered and concentrated to give an off-white solid. This solid was dissolved in 30% TFA in CH$_2$Cl$_2$ (3 mL). After 1 h, the reaction was concentrated. CH$_2$Cl$_2$ was added and the reaction was concentrated again. The above process was repeated again to give a yellow residue. Prep. HPLC [21.2×100 mm; 10 min. gradient; 20-100% B; 20 mL/min.] yielded Example 2 (0.0328 g, 45%) as a white solid. $^1$H-NMR (500 MHz, MeOD$_4$) δ: 8.40 (d, J=6.6 Hz, 1H), 7.74 (dd, J=6.6, 2.8 Hz, 1H), 7.72 (d, J=2.8 Hz, 1H), 7.68-7.66 (m, 2H), 7.52-7.44 (m, 3H), 7.32 (d, J=7.2 Hz, 2H), 7.27 (t, J=7.4 Hz, 2H), 7.19 (t, J=7.2 Hz, 1H), 5.76 (dd, J=9.6, 4.7 Hz, 1H), 3.48 (dd, J=13.8, 4.4 Hz, 1H), 2.91 (dd, J=13.2, 9.9 Hz, 1H), 2.76 (d, J=7.2 Hz, 2H), 2.28-2.22 (m, 1H), 1.87-1.81 (m, 3H), 1.68-1.65 (m, 1H), 1.59-1.51 (m, 1H), 1.43-1.27 (m, 2H), 1.09-0.99 (m, 2H). HRMS m/z calc'd for $C_{27}H_{32}N_3O_2$ (M+H)$^+$: 430.2495. Found 430.2480.

Example 3

3-(2-{1-[(4-Aminomethyl-cyclohexanecarbonyl)-amino]-2-phenyl-ethyl}-pyridin-4-yl)-benzoic acid methyl ester, bis-trifluoroacetic acid salt 3A. 4-Chloro-pyridine-2-carboxylic acid methyl ester (according to a modified procedure described by Varlet, D. et al, *Heterocycles*, 2000, 53(4), 797): A green suspension of 2-picolinic acid (50.0 g, 406 mmol) in thionyl chloride (200 mL) was warmed to reflux. After 41 h, the clear, red-orange solution was cooled to rt and the excess thionyl chloride was removed via rotary evaporation to obtain a red-orange liquid containing a small amount of solid. Dichloroethane (200 mL) was added and the reaction was concentrated. The above process was repeated a second time to obtain an orange residue. Diethyl ether (1.4 L) was added to obtain a suspension and the reaction mixture was cooled to 0° C. and vigorously stirred as methanol (200 mL) was added dropwise. The resulting yellow suspension was stirred at 0° C. for 30 min and then warmed to rt and stirred for 1 h. Filtration provided a yellow solid which was washed with diethyl ether, air-dried, and dried under vacuum to obtain 21.20 g (95% pure) of solid 1. The filtrate was concentrated to dryness and diethyl ether (500 mL) was added and sonication yielded a fine suspension. Filtration provided a yellow solid which was washed with diethyl ether, air-dried, and dried under vacuum to produce 35.5 g (50% pure) of solid 2.

To a cooled (0° C.) suspension of solid 2 (35.5 g) in $CH_2Cl_2$ (500 mL) was added sat. $NaHCO_3$ (300 mL). The suspension was stirred vigorously to dissolve most of the solid. The layers were separated and the aqueous layer was extracted with $CH_2Cl_2$ (200 mL). The combined organic layers were washed with brine, dried over $MgSO_4$, filtered and concentrated to give an orange liquid weighing 28 g. Column chromatography on silica gel (0-10% ethyl acetate in $CH_2Cl_2$ and then 15:1 $CH_2Cl_2$:ethyl acetate) yielded 13.0 g of 3A as a white solid. Solid 1 was neutralized as described in the above procedure to give an additional 17.4 g of 3A as a white solid. A total of 30.4 g (44%) of 3A was obtained. $^1$H-NMR (400 MHz, CDCl$_3$) δ: 8.66 (d, J=5.2 Hz, 1H), 8.15 (d, J=2.6 Hz, 1H), 7.50 (dd, J=5.0, 2.0 Hz, 1H), 4.02 (s, 3H).

3B. 1-(4-Chloro-pyridin-2-yl)-2-phenyl-ethanone: To a cooled (−40° C.) solution of 3A (14.5 g, 84.5 mmol) in THF (192 mL) was added rapidly via cannula a cooled (−40° C.), pale brown solution of 0.6 M benzylmagnesium chloride (142 mL, 84.5 mmol) in THF. The resulting, clear orange solution was stirred at −40° C. for 1 h and then the reaction was quenched with glacial acetic acid (5.4 mL, 93 mmol). The reaction was allowed to warm to rt. The reaction was partitioned between ethyl acetate and sat. $NaHCO_3$. The layers were separated and the aqueous layer was extracted with ethyl acetate. The combined organic layers were washed with brine, dried over $Na_2SO_4$, filtered, and concentrated to give 21.6 g red-brown liquid. Column chromatography on silica gel (1.5:1 $CH_2Cl_2$:hexane) gave 3B (10.1 g, 52%) as an orange liquid. $^1$H-NMR (500 MHz, CDCl$_3$) δ: 8.63 (d, J=5.5 Hz, 1H), 8.03 (d, J=2.2 Hz, 1H), 7.46 (dd, J=5.0, 2.2 Hz, 1H), 7.34-7.28 (m, 4H), 7.27-7.22 (m, 1H), 4.52 (s, 2H). MS 232.1 (M+H)+ and 234.0 (M+2+H)$^+$.

3C. 1-(4-chloropyridin-2-yl)-2-phenylethanamine: To a clear, yellow solution of 3B (3.96 g, 17.1 mmol) in methanol (34 mL) was added hydroxylamine hydrochloride (3.56 g, 51.3 mmol). The suspension was stirred at rt. Over time the hydroxylamine hydrochloride went into solution. After 14 h the reaction was concentrated to produce a yellow solid. The solid was dissolved in ethyl acetate and washed with sat. $NaHCO_3$. The layers were separated and the aqueous layer was extracted with ethyl acetate. The combined organic layers were washed with brine, dried over $Na_2SO_4$, filtered, and concentrated to yield the oxime as a pink solid weighing 4.13 g.

To a cooled (5° C.), clear, yellow solution of oxime (4.13 g) in TFA (39.5 mL) was added zinc dust (11.18 g, 171 mmol) in portions so as to keep the temperature below 25° C. After 1.5 h, the reaction was filtered through a cotton plug to remove most of the zinc and the zinc residue was rinsed with TFA (50 mL). The filtrate was poured slowly into a cold (0° C.), vigorously stirred suspension of 2 M NaOH (700 mL) and $CH_2Cl_2$ (500 mL). The layers were separated and the aqueous layer was extracted with $CH_2Cl_2$. The combined organic layers were washed with brine, dried over $MgSO_4$, filtered and concentrated to obtain 3.64 g of the product as a clear, orange-brown liquid. Column chromatography (5% methanol in $CH_2Cl_2$ with 0.5% ammonium hydroxide) yielded 3C (2.93 g, 74%) as a clear yellow oil. $^1$H-NMR (500 MHz, CDCl$_3$) δ: 8.47 (d, J=5.0 Hz, 1H), 7.31-7.25 (m, 3H), 7.23-7.20 (m, 1H), 7.17-7.14 (m, 3H), 4.21 (dd, J=8.8, 5.5 Hz, 1H), 3.15 (dd, J=13.8, 5.0 Hz, 1H), 2.82 (dd, J=13.8, 8.8 Hz, 1H). MS 233.1 (M+H)$^+$ and 235.1 (M+2+H)$^+$.

3D. {4-[f-(4-Chloro-pyridin-2-yl)-2-phenyl-ethylcarbamoyl]-cyclohexylmethyl}-carbamic acid tert-butyl ester: To a cooled (0° C.), clear, yellow solution of 3C (2.93 g, 12.6 mmol) in DMF (42 mL) was added sequentially, Boc-tranexamic acid (3.56 g, 13.8 mmol), HOBt (2.55 g, 18.8 mmol), and EDC (3.62 g, 18.8 mmol). After 15 min at 0° C., the reaction was warmed to rt. After 4 h, the reaction was poured into vigorously stirred cold water (0° C., 200 mL) to obtain a white suspension. Buchner funnel filtration generated a white solid which was washed with water. The white solid was dissolved in $CH_2Cl_2$ and washed with water, 0.5 M HCl, sat. $NaHCO_3$, brine, dried over $MgSO_4$, filtered and concentrated to give 11 g as a white solid. Column chromatography on silica gel (3:1 $CH_2Cl_2$:ethyl acetate) gave 3D (3.91 g, 66%) as a white solid. $^1$H-NMR (500 MHz, CDCl$_3$) δ: 8.41 (d, J=5.4 Hz, 1H), 7.23-7.16 (m, 4H), 6.93-6.92 (m, 2H), 6.89 (d, J=1.3 Hz, 1H), 6.66 (d, J=8.0 Hz, 1H), 5.22 (dd, J=13.8, 7.7 Hz, 1H), 4.58 (bs, 1H), 3.16 (dd, J=12.8, 6.0 Hz, 1H), 3.03 (dd, J=13.4, 7.4 Hz, 1H), 2.97-2.95 (m, 2H), 2.07-2.02 (m, 1H), 1.89-1.79 (m, 4H), 1.50-1.37 (m, 12H), 0.97-0.88 (m, 2H). HRMS m/z calc'd. for $C_{26}H_{35}N_3O_3C_1$ (M+H)$^+$: 472.2367. Found 472.2357. Separation of the enantiomers of 3D on a Daicel Chiralcel OD column gave enantiomer A $[[\alpha]_D^{25}=$ +1.68 (c=1.0; CHCl$_3$)] as (+)-3D and enantiomer B $[[\alpha]_D^{25}=-1.79$ (c=1.1; CHCl$_3$)] as (−)-3D.

3E. Example 3: To a flame-dried 1 dram vial (with a teflon cap) was added 3D (0.050 g, 0.106 mmol), 3-(methoxycarbonyl)phenylboronic acid (0.0248 g, 0.138 mmol), tris(dibenzylideneacetone)dipalladium (0) (0.0048 g, 0.0053 mmol), tri-t-butylphosphonium tetrafluoroborate (0.0037 g, 0.0127 mmol), and cesium carbonate (0.069 g, 0.212 mmol). The vial was purged with argon for several minutes and degassed dioxane (0.53 mL) was added. The vial was capped with a Teflon-coated cap under a blanket of argon. The purple suspension was stirred at rt for 1 h and then placed in a preheated (90° C.) shaker or oil bath. After 15.5 h, the reaction was cooled to rt, diluted with $CH_2Cl_2$, and filtered through a 0.45 μm nylon filter and the filtrate was concentrated to yield a yellow residue. The residue was dissolved in CH$_2$Cl$_2$ (2.5 mL) followed by the addition of TFA (0.75 mL). The bright yellow solution stirred at rt for 45 min and then concentrated. Prep. HPLC [21.2×100 mm; 10 min. gradient; 0-100% B; 25 mL/min.] afforded Example 3 (0.035 g, 47%) as a white solid. $^1$H-NMR (500 MHz, MeOD$_4$) δ: 8.66 (d, J=6.0 Hz, 1H), 8.35 (bs, 1H), 8.17 (d, J=7.7 Hz, 1H), 7.99 (d, J=6.6 Hz, 1H), 7.87 (dd, J=5.5, 1.6 Hz, 1H), 7.80 (s, 1H), 7.68 (t, J=7.7 Hz, 1H), 7.28-7.25 (m, 2H), 7.22-7.19 (m, 3H), 5.33 (dd, J=8.8, 7.2 Hz, 1H), 3.97 (s, 3H), 3.26 (dd, J=13.8, 7.2 Hz, 1H), 3.18 (dd, J=13.8, 8.8 Hz, 1H), 2.77 (d, J=7.2 Hz, 2H), 2.29-2.25 (m, 3H), 1.86-1.84 (m, 3H), 1.75-1.73 (m, 1H), 1.60-1.53 (m, 1H), 1.42-1.35 (m, 2H), 1.10-1.04 (m, 2H). HRMS m/z calc'd for C$_{29}$H$_{34}$N$_3$O$_3$ (M+H)$^+$: 472.2600. Found 472.2607.

Example 4

4-Aminomethyl-cyclohexanecarboxylic acid {1-[4-(3-acetylamino-phenyl)-pyridin-2-yl]-2-phenyl-ethyl}-amide, bistrifluoroacetic acid salt This compound was prepared from 3D following the procedures described in 3E using 3-acetamidobenzeneboronic acid in place of 3-(methoxycarbonyl)phenylboronic acid. $^1$H-NMR (500 MHz, MeOD$_4$) δ: 8.65 (d, J=5.5 Hz, 1H), 8.27 (s, 1H), 8.03-8.01 (m, 2H), 7.58-7.53 (m, 3H), 7.28-7.25 (m, 2H), 7.23-7.19 (m, 3H), 5.34 (t, J=8.0 Hz, 1H), 3.28 (d, J=8.3 Hz, 2H), 2.76 (d, J=6.6 Hz, 2H), 2.31-2.26 (m, 1H), 2.18 (s, 3H), 1.86-1.84 (m, 3H), 1.77-1.74 (m, 1H), 1.57-1.55 (m, 1H), 1.39-1.34 (m, 2H), 1.09-1.02 (m, 2H). HRMS m/z calc'd for C$_{29}$H$_{35}$N$_4$O$_2$ (M+H)$^+$: 471.2760. Found 471.2772.

Example 5

4-Aminomethyl-cyclohexanecarboxylic acid {1-[4-(3-hydroxy-phenyl)-pyridin-2-yl]-2-phenyl-ethyl}-amide, bistrifluoroacetic acid salt This compound was prepared from 3D following the procedures described in 3E using 3-hydroxyphenylboronic acid in place of 3-(methoxycarbonyl)phenylboronic acid. $^1$H-NMR (500 MHz, DMSO-d$_6$) δ: 8.60 (d, J=5.5 Hz, 1H), 8.36 (d, J=8.2 Hz, 1H), 7.66 (bs, 4H), 7.61 (d, J=4.4 Hz, 1H), 7.33 (t, J=7.7 Hz, 1H), 7.26-7.20 (m, 4H), 7.18-7.16 (m, 2H), 7.12 (s, 1H), 6.90 (dd, J=7.7, 2.2 Hz, 1H), 5.22-5.18 (m, 1H), 3.17 (dd, J=13.8, 5.0 Hz, 1H), 2.98 (dd, J=13.8, 9.9 Hz, 1H), 2.64-2.61 (m, 2H), 2.13-2.09 (m, 1H), 1.73-1.65 (m, 3H), 1.57-1.55 (m, 1H), 1.46-1.40 (m, 1H), 1.22-1.12 (m, 2H), 0.93-0.86 (m, 2H). HRMS m/z calc'd for C$_{27}$H$_{32}$N$_3$O$_2$ (M+H)$^+$: 430.2495. Found 430.2493.

Example 6

4-Aminomethyl-cyclohexanecarboxylic acid {1-[4-(3-amino-phenyl)-pyridin-2-yl]-2-phenyl-ethyl}-amide, tristrifluoroacetic acid salt This compound was prepared from 3D following the procedures described in 3E using 3-aminophenylboronic acid hydrochloride in place of 3-(methoxycarbonyl)phenylboronic acid. $^1$H-NMR (500 MHz, MeOD$_4$) δ: 8.64 (d, J=5.5 Hz, 1H), 7.85 (d, J=5.5 Hz, 1H), 7.82 (s, 1H), 7.51 (t, J=8.0 Hz, 1H), 7.48-7.46 (m, 1H), 7.43 (bs, 1H), 7.27-7.24 (m, 3H), 7.21-7.17 (m, 3H), 5.32 (t, J=8.0 Hz, 1H), 3.24-3.22 (m, 2H), 2.76 (d, J=7.2 Hz, 2H), 2.29-2.24 (m, 1H), 1.85-1.73 (m, 4H), 1.57-1.54 (m, 1H), 1.40-1.34 (m, 2H), 1.08-1.01 (m, 2H). HRMS m/z calc'd for C$_{27}$H$_{33}$N$_4$O (M+H)$^+$: 429.2654. Found 429.2658.

Example 7

4-Aminomethyl-cyclohexanecarboxylic acid [(S)-2-phenyl-1-(4-phenyl-pyrimidin-2-yl)-ethyl]-amide, trifluoroacetic acid salt 7A. ((S)-1-Carbamimidoyl-2-phenyl-ethyl)-carbamic acid tert-butyl ester: To a solution containing (S)-tert-butyl 1-cyano-2-phenylethylcarbamate (500 mg, 2.05 mmol) in MeOH (25 mL) was added N-acetylcysteine (335 mg, 2.05 mmol) and NH$_4$OAc (316 mg, 4.10 mmol). The reaction mixture was heated to reflux overnight. Additional N-acetylcysteine (335 mg, 2.05 mmol) and NH$_4$OAc (335 mg, 2.05 mmol) were added to the reaction mixture and heating at reflux was continued for another 24 h. The reaction was cooled to rt and evaporated in vacuo. The residue was re-dissolved in MeOH/H$_2$O (9:1) containing 0.1% TFA and purified by prep HPLC to yield 228 mg (33%) of 7A. MS 264.1 (M+H)$^+$.

7B. 1-Phenyl-propynone: To a solution of 1-phenylprop-2-yn-1-ol (0.5 g, 3.8 mmol) in CH$_2$Cl$_2$ (10 mL) was added Dess-Martin Periodinane (1.6 g, 3.8 mmol). The reaction was stirred at rt for 5 min. The reaction was diluted with CH$_2$Cl$_2$ (10 mL) and washed with a 1:1 mixture of 10% aqueous Na$_2$S$_2$O$_3$ and saturated aqueous NaHCO$_3$ (200 mL), water and brine. The organic layer was dried over MgSO$_4$, filtered and evaporated in vacuo to provide 1.12 g of a light tan solid. The crude product was purified by silca gel chromatography to produce 600 mg of a white solid which was used without further purification in the next step. $^1$H NMR (500 MHz, d-CHCl$_3$) δ 3.45 (s, 1H) 7.51 (t, J=7.97 Hz, 2H) 7.64 (t, J=7.42 Hz, 1H) 8.17 (d, J=7.15 Hz, 2H).

7C. [(S)-2-Phenyl-1-(4-phenyl-pyrimidin-2-yl)-ethyl]-carbamic acid tert-butyl ester: 7A (57 mg, 0.15 mmol), 7B (16 mg, 0.12 mmol), and Na$_2$CO$_3$ (31 mg, 0.30 mmol) were dissolved in acetonitrile and heated to 120° C. for 40 min using microwave irradiation. The reaction was cooled to rt and filtered. The filtrate was dried in vacuo to yield 75 mg (100%) of 7C which was carried onto the next step without further purification. MS 276.1 (M+1)$^+$.

7D. (S)-2-Phenyl-1-(4-phenylpyrimidin-2-yl)ethanamine: 7C (56 mg, 0.15 mmol) was dissolved in CH$_2$Cl$_2$ (2.7 mL) and treated with TFA (0.3 mL, 10% v/v) for 24 h at rt. The solvent and TFA were evaporated in vacuo and the residue redissolved in MeOH. The MeOH was evaporated to yield 59 mg (100%) of 7D. MS 276.1 (M+1)$^+$.

7E. {4-[(S)-2-Phenyl-1-(4-phenyl-pyrimidin-2-yl)-ethylcarbamoyl]-cyclohexylmethyl}-carbamic acid tert-butyl ester: 7D (59 mg, 0.15 mmol), N-Boc-tranexamic acid (39 mg, 0.15 mmol) and HOBt (24 mg, 0.18 mmol) were dissolved in DMF (1 mL). N-methylmorpholine (61 mg, 0.6 mmol) and EDCI (35 mg, 0.18 mmol) were added sequentially and the reaction mixture was stirred at rt for 4 h. The reaction was diluted with EtOAc, washed with aqueous sodium choloride solution (5×), dried over MgSO$_4$, filtered and evaporated to dryness to yield 75 mg (97%) of 7E. MS 515.1 (M+H)$^+$.

7F. Example 7: 7E was treated according to the procedure described for 1E. The crude product was re-dissolved in MeOH/H$_2$O (9:1) containing 0.1% TFA and purified by prep HPLC to yield 40 mg (42%) of Example 7. $^1$H NMR (500 MHz, d$_4$-MeOH) δ 1.40 (m, 2H) 1.57 (m, 1H) 1.76 (br d, J=13.20 Hz, 1H) 1.84 (br d, J=12.65 Hz, 3H) 2.29 (tt, J=12.10, 3.57 Hz, 1H) 2.77 (d, J=6.60 Hz, 2H) 3.14 (dd, J=13.75, 8.80 Hz, 1H) 3.37 (dd, J=13.92, 6.25 Hz, 1H) 5.42 (dd, J=8.80, 6.05 Hz, 1H) 7.16 (m, 3H) 7.21 (m, 2H) 7.53 (m, 3H) 7.83 (d, J=5.50 Hz, 1H) 8.17 (d, J=7.70 Hz, 2H) 8.73 (d, J=5.50 Hz, 1H). HRMS m/z calc'd for $C_{26}H_{31}N_4O$ (M+H)$^+$: 415.2498. Found 415.2488.

Example 8

4-Aminomethyl-cyclohexanecarboxylic acid [(S)-1-(6-oxo-4-phenyl-1,6-dihydro-pyrimidin-2-yl)-2-phenyl-ethyl]-amide, trifluoroacetic acid salt 8A: [(S)-1-(6-Oxo-4-phenyl-1,6-dihydro-pyrimidin-2-yl)-2-phenyl-ethyl]-carbamic acid tert-butyl ester: 7A (50 mg, 0.13 mmol), ethyl 3-phenylpropiolate (46 mg, 0.26 mmol), and Hunig's base (34 mg, 0.26 mmol) were dissolved in EtOH (1 mL) and heated to reflux for 3 d. The reaction was cooled to rt and the solvent evaporated to dryness in vacuo. The residue was re-dissolved in MeOH/H$_2$O (9:1) containing 0.1% TFA and isolated by prep HPLC to yield 16 mg of the desired product (31% yield). MS 392.1 (M+H)$^+$.

8B. Example 8: 8A (16 mg, 0.041 mmol) was converted to Example 8 using the procedures described in 7D-F with the exception that HOAt was used in place of HOBt. $^1$H NMR (500 MHz, d$_4$-MeOH) δ 1.05 (m, 2H) 1.39 (m, 2H) 1.56 (m, 1H) 1.73 (br d, J=12.10 Hz, 1H) 1.85 (br t, J=14.57 Hz, 3H) 2.26 (tt, J=12.40, 3.60 Hz, 1H) 2.76 (d, J=7.15 Hz, 2H) 3.13 (dd, J=13.20, 8.80 Hz, 1H) 5.06 (m, 1H) 6.74 (s, 1H) 7.23 (m, 5H) 7.48 (m, 3H) 8.05 (d, J=8.25 Hz, 2H) 8.47 (d, J=7.70 Hz, 0.5H). HRMS m/z calc'd for $C_{26}H_{30}N_4O_2$ (M+H)$^+$: 431.2447. Found 431.2467.

Example 10

3-(2-{1-[(4-Aminomethyl-cyclohexanecarbonyl)-amino]-2-phenyl-ethyl}-pyridin-4-yl)-benzoic acid, bis-trifluoroacetic acid salt A clear colorless solution of 3E (0.013 g, 0.018 mmol) in MeOH (0.55 mL) and 1.0 N NaOH (0.15 mL, 0.15 mmol) was heated to 60° C. After 1 h, the reaction was cooled to rt, acidified with TFA and concentrated. Prep. HPLC [21.2×100 mm; 10 min. gradient; 0-100% B, 25 mL/min] gave Example 10 (0.013 g, quantitative) as a white solid. $^1$H NMR (500 MHz, CD$_3$OD) δ: 8.72 (d, J=6.0 Hz, 1H), 8.44 (s, 1H), 8.24 (d, J=7.7 Hz, 1H), 8.11-8.06 (m, 3H), 7.72 (t, J=8.0 Hz, 1H), 7.29-7.26 (m, 2H), 7.24-7.21 (m, 3H), 5.38 (t, J=8.0 Hz, 1H), 3.31-3.28 (m, 2H), 2.77 (d, J=7.2 Hz, 2H), 2.32-2.28 (m, 1H), 1.86-1.84 (m, 3H), 1.77-1.75 (m, 1H), 1.58-1.55 (m, 1H), 1.42-1.32 (m, 2H), 1.10-1.02 (m, 2H). HRMS m/z calc'd for $C_{28}H_{32}N_3O_3$ (M+H)$^+$: 458.2444. Found 458.2453.

Example 13

4-Aminomethyl-cyclohexanecarboxylic acid {2-phenyl-1-[4-(1H-pyrrol-3-yl)-pyridin-2-yl]-ethyl}-amide, bis-trifluoroacetic acid 13A. 4-Aminomethyl-cyclohexanecarboxylic acid {2-phenyl-1-[4-(1-triisopropylsilanyl-1H-pyrrol-3-yl)-pyridin-2-yl]-ethyl}-amide, bis-trifluoroacetic acid salt: This compound was prepared from 3D following the procedures described in example 3E using 1-(Triisopropylsilyl)pyrrole-3-boronic acid in place of 3-(methoxycarbonyl)phenylboronic acid to give 13A (0.013 g, 16%) as a brown residue. MS 559.3 (M+H)$^+$.

13B. Example 13: To a clear, brown solution of 13A (0.013 g, 0.0165 mmol) in THF (0.23 mL) was added 1.0 M TBAF in THF (0.046 mL, 0.046 mmol). After 30 min, a few drops of water were added and the reaction was concentrated to give a brown residue. Prep. HPLC [21.2×100 mm; 8 min. gradient; 0-100% B, 25 mL/min.] provided Example 13 (0.0044 g, 42%) as an off-white solid.

hu 1H NMR (500 MHz, CD$_3$OD) δ: 8.29 (d, J=6.6 Hz, 1H), 7.92 (bs, 1H), 7.89 (dd, J=6.6, 1.6 Hz, 1H), 7.75 (t, J=1.6 Hz, 1H), 7.29-7.26 (m, 2H), 7.24-7.20 (m, 3H), 6.96 (dd, J=3.3, 1.6 Hz, 1H), 6.76 (dd, J=3.3, 1.6 Hz, 1H), 5.23 (t, J=8.2 Hz, 1H), 3.27-3.21 (m, 2H), 2.77 (d, J=7.2 Hz, 2H), 2.29-2.25 (m, 1H), 1.89-1.83 (m, 3H), 1.76-1.73 (m, 1H), 1.70-1.64 (m, 1H), 1.43-1.33 (m, 2H), 1.10-1.04 (m, 2H). HRMS m/z calc'd for $C_{25}H_{31}N_4O$ (M+H)$^+$: 403.2498. Found 403.2483.

Example 15

4-Aminomethyl-cyclohexanecarboxylic acid [1-(2'-amino-[4,4']bipyridinyl-2-yl)-2-phenyl-ethyl]-amide, tris-trifluoroacetic acid salt To a sealable vial with a teflon cap was added 3D (0.094 g, 0.2 mmol), Pd(dppf)Cl$_2$•CH$_2$Cl$_2$ complex (0.122 g, 0.15 mmol), K$_3$PO$_4$ (0.106 g, 0.5 mmol), 2-fluropyridine-4-boronic acid (0.042 g, 0.3 mmol), and DMSO (3 mL). The mixture was degassed by bubbling argon for 10 min, the tube was sealed, and the reaction was placed in a preheated oil bath (95° C.). After 18 h, the reaction mixture was cooled to rt, diluted with EtOAc (10 mL), washed with water (10 mL), brine (10 mL), dried over Na$_2$SO$_4$, filtered and concentrated. The residue was dissolved in 50% TFA/CH$_2$Cl$_2$ (2 mL). After 18 h the reaction was concentrated. Prep. HPLC [30×100 mm, 12 min. gradient, 30 to 100% B, 30 mL/min.) provided 0.096 g of the bipyridyl derivative as a white solid.

A suspension of the bipyridyl derivative in concentrated NH$_4$OH (5 mL) was microwaved at 140° C. for 140 min. The reaction mixture was cooled to rt, filtered, and concentrated. Prep. HPLC [30×100 mm, 10 min. gradient, 20 to 100% B, 30 mL/min.) gave Example 15 (0.0030 g, 1.9%) as a white solid. $^1$H NMR (500 MHz, CD$_3$OD) δ: 0.98-1.09 (m, 2H), 1.33-1.44 (m, 2H), 1.54-1.59 (m, 1H), 1.72-1.85 (in, 4H), 2.21-2.27 (m, 1H), 2.76 (d, J=7.2 Hz, 2H), 3.12-3.23 (m, 2H), 5.30-5.33 (m, 1H), 7.10-7.23 (m, 7H), 7.50 (s, 1H), 7.61 (d, J=5.5 Hz, 1H), 7.94 (d, J=6.6 Hz, 1H), 8.74 (d, J=5.5 Hz, 1H). HRMS m/z calc'd for $C_{26}H_{32}N_5O$ (M+H)$^+$: 430.2607. Found 430.2601.

Example 21

4-Aminomethyl-cyclohexanecarboxylic acid {1-[4-(4-cyano-3-fluoro-phenyl)-pyridin-2-yl]-2-phenyl-ethyl}-amide, bis-trifluoroacetic acid salt To a flame-dried flask was added 3D (0.150 g, 0.318 mmol), 4-cyano-3-fluoro phenylboronic acid (0.131 g, 0.795 mmol), tris(dibenzylideneacetone)dipalladium (0) (0.0146 g, 0.0159 mmol), tri-t-butylphosphonium tetrafluoroborate (0.0111 g, 0.038 mmol), and cesium carbonate (0.207 g, 0.636 mmol). The flask was purged with argon for several minutes and degassed dioxane (1.6 mL) was added. The purple suspension was stirred at rt for 1 h and then placed in a preheated (90° C.) oil bath. After 14 h, the reaction was cooled to rt, diluted with CH$_2$Cl$_2$, and filtered through a 0.45 μm nylon filter and the filtrate was concentrated to yield a yellow solid. The solid was dissolved in CH$_2$Cl$_2$ and NH$_4$OH was added and the biphasic mixture was stirred vigorously for 10 min. The layers were separated and the organic layer was washed with brine, dried over MgSO$_4$, filtered, and concentrated to give an off-white solid weighing 0.200 g. The solid was dissolved in 30% TFA in CH$_2$Cl$_2$ (10 mL). The reaction was stirred at rt for 1 h and then concentrated. Prep. HPLC [21.2×100 mm; 8 min. gradient; 0-100% B; 25 mL/min.] afforded Example 21 (0.146 g, 67%) as a white solid. $^1$H NMR (500 MHz, CD$_3$OD) δ: 8.70 (d, J=5.0 Hz, 1H), 7.93-7.90 (m, 1H), 7.77 (dd, J=5.5, 1.6 Hz, 1H), 7.74 (dd, J=10.4, 1.6 Hz, 1H), 7.71-7.68 (m, 2H), 7.25-7.23 (m, 2H), 7.20-7.17 (m, 3H), 5.33 (dd, J=8.8, 7.2 Hz, 1H), 3.24 (dd, J=13.5, 6.9 Hz, 1H), 3.16 (dd, J=13.5, 8.5 Hz, 1H), 2.76 (d, J=7.2 Hz, 2H), 2.28-2.23 (m, 1H), 1.85-1.72 (m, 4H), 1.58-1.54 (m, 1H), 1.41-1.34 (m, 2H), 1.08-1.00 (m, 2H).
$^{19}$F NMR (470 MHz, CD$_3$OD) δ: −77.27, −108.45. HRMS m/z calc'd for C$_{28}$H$_{30}$N$_4$° F. (M+H)$^+$: 457.2404. Found 457.2420.

Example 22

4-Aminomethyl-cyclohexanecarboxylic acid {1-[4-(4-cyano-3-fluoro-phenyl)-pyridin-2-yl]-2-phenyl-ethyl}-amide, bis-trifluoroacetic acid salt To a flame-dried flask was added (+)-3D (0.258 g, 0.546 mmol), 4-cyano-3-fluoro phenylboronic acid (0.225 g, 1.36 mmol), tris(dibenzylideneacetone)dipalladium (0) (0.0247 g, 0.027 mmol), tri-t-butylphosphonium tetrafluoroborate (0.0188 g, 0.065 mmol), and cesium carbonate (0.355 g, 1.09 mmol). The flask was purged with argon for several minutes and degassed dioxane (2.7 mL) was added. The purple suspension was stirred at rt for 1 h and then placed in a preheated (90° C.) oil bath. After 14 h, the reaction was cooled to rt, diluted with CH$_2$Cl$_2$, and filtered through a 0.45 μm nylon filter and the filtrate was concentrated to yield a yellow residue weighing 0.419 g. The residue was dissolved in CH$_2$Cl$_2$ (10 mL) followed by the addition of TFA (4.0 mL). The reaction was stirred at rt for 1 h and then concentrated. Prep. HPLC [30×100 mm; 12 min. gradient; 25-100% B; 30 mL/min.] afforded Example 22 (0.119 g, 32%) as a white solid.

Example 23

4-Aminomethyl-cyclohexanecarboxylic acid {1-[4-(4-cyano-3-fluoro-phenyl)-pyridin-2-yl]-2-phenyl-ethyl}-amide, bis-trifluoroacetic acid salt To a flame-dried flask was added (−)-3D (0.234 g, 0.495 mmol), 4-cyano-3-fluoro phenylboronic acid (0.204 g, 1.24 mmol), tris(dibenzylideneacetone)dipalladium (0) (0.0226 g, 0.025 mmol), tri-t-butylphosphonium tetrafluoroborate (0.0172 g, 0.059 mmol), and cesium carbonate (0.322 g, 0.99 mmol). The flask was purged with argon for several minutes and degassed dioxane (2.5 mL) was added. The purple suspension was stirred at rt for 1 h and then placed in a preheated (90° C.) oil bath. After 14 h, the reaction was cooled to rt, diluted with CH$_2$Cl$_2$, and filtered through a 0.45 μm nylon filter and the filtrate was concentrated to yield a yellow residue weighing 0.420 g. The residue was dissolved in CH$_2$Cl$_2$ (10 mL) followed by the addition of TFA (4.0 mL). The reaction was stirred at rt for 1 h and then concentrated. Preparatory HPLC [30×100 mm; 12 min. gradient; 25-100% B; 30 mL/min.] afforded Example 23 (0.142 g, 42%) as a white solid.
Alternative coupling procedure: To a flame-dried flask was placed chiral, nonracemic (−)-3D (0.300 g, 0.635 mmol), 4-cyano-3-fluoro phenylboronic acid (0.262 g, 1.59 mmol), Pd(dppf)Cl$_2$•CH$_2$Cl$_2$ (0.0518 g, 0.0635 mmol) and K$_3$PO$_4$ (0.337 g, 1.59 mmol). The flask was purged with Argon for several minutes and then DMSO (degassed, 4.20 mL) was added. The suspension was heated to 90° C. After 15 h, the reaction was cooled to rt and additional 4-cyano-3-fluoro phenylboronic acid (0.105 g, 0.635 mmol), Pd(dppf)Cl$_2$•CH$_2$Cl$_2$ (0.0518 g, 0.0635 mmol) and K$_3$PO$_4$ (0.134 g, 0.635 mmol) were added. Argon was bubbled through the reaction for 5 min. and then the reaction was placed in a preheated oil bath (90° C.). After 5 h, the reaction was cooled to rt, diluted with CH$_2$Cl$_2$ (400 mL), washed with water, 2.0 N Na$_2$CO$_3$, brine, dried over MgSO$_4$, filtered and concentrated to give 0.575 g as a red-brown solid. The red-brown solid was dissolved in 30% TFA/CH$_2$Cl$_2$ (30 mL). After 30 min, the reaction was concentrated. Prep. HPLC [30×250 mm, 30 min gradient, 30-100% B, 30 mL/min.] gave Example 23 (0.234 g, 54%) as a white solid.

Example 25

4-Aminomethyl-cyclohexanecarboxylic acid {1-[4-(3-amino-1H-indazol-6-yl)-pyridin-2-yl]-2-phenyl-ethyl}-amide, bis-trifluoroacetic acid A suspension of Example 21 (0.0261 g, 0.038 mmol) in n-butanol (0.38 mL) and hydrazine monohydrate (0.14 mL, 4.56 mmol) was microwaved at 150° C. for 10 min. The resulting clear, yellow solution was concentrated. Prep HPLC [21.2×100 mm; 8 min. gradient; 0-100% B, 25 mL/min] gave Example 25 (0.0195 g, 63%) as a yellow solid. $^1$H NMR (500 MHz, CD$_3$OD) δ: 8.69 (d, J=5.5 Hz, 1H), 8.02 (d, J=8.2 Hz, 1H), 7.92 (dd, J=5.8, 1.9 Hz, 1H), 7.85 (bs, 1H), 7.75 (bs, 1H), 7.49 (dd, J=8.5, 1.4 Hz, 1H), 7.28-7.25 (m, 2H), 7.22-7.19 (m, 3H), 5.35 (t, J=7.7 Hz, 1H), 3.25 (d, J=8.2 Hz, 2H), 2.77 (d, J=6.6 Hz, 2H), 2.30-2.25 (m, 1H), 1.86-1.74 (m, 4H), 1.59-1.54 (m, 1H), 1.43-1.33 (m, 2H), 1.10-1.01 (m, 2H). HRMS m/z calc'd for C$_{28}$H$_{33}$N$_6$O (M+H)$^+$: 469.2716. Found 469.2699.

Example 26

(+)-4-Aminomethyl-cyclohexanecarboxylic acid {1-[4-(3-amino-1H-indazol-6-yl)-pyridin-2-yl]-2-phenyl-ethyl}-amide, bis-trifluoroacetic acid A suspension of Example 23 (0.095 g) in n-butanol (3.0 mL) and hydrazine monohydrate (1.0 mL) was microwaved at 150° C. for 10 min. The resulting clear, bright yellow solution was concentrated. Prep HPLC [21.2×100 mm; 8 min. gradient; 20-100% B, 20 mL/min.] gave Example 26 (0.069 g, 71%) as a yellow solid. [α]$_D^{25.2}$=+5.52 (c=0.80; MeOH).

Example 27

4-Aminomethyl-cyclohexanecarboxylic acid {1-[4-(3-amino-1,2-benzisoxazol-6-yl)-pyridin-2-yl]-2-phenyl-ethyl}-amide, bis-trifluoroacetic acid To a clear, colorless solution of acetohydroxamic acid (0.0148 g, 0.197 mmol) in DMF (0.66 mL) was added potassium tert-butoxide (0.0221 g, 0.197 mmol). The resulting white suspension was stirred vigorously for 30 min. and then Example 21 (0.030 g, 0.0438 mmol) was added. After 7.5 h, the reaction was stopped by adding brine and extracting with EtOAc (5×). The combined organic layers were washed with brine, dried over Na$_2$SO$_4$, filtered, and concentrated to give a clear, colorless residue. Prep. HPLC [21.2×100 mm; 8 min. gradient; 0-100% B, 20 mL/min.] gave Example 27 (0.0073 g, 20%) as a pale, yellow solid. $^1$H NMR (500 MHz, CD$_3$OD) δ: 8.69 (d, J=6.0 Hz, 1H), 8.00 (dd, J=5.8, 2.0 Hz, 1H), 7.97 (bs, 1H), 7.94 (d, J=8.2 Hz, 1H), 7.82 (s, 1H), 7.65 (dd, J=8.2, 1.6 Hz, 1H), 7.29-7.26 (m, 2H), 7.23-7.20 (m, 3H), 5.36 (t, J=8.0 Hz, 1H), 3.28-3.25 (m, 2H), 2.77 (d, J=7.2 Hz, 2H), 2.31-2.26 (m, 1H), 1.85-1.82 (m, 3H), 1.76-1.74 (m, 1H), 1.57-1.54 (m, 1H), 1.41-1.34 (m, 2H), 1.10-1.04 (m, 2H). HRMS m/z calc'd for C$_{28}$H$_{32}$N$_5$O$_2$ (M+H)$^+$: 470.2556. Found 470.2549.

Example 28

(+)-4-Aminomethyl-cyclohexanecarboxylic acid {1-[4-(3-amino-1,2-benzisoxazol-6-yl)-pyridin-2-yl]-2-phenyl-ethyl}-amide, bis-trifluoroacetic acid Example 28 was prepared from Example 22 following the procedures described in Example 27. [α]$_D^{25}$=+3.14 (c=1.0; MeOH).

Example 29

(−)-4-Aminomethyl-cyclohexanecarboxylic acid {1-[4-(3-amino-1,2-benzisoxazol-6-yl)-pyridin-2-yl]-2-phenyl-ethyl}-amide, bis-trifluoroacetic acid Example 29 was prepared from 23 following the procedures described in Example 27.

Example 33

4-Aminomethyl-cyclohexanecarboxylic acid {1-[4-(3-hydroxy-1H-indazol-5-yl)-pyridin-2-yl]-2-phenyl-ethyl}-amide, bis-trifluoroacetic acid salt 33A. 2-Fluoro-5-(4,4,5,5-tetramethyl-1,3,2-dioxaborolan-2-yl)-benzoic acid methyl ester: A suspension of 5-bromo-2-fluorobenzoic acid (1.116 g, 5.1 mmol) and thionyl chloride (1.49 mL, 20.4 mmol) in 1,2-dichloroethane (10 mL) was heated at 85° C. After 3.5 h, the reaction was cooled to rt and concentrated. Methanol (10 mL) was added carefully, and the resulting solution was stirred at rt. After 30 min, the reaction was concentrated. The residue was dissolved in EtOAc (25 mL), washed with sat. NaHCO$_3$, brine, dried over Na$_2$SO$_4$, filtered and concentrated to give the ester (1.18 g, 99%) as a colorless oil. MS 233.0 (M+H)$^+$.

To a round-bottomed flask equipped with a condenser was added the ester (0.7 g, 3.0 mmol), Pd(dppf)Cl$_2$•CH$_2$Cl$_2$ complex (0.073 g, 0.090 nmol), KOAc (0.884 g, 9.0 mmol), bis(pinacolato)diboron (1.524 g, 6.0 mmol), and DMSO (20 mL). The mixture was degassed by bubbling argon for 10 min, and then the reaction was heated at 80° C. After 4 h, the reaction was cooled to rt, diluted with EtOAc, washed with water, brine, dried over Na$_2$SO$_4$, filtered and concentrated. Column chromatography on silica gel (gradient elution 0-10% EtOAc/Hexane, then 10% EtOAc/Hexane) gave 33A (1.2 g) as a white solid. MS 281.09 (M+H)$^+$.

33B. Example 33:To a sealable tube was added Pd(dppf)Cl$_2$•CH$_2$Cl$_2$ complex (0.016 g, 0.15 mmol), K$_3$PO$_4$ (0.106 g, 0.5 mmol), 33A (0.168 g, 0.6 mmol), 3D (0.095 g, 0.2 mmol), and DMSO (3 mL). The mixture was degassed by bubbling argon for 10 min, and then the reaction was heated at 95° C. After 18 h, the reaction was cooled to rt, diluted with EtOAc (10 mL), washed with water (10 mL), brine (10 mL), dried over Na$_2$SO$_4$, filtered and concentrated. The residue was dissolved in 50% TFA/CH$_2$Cl$_2$ (2 mL) and stirred at rt. After 2 h, the reaction was concentrated. Prep. HPLC (30×100 mm, 12 min. gradient, 30 to 100% B, 30 mL/min.) provided the biphenyl compound (0.054 g) as a white solid.

A suspension of the biphenyl compound (0.054 g) in 1-butanol (3 mL) and hydrazine monohydrate (1 mL) was microwaved at 150° C. for 10 min. The reaction was cooled to rt and concentrated. Prep. HPLC (21.2×100 mm, 8 min. gradient, 20 to 100% B, 20 mL/min.) gave Example 33 (0.008 g, 6%) as a yellow solid. $^1$H NMR (500 MHz, CD$_3$OD) δ: 1.03-1.10 (m, 2 H), 1.32-1.43 (m, 2 H), 1.54-1.60 (m, 1 H), 1.75-1.77 (m, 1 H), 1.84-1.86 (m, 3 H), 2.27-2.32 (m, 1 H), 2.77 (d, J=7.1 Hz, 2 H), 3.27-3.34 (m, 2 H), 5.33-5.36 (m, 1 H), 7.21-7.29 (m, 5 H), 7.48 (d, J=8.8 Hz, 1 H), 7.91 (dd, J=1.6 Hz, 8.8 Hz, 1 H), 8.05-8.06 (m, 2 H), 8.26 (d, J=1.6 Hz, 1 H), 8.59 (d, J=6.6 Hz, 1 H). HRMS m/z Calc'd for C$_{28}$H$_{32}$N$_5$O$_2$ (M+H)$^+$: 470.2556. Found 470.2566.

Alternative preparation of Example 33: A mixture of Example 52 in 1-butanol and hydrazine monohydrate was microwaved at 160° C. for 1 h. Concentration and purification by Prep HPLC as described above gave Example 33.

Example 34

4-Aminomethyl-cyclohexanecarboxylic acid [1-(6-methoxy-4-phenyl-pyridin-2-yl)-2-phenyl-ethyl]-amide, bis-trifluoroacetic acid salt 34A. 2-methoxy-6-methyl-4-phenylpyridine: To a solution of 6-methyl-4-phenyl-1H-pyridin-2-one (0.185 g, 1 mmol, prepared according to a modified procedure described by Thesing, J. and Muller, A. Chem. Ber., 1957, 90, 711.) in chloroform (4 mL) was added Ag$_2$CO$_3$ (0.386 g, 1.4 mmol) and iodomethane (0.62 mL, 10 mmol). The resulting suspension was stirred in the dark for 18 h. The reaction was filtered and the solid was washed with CH$_2$Cl$_2$. The filtrate was concentrated to give a residue. Column chromatography on silica gel (0-10% EtOAc/Hexane) afforded 34A (0.14 g, 70%) as a clear, colorless oil. MS 200.2 (M+H)$^+$.

34B. 6-Methoxy-4-phenyl-pyridine-2-carbaldehyde: A solution of compound of 34A (0.14 g, 0.7 mmol), N-bromo-succinimide (0.25 g, 1.4 mmol), and benzoyl peroxide (0.0085 g, 0.035 mmol) in CCl$_4$ (3 mL) was heated at 80° C. After 24 h, the reaction was cooled to rt, diluted with EtOAc (10 mL), washed with water, sat. NaHCO$_3$, brine, dried over Na$_2$SO$_4$, filtered and concentrated to give a brown residue. The brown residue was dissolved in morpholine (2 mL), heated at 60° C. for 3 h, and then cooled to rt. The reaction mixture was diluted with EtOAc (15 mL), washed with 5% citric acid solution (until the aqueous layer had a pH 4), sat. NaHCO$_3$, brine, dried over Na$_2$SO$_4$, filtered and concentrated. Column chromatography on silica gel (0-5% EtOAc) afforded 34B (0.055 g, 37%) as a white solid. $^1$H NMR (400 MHz, CDCl$_3$) δ: 4.08 (s, 3 H), 7.18 (d, J=1.3 Hz, 1 H), 7.46-7.52 (m, 3 H), 7.64-7.67 (m, 2 H), 7.83 (d, J=1.3 Hz, 1 H), 10.02 (s, 1 H). HRMS m/z Calc'd for C$_{13}$H$_{12}$NO$_2$ (M+H)$^+$: 214.0868. Found 214.0868.

34C. 1-(6-Methoxy-4-phenyl-pyridin-2-yl)-2-phenyl-ethylamine, bis-trifluoroacetic acid salt: To a cooled (0° C.) solution of 34B (0.055 g, 0.26 mmol) in THF (0.52 mL) was added 1.0 M LiHMDS in THF (0.28 mL, 0.28 mmol). After 15 min, 2.0 M BnMgCl in THF (0.15 mL, 0.30 mmol) was added dropwise. The resulting solution was stirred at 0° C. for 30 min and then quenched with sat. NH$_4$Cl (1 mL) and then diluted with water. The reaction was extracted with EtOAc (15 mL). The combined organic layers were washed with sat. NaHCO$_3$, brine, dried over Na$_2$SO$_4$, filtered and concentrated. Prep. HPLC (30×100 mm, 12 min. gradient, 30 to 100% B, 30 mL/min.) gave 34C (0.067 g, 48%) as a white solid. $^1$H NMR (500 MHz, CD$_3$OD) δ: 3.24 (dd, J=9.3 Hz, 13.2 Hz, 1 H), 3.30-3.35 (m, 1 H), 4.04 (s, 3 H), 4.65 (dd, J=6.1 Hz, 8.8 Hz, 1 H), 6.82 (d, J=1.1 Hz, 1 H), 6.98 (d, J=1.1 Hz, 1 H), 7.11-7.13 (m, 2 H), 7.23-7.30 (m, 3 H), 7.39-7.49 (m, 5 H). HRMS m/z Calc'd for C$_{20}$H$_{21}$N$_2$O (M+H)$^+$: 305.1654. Found 305.1645.

34D. Example 34: To a solution of 34C (0.067 g, 0.13 mmol) in DMF (2 mL) was added Boc-tranexamic acid (0.036 mL, 0.14 mmol), triethylamine (0.088 mL, 0.63 mmol), HOBt (0.026 g, 0.19 mmol), and EDCI (0.036 g, 0.19 mmol). The reaction mixture was stirred at rt for 2 h, at 40° C. for 2 h, and then at rt for 18 h. The reaction mixture was diluted with EtOAc (25 mL), washed with water, sat. NaHCO$_3$, brine, dried over Na$_2$SO$_4$, filtered and concentrated to give the amide (0.090 g) as a yellow solid. MS 544.4 (M+H)$^+$.

The yellow solid (0.045 g, 0.08 mmol) was dissolved in 50% TFA/CH$_2$Cl$_2$ (2 mL). After 2 h, the reaction was concentrated to give a residue. Prep. HPLC (30×250 mm, 20 min. gradient, 30 to 100% B, 30 mL/min.) gave Example 34 (0.024 g, 57%) as a white solid. $^1$H NMR (500 MHz, CD$_3$OD) δ: 1.01-1.09 (m, 2 H), 1.34-1.48 (m, 2 H), 1.53-1.60 (m, 1 H), 1.70-1.73 (m, 1 H), 1.83-1.85 (m, 3 H), 2.22-2.29 (m, 1 H), 2.76 (d, J=7.2 Hz, 2 H), 3.07 (dd, J=8.8 Hz, 13.8 Hz, 1 H), 3.27-3.31 (m, 1 H), 4.00 (s, 3 H), 5.21-5.24 (m, 1 H), 6.91 (d, J=1.1 Hz, 1 H), 7.04 (d, J=0.8 Hz, 1 H), 7.15-7.25 (m, 5 H), 7.40-7.47 (m, 3 H), 7.58-7.60 (m, 2 H). HRMS m/z Calc'd for C$_{28}$H$_{34}$N$_3$O$_2$ (M+H)$^+$: 444.2651. Found 444.2646.

Example 35

4-Aminomethyl-cyclohexanecarboxylic acid [1-(6-oxo-4-phenyl-1,6-dihydro-pyridin-2-yl)-2-phenyl-ethyl]-amide, trifluoroacetic acid salt To a cooled (0° C.) solution of the amide from 34D (0.045 g, 0.08 mmol) in CH$_2$Cl$_2$ (1 mL) was added BBr$_3$ (0.078 mL, 0.8 mmol). The reaction was warmed to rt. After 2 h, the reaction was cooled to 0° C., quenched with MeOH, and then concentrated. Prep. HPLC (30×250 mm, 20 min. gradient, 30 to 100% B, 30 mL/min.) gave the bis-TFA salt of the cyclohexyl methylamine derivative (0.034 g, 61%) as a white solid.

A solution of the bis-TFA salt of the cyclohexyl methylamine derivative (0.028 g, 0.042 mmol) and BBr$_3$ (1.0 M in CH$_2$Cl$_2$, 0.42 mL, 0.42 mmol) in CH$_2$Cl$_2$ (1 mL) was heated at 60° C. After 2 h, the reaction was cooled to 0° C., quenched with MeOH, and concentrated. Prep. HPLC (21.2×100 mm, 8 min. gradient, 20 to 100% B, 20 mL/min.) afforded Example 35 (0.008 g, 35%) as a pink solid. $^1$H NMR (500 MHz, CD$_3$OD) δ: 0.96-1.09 (m, 2 H), 1.27-1.46 (m, 2 H), 1.51-1.62 (m, 2 H), 1.81-1.85 (m, 3 H), 2.15-2.22 (in, 1 H), 2.76 (d, J=7.2 Hz, 2 H), 3.02 (dd, J=9.9 Hz, 13.7 Hz, 1 H), 3.23 (dd, J=6.0 Hz, 13.7 Hz, 1 H), 5.11 (dd, J=6.0 Hz, 9.9 Hz, 1 H), 6.62 (s, 2 H), 7.18-7.31 (m, 5 H), 7.46-7.51 (m, 3 H), 7.60-7.62 (m, 2 H). HRMS m/z Calc'd for C$_{27}$H$_{32}$N$_3$O$_2$ (M+H)$^+$: 430.2495. Found 430.2497.

Example 36

4-Aminomethyl-cyclohexanecarboxylic acid [1-(1-methyl-6-oxo-4-phenyl-1,6-dihydro-pyridin-2-yl)-2-phenyl-ethyl]-amide, trifluoroacetic acid salt 36A. 6-(1-Amino-2-phenyl-ethyl)-1-methyl-4-phenyl-1H-pyridin-2-one: A solution of 34C (0.15 g, 0.28 mmol) in concentrated HCl (1 mL) was heated at 130° C. After 3 h, the reaction was cooled to rt and concentrated. The residue was suspended in CH$_2$Cl$_2$ (4 mL) and benzophenone imine (0.047 mL, 0.28 mmol) was added. The reaction was stirred at rt with exclusion of moisture via a drying tube. After 18 h, triethylamine (0.039 mL, 0.28 mmol) and additional benzophenone imine (0.047 mL, 0.28 mmol) were added and the mixture was refluxed. After 18 h, the reaction was cooled to rt, diluted with CH$_2$Cl$_2$, washed with brine, dried over Na$_2$SO$_4$, filtered, and concentrated. Column chromatography on silica gel (0-10% EtOAc/hexane, then 10% EtOAc/hexanes, and then 100% EtOAc) afforded the imine (0.18 g) as an off-white gum. HRMS m/z Calc'd for C$_{32}$H$_{27}$N$_2$O (M+H)$^+$: 455.2123. Found 455.2114.

To a solution of the imine in DMF (4 mL) was added NaH (60% dispersion in mineral oil, 0.018 g, 0.44 mmol). The brown suspension was stirred at rt for 30 min and then iodomethane (0.027 mL, 0.44 mmol) was added. After 1 h, the reaction was quenched with water and extracted with EtOAc. The combined organic layers were washed with sat. NaHCO$_3$, brine, dried over Na$_2$SO$_4$, filtered, and concentrated. Column chromatography on silica gel (0-50% EtOAc/hexane) afforded a 2:1 mixture of the N-methylpyridone and O-methylpyridone (0.12 g) as a brown oil.

A solution of the N-methylpyridone and O-methylpyridone mixture (0.12 g, 0.26 mmol) in ether (4 mL) and 1.0 N HCl (3 mL) was stirred at rt. After 18 h, the reaction was concentrated. Prep. HPLC (21.2×250 mm, 30 min. gradient, 30 to 100% B, 30 mL/min.) afforded 36A (0.050 g, 43%) as a white solid. $^1$H NMR (500 MHz, CD$_3$OD) δ: 3.29-3.34 (m, 4H), 3.41 (dd, J=6.1 Hz, 13.2 Hz, 1H), 5.03 (dd, J=6.6 Hz, 8.8 Hz, 1 H), 6.80 (d, J=2.2 Hz, 1 H), 7.05 (d, J=1.6 Hz, 1 H), 7.20-7.22 (m, 2 H), 7.29-7.35 (m, 3 H), 7.49-7.54 (m, 3 H), 7.71-7.73 (m, 2 H). HRMS m/z Calc'd for C$_{20}$H$_{21}$N$_2$O (M+H)$^+$: 305.1654. Found 305.1645.

36B. Example 36: Compound 36A was converted to Example 36 according to the procedures described in 34D. $^1$H NMR (500 MHz, CD$_3$OD) δ: 0.99-1.08 (m, 2 H), 1.36-1.43 (m, 2 H), 1.53-1.58 (m, 1 H), -1.69-1.71 (m, 1 H), 1.79-1.85 (m, 3 H), 2.18-2.24 (m, 1 H), 2.75 (d, J=7.2 Hz, 2 H), 3.10 (dd, J=8.8 Hz, 13.8 Hz, 1 H), 3.23 (dd, J=6.6 Hz, 13.8 Hz, 1 H), 3.55 (s, 3 H), 5.37-5.41 (m, 1 H), 6.70 (d, J=1.6 Hz, 1H), 6.85 (d, J=2.2 Hz, 1H), 7.21-7.30 (m, 5H), 7.46-7.53 (m, 3H), 7.66-7.68 (m, 2 H). HRMS m/z Calc'd for C$_{28}$H$_{33}$N$_3$O$_2$ (M+H)$^+$: 444.2651. Found 444.2669.

Example 37

4-Aminomethyl-cyclohexanecarboxylic acid [1-(6-amino-4-phenyl-pyridin-2-yl)-2-phenyl-ethyl]-amide, bis-trifluoroacetic acid salt 37A. 2-chloro-6-methyl-4-phenylpyridine: A suspension 6-methyl-4-phenyl-1H-pyridin-2-one (0.185 g, 1.0 mmol) and POCl$_3$ (0.56 mL, 6 mmol) in DMF (1 mL) was heated to 110° C. After 1.5 h, the reaction was cooled to rt, quenched with water and extracted with EtOAc. The combined organic layers were washed with sat. NaHCO$_3$, brine, dried over Na$_2$SO$_4$, filtered, and concentrated. Column chromatography on silica gel (0-10% EtOAc/Hexane) provided 37A (0.143 g, 70%) as a yellow oil. MS 204.1 (M+H)+ and 206.1 (M+2+H)$^+$.

37B. 1-(6-chloro-4-phenyl-pyridin-2-yl)-2-phenyl-ethylamine, bis-trifluoroacetic acid salt: Compound 37A was converted to 37B according to the procedures described in examples 34B and 34C. $^1$H NMR (400 MHz, CD$_3$OD) δ: 3.16-3.35 (m, 2 H), 4.74 (dd, J=6.6 Hz, 8.8 Hz, 1 H), 7.14 (d, J=6.2 Hz, 1H), 7.20 (d, J=1.8 Hz, 1 H), 7.25-7.33 (m, 4 H), 7.46-7.54 (m, 5 H), 7.71 (d, J=1.8 Hz, 1 H). HRMS m/z Calc'd for $C_{19}H_{18}ClN_2$ (M+H)$^+$: 309.1159. Found 309.1151.

37C. {4-[1-(6-Chloro-4-phenyl-pyridin-2-yl)-2-phenyl-ethylcarbamoyl]-cyclohexylmethyl}-carbamic acid tert-butyl ester: To a solution of 37B (0.067 g, 0.12 mmol) in DMF (3 mL) was added Boc-tranexamic acid (0.035 mL, 0.14 mmol), triethylamine (0.087 mL, 0.62 mmol), HOBt (0.025 g, 0.19 mmol), and EDCI (0.036 g, 0.19 mmol). The reaction mixture was stirred at rt for 18 h. The reaction mixture was diluted with EtOAc (25 mL), washed with water, sat. NaHCO$_3$, brine, dried over Na$_2$SO$_4$, filtered and concentrated. Column chromatography on silica gel (0-50% EtOAc/hexane) gave the amide 37C (0.045 g, 68%) as a white solid. MS 548.3 (M+H)+ and 550.4 (M+2+H)$^+$.

37D. Example 37: To a sealable tube was added 37C (0.045 g, 0.082 mmol), benzophenone imine (0.028 mL, 0.16 mmol), Pd(OAc)$_2$ (0.0018 g, 0.0082 mmol), BINAP (0.0077 g, 0.012 mmol), CS$_2$CO$_3$ (0.064 g, 0.2 mmol) and DMSO (0.55 mL). The mixture was degassed by bubbling argon for 10 min, the tube was sealed, and the reaction was heated at 85° C. After 18 h, the reaction was cooled to rt, poured into water and extracted with CH$_2$Cl$_2$ (3×). The combined organic layers were washed with brine, dried over Na$_2$SO$_4$, filtered and concentrated to give the benzophenone imine derivative (0.10 g) as a yellow oil. MS 693.2 (M+H)$^+$.

The benzophenone imine derivative was dissolved in THF (1 mL) and 4.0 M HCl in 1,4-dioxane (1.0 mL) was added, followed by water (0.5 mL). After 1 h, the solvent was removed, and the residue was dissolved in 50% TFA/CH$_2$Cl$_2$ (4 mL). After 0.5 h, the reaction was concentrated. Prep. HPLC (21.2×100 mm, 8 min. gradient, 20 to 100% B. 0.20 mL/min.) gave Example 37 (0.020 g, 37%) as a white solid. $^1$H NMR (500 MHz, CD$_3$OD) δ: 1.00-1.08 (m, 2H), 1.28-1.44 (m, 2H), 1.52-1.60 (m, 1 H), 1.69-1.72 (m, 1 H), 1.82-1.85 (m, 3 H), 2.21-2.26 (m, 1 H), 2.76 (d, J=7.2 Hz, 2 H), 3.15-3.26 (m, 2 H), 5.15-5.18 (m, 1 H), 7.05 (s, 2 H), 7.22-7.31 (m, 5H), 7.53-7.56 (m, 3 H), 7.68-7.70 (m, 2 H). HRMS m/z Calc'd for $C_{27}H_{33}N_4O$ (M+H)$^+$: 429.2654. Found 429.2655.

Example 38

4-Aminomethyl-cyclohexanecarboxylic acid [1-(6-chloro-4-phenyl-pyridin-2-yl)-2-phenyl-ethyl]-amide, bis-trifluoroacetic acid salt Example 38 can be prepared by deprotection of the Boc-protected 37C with TFA as was previously described. $^1$H NMR (500 MHz, CD$_3$OD) δ: 1.00-1.09 (m, 2 H), 1.31-1.46 (m, 2 H), 1.51-1.59 (m, 1 H), 1.67-1.73 (m, 1 H), 1.80-1.87 (m, 3H), 2.20-2.27 (m, 1 H), 2.76 (d, J=7.2 Hz, 2 H), 3.07 (dd, J=9.6 Hz, 13.5 Hz, 1 H), 3.21 (dd, J=6.3 Hz, 13.5 Hz, 1 H), 5.24-5.27 (m, 1 H), 7.15-7.26 (m, 5 H), 7.37 (s, 1H), 7.44-7.51 (m, 3 H), 7.58 (d, J=1.6 Hz, 1 H), 7.61-7.63 (m, 2 H). HRMS m/z Calc'd for $C_{27}H_{31}ClN_3O$ (M+H)$^+$: 448.2156. Found 448.2157.

Example 39

4-Aminomethyl-cyclohexanecarboxylic acid {1-[4-(3-amino-1H-indazol-6-yl)-6-oxo-1,6-dihydro-pyridin-2-yl]-2-phenyl-ethyl}-amide, trifluoroacetic acid salt 39A. [(E)-1-Benzyl-4-(4-cyano-3-fluoro-phenyl)-2-oxo-but-3-enyl]-carbamic acid tert-butyl ester: To a clear colorless solution of (3-tert-Butoxycarbonylamino-2-oxo-4-phenyl-butyl)-phosphonic acid dimethyl ester (5.45 g, 14.7 mmol; Resmini, M. et al., Tetrahedron Asymmetry, 2004, 15, 1847.) and 2-fluoro-4-formyl-benzonitrile (2.19 g, 14.7 mmol; Graham, S., J. Med. Chem., 2003, 46(14), 2973) in THF (210 mL) was added potassium carbonate (2.02 g, 14.7 mmol). The resulting suspension was vigorously stirred at rt to give a cloudy yellow suspension. After 54 h, additional (3-tert-Butoxycarbonylamino-2-oxo-4-phenyl-butyl)-phosphonic acid dimethyl ester (2, 72 g, 7.35 mmol) and potassium carbonate (1.0 g, 7.35 mmol) were added. After 2 h the reaction was stopped, filtered to remove the solid, and the solid was rinsed with ethyl acetate. The filtrate was diluted with ethyl acetate and then washed with water, brine, dried over Na$_2$SO$_4$, filtered and concentrated to give 10.38 g as a yellow solid. Column chromatography on silica gel (20% CH$_2$Cl$_2$/hexane, then 20-100% CH$_2$Cl$_2$/hexane, then 40% EtOAc/hexane) gave 39A (4.37 g, 75%) as a pale yellow solid. $^1$H NMR (500 MHz, CDCl$_3$) δ: 7.63 (t, J=7.2 Hz, 1H), 7.48 (d, J=16.5 Hz, 1H), 7.31-7.22 (m, 5H), 7.17 (d, J=8.2 Hz, 2H), 6.65 (d, J=16.0 Hz, 1H), 5.27 (d, J=7.2 Hz, 1H), 4.86-4.82 (m, 1H), 3.14-3.05 (m, 2H), 1.43 (bs, 9H). $^{19}$F NMR (470 MHz, CDCl$_3$) δ: −105.4. MS 417.1 (M+Na)$^+$ and 295.1 (M-C$_5$H$_9$O$_2$+H)$^+$.

39B. 4-[6-(1-Amino-2-phenyl-ethyl)-2-oxo-1,2-dihydro-pyridin-4-yl]-2-fluoro-benzonitrile: A suspension of 39A (3.17 g, 8.0 mmol), (1.62 g, 8.0 mmol), and ammonium acetate (12.4 g, 161 mmol) in ethanol (40 mL) was stirred at rt for 10 min. and then placed in a preheated oil bath (80° C.). After 20-30 min, a clear orange solution formed and then a precipitate formed. Additional ethanol (100 mL) was added to facilitate stirring. After 4 h, the reaction was cooled to rt, filtered to collect solid, the solid was rinsed with ethanol, air-dried, dried under vacuum to give the pyridone (2.09 g, 60%) as a white cloth-like solid. $^1$H NMR (500 MHz, DMSO-d$_6$) δ: 8.07 (t, J=7.7 Hz, 1H), 7.84 (d, J=11.0 Hz, 1H), 7.68 (d, J=7.7 Hz, 1H), 7.33-7.26 (m, 4H), 7.20-7.16 (m, 1H), 6.63 (bs, 1H), 6.53 (bs, 1H), 4.76-4.70 (m, 1H), 3.16-2.99 (m, 1H), 2.83-2.76 (m, 1H), 1.25 (s, 9H). $^{19}$F NMR (470 MHz, DMSO-d$_6$) δ: −107.6. HRMS m/z Calc'd for $C_{25}H_{25}N_3O_3F$ (M+H)$^+$: 434.1880. Found 434.1885.

To a suspension of the pyridone (2.09 g, 4.82 mmol) in dichloromethane (120 mL) was added TFA (30 mL) to give a clear, slightly yellow solution. After 1.5 h, the reaction was concentrated, redissolved in dichloromethane, and then concentrated. The above process was repeated. The residue was dissolved in dichloromethane and washed with sat. NaHCO$_3$. The layers were separated and the aqueous layer was extracted with dichloromethane. The combined organic layers were washed with brine, dried MgSO$_4$, filtered and concentrated to give 39B (1.60 g, 100%) as a pale yellow solid. $^1$H NMR (400 MHz, CDCl$_3$) δ: 7.71 (dd, J=7.9, 6.6 Hz, 1H), 7.40 (dd, J=7.9, 1.3 Hz, 1H), 7.35-7.31 (m, 3H), 7.28-7.22 (m, 3H), 6.65 (d, J=1.8 Hz, 1H), 6.26 (d, J=1.6 Hz, 1H), 4.20 (dd, J=8.4, 5.7 Hz, 1H), 3.17 (dd, J=13.2, 5.7 Hz, 1H), 2.95 (dd, J=13.2, 8.5 Hz, 1H). $^{19}$F NMR (375 MHz, CDCl$_3$) δ: −105.1 (d, J=9.2 Hz). HRMS m/z Calc'd for $C_{20}H_{17}N_3°F$ (M+H)$^+$: 334.1356. Found 334.1363.

39C. 4-Aminomethyl-cyclohexanecarboxylic acid {1-[4-(4-cyano-3-fluoro-phenyl)-6-oxo-1,6-dihydro-pyridin-2-yl]-2-phenyl-ethyl}-amide: To a solution of 39B (0.096 g, 0.29 mmol) in DMF (4 mL) was added Boc-tranexamic acid (0.082 mL, 0.32 mmol), triethylamine (0.2 mL, 1.44 mmol), HOBt (0.058 g, 0.43 mmol), and EDCI (0.083 g, 0.43 mmol). The reaction mixture was stirred at rt for 2 h and additional DMF (3 mL) was added. After 2 h, water was added to afford a white solid. The solid was collected to give the amide (0.16 g, 96%) as a white solid. MS 573.3 (M+H)$^+$.

To a suspension of the amide (0.16 g, 0.28 mmol)) in CH$_2$Cl$_2$ (2 mL) was added TFA (2 mL). The resulting clear solution was stirred for 2 h and then concentrated to give 39C (0.25 g) as a white solid. $^1$H NMR (400 MHz, CD$_3$OD) δ: 0.98-1.08 (m, 2 H), 1.25-1.45 (m, 2 H), 1.50-1.65 (m, 2 H), 1.80-1.86 (m, 3 H), 2.15-2.21 (m, 1 H), 2.76 (d, J=7.0 Hz, 2 H), 2.99-3.05 (dd, J=10.1 Hz, 14.1 Hz, 1 H), 3.22 (dd, J=6.2 Hz, 14.1 Hz, 1 H), 5.08-5.12 (m, 1 H), 6.57 (s, 1 H), 6.68 (d, J=1.8 Hz, 1 H), 7.20-7.30 (m, 5 H), 7.60-7.65 (m, 2 H), 7.86-7.90 (m, 1 H). MS 473.2 (M+H)$^+$.

39D. Example 39: A suspension of 39C (0.125 g), 1-butanol (3 mL) and hydrazine monohydrate (1 mL) was microwaved at 150° C. for 10 min. The reaction mixture was cooled to rt and concentrated to give a residue. Prep. HPLC (30×250 mm, 20 min. gradient, 30 to 100% B, 30 mL/min.) gave Example 39 (0.029 g, 33% over three steps) as a white solid. $^1$H NMR (500 MHz, CD$_3$OD) δ: 0.98-1.08 (m, 2 H), 1.28-1.46 (m, 2 H), 1.52-1.66 (m, 2 H), 1.81-1.85 (m, 3 H), 2.17-2.24 (m, 1 H), 2.75 (d, J=7.2 Hz, 2 H), 3.06 (dd, J=9.9 Hz, 13.7 Hz, 1 H), 3.06 (dd, J=6.3 Hz, 13.7 Hz, 1 H), 5.08-5.15 (m, 1 H), 6.63 (d, J=1.1 Hz, 1 H), 6.68 (d, J=1.7 Hz, 1 H), 7.20-7.31 (m, 5 H), 7.38-7.40 (m, 1 H), 7.61 (s, 1 H), 7.98 (d, J=8.2 Hz, 1 H). HRMS m/z Calc'd for C$_{28}$H$_{33}$N$_6$O$_2$ (M+H)$^+$: 485.2665. Found 485.2686.

Example 40

4-Aminomethyl-cyclohexanecarboxylic acid {1-[4-(3-amino-1,2-benzisoxazol-6-yl)-6-oxo-1,6-dihydro-pyridin-2-yl]-2-phenyl-ethyl}-amide, trifluoroacetic acid salt To a solution of acetohydroxamic acid (0.023 g, 0.31 mmol) in DMF (2 mL) was added t-BuOK (0.034 g, 0.31 mmol). This suspension was vigorously stirred for 30 min, then 39C (0.040 g, 0.068 mmol) was added. After 18 h, the reaction mixture was quenched with water and extracted with EtOAc (3×10 mL). The combined organic layers were washed with brine, dried over Na$_2$SO$_4$, filtered and concentrated. Prep HPLC (21.2×100 mm, 8 min. gradient, 20 to 100% B, 20 mL/min.) provided Example 40 (0.0050 g, 12%) as a white solid. $^1$H NMR (500 MHz, CD$_3$OD) δ: 0.98-1.08 (m, 2 H), 1.28-1.45 (m, 2 H), 1.50-1.65 (m, 2 H), 1.81-1.85 (m, 3 H), 2.16-2.22 (m, 1 H), 2.75 (d, J=6.6 Hz, 2 H), 3.02 (dd, J=9.9 Hz, 13.8 Hz, 1 H), 3.24 (dd, J=6.0 Hz, 13.8 Hz, 1 H), 5.10-5.15 (m, 1 H), 6.65 (s, 1 H), 6.69 (s, 1 H), 7.21-7.31 (m, 5 H), 7.50 (d, J=8.2 Hz, 1 H), 7.63 (s, 1 H), 7.86 (d, J=8.2 Hz, 1 H). HRMS m/z Calc'd for C$_{28}$H$_{32}$N$_5$O$_3$ (M+H)$^+$: 486.2505. Found 486.2519.

Example 52

5-(2-{1-[(4-Aminomethyl-cyclohexanecarbonyl)-amino]-2-phenyl-ethyl}-pyridin-4-yl)-2-fluoro-benzoic acid, bis-trifluoroacetic acid salt Example 52 was prepared from 3D following the procedures described in 3E using 3-carboxy-4-fluorophenylboronic acid in place of 3-(methoxycarbonyl)phenylboronic acid. $^1$H NMR (500 MHz, CD$_3$OD) δ: 1.01-1.10 (m, 2 H), 1.32-1.43 (m, 2 H), 1.52-1.60 (m, 1 H), 1.73-1.86 (m, 4 H), 2.26-2.31 (m, 1 H), 2.77 (d, J=7.2 Hz, 2 H), 3.23-3.26 (m, 2 H), 5.33-5.36 (m. 1 H), 7.19-7.28 (m, 5H), 7.43 (dd, J=8.8 Hz, 9.9 Hz, 1 H), 7.92 (s, 1 H), 7.96 (dd, J=1.6 Hz, 6.0 Hz, 1H), 8.03-8.05 (m, 1 H), 8.33 (dd, J=2.7 Hz, 6.6 Hz, 1 H), 8.67 (d, J=5.5 Hz, 1 H). HRMS m/z Calc'd for C$_{28}$H$_{31}$FN$_3$O$_3$ [M+H]$^+$: 476.2349. Found 476.2342.

Example 54

2-Amino-5-(2-{1-[(4-aminomethyl-cyclohexanecarbonyl)-amino]-2-phenyl-ethyl}-pyridin-4-yl)-benzoic acid methyl ester, tris-trifluroacetic acid salt 54A. 2-Amino-5-(5,5-dimethyl-1,3,2-dioxaborinan-2-yl)-benzoic acid methyl ester: To a flame-dried, round-bottom flask equipped with a condenser was added 2-Amino-5-bromo-benzoic acid methyl ester (0.7 g, 3.0 mmol), Pd(dppf)Cl$_2$•CH$_2$Cl$_2$ complex (0.106 g, 0.130 mmol), KOAc (1.28 g, 13.0 mmol), and bis(neopentyl glycolato)diboron (1.08 g, 4.78 mmol). Next degassed DMSO (29 mL) was added and the reaction was stirred at 80° C. After 5 h, the reaction was cooled to rt, diluted with EtOAc (100 mL), washed with water, brine, dried over Na$_2$SO$_4$, filtered and concentrated. Column chromatography on silica gel (gradient elution 0-20% EtOAc/Hexane) gave 54A (0.858 g, 75%) as a white solid. $^1$H NMR (400 MHz, CDCl$_3$)δ: 1.01 (s, 6 H), 3.74 (s, 4 H), 3.86 (s, 3 H), 5.91 (bs, 2 H), 6.63 (d, J=8.3 Hz, 1 H), 7.66-7.68 (m, 1 H), 8.33 (s, 1 H). MS 196.1 (M−C$_5$H$_8$+H)

54B. 2-Amino-5-[2-(1-{[4-(tert-butoxycarbonylamino-methyl)-cyclohexanecarbonyl]-amino}-2-phenyl-ethyl)-pyridin-4-yl]-benzoic acid methyl ester: 54B was prepared from 3D following the procedures described in 3E using 54A in place of 3-(methoxycarbonyl)phenylboronic acid. MS 587.41 (M+H)$^+$.

54C. Example 54: Deprotection of 54B following the procedure from 1E gave Example 54. $^1$H NMR (500 MHz, CD$_3$OD) δ: 1.03-1.12 (m, 2 H), 1.32-1.43 (m, 2 H), 1.52-1.60 (m, 1 H), 1.73-1.86 (m, 4 H), 2.26-2.31 (m, 1 H), 2.77 (d, J=6.6 Hz, 2 H), 3.25-3.31 (m, 2 H), 3.03 (s, 3 H), 5.28-5.31 (m, 1 H), 6.95 (d, J=8.8 Hz, 1 H), 7.20-7.30 (m, 5 H), 7.86 (dd, J=2.2 Hz, 8.8 Hz, 1 H), 8.02-8.05 (m, 2 H), 8.43 (d, J=2.2 Hz, 1 H), 8.47 (d, J=6.6 Hz, 1 H). HRMS m/z Calc'd for C$_{29}$H$_{35}$N$_4$O$_3$ [M+H]$^+$: 487.2709. Found 487.2710.

Example 55

4-Aminomethyl-cyclohexanecarboxylic acid {1-[4-(4-oxo-3,4-dihydro-quinazolin-6-yl)-pyridin-2-yl]-2-phenyl-ethyl}-amide, bis-trifluoroacefic acid salt A yellow suspension of 54B (0.085 g, 0.145 mmol), ammonium acetate (0.112 g, 1.45 mmol), and trimethyl orthoformate (0.15 mL, 1.45=mmol) in methanol (1.4 mL) was heated to 100° C. in a sealed tube. After 8 h, the reaction was filtered hot, and the solid was rinsed with methanol, air-dried, and dried under vacuum to give a white solid. The solid was dissolved in 30% TFA/CH$_2$Cl$_2$ (5 mL). After 30 min, the reaction was concentrated. Prep HPLC [21.1×100 mm; 8 min. grad.; 30-100% B; 20 mL/min) gave, after lyophilization, Example 55 (0.034 g, 33%) as a white solid. $^1$H NMR (500 MHz, CD$_3$OD) δ: 8.69 (t, J=4.7 Hz, 1H), 8.63 (bs, 1H), 8.26-8.23 (m. 2H), 8.18-7.96 (m, 2H), 7.88 (d, J=8.8 Hz, 1H), 7.29-7.26 (m, 2H), 7.22-7.18 (m, 3H), 5.40-5.35 (m, 1H), 3.30-3.20 (m, 2H), 2.77 (d, J=6.6 Hz, 2H), 2.32-2.26 (m, 1H), 1.87-1.82 (m, 3H), 1.77-1.74 (m, 1H), 1.62-1.52 (m, 1H), 1.42-1.34 (m, 2H), 1.10-1.02 (m, 2H). HRMS m/z Calc'd for C$_{29}$H$_{32}$N$_5$O$_2$ (M+H)$^+$: 485.2556. Found 485.2532.

Example 56

2-Amino-5-(2-{1-[(4-aminomethyl-cyclohexanecarbonyl)-amino]-2-phenyl-ethyl}-pyridin-4-yl)-benzoic acid, tris-trifluoroacefic acid salt A yellow suspension of 54B (0.036 g, 0.061 mmol) and 1.0 N NaOH (0.31 mL) in methanol (0.60 mL) was heated to 60° C. After 4 h, the clear, yellow solution was concentrated to give a yellow residue. The yellow residue was dissolved in 30% TFA/CH₂Cl₂ (5 mL). After 30 min., the reaction was concentrated. Prep HPLC [21.1×100 mm; 8 min. grad.; 30-100% B; 20 mL/min) gave Example 56 (0.0031 g, 7%) as a yellow solid. $^1$H NMR (500 MHz, CD₃OD) δ: 8.47-8.44 (m, 2H), 8.01-7.97 (m, 2H), 7.85-7.81 (m, 1H), 7.31-7.26 (m, 2H), 7.25-7.19 (m, 3H), 6.93 (d, J=8.8 Hz, 1H), 5.29 (t, J=8.0 Hz, 1H), 3.29-3.22 (m, 2H), 2.77 (d, J=7.2 Hz, 2H), 2.33-2.26 (m, 1H), 1.89-1.83 (m, 3H), 1.79-1.73 (m, 1H), 1.62-1.54 (m, 1H), 1.42-1.32 (m, 2H), 1.10-1.03 (m, 2H). HRMS m/z Calc'd for C₂₈H₃₃N₄O₃ (M+H)⁺: 473.2553. Found 473.2531.

Example 57

4-Aminomethyl-cyclohexanecarboxylic acid {1-[4-(4-methoxy-quinolin-6-yl)-pyridin-2-yl]-2-phenyl-ethyl}-amide, tris-trifluoroacetic acid salt Example 57 was prepared from 3D following the procedures described in 3E using 6-(5,5-Dimethyl-1,3,2-dioxaborinan-2-yl)-4-methoxy-quinoline, prepared following the procedure in 54A, in place of 3-(methoxycarbonyl)phenylboronic acid. $^1$H NMR (500 MHz, CD₃OD) δ: 1.01-1.12 (m, 2 H), 1.32-1.46 (m, 2 H), 1.53-1.60 (m, 1 H), 1.75-1.86 (m, 4 H), 2.26-2.31 (m, 1 H), 2.77 (d, J=7.2 Hz, 2 H), 3.25 (d, J=7.7 Hz, 2 H), 4.44 (s, 3 H), 5.36 (t, J=7.7 Hz, 1 H), 7.19-7.28 (m, 5H), 7.60 (d, J=6.6 Hz, 1 H), 7.85 (s, 1 H), 7.95 (dd, J=1.7 Hz, 5.5 Hz, 1 H), 8.25 (d, J=9.3 Hz, 1 H), 8.43 (dd, J=2.2 Hz, 9.3 Hz, 1 H), 8.73 (d, J=2.2 Hz, 1 H), 8.77 (d, J=5.5 Hz, 1 H), 9.10 (d, J=6.6 Hz, 1 H). HRMS m/z Calc'd for C₃₁H₃₅N₄O₂ [M+H]⁺: 495.2760. Found 495.2773.

Example 58

4-Aminomethyl-cyclohexanecarboxylic acid {1-[4-(4-oxo-1,4-dihydro-quinolin-6-yl)-pyridin-2-yl]-2-phenyl-ethyl}-amide, tris-trifluoroacetic acid salt 58A. 6-[2-(1-Amino-2-phenyl-ethyl)-pyridin-4-yl]-1H-quinolin-4-one, tris-trifluoroacetic acid salt: A mixture of 57 (0.062 g, 0.074 mmol) in concentrated HCl (0.5 mL) and 1,2-dichloroethane (1.0 mL) was heated to 130° C. in a sealed tube. After 22 h, the reaction was concentrated. Prep. HPLC (Phenomenex Luna 5u 21.2×100 nun; 8 min. gradient, 20 to 100% B; 20 mL/min.) gave 58A (0.031 g, 92%) as a clear, colorless oil. MS 342.2 (M+H)⁺.

58B. Example 58: To a solution of the oil in DMF (2 mL) was added Boc-tranexamic acid (0.023 g, 0.089 mmol), BOP reagent (0.0393 g, 0.089 mmol) and triethylamine (0.041 mL, 0.30 mmol). After 2 h, water was added and the reaction was extracted with EtOAc. The combined organic layers were washed with brine, dried over Na₂SO₄, filtered and concentrated. Prep. HPLC (Phenomenex Luna 5u 21.2×100 mm; 8 min. gradient; 30 to 100% B; 20 mL/min.) gave 0.014 g of the amide as a white solid. The solid was dissolved in 50% TFA in CH₂Cl₂ (2 mL). After 1 h the reaction was concentrated. Prep. HPLC (Phenomenex Luna 5u 21.2×100 mm; 8 min. gradient; 20 to 100% B; 25 mL/min.) gave, after lyophilization, Example 58 (0.010 g, 16% over three steps) as a pale, yellow solid. $^1$H NMR (500 MHz, CD₃OD) δ: 1.01-1.11 (m, 2 H), 1.34-1.45 (m, 2 H), 1.55-1.60 (m, 1 H), 1.75-1.90 (m, 4 H), 2.28-2.33 (m, 1 H), 2.78 (d, J=7.2 Hz, 2 H), 3.27-3.31 (m, 2H), 5.35-5.38 (m, 1 H), 6.53 (d, J=7.2 Hz, 1 H), 7.22-7.30 (m, 5 H), 7.85 (d, J=8.8 Hz, 1 H), 8.11-8.13 (m, 2 H), 8.16 (d, J=7.2 Hz, 1 H), 8.23 (dd, J=1.6 Hz, 8.8 Hz, 1H), 8.69 (d, J=6.1 Hz, 1 H), 8.76 (d, J=1.6 Hz, 1 H). MS 481.4 (M+H)⁺.

Examples 9, 11-12, 14, 16-20, 24, 30-32, 41-51, 53, and 59-60 were prepared using procedures similar to those described above. Table 1 below summarizes representative examples of the compounds in the present invention.

TABLE 1

(Id)

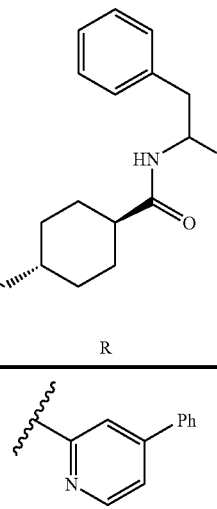

| Ex # | R | MS (M + H)⁺ |
|---|---|---|
| 1 | 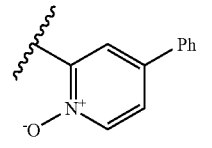 | 414.2 |
| 2 | 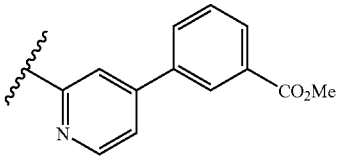 | 430.2 |
| 3 | 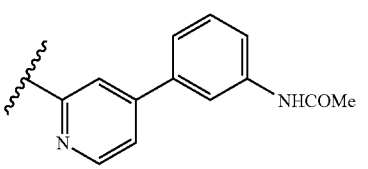 | 472.2 |
| 4 | 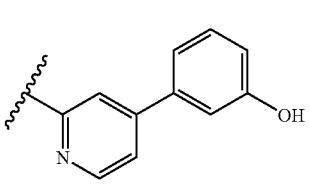 | 471.4 |
| 5 | 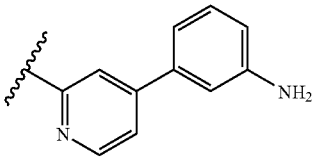 | 430.3 |
| 6 | 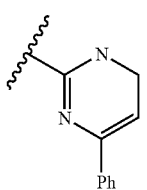 | 429.4 |
| 7 |  | 415.2 |

TABLE 1-continued (Id) Structure: N-(1-benzyl) amide of 4-(aminomethyl)cyclohexanecarboxamide with substituent R

| Ex # | R | MS (M + H)+ |
|---|---|---|
| 8 | 2-(6-oxo-4-phenyl-pyrimidinyl) | 431.2 |
| 9 | 4-(3-cyanophenyl)pyridin-2-yl | 439.3 |
| 10 | 4-(3-carboxyphenyl)pyridin-2-yl | 458.3 |
| 11 | 4-(4-methoxyphenyl)pyridin-2-yl | 444.3 |
| 12 | 4-(3-methoxyphenyl)pyridin-2-yl | 444.3 |
| 13 | 4-(1H-pyrrol-3-yl)pyridin-2-yl | 403.4 |
| 14 | 4-(pyridin-3-yl)pyridin-2-yl | 415.4 |
| 15 | 4-(2-aminopyridin-4-yl)pyridin-2-yl | 430.1 |
| 16 | 4-(2-methoxyphenyl)pyridin-2-yl | 444.4 |
| 17 | 4-(4-fluoro-3-cyanophenyl)pyridin-2-yl | 457.4 |
| 18 | 4-(3-carbamoylphenyl)pyridin-2-yl | 457.4 |
| 19 | 4-(4-carboxyphenyl)pyridin-2-yl | 458.4 |
| 20 | 4-(4-cyanophenyl)pyridin-2-yl | 439.4 |

TABLE 1-continued
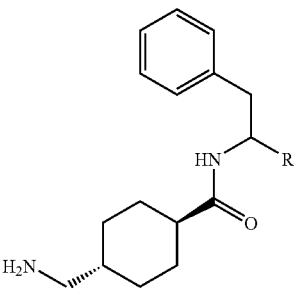
(Id)
| Ex # | R | MS (M + H)+ |
|---|---|---|
| 21 | 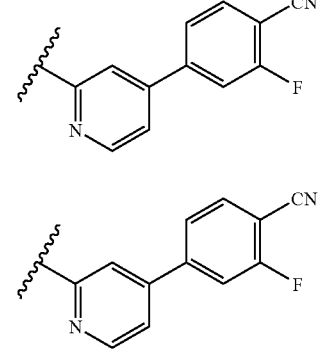 | 457.4 |
| (+)-22 | 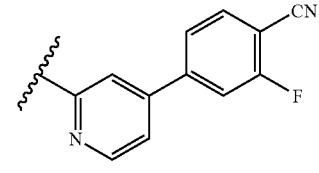 | 457.4 |
| (−)-23 | 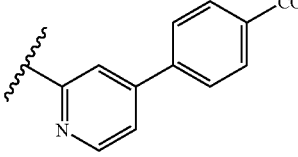 | 457.4 |
| 24 | 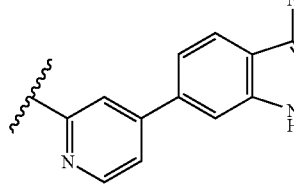 | 457.4 |
| 25 | 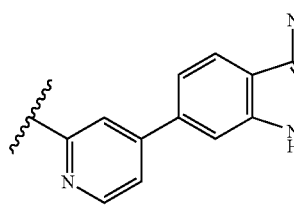 | 469.4 |
| (+)-26 | 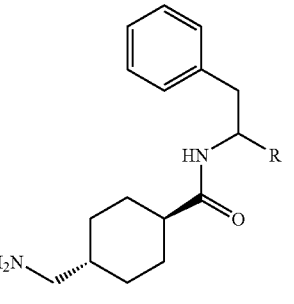 | 469.4 |
TABLE 1-continued
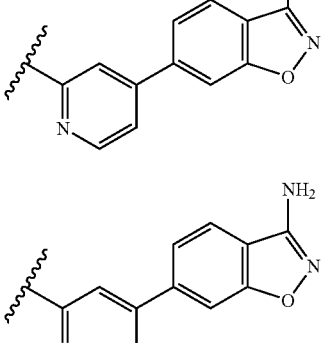
(Id)
| Ex # | R | MS (M + H)+ |
|---|---|---|
| 27 | 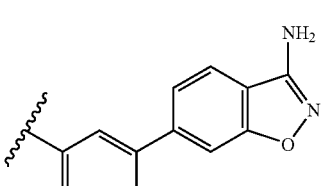 | 470.4 |
| (+)-28 | | 470.4 |
| (−)-29 | | 470.4 |
| 30 | | 470.4 |
| 31 | | 469.4 |
| 32 | | 470.4 |

TABLE 1-continued
(Id)
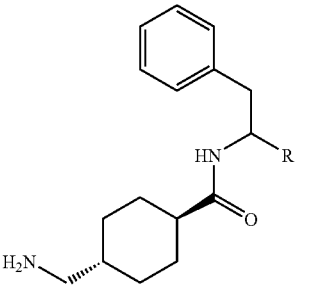
| Ex # | R | MS (M + H)+ |
|---|---|---|
| 33 | 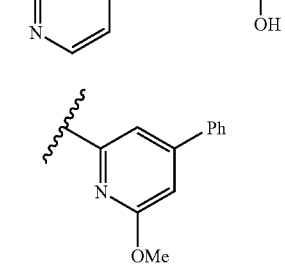 | 470.3 |
| 34 | 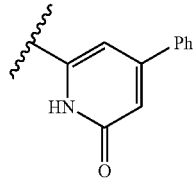 | 444.3 |
| 35 | 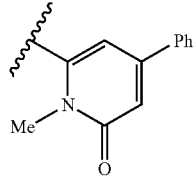 | 430.2 |
| 36 | 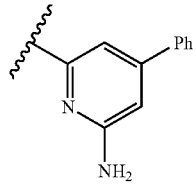 | 444.3 |
| 37 | 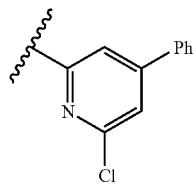 | 429.3 |
| 38 | 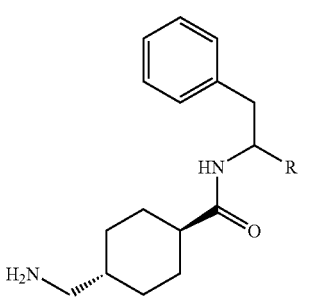 | 448.2 |
TABLE 1-continued
(Id)
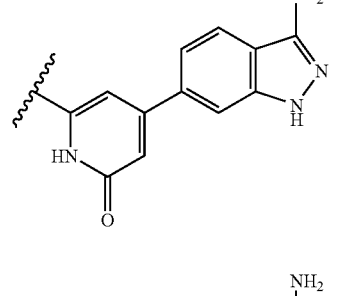
| Ex # | R | MS (M + H)+ |
|---|---|---|
| 39 | 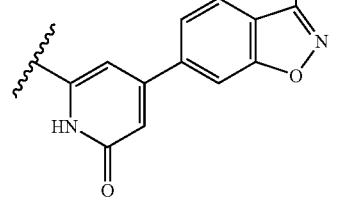 | 485.3 |
| 40 | 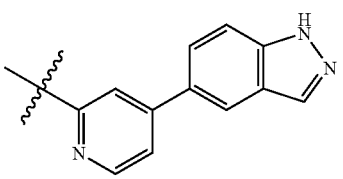 | 486.2 |
| 41 | 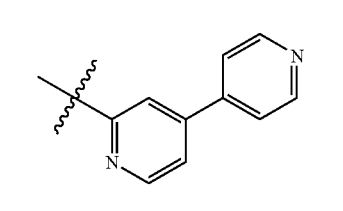 | 454.2 |
| 42 | 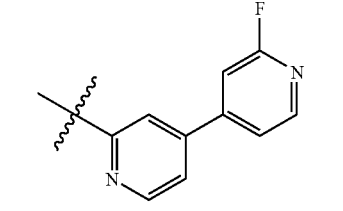 | 415.2 |
| 43 |  | 433.2 |

US 7,429,604 B2
TABLE 1-continued
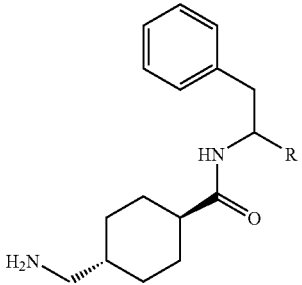
| Ex # | R | MS (M + H)+ |
|---|---|---|
| 44 | 2-(4-(2-NHMe-pyridyl))pyridyl | 444.3 |
| 45 | 2-(4-(2-NMe₂-pyridyl))pyridyl | 458.3 |
| 46 | 2-(4-(2-OMe-pyridyl))pyridyl | 445.3 |
| 47 | 2-(4-(2-oxo-1H-pyridyl))pyridyl | 431.2 |
| 48 | 2-(5-(2-F-pyridyl))pyridyl | 433.2 |
| 49 | 2-(5-(2-NH₂-pyridyl))pyridyl | 430.3 |
| 50 | 2-(5-(2-OMe-pyridyl))pyridyl | 445.3 |
| 51 | 2-(5-(2-oxo-1H-pyridyl))pyridyl | 431.3 |
| 52 | 5-(2-F,5-CO₂H-phenyl)-2-pyridyl | 476.2 |
| 53 | 2-(4-(1H-pyrazolyl))pyridyl | 404.2 |
| 54 | 5-(2-NH₂,5-CO₂Me-phenyl)-2-pyridyl | 487.3 |
| 55 | 2-(6-(4-oxo-3H-quinazolinyl))pyridyl | 482.4 |
| 56 | 5-(2-NH₂,5-CO₂H-phenyl)-2-pyridyl | 473.4 |

TABLE 1-continued (Id)

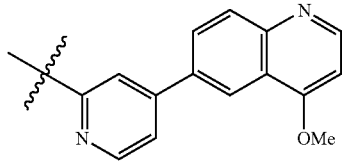

| Ex # | R | MS (M + H)+ |
|---|---|---|
| 57 | 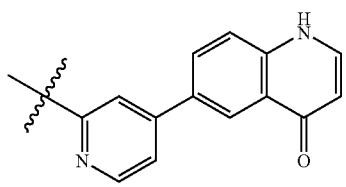 | 495.3 |
| 58 | 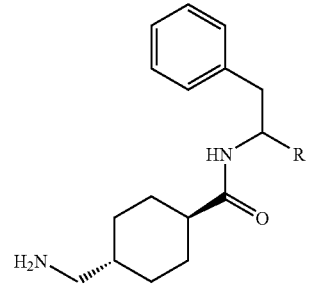 | 481.4 |

TABLE 1-continued (Id)

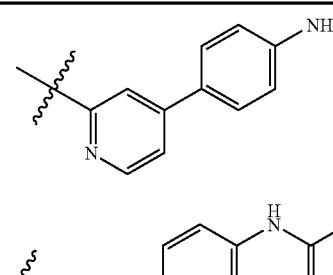

| Ex # | R | MS (M + H)+ |
|---|---|---|
| 59 | 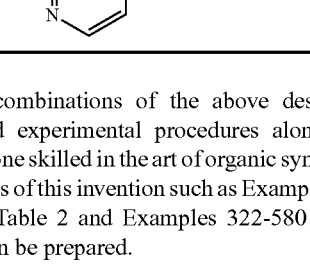 | 429.4 |
| 60 | 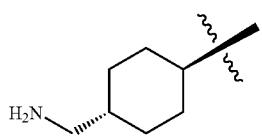 | 487.4 |

Using combinations of the above described synthetic routes and experimental procedures along with methods known to one skilled in the art of organic synthesis, additional compounds of this invention such as Examples 61-321 shown below in Table 2 and Examples 322-580 shown below in Table 3 can be prepared.

TABLE 2

(Ie)

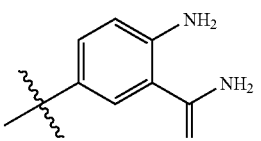

| Ex # | A | R11 | R3 |
|---|---|---|---|
| 61 | 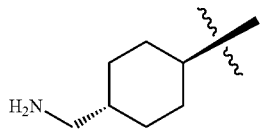 | benzyl | 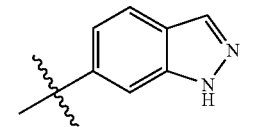 |
| 62 | 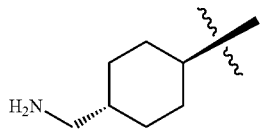 | benzyl | 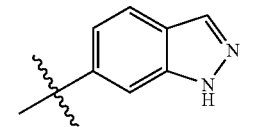 |

TABLE 2-continued
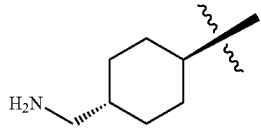
(Ie)
| Ex # | A | R[11] | R[3] |
|---|---|---|---|
| 63 | 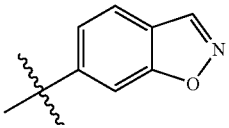 | benzyl | 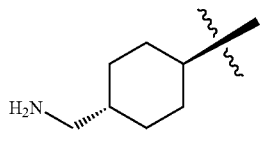 |
| 64 | 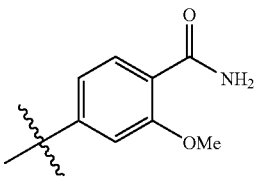 | benzyl | 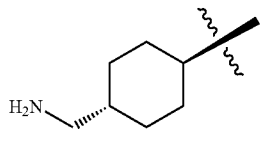 |
| 65 | 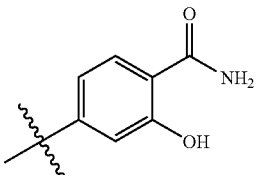 | benzyl | 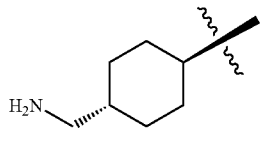 |
| 66 | 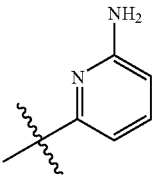 | benzyl | 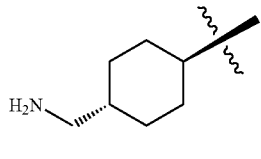 |
| 67 | 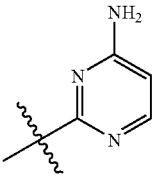 | benzyl | 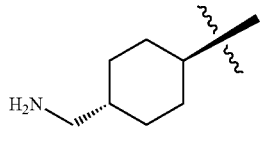 |
| 68 | 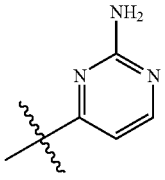 | benzyl | 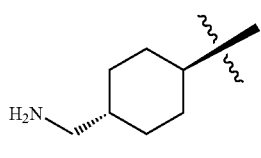 |
| 69 | 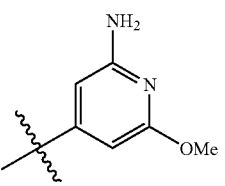 | benzyl | 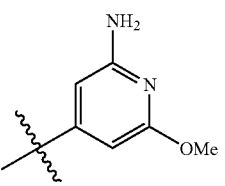 |

TABLE 2-continued (Ie)

| Ex # | A | R11 | R3 |
|---|---|---|---|
| 70 | H2N-CH2-cyclohexyl- | benzyl | 6-amino-pyrimidin-4-yl |
| 71 | H2N-CH2-cyclohexyl- | benzyl | 2-amino-pyrimidin-5-yl |
| 72 | H2N-CH2-cyclohexyl- | benzyl | 2-carbamoyl-pyridin-4-yl |
| 73 | H2N-CH2-cyclohexyl- | benzyl | 2-carboxy-pyridin-4-yl |
| 74 | H2N-CH2-cyclohexyl- | benzyl | 6-carbamoyl-pyridin-3-yl |
| 75 | H2N-CH2-cyclohexyl- | benzyl | 3-amino-1H-pyrazol-5-yl |
| 76 | H2N-CH2-cyclohexyl- | benzyl | 2-methyl-3-oxo-2,3-dihydro-1H-indazol-5-yl |
| 77 | H2N-CH2-cyclohexyl- | benzyl | 3-methoxy-1H-indazol-5-yl |

TABLE 2-continued (Ie)

| Ex # | A | R¹¹ | R³ |
|---|---|---|---|
| 78 | 4-(aminomethyl)cyclohexyl (trans) | benzyl | 5-(2,3-dioxoindolin-5-yl) (isatin-5-yl) |
| 79 | 4-(aminomethyl)cyclohexyl (trans) | benzyl | 3-hydroxy-2-oxoindolin-5-yl |
| 81 | 1-aminoisoquinolin-6-yl | benzyl | 3-aminobenzo[d]isoxazol-6-yl |
| 82 | 4-carbamoylphenyl | benzyl | 3-aminobenzo[d]isoxazol-6-yl |
| 83 | 4-(aminomethyl)phenyl | benzyl | 3-aminobenzo[d]isoxazol-6-yl |
| 84 | 3-amino-1H-indazol-6-yl | benzyl | 3-aminobenzo[d]isoxazol-6-yl |
| 85 | 3-aminobenzo[d]isoxazol-6-yl | benzyl | 3-aminobenzo[d]isoxazol-6-yl |

TABLE 2-continued (Ie) structure: A-C(O)-NH-CH(R11)-(2-pyridyl with R3 at 4-position)

| Ex # | A | R11 | R3 |
|---|---|---|---|
| 86 | trans-4-(aminomethyl)cyclohexyl (H2N-CH2-C6H10-) | N-methyl-N-phenyl-3-(methylene)benzamide | 3-amino-1,2-benzisoxazol-6-yl |
| 87 | trans-4-(aminomethyl)cyclohexyl | benzyl | 4-aminoquinazolin-7-yl |
| 88 | trans-4-(aminomethyl)cyclohexyl | benzyl | 2,4-diaminoquinazolin-7-yl |
| 89 | trans-4-(aminomethyl)cyclohexyl | N-(phenylsulfonyl)-3-(methylene)aniline | 3-amino-1,2-benzisoxazol-6-yl |
| 91 | trans-4-(aminomethyl)cyclohexyl | N-benzyl-N-methyl-3-(methylene)benzamide | 3-amino-1,2-benzisoxazol-6-yl |

TABLE 2-continued
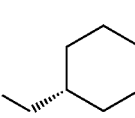
| Ex # | A | R{11} | R{3} |
|---|---|---|---|
| 92 | 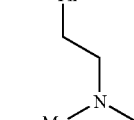 | 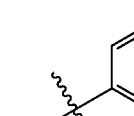 | 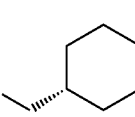 |
| 93 | 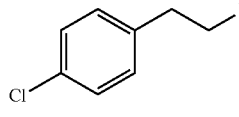 | 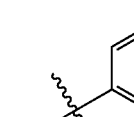 | 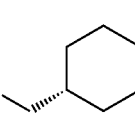 |
| 94 | 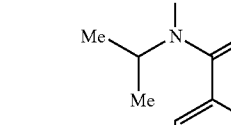 | 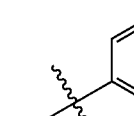 | 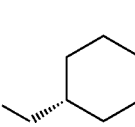 |
| 95 | 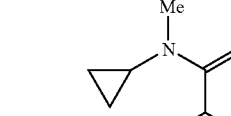 | 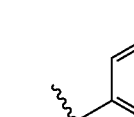 | |

TABLE 2-continued (Ie)

| Ex # | A | R11 | R3 |
|---|---|---|---|
| 96 | 4-(aminomethyl)cyclohexyl | PhS(O)2N(Me)-(3-phenyl) | 3-amino-1,2-benzisoxazol-6-yl |
| 97 | 1-amino-5,6,7,8-tetrahydroisoquinolin-6-yl | N-methyl-N-phenyl-3-benzamide | 4-(NHCO2Me)phenyl |
| 98 | 1-amino-5,6,7,8-tetrahydroisoquinolin-6-yl | N-methyl-N-phenyl-3-benzamide | 6-aminopyridin-3-yl |
| 99 | 1-amino-5,6,7,8-tetrahydroisoquinolin-6-yl | N-methyl-N-phenyl-3-benzamide | 5-(C(O)NH2)thiophen-2-yl |

TABLE 2-continued
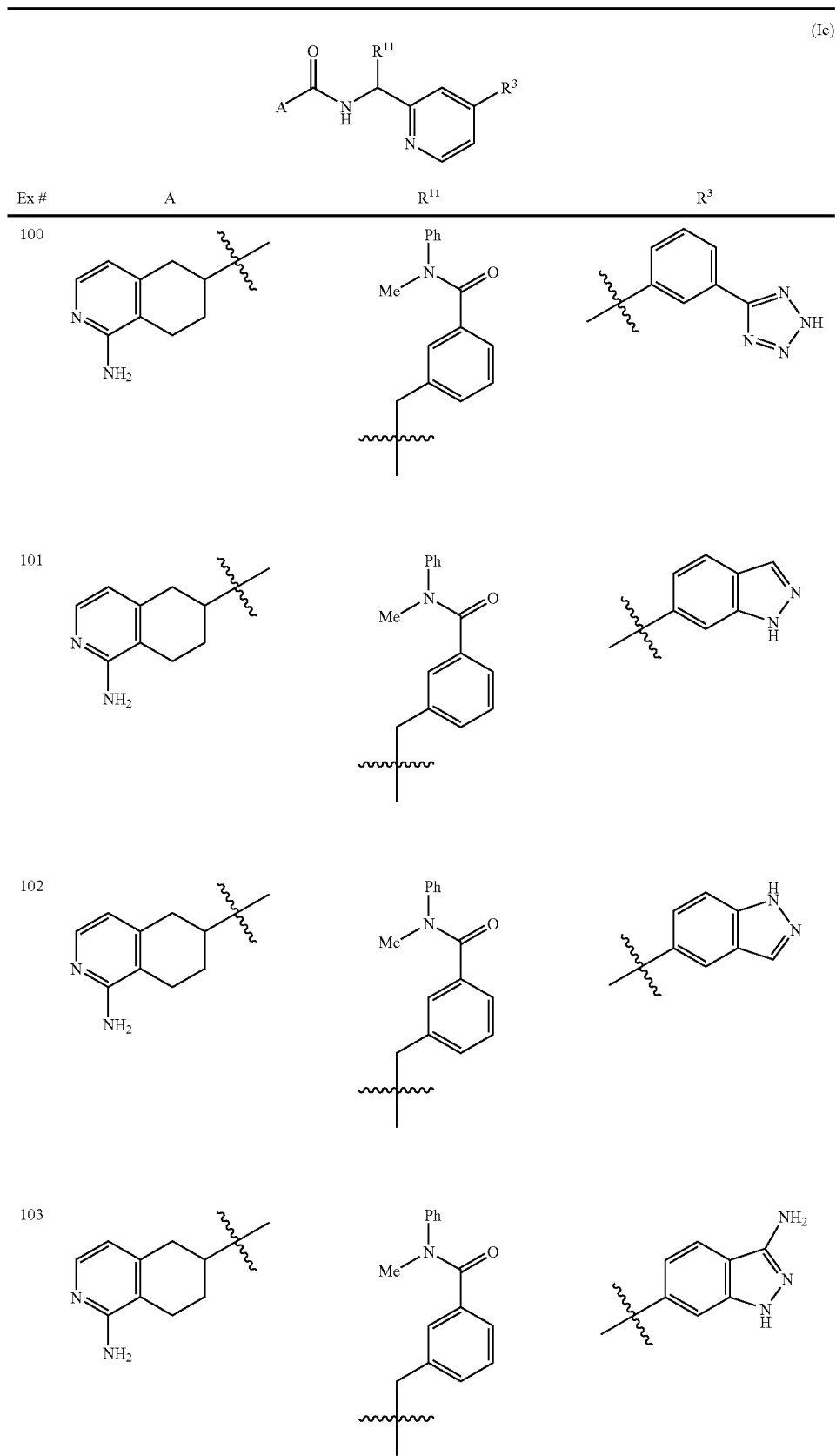

TABLE 2-continued
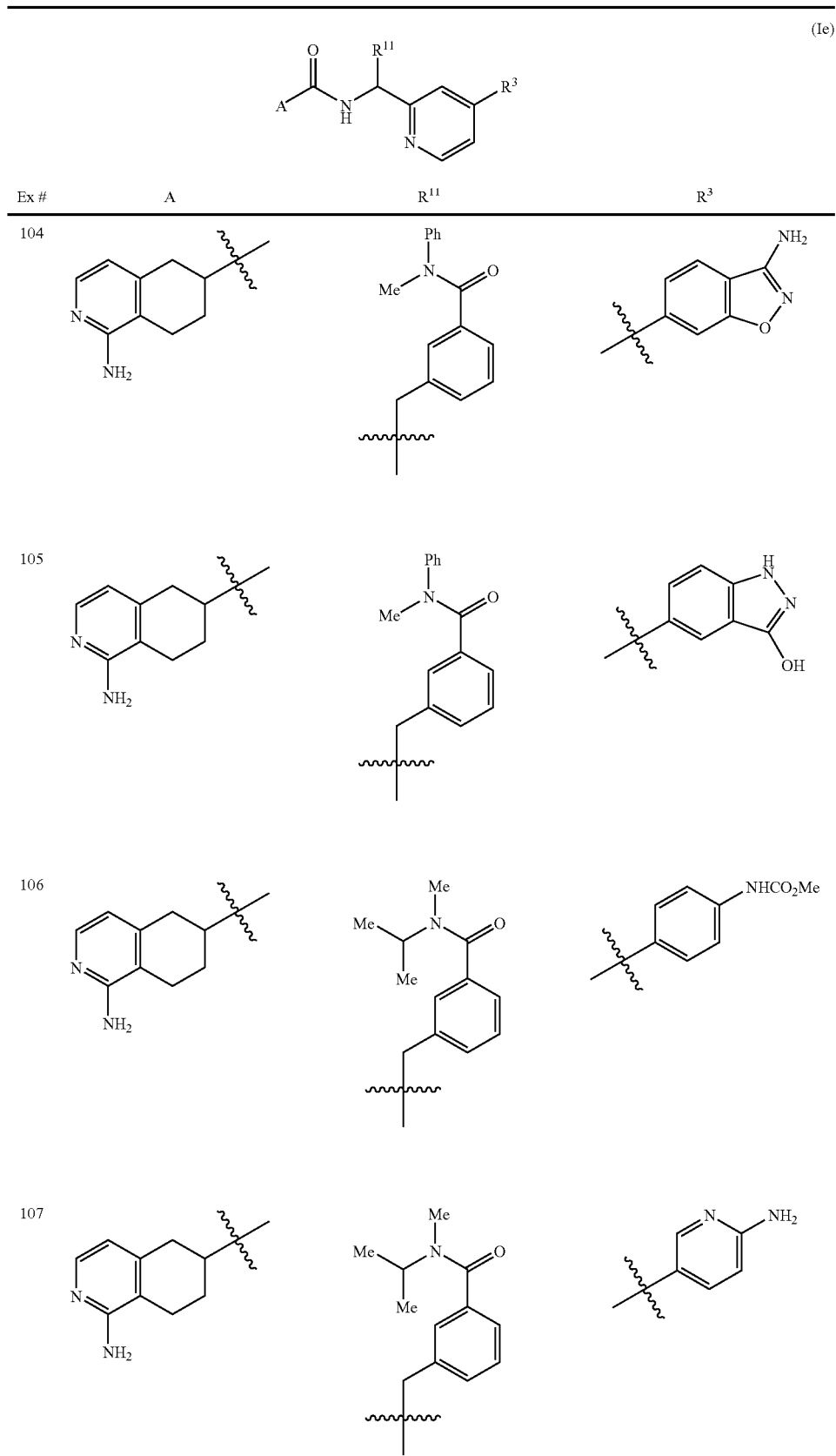

TABLE 2-continued
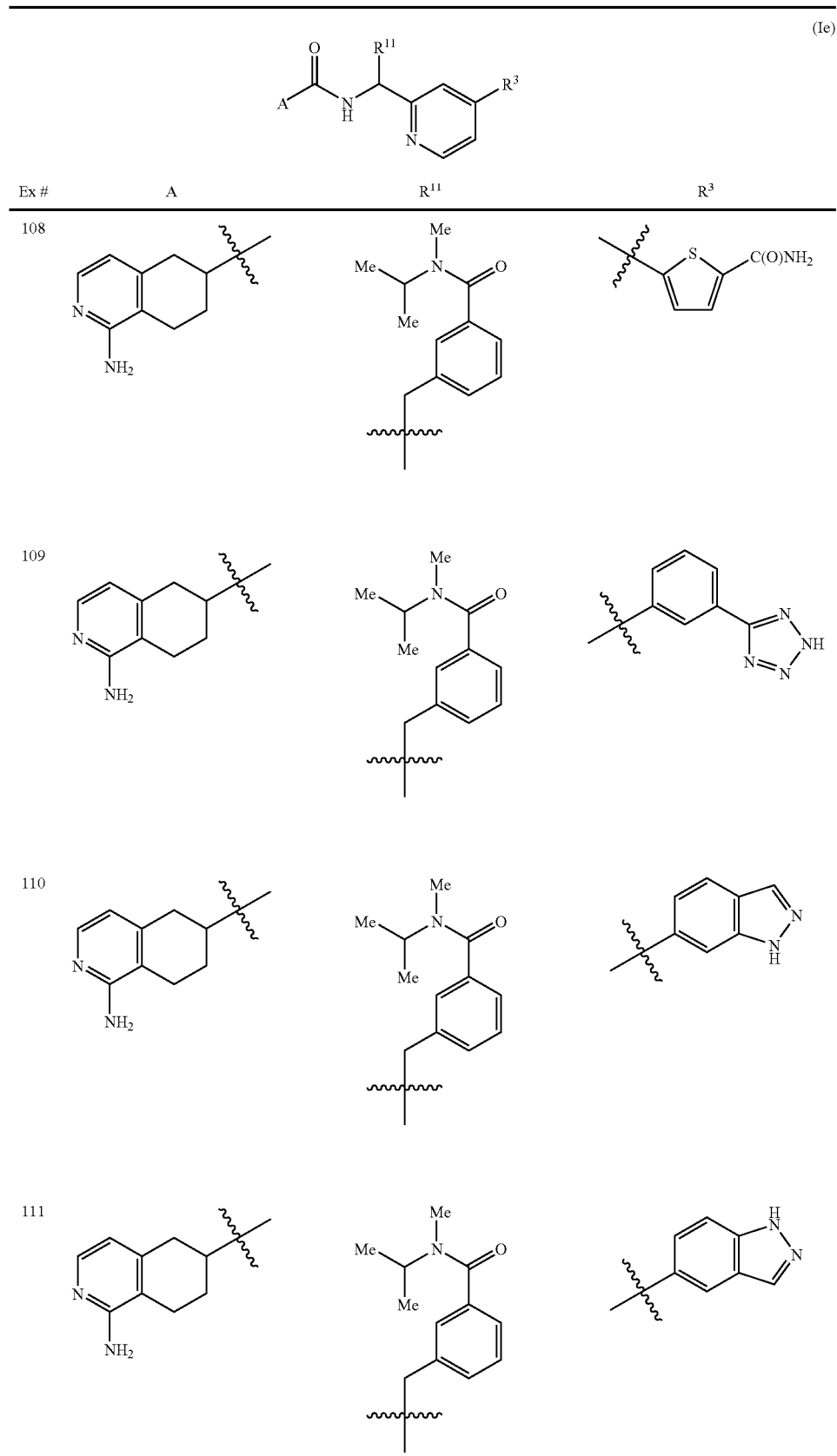

TABLE 2-continued
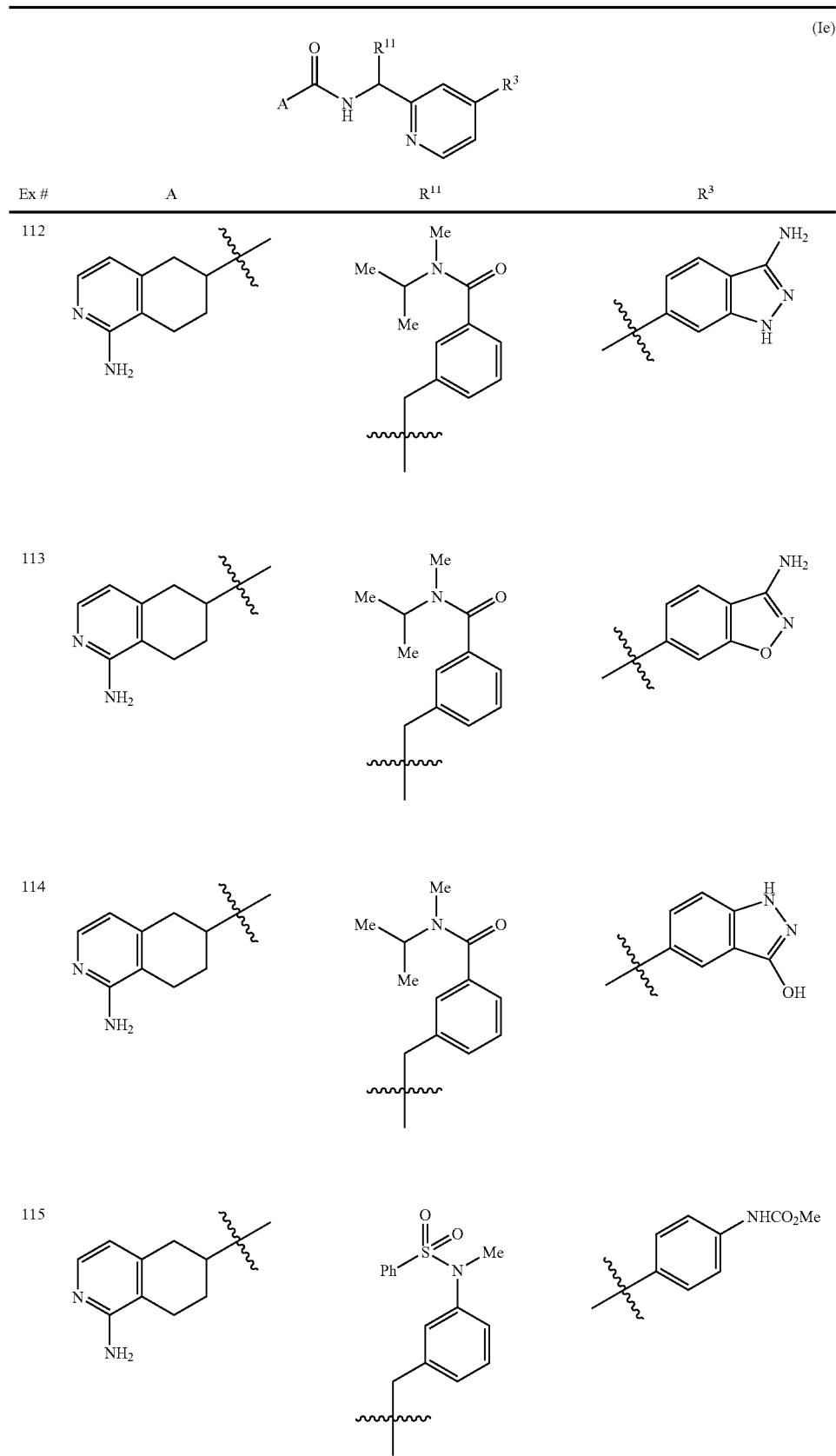

TABLE 2-continued
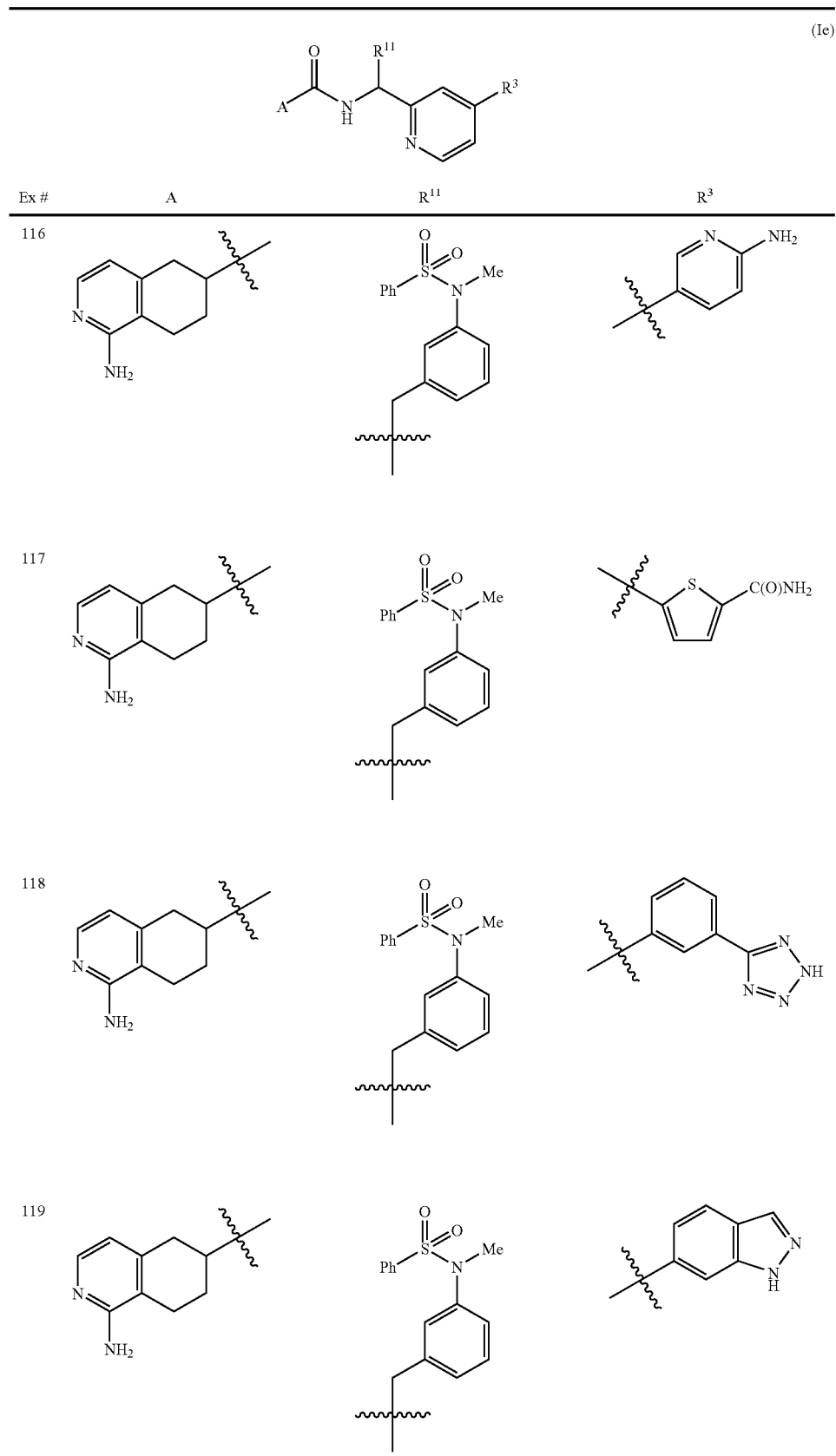

TABLE 2-continued
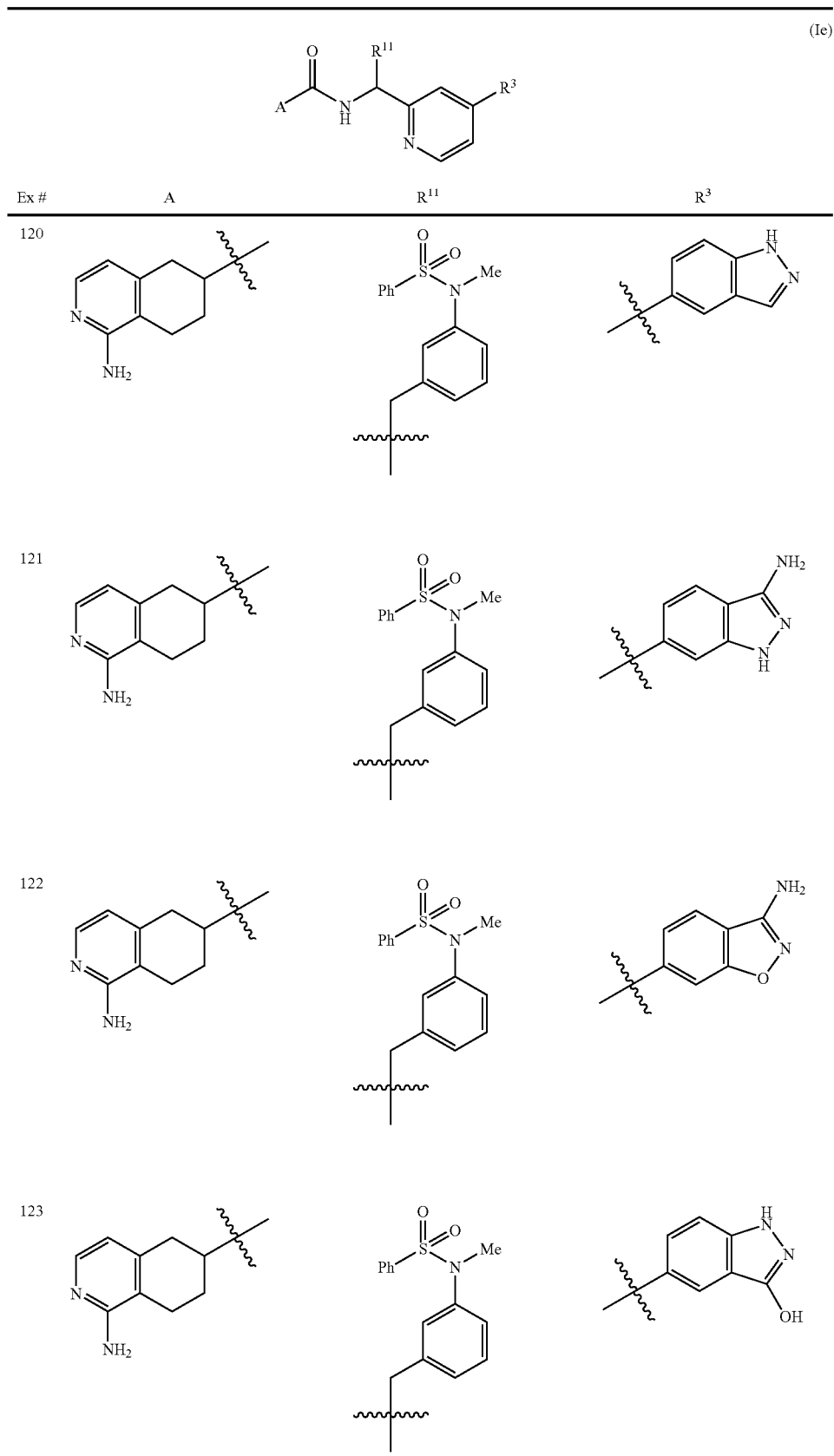

TABLE 2-continued
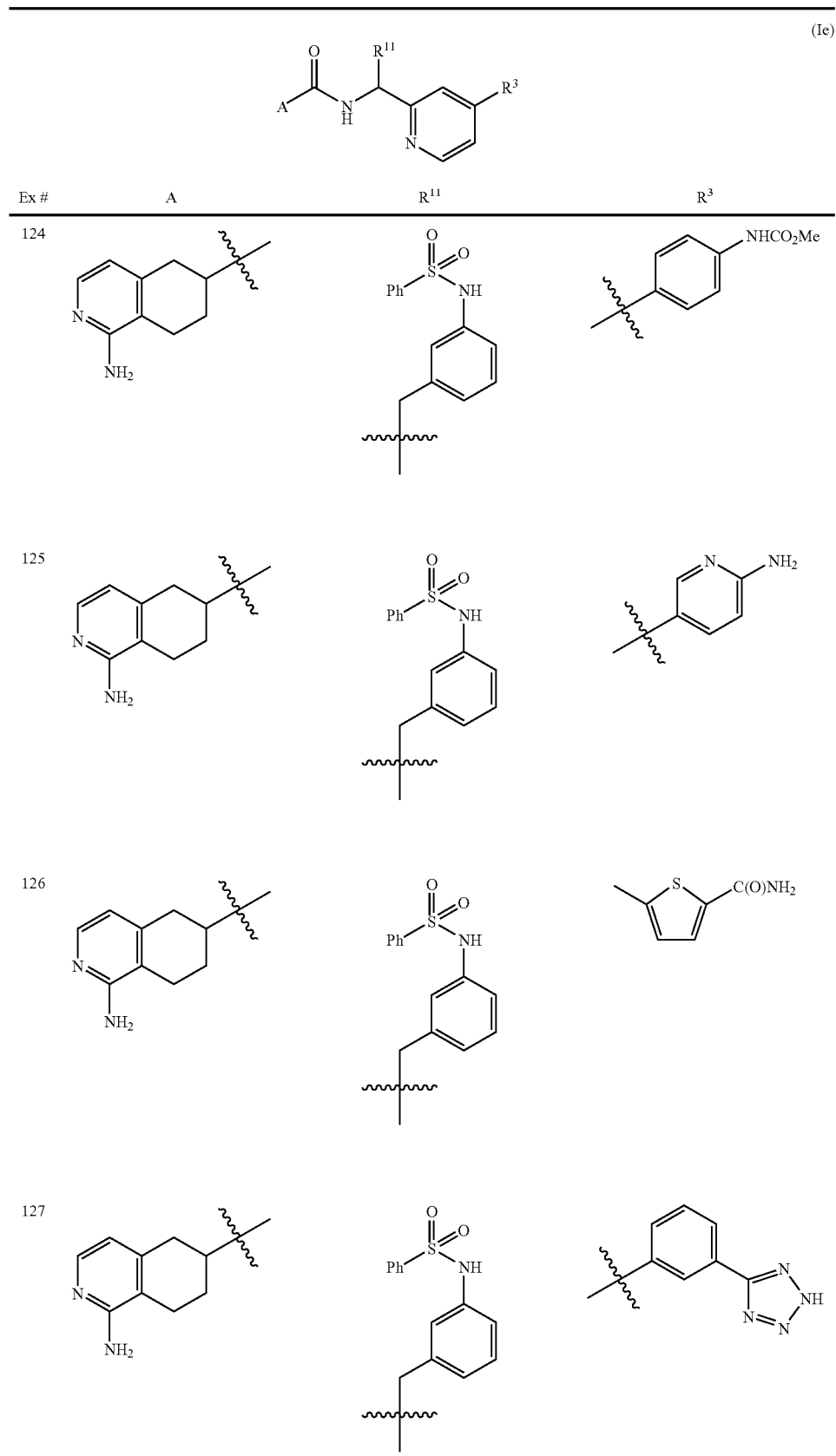

TABLE 2-continued
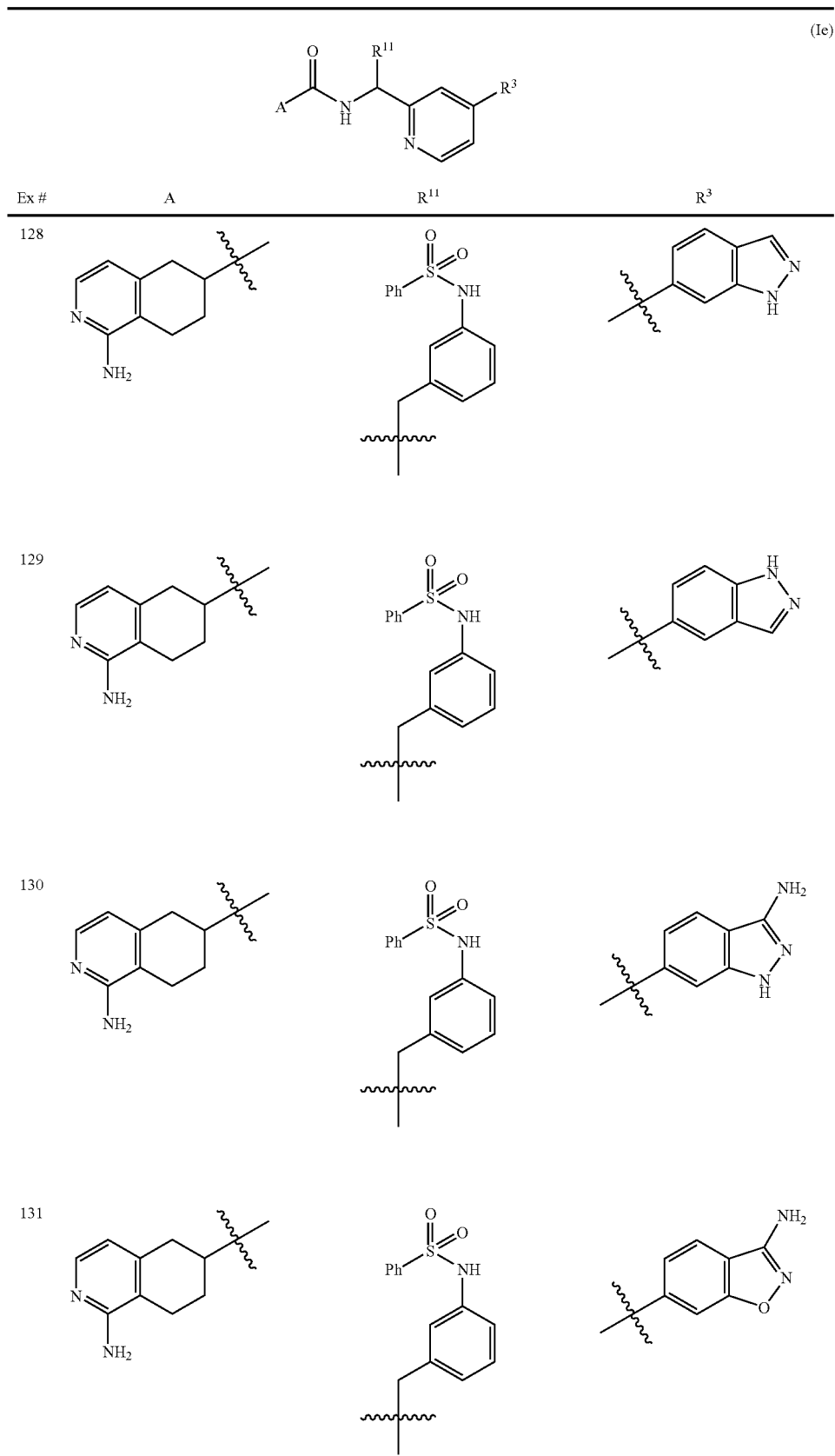

TABLE 2-continued
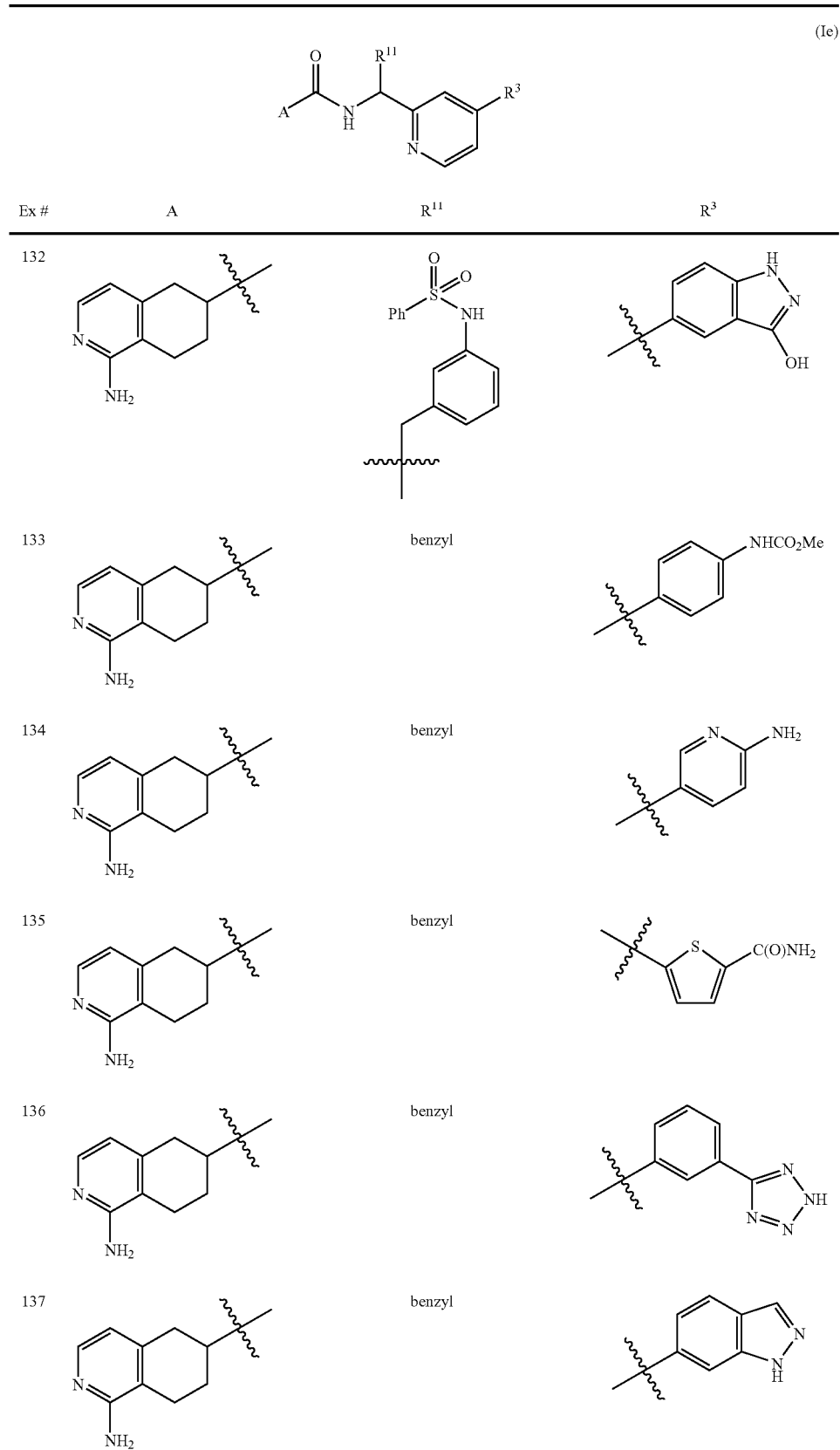

TABLE 2-continued (Ie)

| Ex # | A | R¹¹ | R³ |
|---|---|---|---|
| 138 | 1-amino-tetrahydroisoquinolin-6-yl | benzyl | 1H-indazol-5-yl |
| 139 | 1-amino-tetrahydroisoquinolin-6-yl | benzyl | 3-amino-1H-indazol-6-yl |
| 140 | 1-amino-tetrahydroisoquinolin-6-yl | benzyl | 3-amino-benzo[d]isoxazol-6-yl |
| 141 | 1-amino-tetrahydroisoquinolin-6-yl | benzyl | 3-hydroxy-1H-indazol-5-yl |
| 142 | 2-fluoro-4-methylphenyl | 3-(N-methyl-N-phenyl-carbamoyl)benzyl | 4-(NHCO₂Me)phenyl |
| 143 | 3-fluoro-4-methylphenyl | 3-(N-methyl-N-phenyl-carbamoyl)benzyl | 6-amino-pyridin-3-yl |

TABLE 2-continued

| Ex # | A | R¹¹ | R³ |
|---|---|---|---|
| 144 | 2-F, 4-Me phenyl | N-Me-N-Ph, 3-CH₂-benzamide | 5-(C(O)NH₂)-thiophen-2-yl |
| 145 | 2-F, 4-Me phenyl | N-Me-N-Ph, 3-CH₂-benzamide | 3-(2H-tetrazol-5-yl)phenyl |
| 146 | 2-F, 4-Me phenyl | N-Me-N-Ph, 3-CH₂-benzamide | 1H-indazol-6-yl |
| 147 | 2-F, 4-Me phenyl | N-Me-N-Ph, 3-CH₂-benzamide | 1H-indazol-5-yl |

TABLE 2-continued
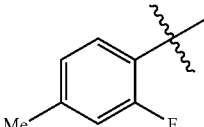
| Ex # | A | R[11] | R[3] |
|---|---|---|---|
| 148 | 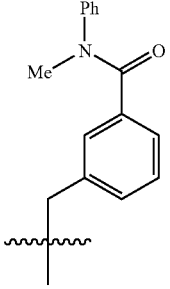 | 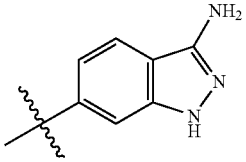 | 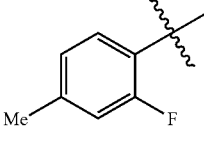 |
| 149 | 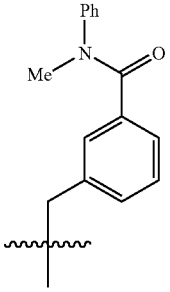 | 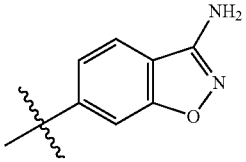 | 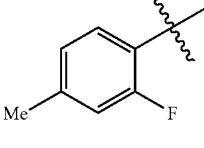 |
| 150 | 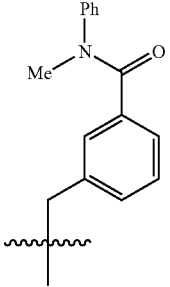 | 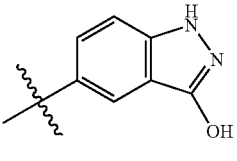 | 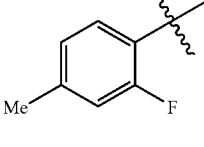 |
| 151 | 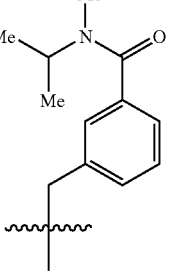 | 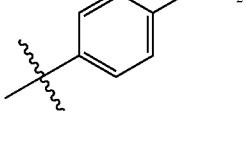 | | |

TABLE 2-continued (Ie)

| Ex # | A | R11 | R3 |
|---|---|---|---|
| 152 | 2-F-4-Me-phenyl | N-methyl-N-isopropyl-3-(CH2-)benzamide | 5-(2-aminopyridyl) |
| 153 | 2-F-4-Me-phenyl | N-methyl-N-isopropyl-3-(CH2-)benzamide | 5-(2-carboxamido)thienyl |
| 154 | 2-F-4-Me-phenyl | N-methyl-N-isopropyl-3-(CH2-)benzamide | 3-(2H-tetrazol-5-yl)phenyl |
| 155 | 2-F-4-Me-phenyl | N-methyl-N-isopropyl-3-(CH2-)benzamide | 1H-indazol-6-yl |

TABLE 2-continued
(Ie)
| Ex # | A | R11 | R3 |
|---|---|---|---|
| 156 | 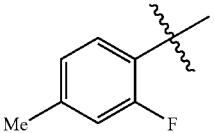 | 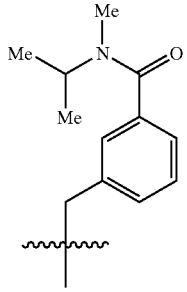 | 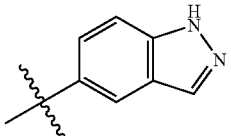 |
| 157 | 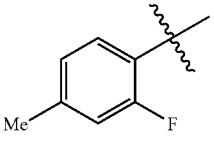 | 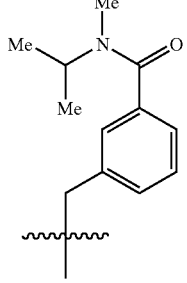 | 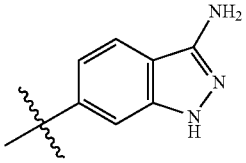 |
| 158 | 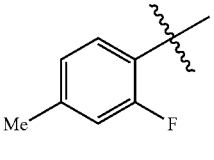 | 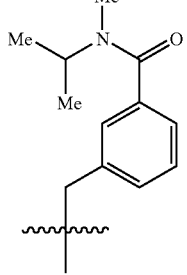 | 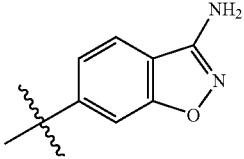 |
| 159 | 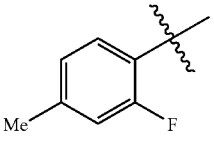 | 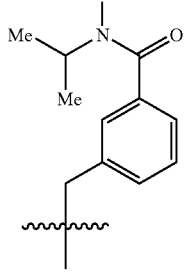 | 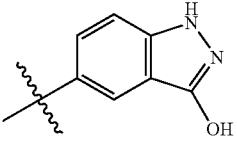 |

TABLE 2-continued
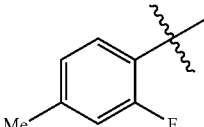
(Ie)
| Ex # | A | R<sup>11</sup> | R<sup>3</sup> |
|---|---|---|---|
| 160 | 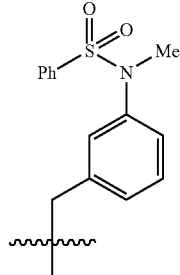 | 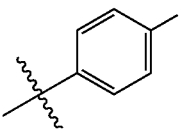 | 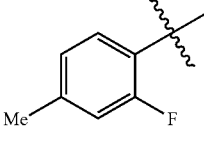 |
| 161 | 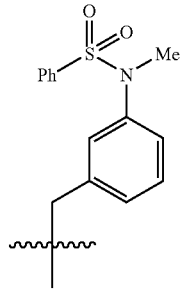 | 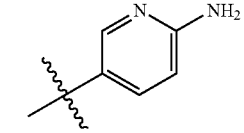 | 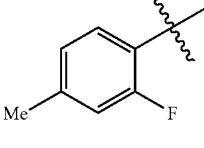 |
| 162 | 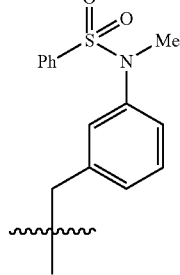 | 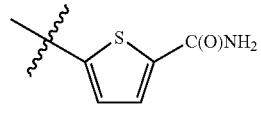 | 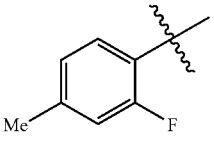 |
| 163 | 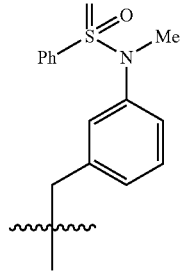 | 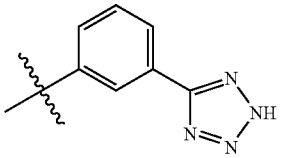 | |

TABLE 2-continued
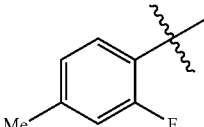
(Ie)
| Ex # | A | R[11] | R[3] |
|---|---|---|---|
| 164 | 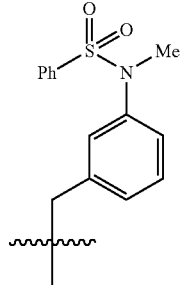 | 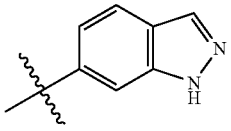 | 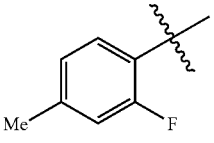 |
| 165 | 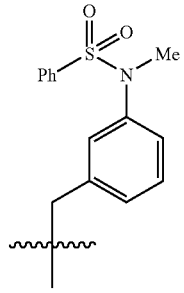 | 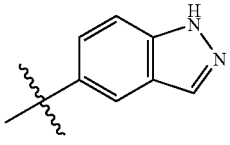 | 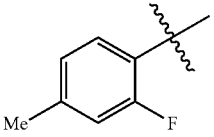 |
| 166 | 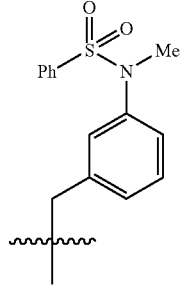 | 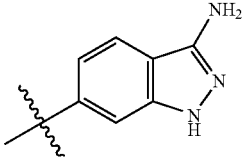 | 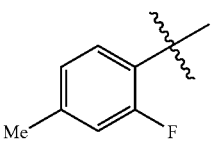 |
| 167 | 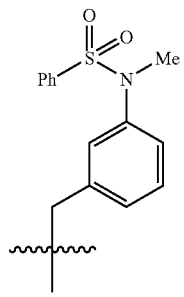 | 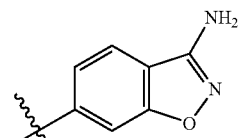 | |

TABLE 2-continued (Ie)

| Ex # | A | R<sup>11</sup> | R<sup>3</sup> |
|---|---|---|---|
| 168 | 2-F, 4-Me-phenyl | N-methyl-N-(phenylsulfonyl)-3-aminobenzyl | 3-hydroxy-1H-indazol-5-yl |
| 169 | 2-F, 4-Me-phenyl | N-(phenylsulfonyl)-3-aminobenzyl | 4-(NHCO<sub>2</sub>Me)phenyl |
| 170 | 2-F, 4-Me-phenyl | N-(phenylsulfonyl)-3-aminobenzyl | 6-amino-pyridin-3-yl |
| 171 | 2-F, 4-Me-phenyl | N-(phenylsulfonyl)-3-aminobenzyl | 5-(C(O)NH<sub>2</sub>)thiophen-2-yl |

TABLE 2-continued
(Ie)
| Ex # | A | R11 | R3 |
|---|---|---|---|
| 172 | 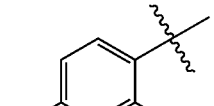 | 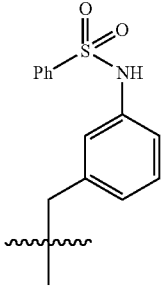 |  |
| 173 | 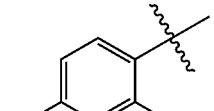 | 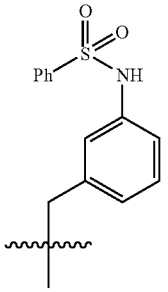 | 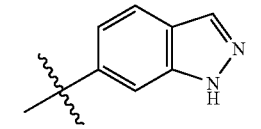 |
| 174 | 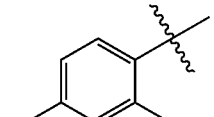 | 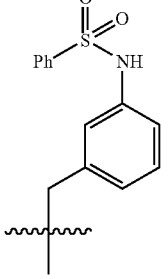 | 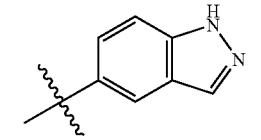 |
| 175 | 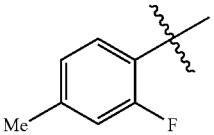 | 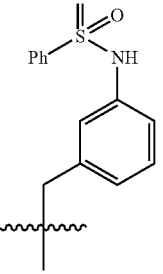 | 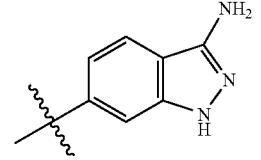 |

TABLE 2-continued (Ie) Structure: A-C(O)-NH-CH(R11)-(2-pyridyl with R3 at 4-position)

| Ex # | A | R11 | R3 |
|---|---|---|---|
| 176 | 2-F-4-Me-phenyl | 3-(PhSO2NH)-benzyl | 3-amino-benzo[d]isoxazol-6-yl |
| 177 | 2-F-4-Me-phenyl | 3-(PhSO2NH)-benzyl | 3-hydroxy-1H-indazol-5-yl |
| 178 | 2-F-4-Me-phenyl | benzyl | 4-(NHCO2Me)-phenyl |
| 179 | 2-F-4-Me-phenyl | benzyl | 6-amino-pyridin-3-yl |
| 180 | 2-F-4-Me-phenyl | benzyl | 5-(C(O)NH2)-thiophen-2-yl |
| 181 | 2-F-4-Me-phenyl | benzyl | 3-(2H-tetrazol-5-yl)-phenyl |
| 182 | 2-F-4-Me-phenyl | benzyl | 1H-indazol-6-yl |

TABLE 2-continued
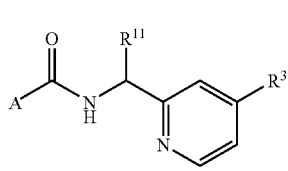
(Ie)
| Ex # | A | R[11] | R[3] |
|---|---|---|---|
| 183 | 4-Me, 2-F-phenyl | benzyl | 1H-indazol-5-yl |
| 184 | 4-Me, 2-F-phenyl | benzyl | 3-amino-1H-indazol-6-yl |
| 185 | 4-Me, 2-F-phenyl | benzyl | 3-amino-1,2-benzisoxazol-6-yl |
| 186 | 4-Me, 2-F-phenyl | benzyl | 3-hydroxy-1H-indazol-5-yl |
| 187 | 4-(H2N-CH2), 2-F-phenyl | N-methyl-N-phenyl-3-benzamidomethyl | 4-(NHCO2Me)-phenyl |
| 188 | 4-(H2N-CH2), 2-F-phenyl | N-methyl-N-phenyl-3-benzamidomethyl | 6-amino-pyridin-3-yl |

TABLE 2-continued
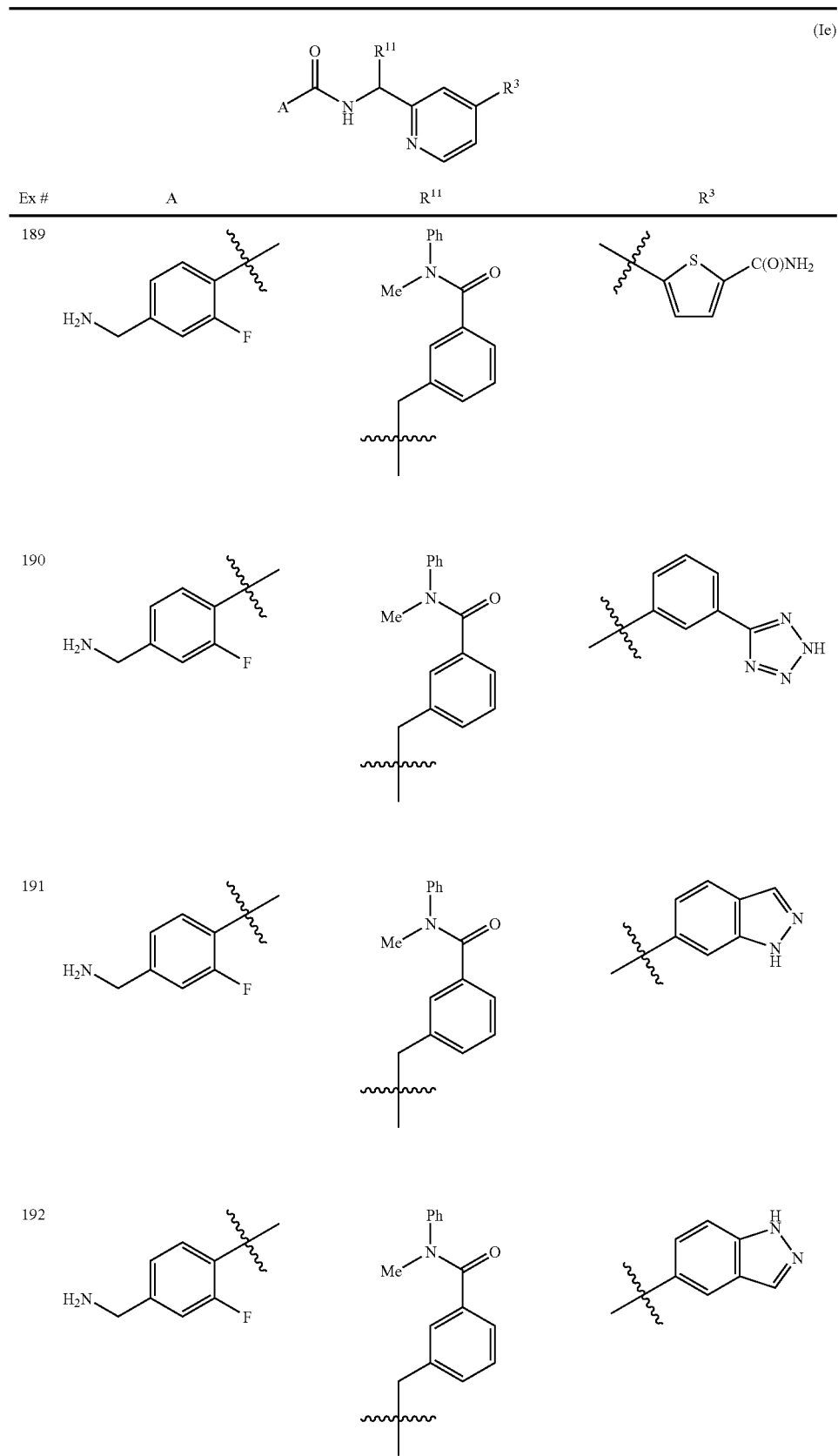

TABLE 2-continued (Ie)

| Ex # | A | R^11 | R^3 |
|---|---|---|---|
| 193 | 4-(aminomethyl)-2-fluorophenyl | N-methyl-N-phenyl-3-(methylene)benzamide | 3-amino-1H-indazol-6-yl |
| 194 | 4-(aminomethyl)-2-fluorophenyl | N-methyl-N-phenyl-3-(methylene)benzamide | 3-amino-1,2-benzisoxazol-6-yl |
| 195 | 4-(aminomethyl)-2-fluorophenyl | N-methyl-N-phenyl-3-(methylene)benzamide | 3-hydroxy-1H-indazol-5-yl |
| 196 | 4-(aminomethyl)-2-fluorophenyl | N-isopropyl-N-methyl-3-(methylene)benzamide | 4-(NHCO$_2$Me)phenyl |

TABLE 2-continued
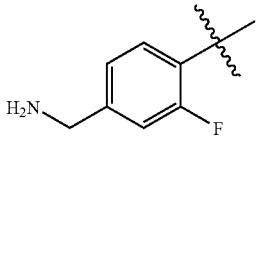
(Ie)
| Ex # | A | R[11] | R[3] |
|---|---|---|---|
| 197 | 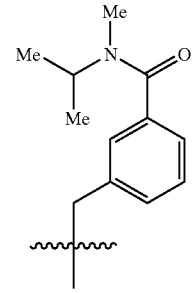 | 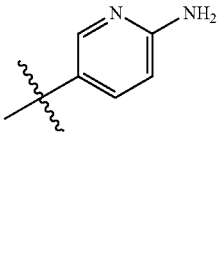 | 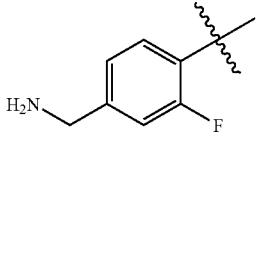 |
| 198 | 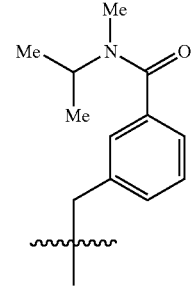 | 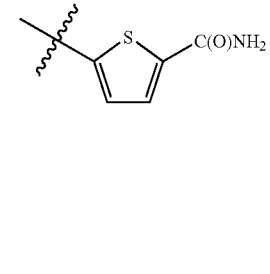 | 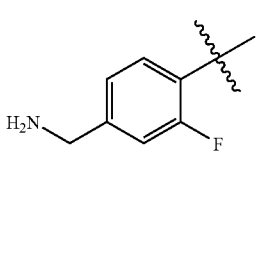 |
| 199 | 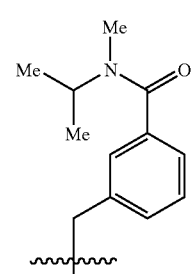 | 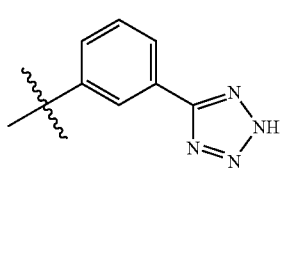 | 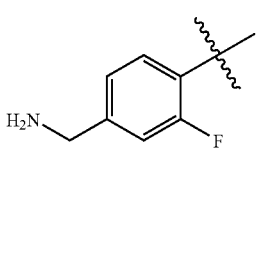 |
| 200 | 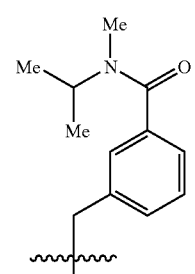 | 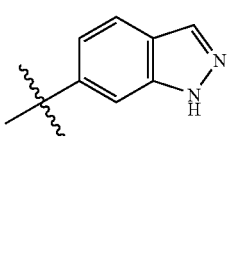 |  |

TABLE 2-continued (Ie)

| Ex # | A | R11 | R3 |
|------|---|-----|-----|
| 201 | 3-fluoro-4-(aminomethyl)phenyl (H2N-CH2- attached to phenyl with F) | N-isopropyl-N-methyl-3-substituted benzamide | 1H-indazol-5-yl |
| 202 | 3-fluoro-4-(aminomethyl)phenyl | N-isopropyl-N-methyl-3-substituted benzamide | 3-amino-1H-indazol-6-yl |
| 203 | 3-fluoro-4-(aminomethyl)phenyl | N-isopropyl-N-methyl-3-substituted benzamide | 3-amino-1,2-benzisoxazol-6-yl |
| 204 | 3-fluoro-4-(aminomethyl)phenyl | N-isopropyl-N-methyl-3-substituted benzamide | 3-hydroxy-1H-indazol-5-yl |

TABLE 2-continued
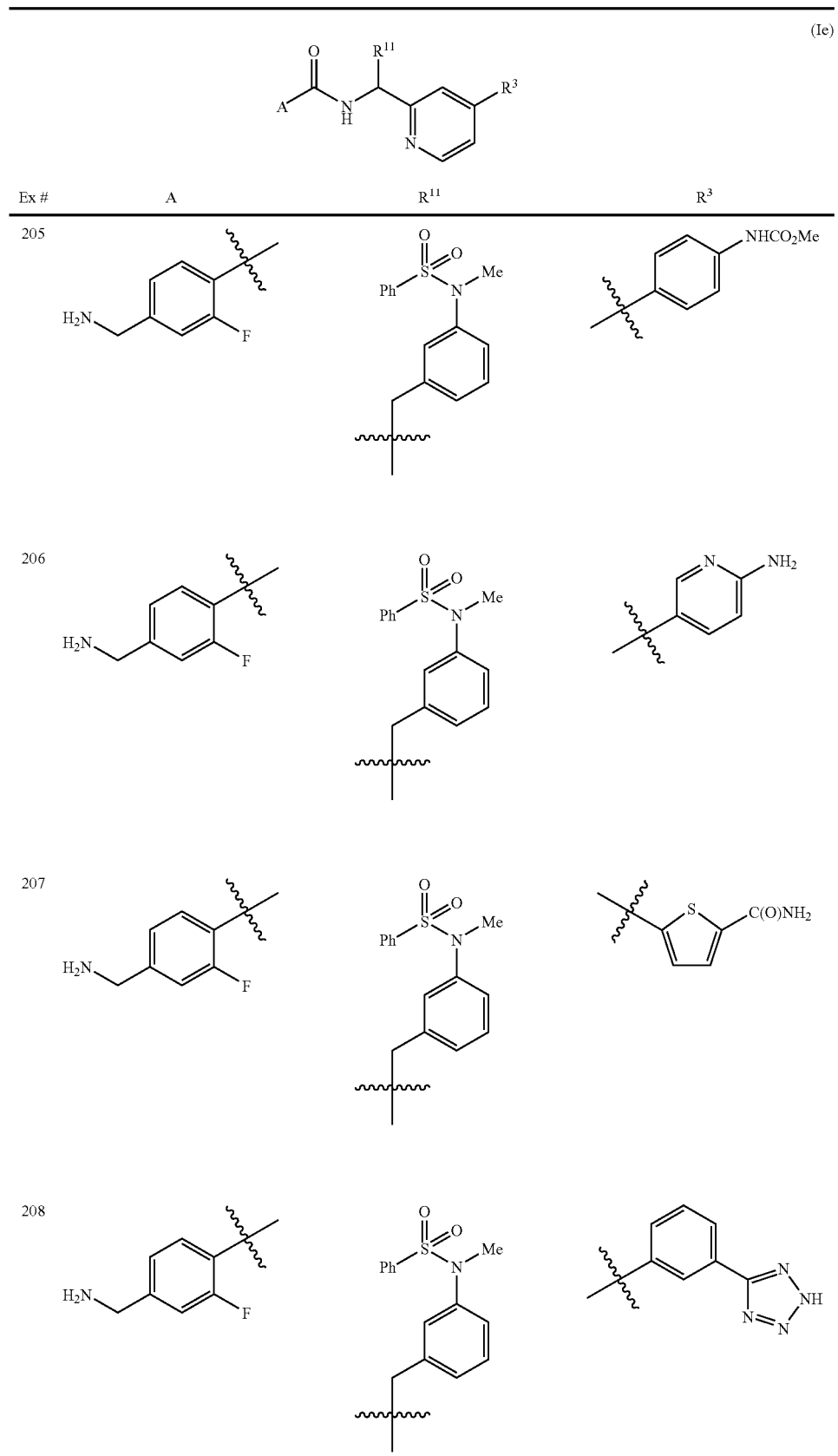

TABLE 2-continued
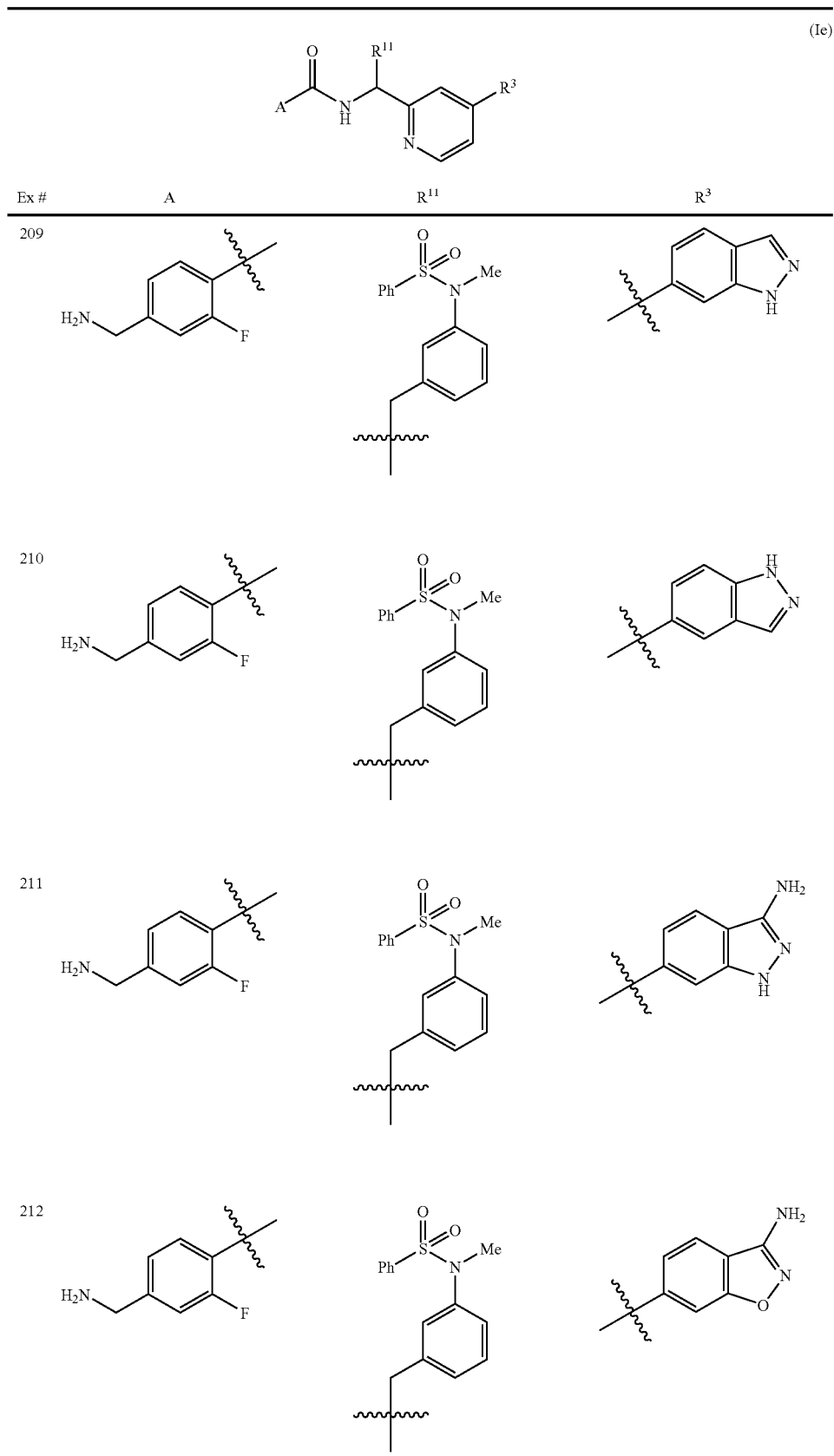

TABLE 2-continued (Ie)

| Ex # | A | R¹¹ | R³ |
|---|---|---|---|
| 213 | 4-(aminomethyl)-2-fluorophenyl | 3-[N-methyl-N-(phenylsulfonyl)amino]benzyl | 3-hydroxy-1H-indazol-5-yl |
| 214 | 4-(aminomethyl)-2-fluorophenyl | 3-[(phenylsulfonyl)amino]benzyl | 4-(NHCO₂Me)phenyl |
| 215 | 4-(aminomethyl)-2-fluorophenyl | 3-[(phenylsulfonyl)amino]benzyl | 6-amino-pyridin-3-yl |
| 216 | 4-(aminomethyl)-2-fluorophenyl | 3-[(phenylsulfonyl)amino]benzyl | 5-(C(O)NH₂)thiophen-2-yl |

TABLE 2-continued
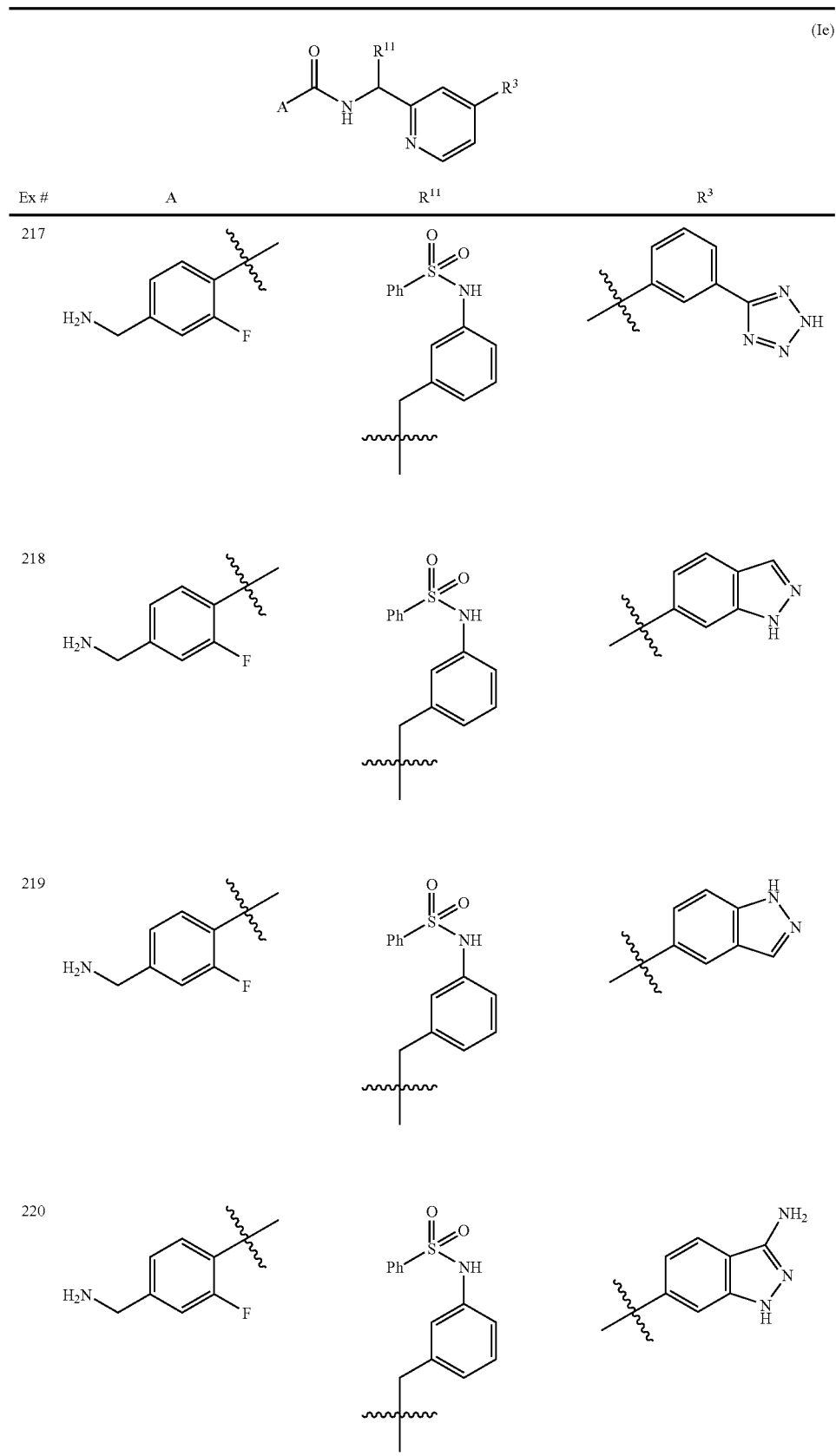

TABLE 2-continued
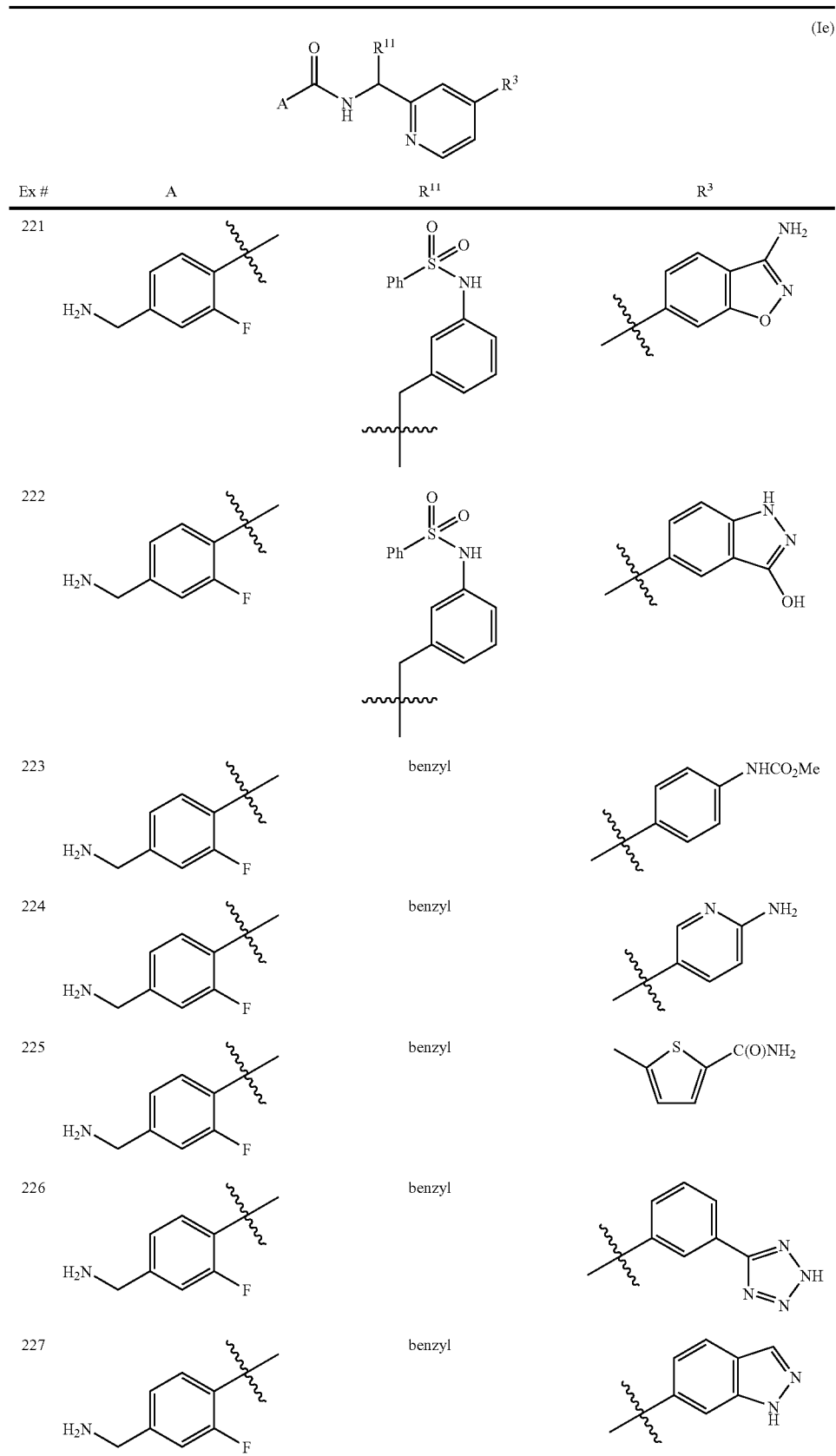

TABLE 2-continued
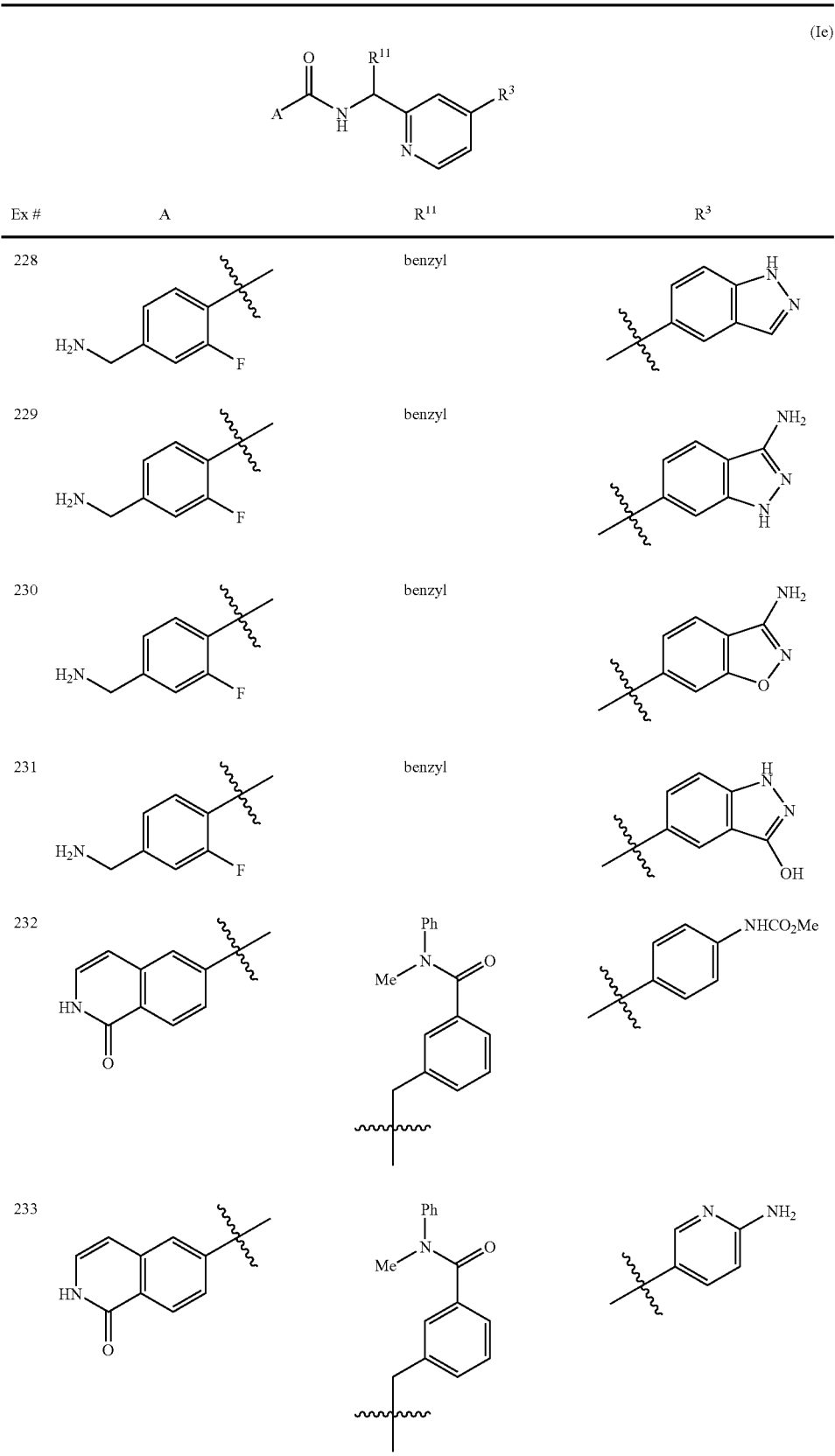

TABLE 2-continued (Ie)

| Ex # | A | R[11] | R[3] |
|---|---|---|---|
| 234 | 1-oxo-1,2-dihydroisoquinolin-6-yl | 3-(N-methyl-N-phenylcarbamoyl)benzyl | 5-carbamoylthiophen-2-yl |
| 235 | 1-oxo-1,2-dihydroisoquinolin-6-yl | 3-(N-methyl-N-phenylcarbamoyl)benzyl | 3-(2H-tetrazol-5-yl)phenyl |
| 236 | 1-oxo-1,2-dihydroisoquinolin-6-yl | 3-(N-methyl-N-phenylcarbamoyl)benzyl | 1H-indazol-6-yl |
| 237 | 1-oxo-1,2-dihydroisoquinolin-6-yl | 3-(N-methyl-N-phenylcarbamoyl)benzyl | 1H-indazol-5-yl |

TABLE 2-continued
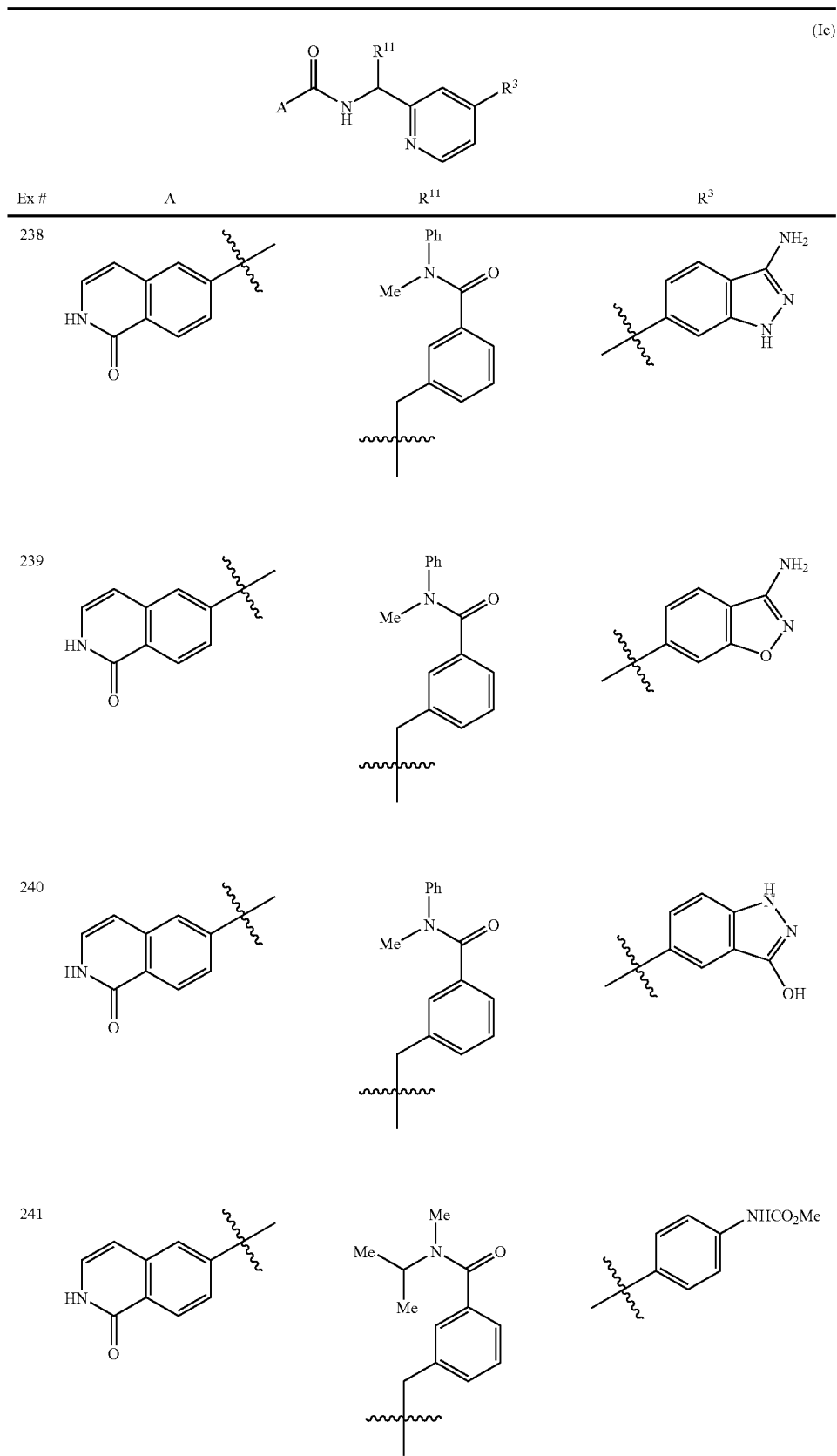

TABLE 2-continued
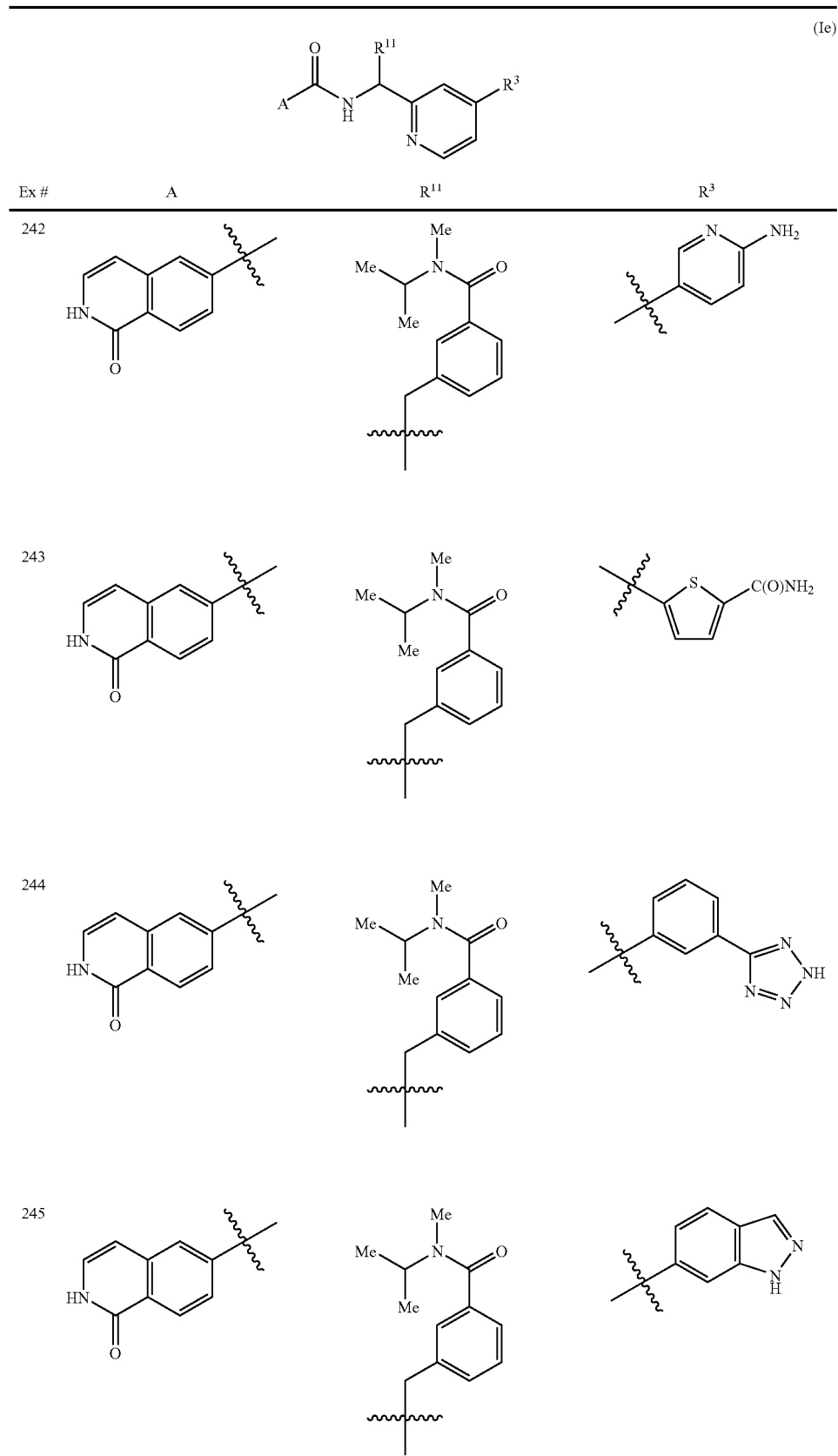

TABLE 2-continued
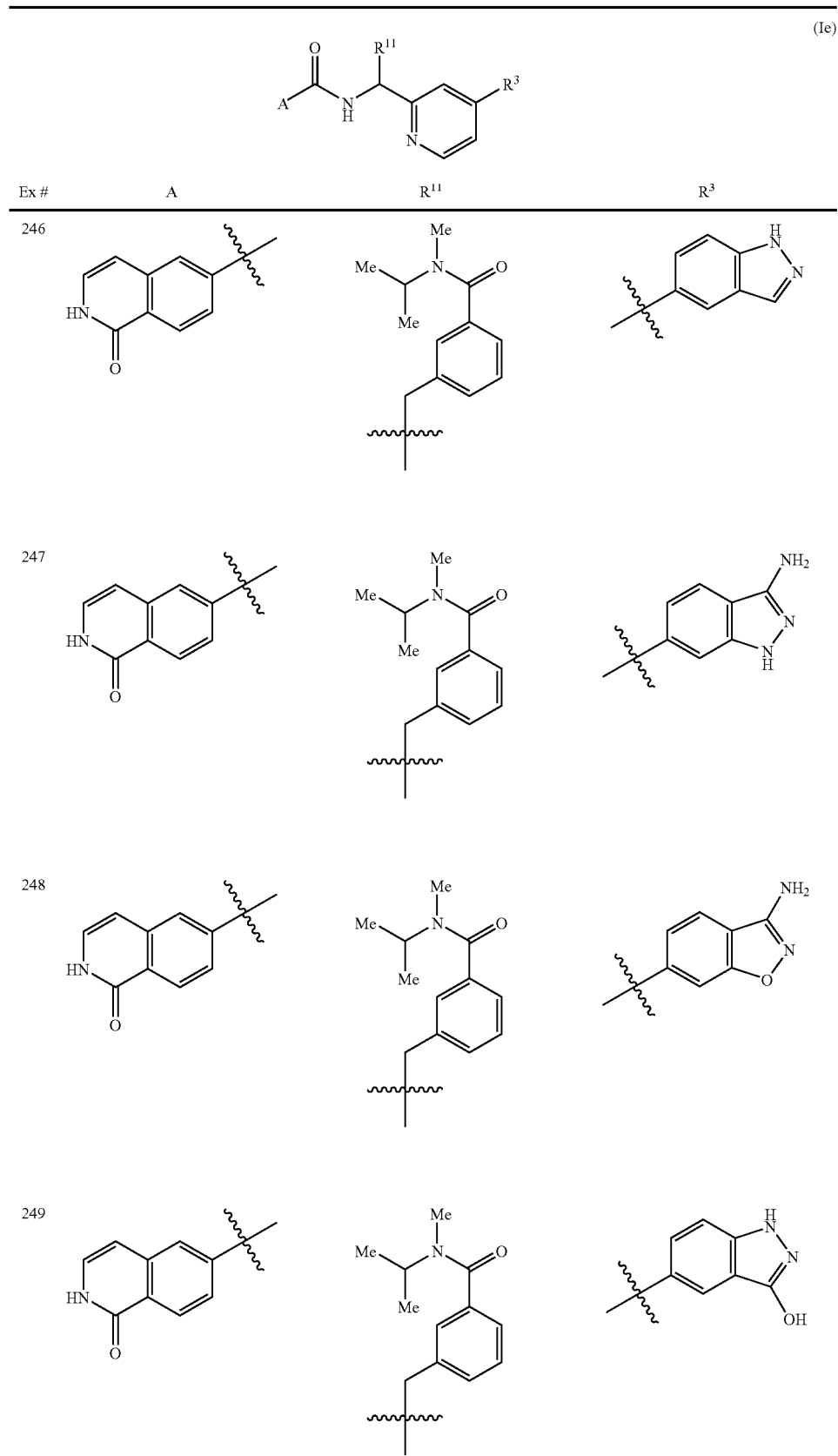

TABLE 2-continued
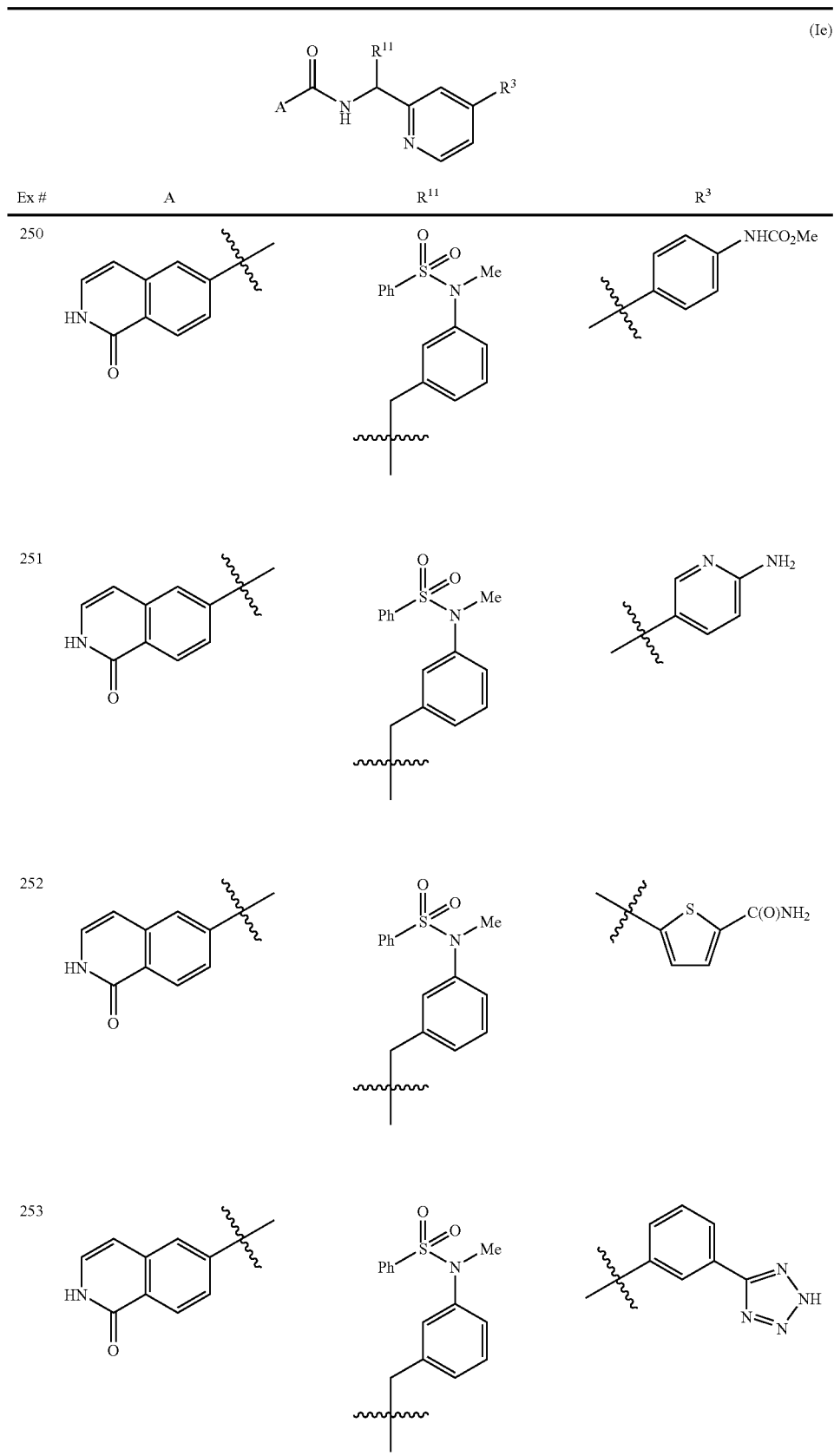

TABLE 2-continued
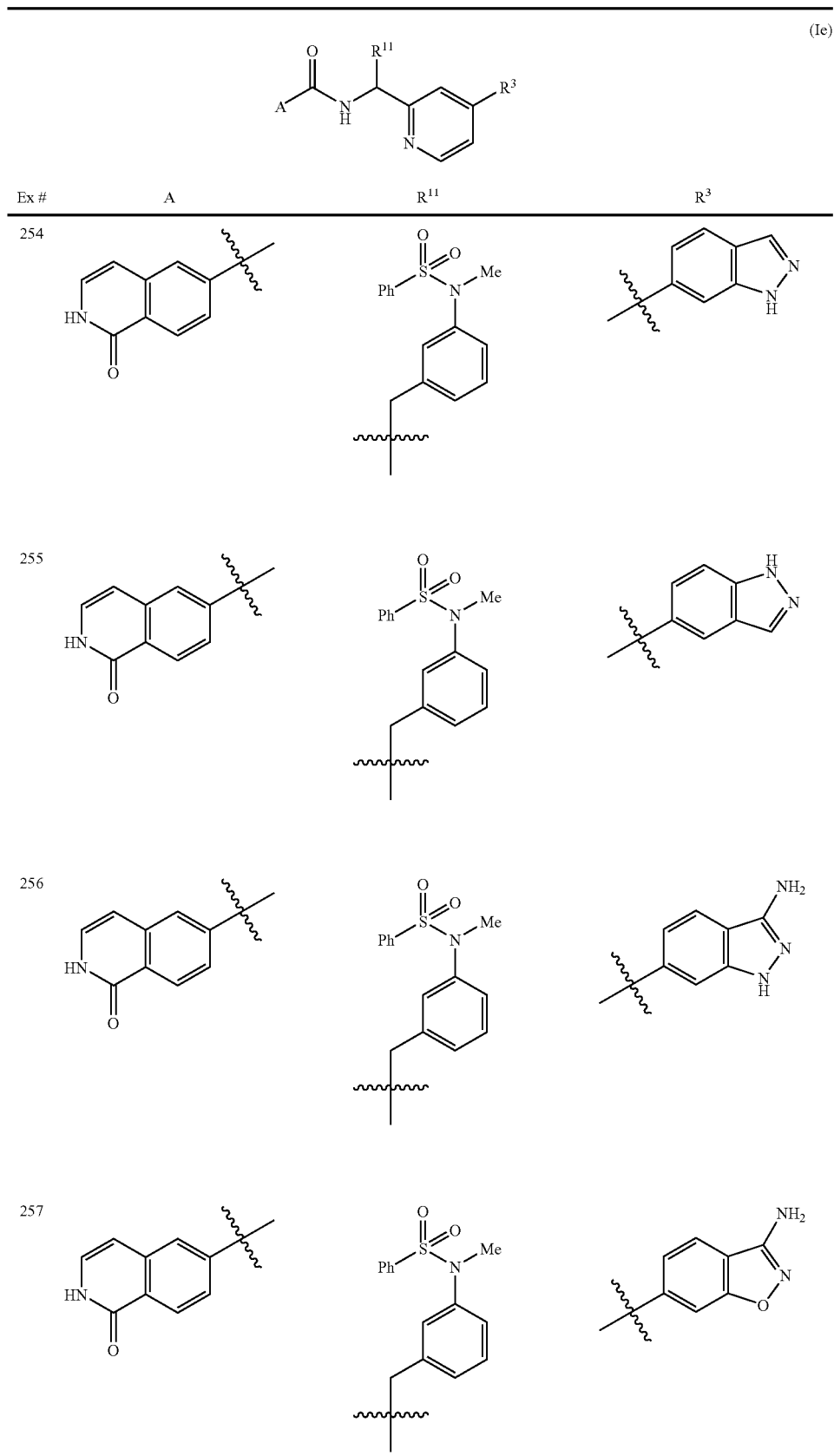

TABLE 2-continued (Ie)

| Ex # | A | R[11] | R[3] |
|---|---|---|---|
| 258 | 6-(1-oxo-1,2-dihydroisoquinolinyl) | 3-(N-methyl-N-phenylsulfonylamino)benzyl | 5-(3-hydroxy-1H-indazolyl) |
| 259 | 6-(1-oxo-1,2-dihydroisoquinolinyl) | 3-(phenylsulfonylamino)benzyl | 4-(NHCO$_2$Me)phenyl |
| 260 | 6-(1-oxo-1,2-dihydroisoquinolinyl) | 3-(phenylsulfonylamino)benzyl | 5-(2-aminopyridinyl) |
| 261 | 6-(1-oxo-1,2-dihydroisoquinolinyl) | 3-(phenylsulfonylamino)benzyl | 5-(2-carboxamidothienyl) |

TABLE 2-continued
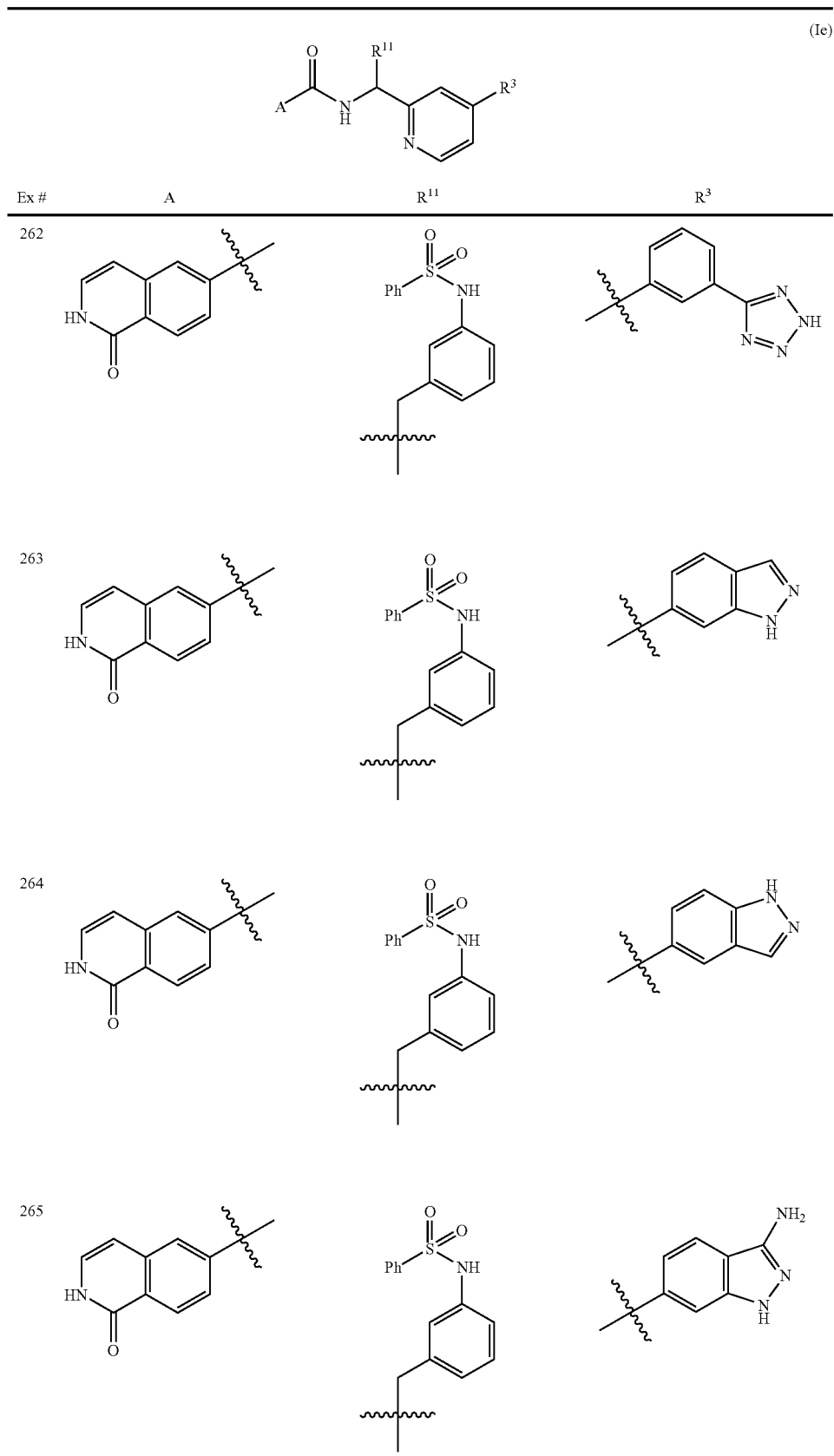

TABLE 2-continued
(Ie)
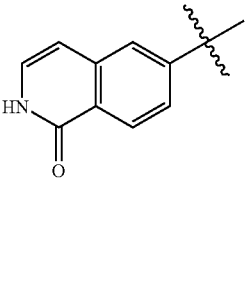
| Ex # | A | R[11] | R[3] |
|------|---|-------|------|
| 266 | 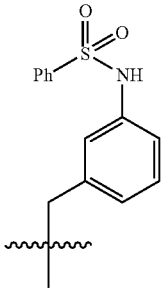 | 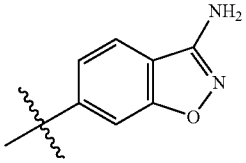 | 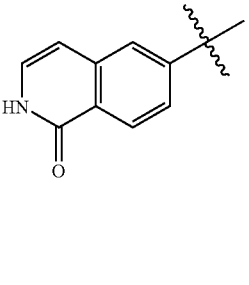 |
| 267 | 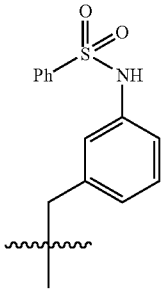 | 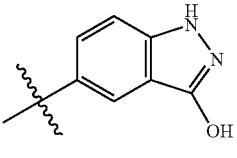 | 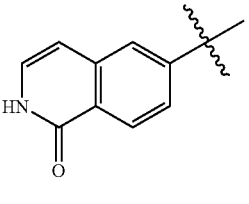 |
| 268 | 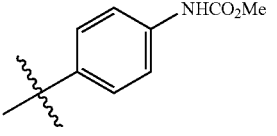 | benzyl | 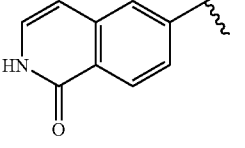 |
| 269 | 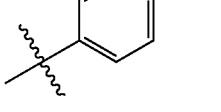 | benzyl | 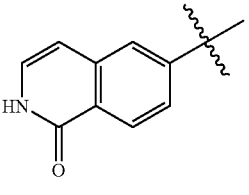 |
| 270 | 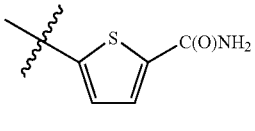 | benzyl | 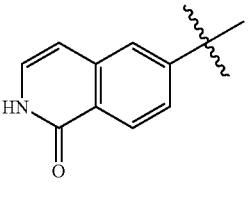 |
| 271 | 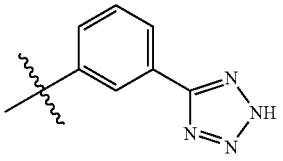 | benzyl | |

TABLE 2-continued (Ie)

| Ex # | A | R[11] | R[3] |
|---|---|---|---|
| 272 | 1-oxo-1,2-dihydroisoquinolin-6-yl | benzyl | 1H-indazol-6-yl |
| 273 | 1-oxo-1,2-dihydroisoquinolin-6-yl | benzyl | 1H-indazol-5-yl |
| 274 | 1-oxo-1,2-dihydroisoquinolin-6-yl | benzyl | 3-amino-1H-indazol-6-yl |
| 275 | 1-oxo-1,2-dihydroisoquinolin-6-yl | benzyl | 3-amino-1,2-benzisoxazol-6-yl |
| 276 | 1-oxo-1,2-dihydroisoquinolin-6-yl | benzyl | 3-hydroxy-1H-indazol-5-yl |
| 277 | 4-carbamoyl-2-fluorophenyl | N-methyl-N-phenyl-3-(methylene)benzamide | 4-(NHCO$_2$Me)phenyl |

TABLE 2-continued

| Ex # | A | R11 | R3 |
|---|---|---|---|
| 278 | 4-carbamoyl-2-fluorophenyl | N-methyl-N-phenyl-3-(methylene)benzamide | 6-amino-pyridin-3-yl |
| 279 | 4-carbamoyl-2-fluorophenyl | N-methyl-N-phenyl-3-(methylene)benzamide | 5-carbamoyl-thiophen-2-yl |
| 280 | 4-carbamoyl-2-fluorophenyl | N-methyl-N-phenyl-3-(methylene)benzamide | 3-(2H-tetrazol-5-yl)phenyl |
| 281 | 4-carbamoyl-2-fluorophenyl | N-methyl-N-phenyl-3-(methylene)benzamide | 1H-indazol-6-yl |

TABLE 2-continued (Ie)

| Ex # | A | R¹¹ | R³ |
|---|---|---|---|
| 282 | 4-carbamoyl-2-fluorophenyl | N-methyl-N-phenyl-3-(methylene)benzamide | 1H-indazol-5-yl |
| 283 | 4-carbamoyl-2-fluorophenyl | N-methyl-N-phenyl-3-(methylene)benzamide | 3-amino-1H-indazol-6-yl |
| 284 | 4-carbamoyl-2-fluorophenyl | N-methyl-N-phenyl-3-(methylene)benzamide | 3-amino-1,2-benzisoxazol-6-yl |
| 285 | 4-carbamoyl-2-fluorophenyl | N-methyl-N-phenyl-3-(methylene)benzamide | 3-hydroxy-1H-indazol-5-yl |

TABLE 2-continued
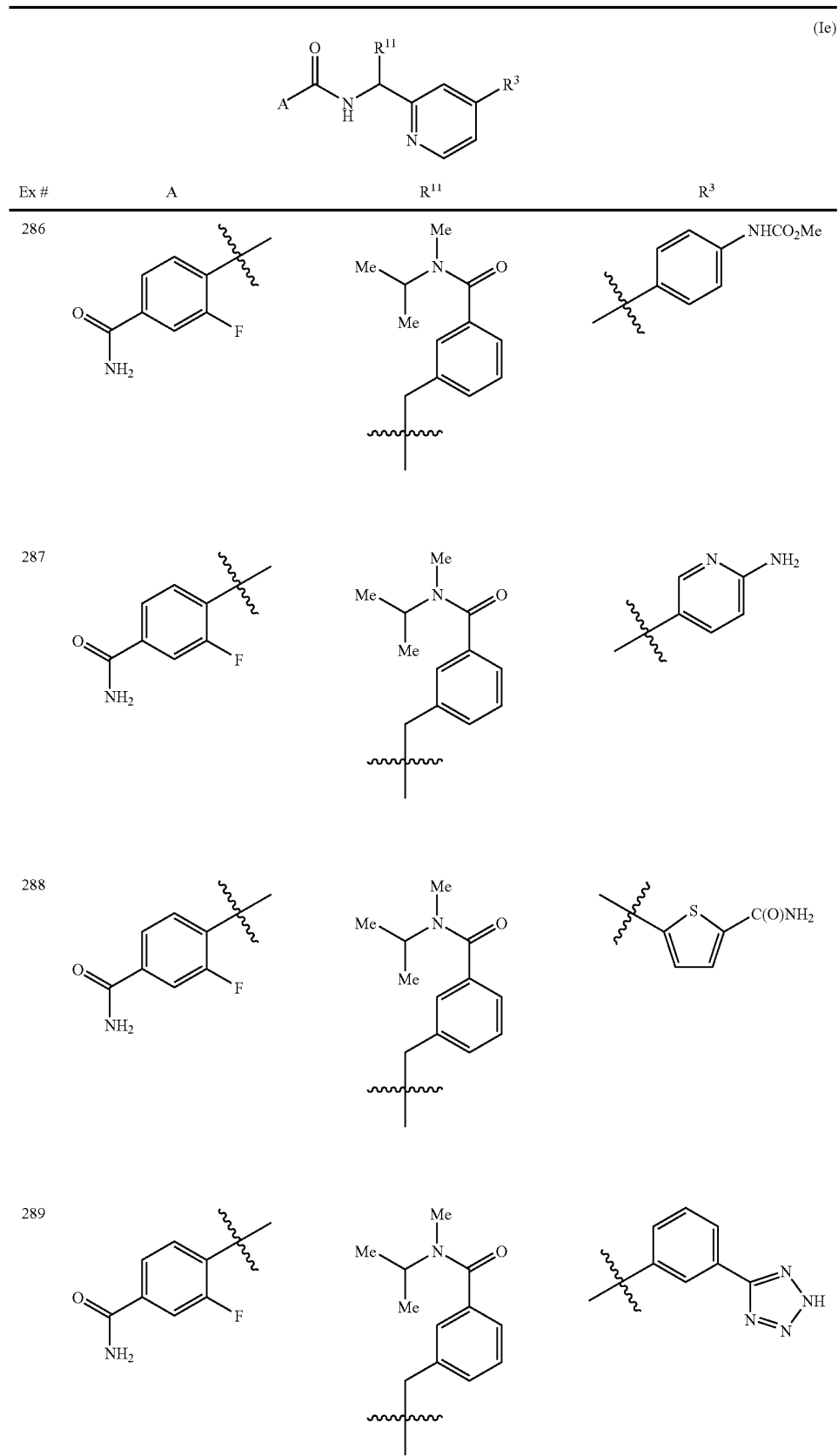

TABLE 2-continued
(Ie)
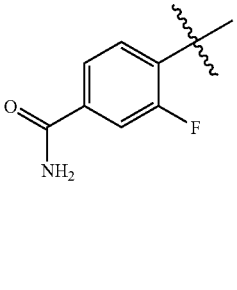
| Ex # | A | R¹¹ | R³ |
|------|---|-----|-----|
| 290 | 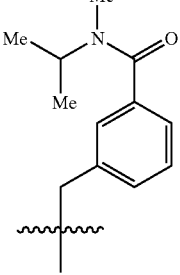 | 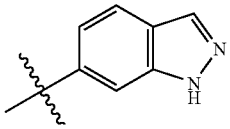 | 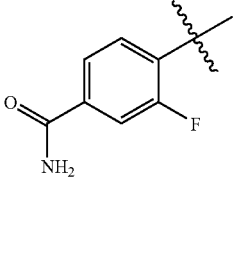 |
| 291 | 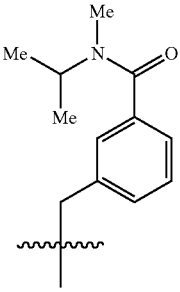 | 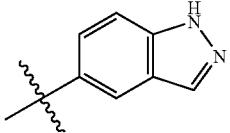 | 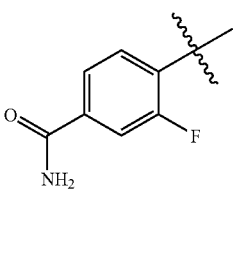 |
| 292 | 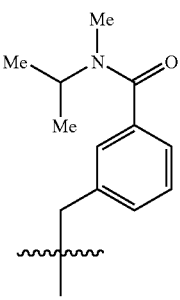 | 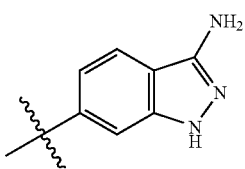 | 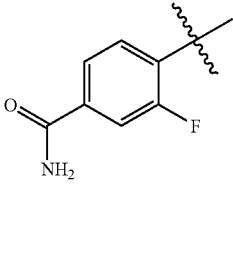 |
| 293 | 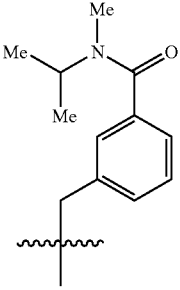 | 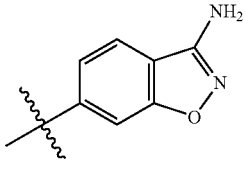 | |

TABLE 2-continued (Ie)

| Ex # | A | R¹¹ | R³ |
|---|---|---|---|
| 294 | 4-carbamoyl-2-fluorophenyl | N-isopropyl-N-methyl-3-(methylene)benzamide | 5-(1H-indazol-3-ol-5-yl) |
| 295 | 4-carbamoyl-2-fluorophenyl | N-methyl-N-(3-(methylene)phenyl)benzenesulfonamide | 4-(NHCO₂Me)phenyl |
| 296 | 4-carbamoyl-2-fluorophenyl | N-methyl-N-(3-(methylene)phenyl)benzenesulfonamide | 6-aminopyridin-3-yl |
| 297 | 4-carbamoyl-2-fluorophenyl | N-methyl-N-(3-(methylene)phenyl)benzenesulfonamide | 5-(C(O)NH₂)thiophen-2-yl |

TABLE 2-continued (Ie)

| Ex # | A | R¹¹ | R³ |
|---|---|---|---|
| 298 | 4-carbamoyl-2-fluorophenyl | N-methyl-N-(3-methylenephenyl)benzenesulfonamide | 3-(2H-tetrazol-5-yl)phenyl |
| 299 | 4-carbamoyl-2-fluorophenyl | N-methyl-N-(3-methylenephenyl)benzenesulfonamide | 1H-indazol-6-yl |
| 300 | 4-carbamoyl-2-fluorophenyl | N-methyl-N-(3-methylenephenyl)benzenesulfonamide | 1H-indazol-5-yl |
| 301 | 4-carbamoyl-2-fluorophenyl | N-methyl-N-(3-methylenephenyl)benzenesulfonamide | 3-amino-1H-indazol-6-yl |

TABLE 2-continued (Ie)

| Ex # | A | R11 | R3 |
|---|---|---|---|
| 302 | 4-carbamoyl-2-fluorophenyl | 3-(N-methyl-N-phenylsulfonylamino)benzyl | 6-(3-amino-1,2-benzisoxazolyl) |
| 303 | 4-carbamoyl-2-fluorophenyl | 3-(N-methyl-N-phenylsulfonylamino)benzyl | 5-(3-hydroxy-1H-indazolyl) |
| 304 | 4-carbamoyl-2-fluorophenyl | 3-(phenylsulfonylamino)benzyl | 4-(NHCO2Me)phenyl |
| 305 | 4-carbamoyl-2-fluorophenyl | 3-(phenylsulfonylamino)benzyl | 5-(2-aminopyridyl) |

TABLE 2-continued (Ie)

| Ex # | A | R¹¹ | R³ |
|---|---|---|---|
| 306 | 4-carbamoyl-3-fluorophenyl | 3-(PhS(O)₂NH)benzyl (via CH) | 5-(C(O)NH₂)thiophen-2-yl |
| 307 | 4-carbamoyl-3-fluorophenyl | 3-(PhS(O)₂NH)benzyl (via CH) | 3-(2H-tetrazol-5-yl)phenyl |
| 308 | 4-carbamoyl-3-fluorophenyl | 3-(PhS(O)₂NH)benzyl (via CH) | 1H-indazol-6-yl |
| 309 | 4-carbamoyl-3-fluorophenyl | 3-(PhS(O)₂NH)benzyl (via CH) | 1H-indazol-5-yl |

TABLE 2-continued (Ie)

| Ex # | A | R¹¹ | R³ |
|---|---|---|---|
| 310 | 4-carbamoyl-2-fluorophenyl | N-(3-substituted-phenyl)benzenesulfonamide (CH₂ linker) | 3-amino-1H-indazol-6-yl |
| 311 | 4-carbamoyl-2-fluorophenyl | N-(3-substituted-phenyl)benzenesulfonamide (CH₂ linker) | 3-amino-1,2-benzisoxazol-6-yl |
| 312 | 4-carbamoyl-2-fluorophenyl | N-(3-substituted-phenyl)benzenesulfonamide (CH₂ linker) | 3-hydroxy-1H-indazol-5-yl |
| 313 | 4-carbamoyl-2-fluorophenyl | benzyl | 4-(NHCO₂Me)phenyl |
| 314 | 4-carbamoyl-2-fluorophenyl | benzyl | 6-aminopyridin-3-yl |

TABLE 2-continued
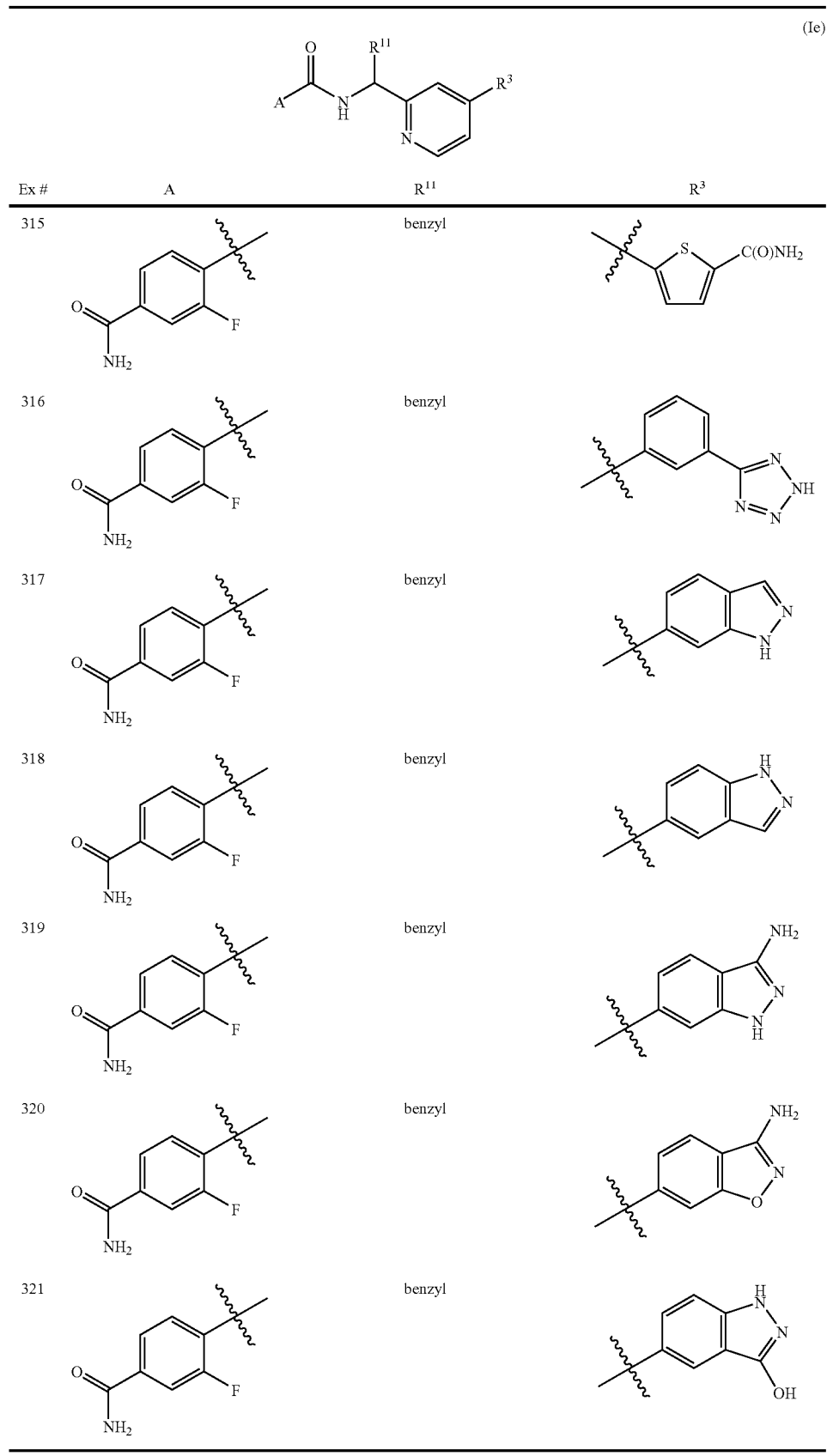

TABLE 3

(Ie)

| Ex # | A | R[11] | R[3] |
|---|---|---|---|
| 322 | 4-(aminomethyl)cyclohexyl | benzyl | 2-amino-5-yl benzamide |
| 323 | 4-(aminomethyl)cyclohexyl | benzyl | 1H-indazol-6-yl |
| 324 | 4-(aminomethyl)cyclohexyl | benzyl | benzo[d]isoxazol-6-yl |
| 325 | 4-(aminomethyl)cyclohexyl | benzyl | 4-carbamoyl-3-methoxyphenyl |
| 326 | 4-(aminomethyl)cyclohexyl | benzyl | 4-carbamoyl-3-hydroxyphenyl |
| 327 | 4-(aminomethyl)cyclohexyl | benzyl | 6-aminopyridin-2-yl |
| 328 | 4-(aminomethyl)cyclohexyl | benzyl | 4-aminopyrimidin-2-yl |

TABLE 3-continued (Ie)

| Ex # | A | R¹¹ | R³ |
|---|---|---|---|
| 329 | H₂N-cyclohexyl-CH₂- | benzyl | 2-amino-pyrimidin-4-yl |
| 330 | H₂N-cyclohexyl-CH₂- | benzyl | 2-amino-6-methoxy-pyridin-4-yl |
| 331 | H₂N-cyclohexyl-CH₂- | benzyl | 6-amino-pyrimidin-4-yl |
| 332 | H₂N-cyclohexyl-CH₂- | benzyl | 2-amino-pyrimidin-5-yl |
| 333 | H₂N-cyclohexyl-CH₂- | benzyl | 2-carboxamido-pyridin-4-yl |
| 334 | H₂N-cyclohexyl-CH₂- | benzyl | 2-carboxy-pyridin-4-yl |
| 335 | H₂N-cyclohexyl-CH₂- | benzyl | 6-carboxamido-pyridin-3-yl |

TABLE 3-continued

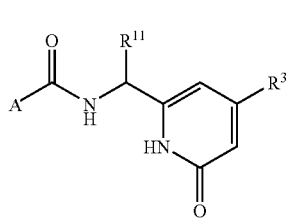

| Ex # | A | R$^{11}$ | R$^3$ |
|---|---|---|---|
| 336 | 4-(aminomethyl)cyclohexyl | benzyl | 3-amino-1H-pyrazol-5-yl |
| 337 | 4-(aminomethyl)cyclohexyl | benzyl | 2-methyl-3-oxo-2,3-dihydro-1H-indazol-5-yl |
| 338 | 4-(aminomethyl)cyclohexyl | benzyl | 3-methoxy-1H-indazol-5-yl |
| 339 | 4-(aminomethyl)cyclohexyl | benzyl | 2,3-dioxoindolin-5-yl |
| 340 | 4-(aminomethyl)cyclohexyl | benzyl | 3-hydroxy-2-oxoindolin-5-yl |
| 341 | 1-aminoisoquinolin-6-yl | benzyl | 3-aminobenzo[d]isoxazol-6-yl |
| 342 | 4-carbamoylphenyl | benzyl | 3-aminobenzo[d]isoxazol-6-yl |

TABLE 3-continued (Ie)

| Ex # | A | R¹¹ | R³ |
|---|---|---|---|
| 343 | 4-(aminomethyl)phenyl | benzyl | 3-amino-1,2-benzisoxazol-6-yl |
| 344 | 3-amino-1H-indazol-6-yl | benzyl | 3-amino-1,2-benzisoxazol-6-yl |
| 345 | 3-amino-1,2-benzisoxazol-6-yl | benzyl | 3-amino-1,2-benzisoxazol-6-yl |
| 346 | trans-4-(aminomethyl)cyclohexyl | 3-[N-methyl-N-phenylcarbamoyl]benzyl | 3-amino-1,2-benzisoxazol-6-yl |
| 347 | trans-4-(aminomethyl)cyclohexyl | benzyl | 4-aminoquinazolin-7-yl |
| 348 | trans-4-(aminomethyl)cyclohexyl | benzyl | 2,4-diaminoquinazolin-7-yl |

TABLE 3-continued (Ie)

| Ex # | A | R11 | R3 |
|---|---|---|---|
| 349 | trans-4-(aminomethyl)cyclohexyl | PhS(O)2NH-(3-substituted phenyl)methyl | 3-amino-1,2-benzisoxazol-6-yl |
| 350 | trans-4-(aminomethyl)cyclohexyl | N-Bn-N-Me-3-substituted benzamide | 3-amino-1,2-benzisoxazol-6-yl |
| 351 | trans-4-(aminomethyl)cyclohexyl | N-(2-phenylethyl)-N-Me-3-substituted benzamide | 3-amino-1,2-benzisoxazol-6-yl |
| 352 | trans-4-(aminomethyl)cyclohexyl | N-[2-(4-chlorophenyl)ethyl]-3-substituted benzamide | 3-amino-1,2-benzisoxazol-6-yl |

TABLE 3-continued (Ie)

| Ex # | A | R11 | R3 |
|---|---|---|---|
| 353 | trans-4-(aminomethyl)cyclohexyl | N-isopropyl-N-methyl-3-benzamide (CH2 linker) | 3-amino-1,2-benzisoxazol-6-yl |
| 354 | trans-4-(aminomethyl)cyclohexyl | N-cyclopropyl-N-methyl-3-benzamide (CH2 linker) | 3-amino-1,2-benzisoxazol-6-yl |
| 355 | trans-4-(aminomethyl)cyclohexyl | N-methyl-N-(phenylsulfonyl)-3-aminophenyl (CH2 linker) | 3-amino-1,2-benzisoxazol-6-yl |
| 356 | 1-amino-5,6,7,8-tetrahydroisoquinolin-6-yl | N-methyl-N-phenyl-3-benzamide (CH2 linker) | 4-(NHCO2Me)phenyl |

TABLE 3-continued (Ie)

| Ex # | A | R[11] | R[3] |
|------|---|-------|------|
| 357 | 1-amino-tetrahydroisoquinolin-6-yl | 3-(N-methyl-N-phenylcarbamoyl)benzyl | 6-aminopyridin-3-yl |
| 358 | 1-amino-tetrahydroisoquinolin-6-yl | 3-(N-methyl-N-phenylcarbamoyl)benzyl | 5-(aminocarbonyl)thiophen-2-yl |
| 359 | 1-amino-tetrahydroisoquinolin-6-yl | 3-(N-methyl-N-phenylcarbamoyl)benzyl | 3-(2H-tetrazol-5-yl)phenyl |
| 360 | 1-amino-tetrahydroisoquinolin-6-yl | 3-(N-methyl-N-phenylcarbamoyl)benzyl | 1H-indazol-6-yl |

TABLE 3-continued (Ie)

| Ex # | A | R¹¹ | R³ |
|------|---|-----|-----|
| 361 | 1-amino-tetrahydroisoquinolin-6-yl | 3-[(N-methyl-N-phenyl)carbamoyl]benzyl | 1H-indazol-5-yl |
| 362 | 1-amino-tetrahydroisoquinolin-6-yl | 3-[(N-methyl-N-phenyl)carbamoyl]benzyl | 3-amino-1H-indazol-6-yl |
| 363 | 1-amino-tetrahydroisoquinolin-6-yl | 3-[(N-methyl-N-phenyl)carbamoyl]benzyl | 3-amino-1,2-benzisoxazol-6-yl |
| 364 | 1-amino-tetrahydroisoquinolin-6-yl | 3-[(N-methyl-N-phenyl)carbamoyl]benzyl | 3-hydroxy-1H-indazol-5-yl |

TABLE 3-continued
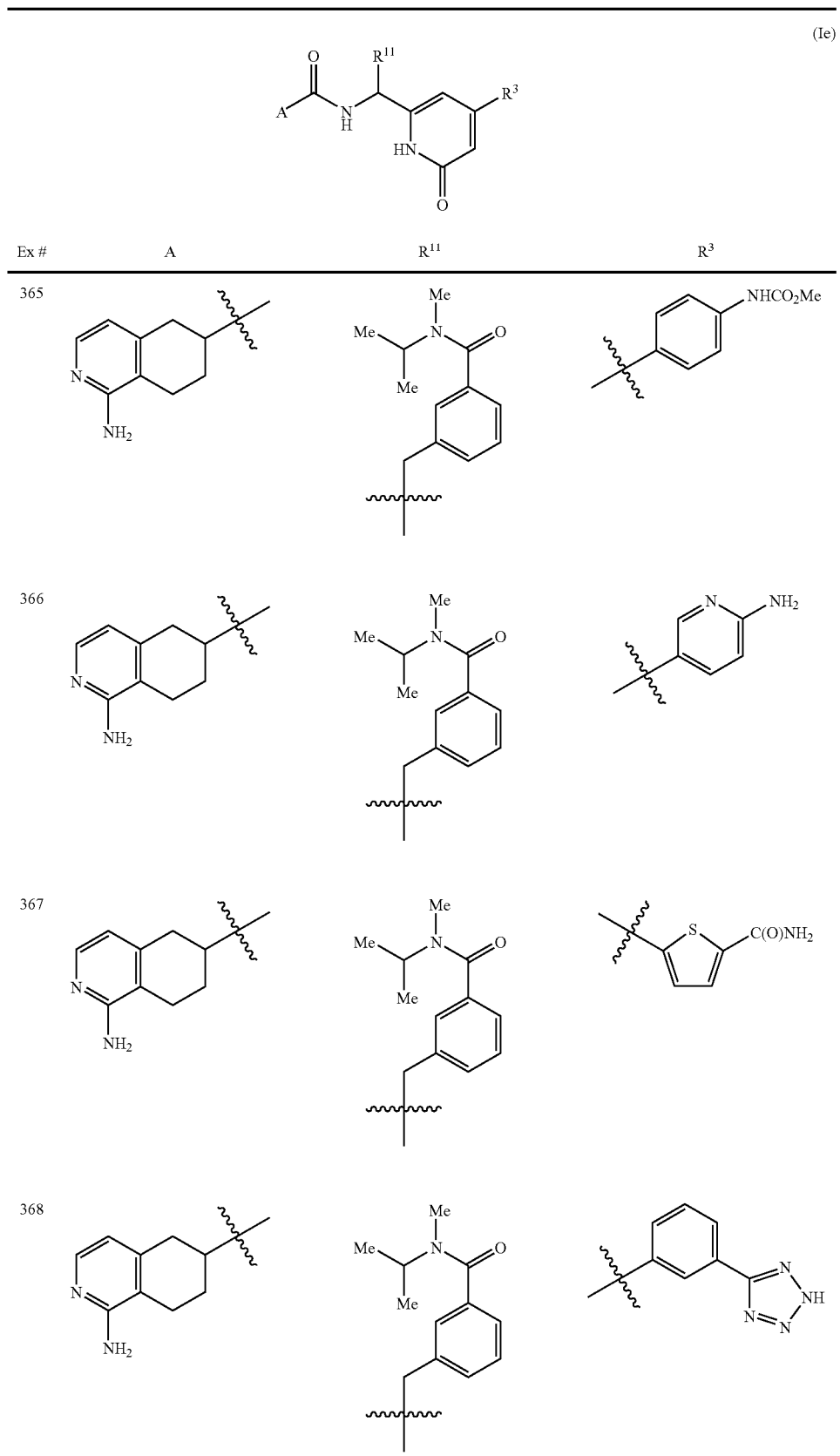

TABLE 3-continued
(Ie)
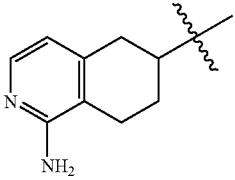
| Ex # | A | R11 | R3 |
|---|---|---|---|
| 369 | 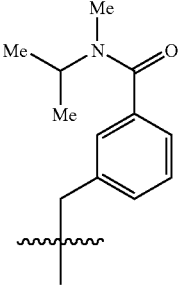 | 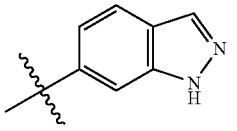 | 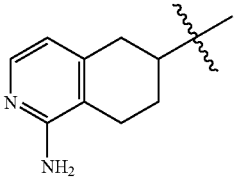 |
| 370 | 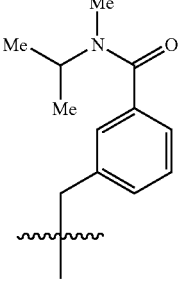 | 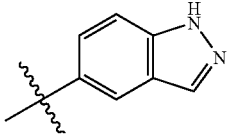 | 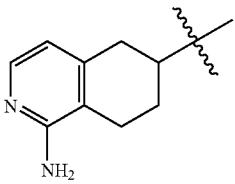 |
| 371 | 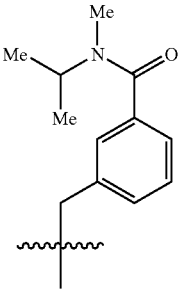 | 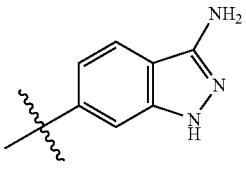 | 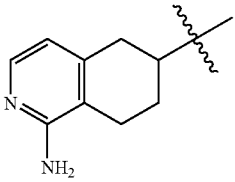 |
| 372 | 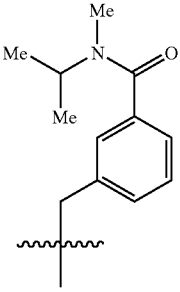 | 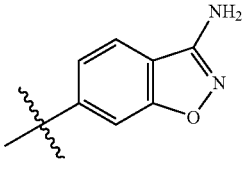 | |

TABLE 3-continued
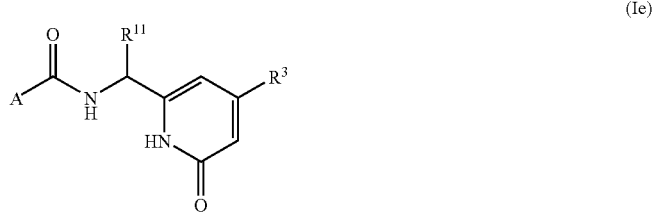
| Ex # | A | R[11] | R[3] |
|---|---|---|---|
| 373 | | | |
| 374 | | | |
| 375 | | | |
| 376 | | | |

TABLE 3-continued

| Ex # | A | R¹¹ | R³ |
|---|---|---|---|
| 377 | 1-amino-tetrahydroisoquinolin-6-yl | N-methyl-N-(3-methylenephenyl)benzenesulfonamide | 3-(2H-tetrazol-5-yl)phenyl |
| 378 | 1-amino-tetrahydroisoquinolin-6-yl | N-methyl-N-(3-methylenephenyl)benzenesulfonamide | 1H-indazol-6-yl |
| 379 | 1-amino-tetrahydroisoquinolin-6-yl | N-methyl-N-(3-methylenephenyl)benzenesulfonamide | 1H-indazol-5-yl |
| 380 | 1-amino-tetrahydroisoquinolin-6-yl | N-methyl-N-(3-methylenephenyl)benzenesulfonamide | 3-amino-1H-indazol-6-yl |

TABLE 3-continued (Ie)

| Ex # | A | R¹¹ | R³ |
|---|---|---|---|
| 381 | 1-amino-5,6,7,8-tetrahydroisoquinolin-6-yl | PhSO₂N(Me)-(3-benzyl) | 3-amino-1,2-benzisoxazol-6-yl |
| 382 | 1-amino-5,6,7,8-tetrahydroisoquinolin-6-yl | PhSO₂N(Me)-(3-benzyl) | 3-hydroxy-1H-indazol-5-yl |
| 383 | 1-amino-5,6,7,8-tetrahydroisoquinolin-6-yl | PhSO₂NH-(3-benzyl) | 4-(NHCO₂Me)phenyl |
| 384 | 1-amino-5,6,7,8-tetrahydroisoquinolin-6-yl | PhSO₂NH-(3-benzyl) | 6-aminopyridin-3-yl |

TABLE 3-continued (Ie)

| Ex # | A | R¹¹ | R³ |
|---|---|---|---|
| 385 | 1-amino-tetrahydroisoquinolin-6-yl | 3-(phenylsulfonylamino)benzyl | 5-(aminocarbonyl)thiophen-2-yl |
| 386 | 1-amino-tetrahydroisoquinolin-6-yl | 3-(phenylsulfonylamino)benzyl | 3-(2H-tetrazol-5-yl)phenyl |
| 387 | 1-amino-tetrahydroisoquinolin-6-yl | 3-(phenylsulfonylamino)benzyl | 1H-indazol-6-yl |
| 388 | 1-amino-tetrahydroisoquinolin-6-yl | 3-(phenylsulfonylamino)benzyl | 1H-indazol-5-yl |

TABLE 3-continued
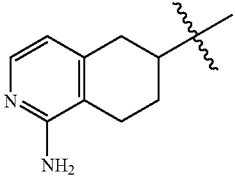
(Ie)
| Ex # | A | R11 | R3 |
|---|---|---|---|
| 389 | 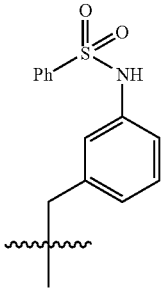 | 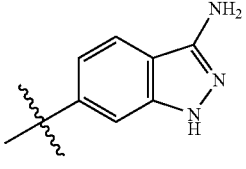 | 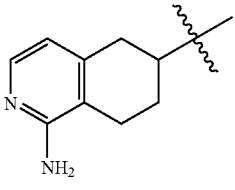 |
| 390 | 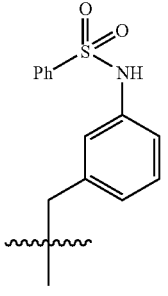 | 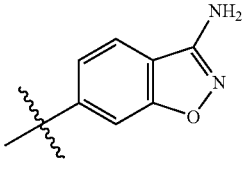 | 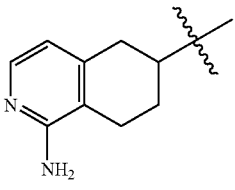 |
| 391 | 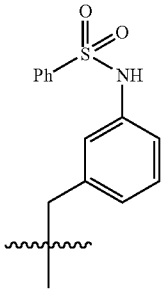 | 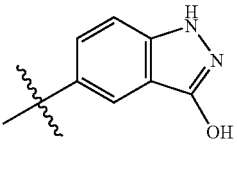 | 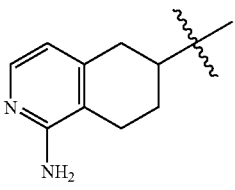 |
| 392 | 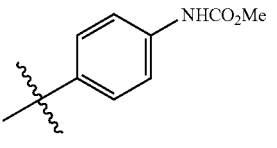 | benzyl | 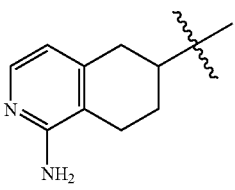 |
| 393 | 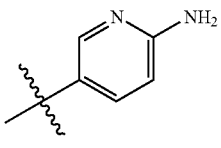 | benzyl | 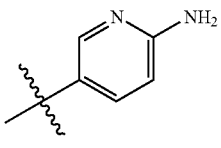 |

TABLE 3-continued

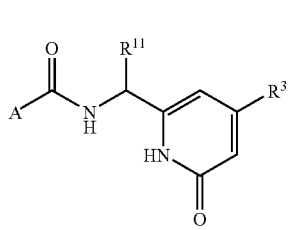

(Ie)

| Ex # | A | R[11] | R[3] |
|---|---|---|---|
| 394 | 1-amino-tetrahydroisoquinolin-6-yl | benzyl | 5-(aminocarbonyl)thiophen-2-yl |
| 395 | 1-amino-tetrahydroisoquinolin-6-yl | benzyl | 3-(2H-tetrazol-5-yl)phenyl |
| 396 | 1-amino-tetrahydroisoquinolin-6-yl | benzyl | 1H-indazol-6-yl |
| 397 | 1-amino-tetrahydroisoquinolin-6-yl | benzyl | 1H-indazol-5-yl |
| 398 | 1-amino-tetrahydroisoquinolin-6-yl | benzyl | 3-amino-1H-indazol-6-yl |
| 399 | 1-amino-tetrahydroisoquinolin-6-yl | benzyl | 3-amino-1,2-benzisoxazol-6-yl |

TABLE 3-continued
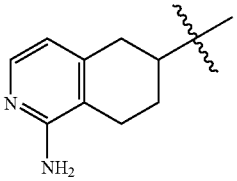
| Ex # | A | R<sup>11</sup> | R<sup>3</sup> |
|---|---|---|---|
| 400 | 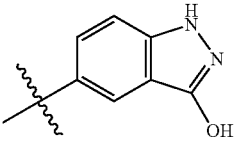 | benzyl | 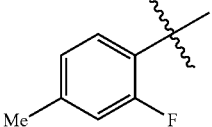 |
| 401 | 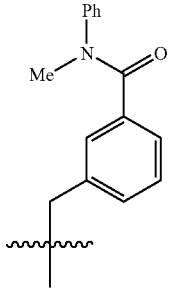 | 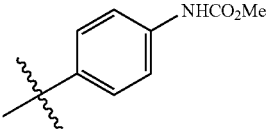 | 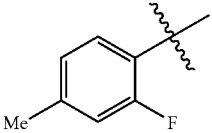 |
| 402 | 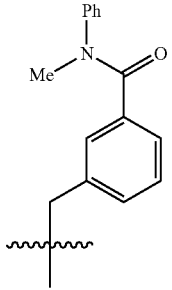 | 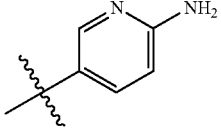 | 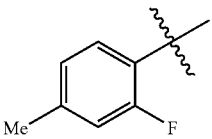 |
| 403 | 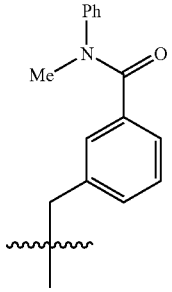 | 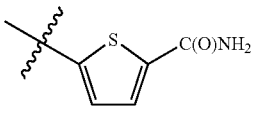 | (not shown) |

TABLE 3-continued
| Ex # | A | R[11] | R[3] |
|---|---|---|---|
| 404 | 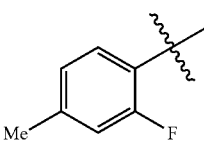 | 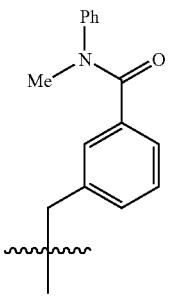 |  |
| 405 | 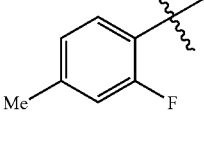 | 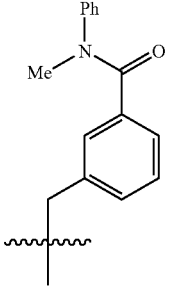 | 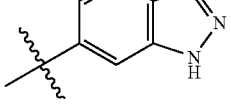 |
| 406 | 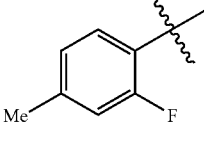 | 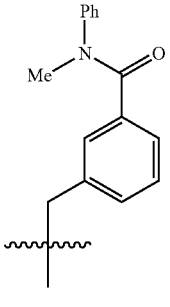 | 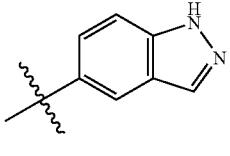 |
| 407 | 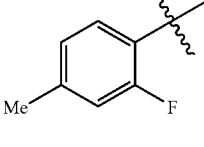 | 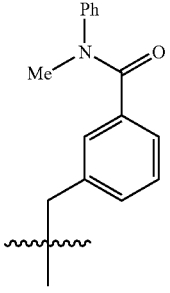 | 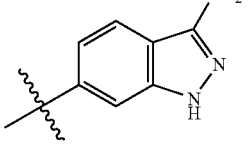 |

TABLE 3-continued
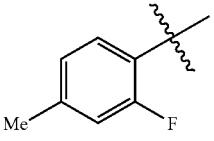
(Ie)
| Ex # | A | R[11] | R[3] |
|---|---|---|---|
| 408 | 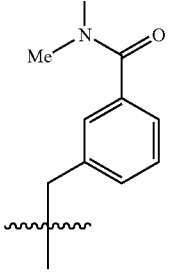 | 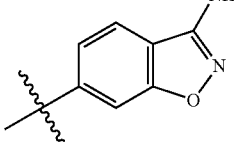 | 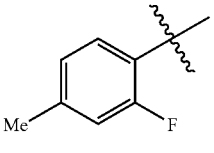 |
| 409 | 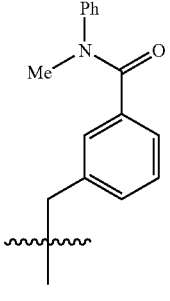 | 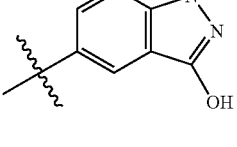 | 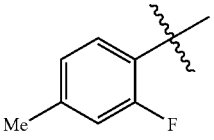 |
| 410 | 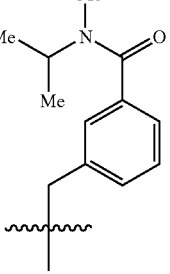 | 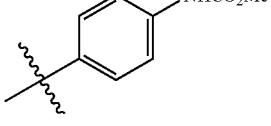 | 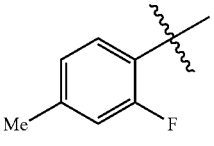 |
| 411 | 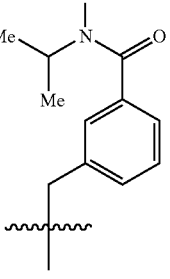 | 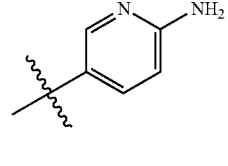 | |

TABLE 3-continued
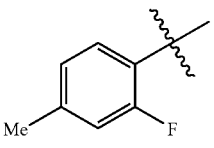
| Ex # | A | R¹¹ | R³ |
|---|---|---|---|
| 412 | 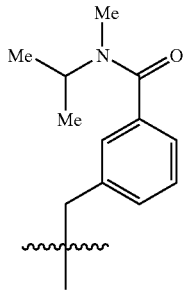 | 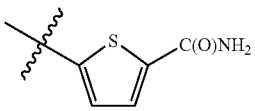 | 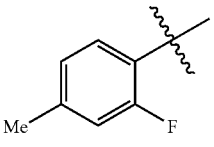 |
| 413 | 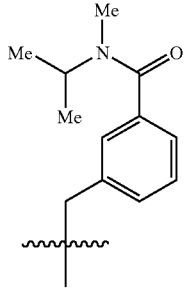 |  | 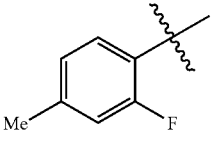 |
| 414 | 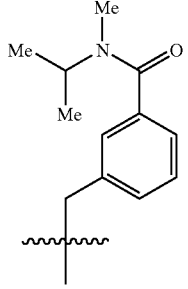 | 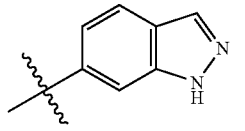 | 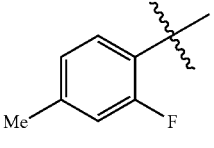 |
| 415 | 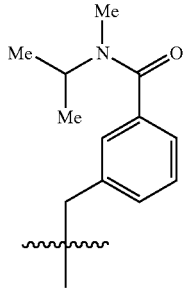 | 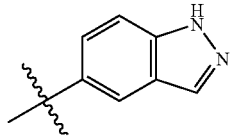 | |

TABLE 3-continued
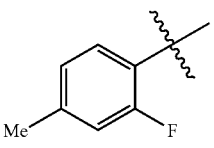
(Ie)
| Ex # | A | R[11] | R[3] |
|------|---|-------|------|
| 416 | 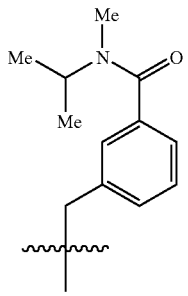 | 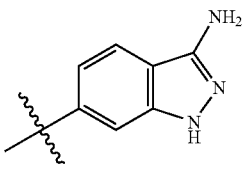 | 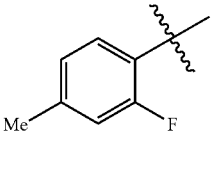 |
| 417 | 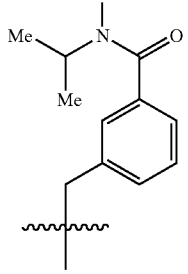 | 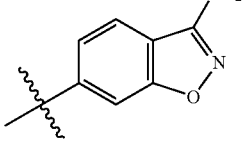 | 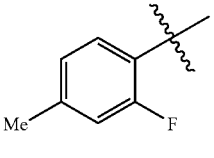 |
| 418 | 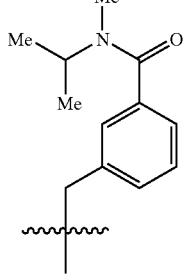 | 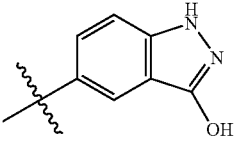 | 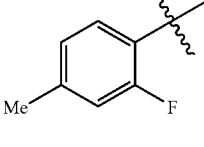 |
| 419 | 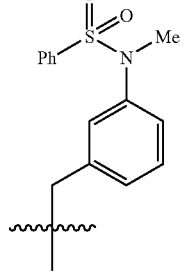 | 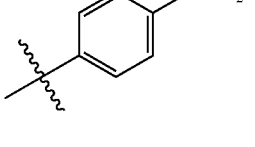 | |

TABLE 3-continued
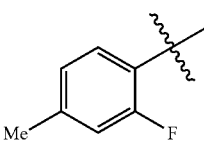
(Ie)
| Ex # | A | R[11] | R[3] |
|---|---|---|---|
| 420 | 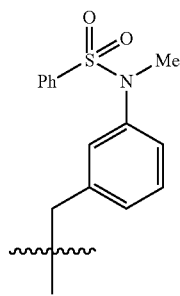 | 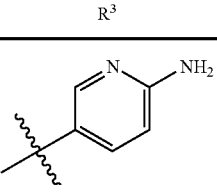 | 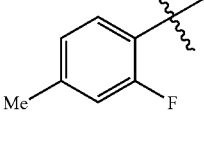 |
| 421 | 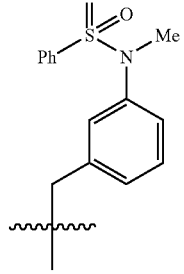 | 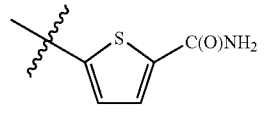 | 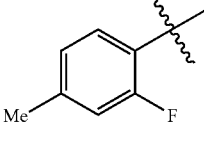 |
| 422 | 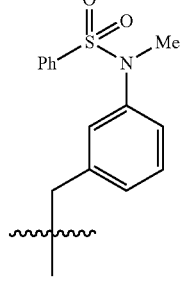 |  | 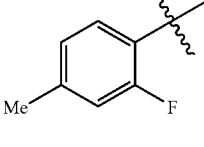 |
| 423 | 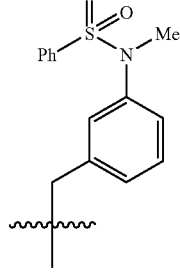 | 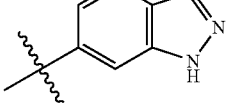 | |

TABLE 3-continued (Ie)

| Ex # | A | R¹¹ | R³ |
|---|---|---|---|
| 424 | 2-F, 4-Me-phenyl | N-methyl-N-(3-methylphenyl)benzenesulfonamide (via CH₂ linker) | 1H-indazol-5-yl |
| 425 | 2-F, 4-Me-phenyl | N-methyl-N-(3-methylphenyl)benzenesulfonamide (via CH₂ linker) | 3-amino-1H-indazol-6-yl |
| 426 | 2-F, 4-Me-phenyl | N-methyl-N-(3-methylphenyl)benzenesulfonamide (via CH₂ linker) | 3-amino-1,2-benzisoxazol-6-yl |
| 427 | 2-F, 4-Me-phenyl | N-methyl-N-(3-methylphenyl)benzenesulfonamide (via CH₂ linker) | 3-hydroxy-1H-indazol-5-yl |

TABLE 3-continued
(Ie)
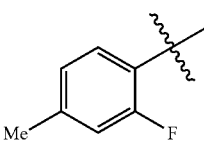
| Ex # | A | R[11] | R[3] |
|---|---|---|---|
| 428 | 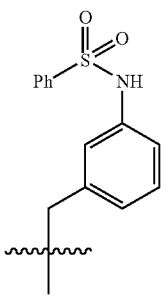 | 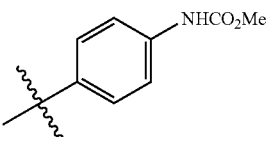 | 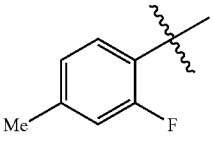 |
| 429 | 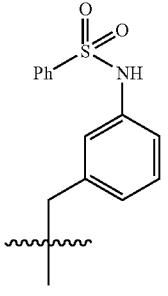 | 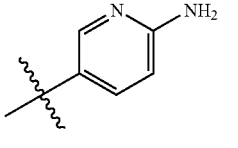 | 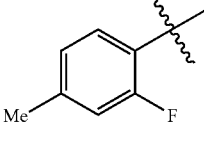 |
| 430 | 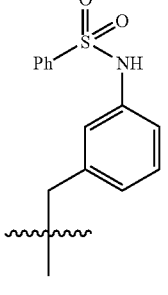 | 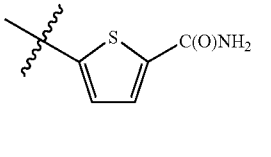 | 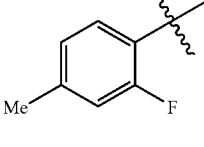 |
| 431 | 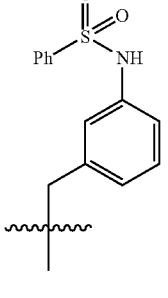 |  |  |

TABLE 3-continued
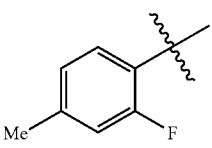
(Ie)
| Ex # | A | R{11} | R{3} |
|---|---|---|---|
| 432 | 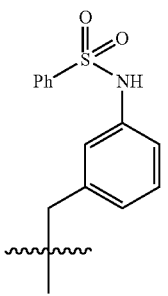 | 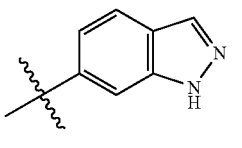 | 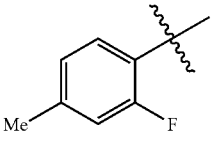 |
| 433 | 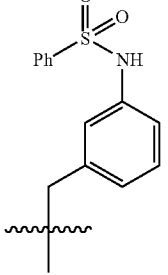 | 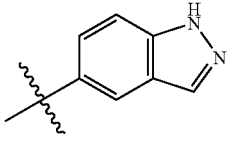 | 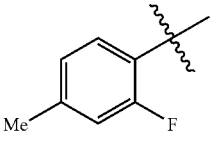 |
| 434 | 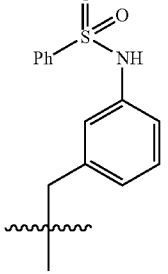 | 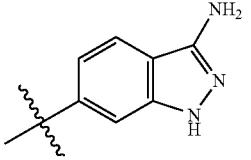 | 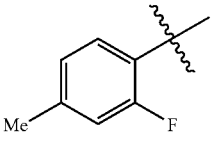 |
| 435 | 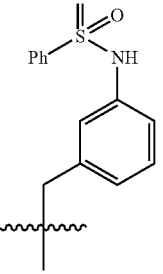 | 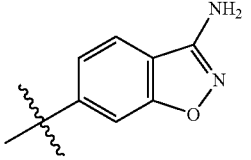 |  |

TABLE 3-continued (Ie)

| Ex # | A | R¹¹ | R³ |
|---|---|---|---|
| 436 | 4-Me, 2-F phenyl | PhS(O)₂NH-(3-substituted phenyl)-CH₂- | 1H-indazol-3-ol-5-yl |
| 437 | 4-Me, 2-F phenyl | benzyl | 4-(NHCO₂Me)phenyl |
| 438 | 4-Me, 2-F phenyl | benzyl | 6-amino-pyridin-3-yl |
| 439 | 4-Me, 2-F phenyl | benzyl | 5-(C(O)NH₂)thiophen-2-yl |
| 440 | 4-Me, 2-F phenyl | benzyl | 3-(2H-tetrazol-5-yl)phenyl |
| 441 | 4-Me, 2-F phenyl | benzyl | 1H-indazol-6-yl |
| 442 | 4-Me, 2-F phenyl | benzyl | 1H-indazol-5-yl |

TABLE 3-continued
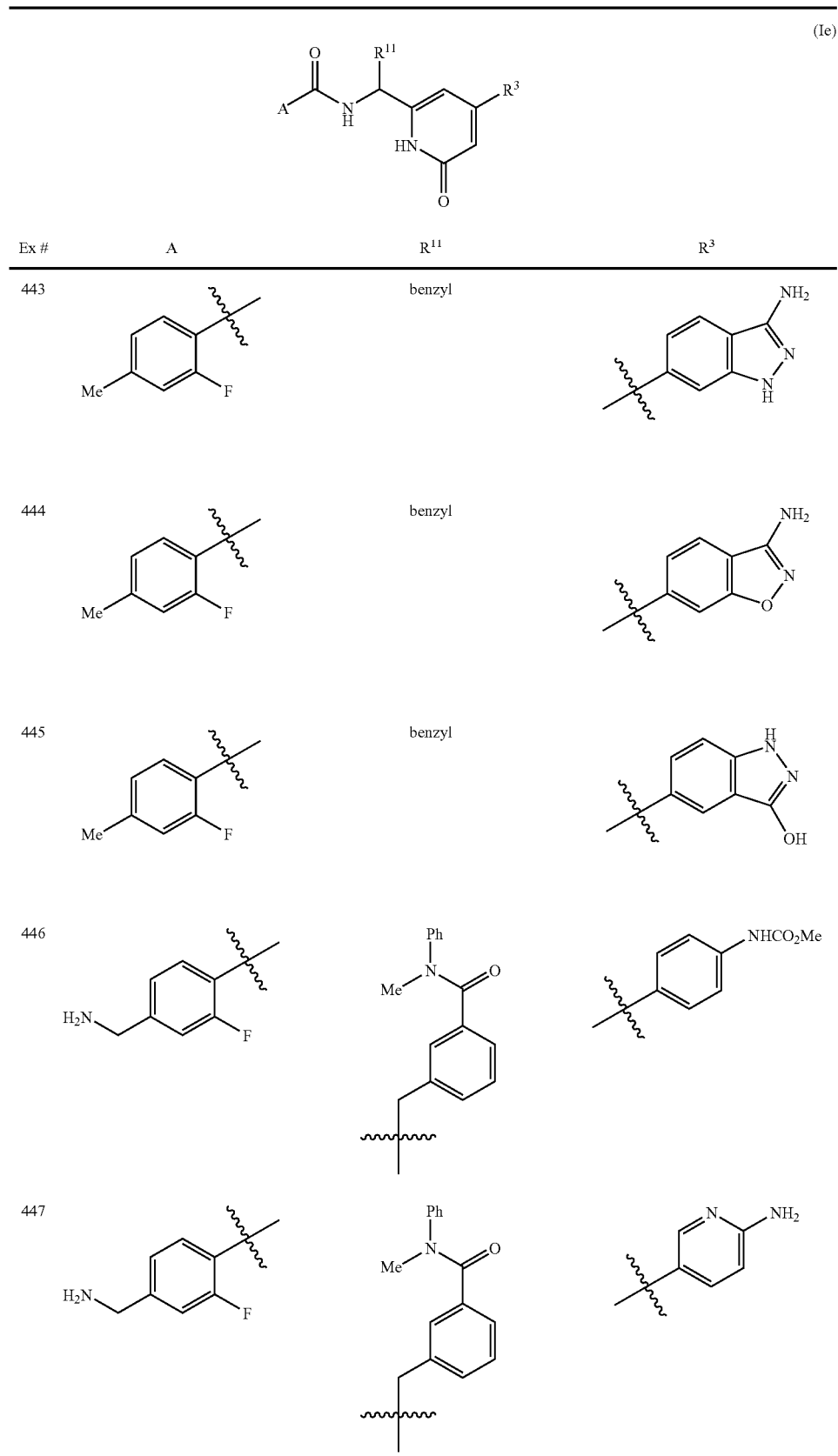

TABLE 3-continued
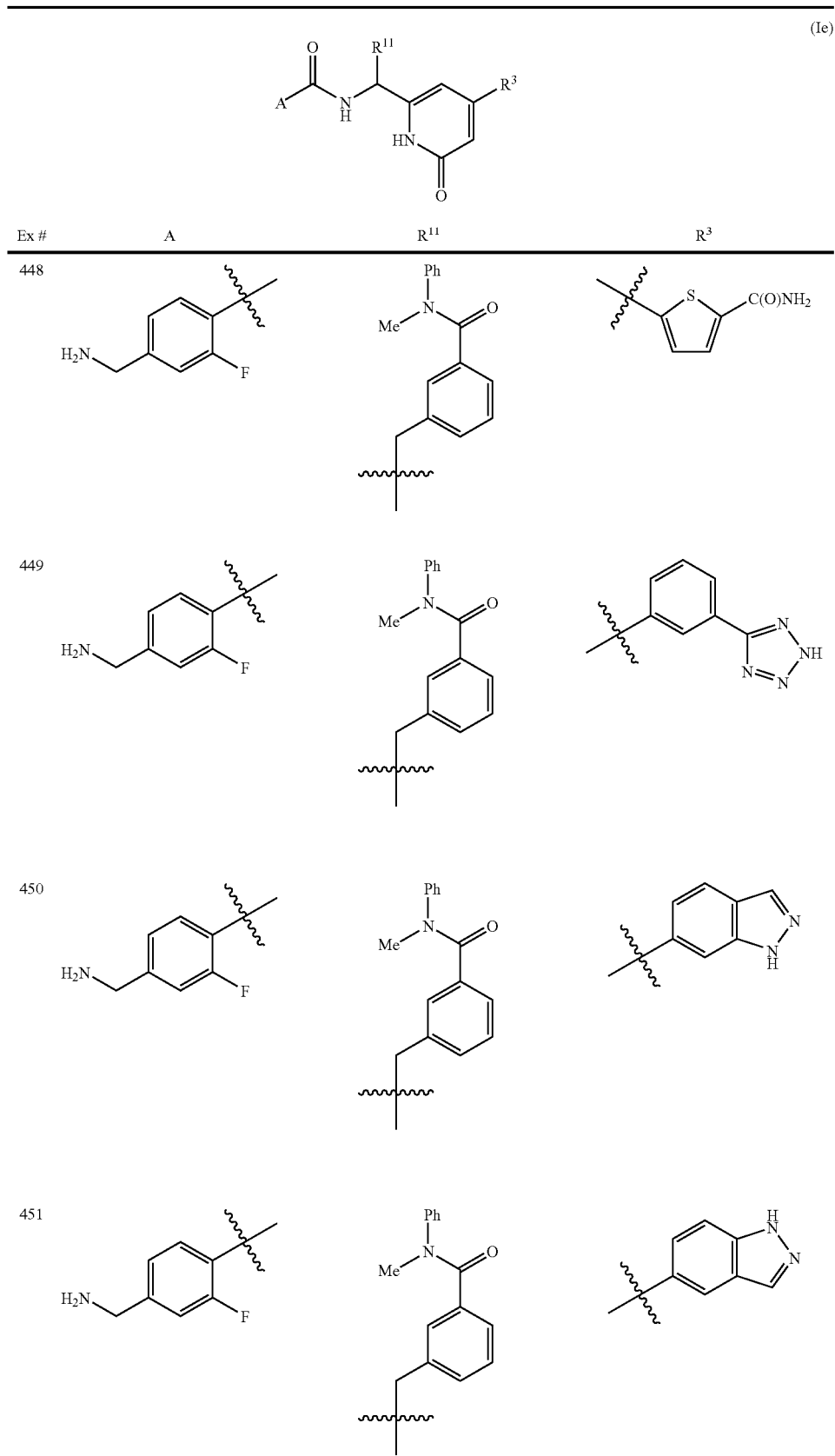

TABLE 3-continued

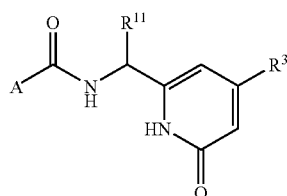

(Ie)

| Ex # | A | R11 | R3 |
|---|---|---|---|
| 452 | 4-(aminomethyl)-2-fluorophenyl | N-methyl-N-phenyl-3-(methylene)benzamide | 3-amino-1H-indazol-6-yl |
| 453 | 4-(aminomethyl)-2-fluorophenyl | N-methyl-N-phenyl-3-(methylene)benzamide | 3-amino-1,2-benzisoxazol-6-yl |
| 454 | 4-(aminomethyl)-2-fluorophenyl | N-methyl-N-phenyl-3-(methylene)benzamide | 3-hydroxy-1H-indazol-5-yl |
| 455 | 4-(aminomethyl)-2-fluorophenyl | N-isopropyl-N-methyl-3-(methylene)benzamide | 4-(NHCO2Me)phenyl |

TABLE 3-continued
(Ie)
| Ex # | A | R11 | R3 |
|---|---|---|---|
| 456 | 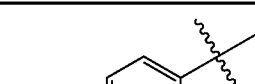 | 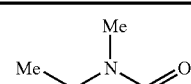 | 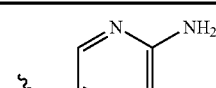 |
| 457 | 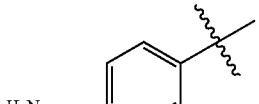 | 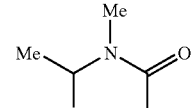 | 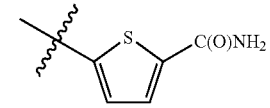 |
| 458 | 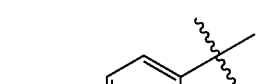 | 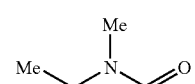 | 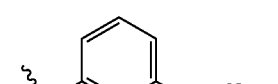 |
| 459 | 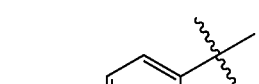 | 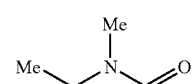 | 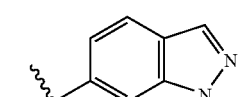 |

TABLE 3-continued
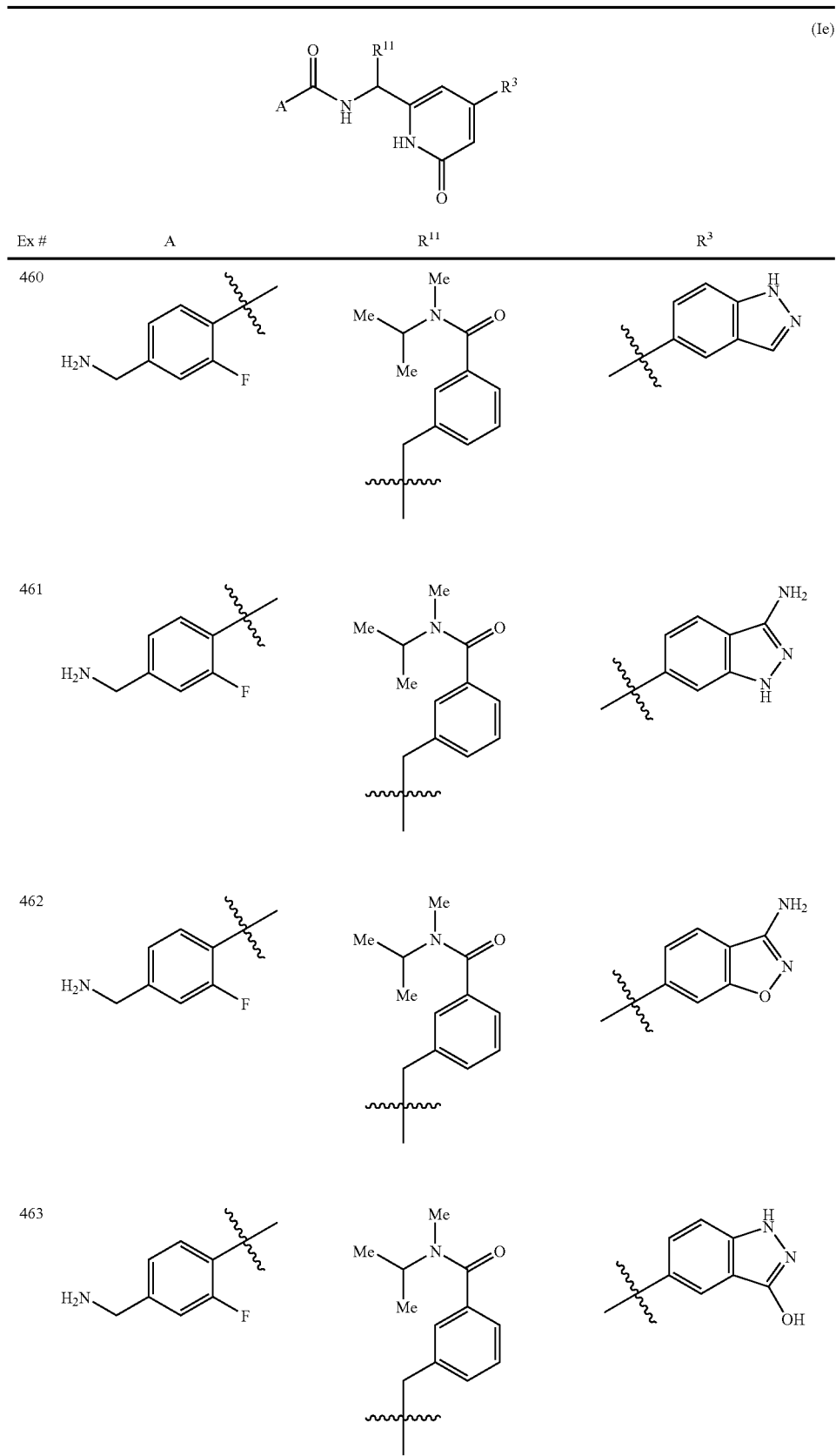

TABLE 3-continued (Ie)

| Ex # | A | R11 | R3 |
|------|---|-----|-----|
| 464 | 4-(aminomethyl)-2-fluorophenyl | N-methyl-N-(3-substituted phenyl)benzenesulfonamide | 4-(NHCO2Me)phenyl |
| 465 | 4-(aminomethyl)-2-fluorophenyl | N-methyl-N-(3-substituted phenyl)benzenesulfonamide | 6-amino-pyridin-3-yl |
| 466 | 4-(aminomethyl)-2-fluorophenyl | N-methyl-N-(3-substituted phenyl)benzenesulfonamide | 5-(C(O)NH2)thiophen-2-yl |
| 467 | 4-(aminomethyl)-2-fluorophenyl | N-methyl-N-(3-substituted phenyl)benzenesulfonamide | 3-(2H-tetrazol-5-yl)phenyl |

TABLE 3-continued
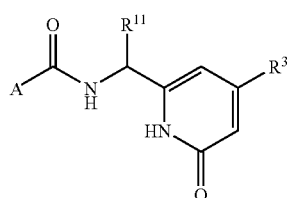
(Ie)
| Ex # | A | R[11] | R[3] |
|---|---|---|---|
| 468 | 4-(H2N-CH2)-3-F-phenyl | N-methyl-N-(3-methylenephenyl)benzenesulfonamide | 1H-indazol-6-yl |
| 469 | 4-(H2N-CH2)-3-F-phenyl | N-methyl-N-(3-methylenephenyl)benzenesulfonamide | 1H-indazol-5-yl |
| 470 | 4-(H2N-CH2)-3-F-phenyl | N-methyl-N-(3-methylenephenyl)benzenesulfonamide | 3-amino-1H-indazol-6-yl |
| 471 | 4-(H2N-CH2)-3-F-phenyl | N-methyl-N-(3-methylenephenyl)benzenesulfonamide | 3-amino-1,2-benzisoxazol-6-yl |

TABLE 3-continued

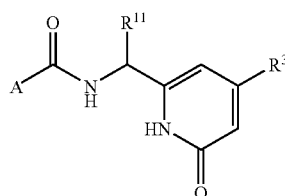

(Ie)

| Ex # | A | R11 | R3 |
|---|---|---|---|
| 472 | 4-(aminomethyl)-2-fluorophenyl | N-methyl-N-(3-methylenephenyl)benzenesulfonamide | 3-hydroxy-1H-indazol-5-yl |
| 473 | 4-(aminomethyl)-2-fluorophenyl | N-(3-methylenephenyl)benzenesulfonamide | 4-(NHCO2Me)phenyl |
| 474 | 4-(aminomethyl)-2-fluorophenyl | N-(3-methylenephenyl)benzenesulfonamide | 6-amino-pyridin-3-yl |
| 475 | 4-(aminomethyl)-2-fluorophenyl | N-(3-methylenephenyl)benzenesulfonamide | 5-(C(O)NH2)thiophen-2-yl |

TABLE 3-continued
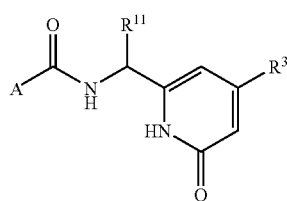
(Ie)
| Ex # | A | R¹¹ | R³ |
|---|---|---|---|
| 476 | 3-F,4-yl-benzylamine | PhSO₂NH-(3-yl-benzyl) | 3-(2H-tetrazol-5-yl)phenyl |
| 477 | 3-F,4-yl-benzylamine | PhSO₂NH-(3-yl-benzyl) | 1H-indazol-6-yl |
| 478 | 3-F,4-yl-benzylamine | PhSO₂NH-(3-yl-benzyl) | 1H-indazol-5-yl |
| 479 | 3-F,4-yl-benzylamine | PhSO₂NH-(3-yl-benzyl) | 3-amino-1H-indazol-6-yl |

TABLE 3-continued (Ie)

| Ex # | A | R¹¹ | R³ |
|---|---|---|---|
| 480 | 4-(aminomethyl)-2-fluorophenyl | PhS(O)₂NH-(3-substituted benzyl) | 3-amino-1,2-benzisoxazol-6-yl |
| 481 | 4-(aminomethyl)-2-fluorophenyl | PhS(O)₂NH-(3-substituted benzyl) | 3-hydroxy-1H-indazol-5-yl |
| 482 | 4-(aminomethyl)-2-fluorophenyl | benzyl | 4-(NHCO₂Me)phenyl |
| 483 | 4-(aminomethyl)-2-fluorophenyl | benzyl | 6-amino-pyridin-3-yl |
| 484 | 4-(aminomethyl)-2-fluorophenyl | benzyl | 5-(C(O)NH₂)thiophen-2-yl |
| 485 | 4-(aminomethyl)-2-fluorophenyl | benzyl | 3-(2H-tetrazol-5-yl)phenyl |

TABLE 3-continued

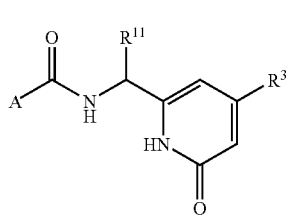

(Ie)

| Ex # | A | R[11] | R[3] |
|---|---|---|---|
| 486 | 4-(aminomethyl)-2-fluorophenyl | benzyl | 1H-indazol-6-yl |
| 487 | 4-(aminomethyl)-2-fluorophenyl | benzyl | 1H-indazol-5-yl |
| 488 | 4-(aminomethyl)-2-fluorophenyl | benzyl | 3-amino-1H-indazol-6-yl |
| 489 | 4-(aminomethyl)-2-fluorophenyl | benzyl | 3-amino-1,2-benzisoxazol-6-yl |
| 490 | 4-(aminomethyl)-2-fluorophenyl | benzyl | 3-hydroxy-1H-indazol-5-yl |
| 491 | 1-oxo-1,2-dihydroisoquinolin-6-yl | 3-[(N-methyl-N-phenylcarbamoyl)]benzyl | 4-(methoxycarbonylamino)phenyl |

TABLE 3-continued
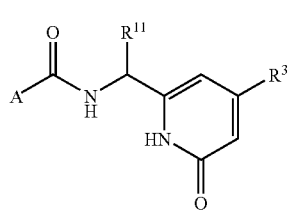
(Ie)
| Ex # | A | R[11] | R[3] |
|---|---|---|---|
| 492 | 1-oxo-1,2-dihydroisoquinolin-6-yl | 3-[(N-methyl-N-phenylcarbamoyl)]benzyl | 6-aminopyridin-3-yl |
| 493 | 1-oxo-1,2-dihydroisoquinolin-6-yl | 3-[(N-methyl-N-phenylcarbamoyl)]benzyl | 5-carbamoylthiophen-2-yl |
| 494 | 1-oxo-1,2-dihydroisoquinolin-6-yl | 3-[(N-methyl-N-phenylcarbamoyl)]benzyl | 3-(2H-tetrazol-5-yl)phenyl |
| 495 | 1-oxo-1,2-dihydroisoquinolin-6-yl | 3-[(N-methyl-N-phenylcarbamoyl)]benzyl | 1H-indazol-6-yl |

TABLE 3-continued (Ie)

| Ex # | A | R[11] | R[3] |
|---|---|---|---|
| 496 | isoquinolinone | N-methyl-N-phenyl-3-(benzyl)benzamide | 1H-indazol-5-yl |
| 497 | isoquinolinone | N-methyl-N-phenyl-3-(benzyl)benzamide | 3-amino-1H-indazol-6-yl |
| 498 | isoquinolinone | N-methyl-N-phenyl-3-(benzyl)benzamide | 3-amino-benzo[d]isoxazol-6-yl |
| 499 | isoquinolinone | N-methyl-N-phenyl-3-(benzyl)benzamide | 3-hydroxy-1H-indazol-5-yl |

TABLE 3-continued
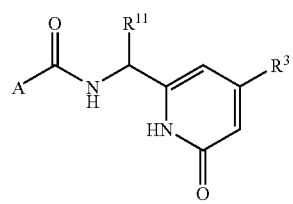
(Ie)
| Ex # | A | R[11] | R[3] |
|---|---|---|---|
| 500 | isoquinolin-1(2H)-one-6-yl | N-methyl-N-isopropyl-3-benzamide | 4-(NHCO₂Me)phenyl |
| 501 | isoquinolin-1(2H)-one-6-yl | N-methyl-N-isopropyl-3-benzamide | 6-amino-pyridin-3-yl |
| 502 | isoquinolin-1(2H)-one-6-yl | N-methyl-N-isopropyl-3-benzamide | 5-(C(O)NH₂)thiophen-2-yl |
| 503 | isoquinolin-1(2H)-one-6-yl | N-methyl-N-isopropyl-3-benzamide | 3-(2H-tetrazol-5-yl)phenyl |

TABLE 3-continued
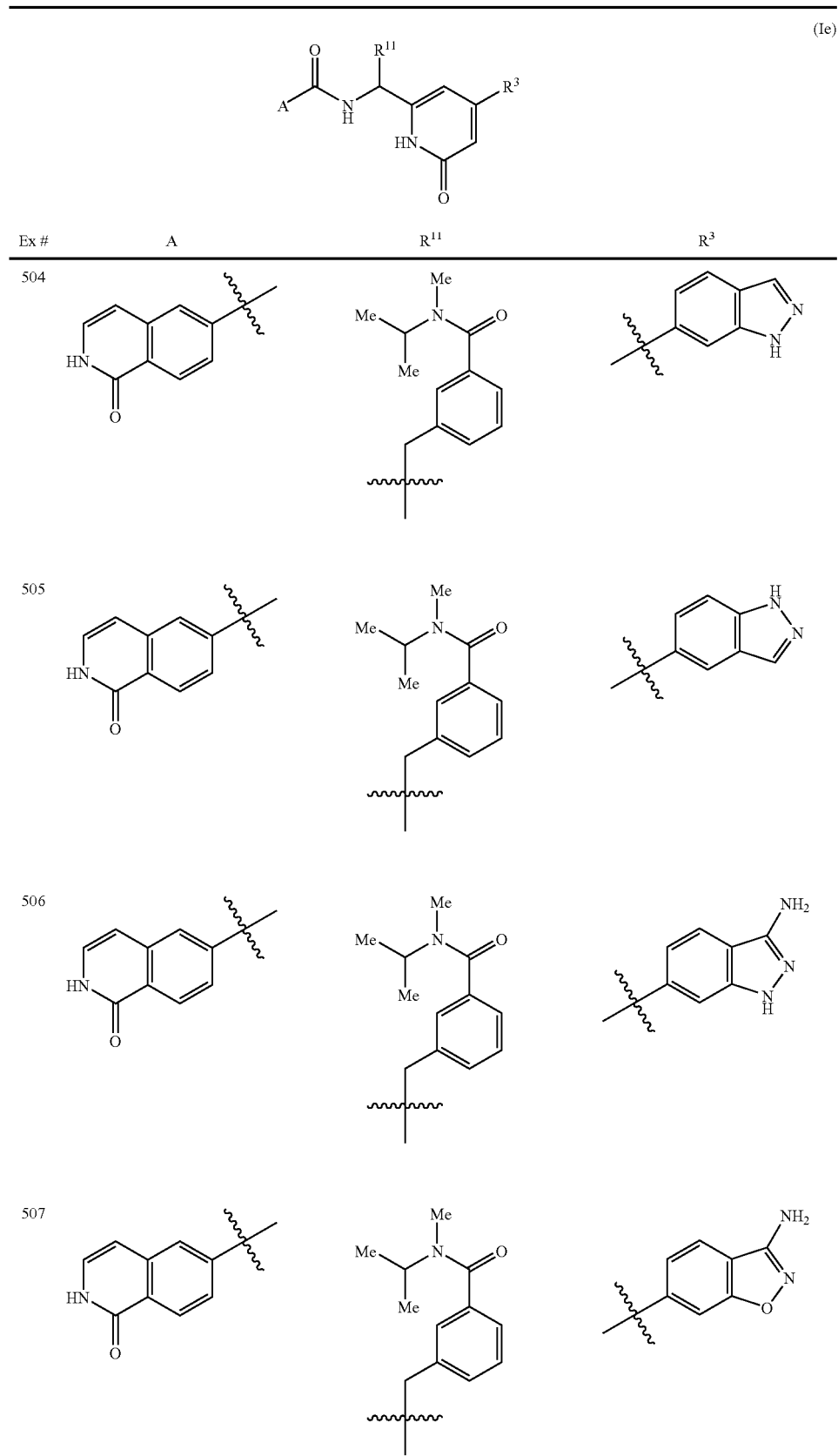

TABLE 3-continued
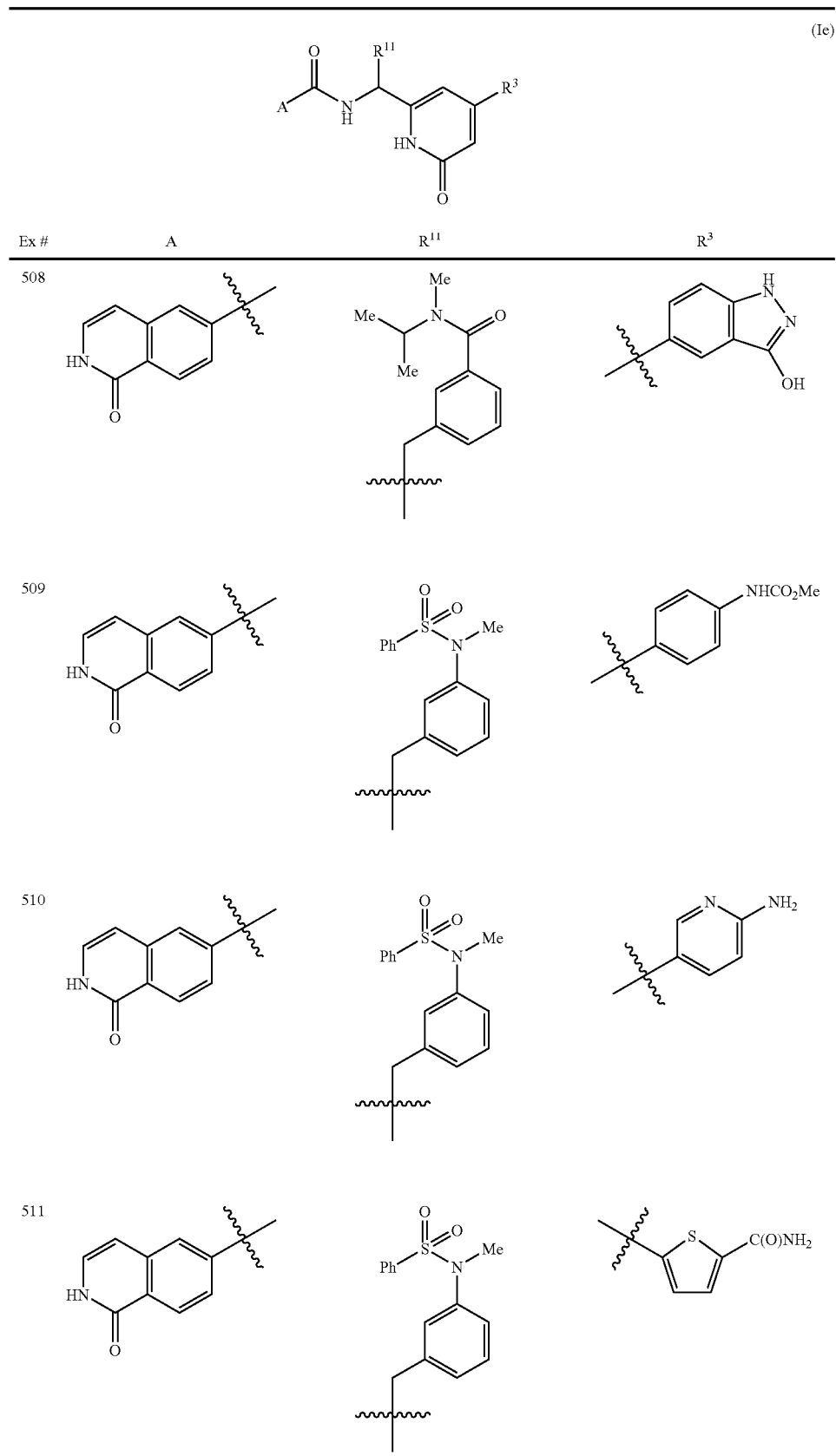

TABLE 3-continued

| Ex # | A | R11 | R3 |
|---|---|---|---|
| 512 | 1-oxo-1,2-dihydroisoquinolin-6-yl | N-methyl-N-(3-methylenephenyl)benzenesulfonamide | 3-(2H-tetrazol-5-yl)phenyl |
| 513 | 1-oxo-1,2-dihydroisoquinolin-6-yl | N-methyl-N-(3-methylenephenyl)benzenesulfonamide | 1H-indazol-6-yl |
| 514 | 1-oxo-1,2-dihydroisoquinolin-6-yl | N-methyl-N-(3-methylenephenyl)benzenesulfonamide | 1H-indazol-5-yl |
| 515 | 1-oxo-1,2-dihydroisoquinolin-6-yl | N-methyl-N-(3-methylenephenyl)benzenesulfonamide | 3-amino-1H-indazol-6-yl |

TABLE 3-continued
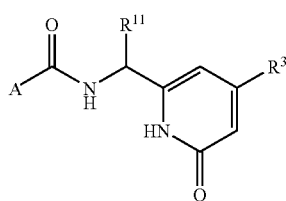
| Ex # | A | R[11] | R[3] |
|---|---|---|---|
| 516 | | | |
| 517 | | | |
| 518 | | | |
| 519 | | | |

TABLE 3-continued
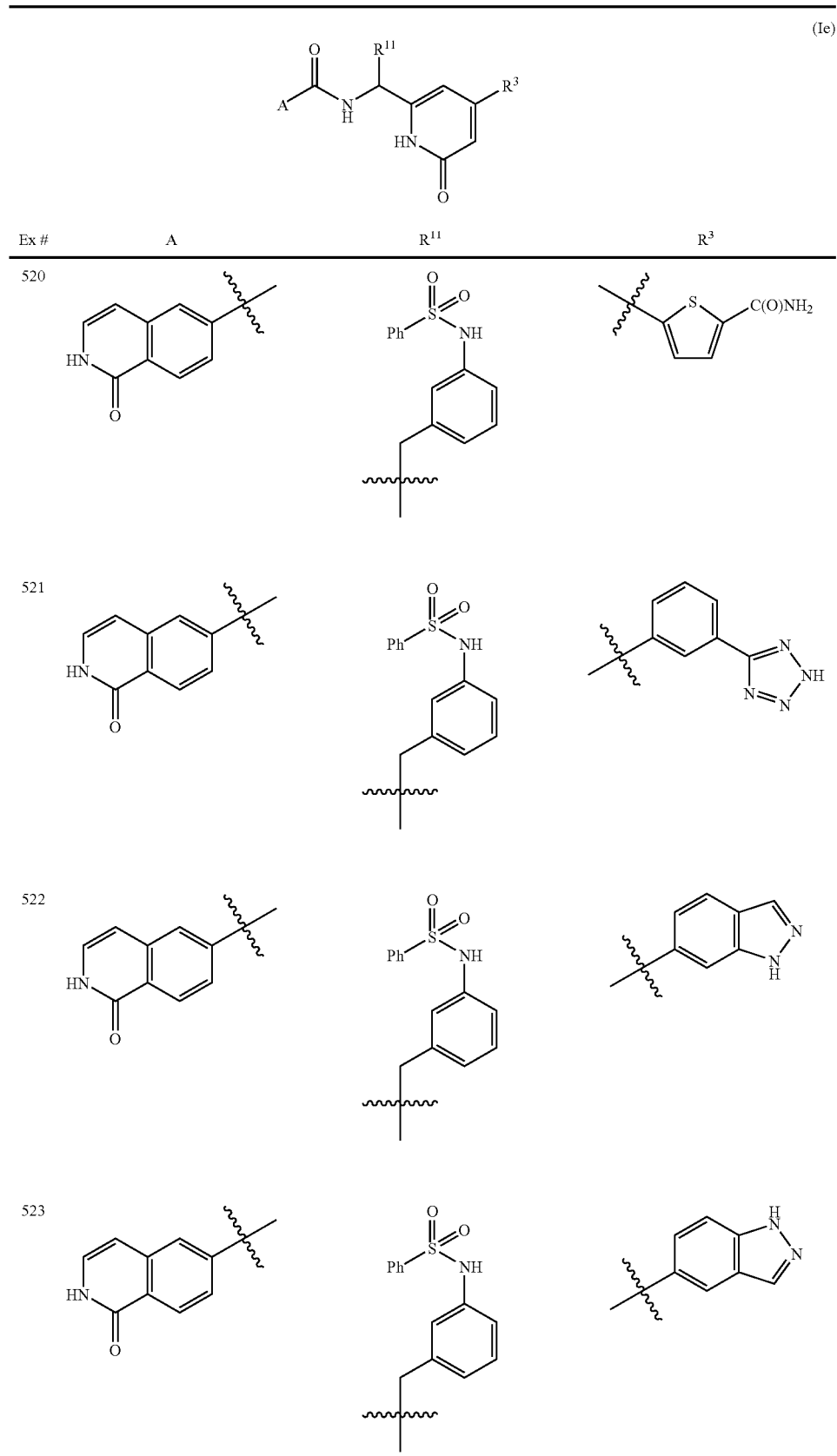

TABLE 3-continued (Ie)

| Ex # | A | R11 | R3 |
|---|---|---|---|
| 524 | isoquinolin-1(2H)-one-6-yl | 3-(PhSO2NH)benzyl | 3-amino-1H-indazol-6-yl |
| 525 | isoquinolin-1(2H)-one-6-yl | 3-(PhSO2NH)benzyl | 3-aminobenzo[d]isoxazol-6-yl |
| 526 | isoquinolin-1(2H)-one-6-yl | 3-(PhSO2NH)benzyl | 3-hydroxy-1H-indazol-5-yl |
| 527 | isoquinolin-1(2H)-one-6-yl | benzyl | 4-(NHCO2Me)phenyl |
| 528 | isoquinolin-1(2H)-one-6-yl | benzyl | 6-aminopyridin-3-yl |

TABLE 3-continued (Ie)

| Ex # | A | R¹¹ | R³ |
|---|---|---|---|
| 529 | 1-oxo-1,2-dihydroisoquinolin-6-yl | benzyl | 5-(aminocarbonyl)thiophen-2-yl |
| 530 | 1-oxo-1,2-dihydroisoquinolin-6-yl | benzyl | 3-(2H-tetrazol-5-yl)phenyl |
| 531 | 1-oxo-1,2-dihydroisoquinolin-6-yl | benzyl | 1H-indazol-6-yl |
| 532 | 1-oxo-1,2-dihydroisoquinolin-6-yl | benzyl | 1H-indazol-5-yl |
| 533 | 1-oxo-1,2-dihydroisoquinolin-6-yl | benzyl | 3-amino-1H-indazol-6-yl |
| 534 | 1-oxo-1,2-dihydroisoquinolin-6-yl | benzyl | 3-aminobenzo[d]isoxazol-6-yl |
| 535 | 1-oxo-1,2-dihydroisoquinolin-6-yl | benzyl | 3-hydroxy-1H-indazol-5-yl |

TABLE 3-continued

| Ex # | A | R11 | R3 |
|---|---|---|---|
| 536 | 4-carbamoyl-2-fluorophenyl | N-methyl-N-phenyl-3-(methylene)benzamide | 4-(NHCO2Me)phenyl |
| 537 | 4-carbamoyl-2-fluorophenyl | N-methyl-N-phenyl-3-(methylene)benzamide | 6-aminopyridin-3-yl |
| 538 | 4-carbamoyl-2-fluorophenyl | N-methyl-N-phenyl-3-(methylene)benzamide | 5-(C(O)NH2)thiophen-2-yl |
| 539 | 4-carbamoyl-2-fluorophenyl | N-methyl-N-phenyl-3-(methylene)benzamide | 3-(2H-tetrazol-5-yl)phenyl |

TABLE 3-continued
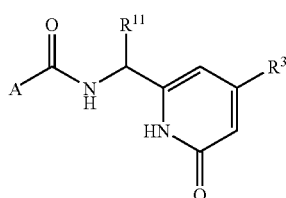
(Ie)
| Ex # | A | R[11] | R[3] |
|------|---|-------|------|
| 540 | 4-carbamoyl-2-fluorophenyl | 3-(N-methyl-N-phenylcarbamoyl)benzyl | 1H-indazol-6-yl |
| 541 | 4-carbamoyl-2-fluorophenyl | 3-(N-methyl-N-phenylcarbamoyl)benzyl | 1H-indazol-5-yl |
| 542 | 4-carbamoyl-2-fluorophenyl | 3-(N-methyl-N-phenylcarbamoyl)benzyl | 3-amino-1H-indazol-6-yl |
| 543 | 4-carbamoyl-2-fluorophenyl | 3-(N-methyl-N-phenylcarbamoyl)benzyl | 3-amino-1,2-benzisoxazol-6-yl |

TABLE 3-continued (Ie)

| Ex # | A | R¹¹ | R³ |
|---|---|---|---|
| 544 | 4-carbamoyl-2-fluorophenyl | N-methyl-N-phenyl-3-(methylene)benzamide | 3-hydroxy-1H-indazol-5-yl |
| 545 | 4-carbamoyl-2-fluorophenyl | N-isopropyl-N-methyl-3-(methylene)benzamide | 4-(NHCO₂Me)phenyl |
| 546 | 4-carbamoyl-2-fluorophenyl | N-isopropyl-N-methyl-3-(methylene)benzamide | 6-aminopyridin-3-yl |
| 547 | 4-carbamoyl-2-fluorophenyl | N-isopropyl-N-methyl-3-(methylene)benzamide | 5-carbamoylthiophen-2-yl |

TABLE 3-continued (Ie)

| Ex # | A | R¹¹ | R³ |
|---|---|---|---|
| 548 | 4-carbamoyl-2-fluorophenyl | N-isopropyl-N-methyl-3-benzamide | 3-(2H-tetrazol-5-yl)phenyl |
| 549 | 4-carbamoyl-2-fluorophenyl | N-isopropyl-N-methyl-3-benzamide | 1H-indazol-6-yl |
| 550 | 4-carbamoyl-2-fluorophenyl | N-isopropyl-N-methyl-3-benzamide | 1H-indazol-5-yl |
| 551 | 4-carbamoyl-2-fluorophenyl | N-isopropyl-N-methyl-3-benzamide | 3-amino-1H-indazol-6-yl |

TABLE 3-continued (Ie)

| Ex # | A | R¹¹ | R³ |
|---|---|---|---|
| 552 | 4-carbamoyl-3-fluorophenyl | N-isopropyl-N-methyl-3-(benzamide)methyl | 3-amino-1,2-benzisoxazol-6-yl |
| 553 | 4-carbamoyl-3-fluorophenyl | N-isopropyl-N-methyl-3-(benzamide)methyl | 3-hydroxy-1H-indazol-5-yl |
| 554 | 4-carbamoyl-3-fluorophenyl | N-methyl-N-(phenylsulfonyl)-3-aminobenzyl | 4-(NHCO₂Me)phenyl |
| 555 | 4-carbamoyl-3-fluorophenyl | N-methyl-N-(phenylsulfonyl)-3-aminobenzyl | 6-amino-pyridin-3-yl |

TABLE 3-continued (Ie)

| Ex # | A | R11 | R3 |
|---|---|---|---|
| 556 | 4-carbamoyl-3-fluorophenyl | N-methyl-N-(3-methylenephenyl)benzenesulfonamide | 5-(aminocarbonyl)thiophen-2-yl |
| 557 | 4-carbamoyl-3-fluorophenyl | N-methyl-N-(3-methylenephenyl)benzenesulfonamide | 3-(2H-tetrazol-5-yl)phenyl |
| 558 | 4-carbamoyl-3-fluorophenyl | N-methyl-N-(3-methylenephenyl)benzenesulfonamide | 1H-indazol-6-yl |
| 559 | 4-carbamoyl-3-fluorophenyl | N-methyl-N-(3-methylenephenyl)benzenesulfonamide | 1H-indazol-5-yl |

TABLE 3-continued (Ie)

| Ex # | A | R¹¹ | R³ |
|---|---|---|---|
| 560 | 4-carbamoyl-2-fluorophenyl | N-methyl-N-(3-CH₂-phenyl)benzenesulfonamide | 3-amino-1H-indazol-6-yl |
| 561 | 4-carbamoyl-2-fluorophenyl | N-methyl-N-(3-CH₂-phenyl)benzenesulfonamide | 3-amino-1,2-benzisoxazol-6-yl |
| 562 | 4-carbamoyl-2-fluorophenyl | N-methyl-N-(3-CH₂-phenyl)benzenesulfonamide | 3-hydroxy-1H-indazol-5-yl |
| 563 | 4-carbamoyl-2-fluorophenyl | N-(3-CH₂-phenyl)benzenesulfonamide | 4-(NHCO₂Me)phenyl |

TABLE 3-continued (Ie)

| Ex # | A | R¹¹ | R³ |
|---|---|---|---|
| 564 | 4-carbamoyl-3-fluorophenyl | 3-(phenylsulfonylamino)benzyl | 6-aminopyridin-3-yl |
| 565 | 4-carbamoyl-3-fluorophenyl | 3-(phenylsulfonylamino)benzyl | 5-carbamoylthiophen-2-yl |
| 566 | 4-carbamoyl-3-fluorophenyl | 3-(phenylsulfonylamino)benzyl | 3-(2H-tetrazol-5-yl)phenyl |
| 567 | 4-carbamoyl-3-fluorophenyl | 3-(phenylsulfonylamino)benzyl | 1H-indazol-6-yl |

TABLE 3-continued (Ie)

| Ex # | A | R11 | R3 |
|---|---|---|---|
| 568 | 3-F-4-(CONH2)-phenyl (attached at 4) | PhSO2NH-(3-CH2-phenyl) | 1H-indazol-5-yl |
| 569 | 3-F-4-(CONH2)-phenyl | PhSO2NH-(3-CH2-phenyl) | 3-amino-1H-indazol-6-yl |
| 570 | 3-F-4-(CONH2)-phenyl | PhSO2NH-(3-CH2-phenyl) | 3-aminobenzo[d]isoxazol-6-yl |
| 571 | 3-F-4-(CONH2)-phenyl | PhSO2NH-(3-CH2-phenyl) | 3-hydroxy-1H-indazol-5-yl |

TABLE 3-continued (Ie)

| Ex # | A | R¹¹ | R³ |
|---|---|---|---|
| 572 | 4-carbamoyl-2-fluorophenyl | benzyl | 4-(NHCO₂Me)phenyl |
| 573 | 4-carbamoyl-2-fluorophenyl | benzyl | 6-amino-pyridin-3-yl |
| 574 | 4-carbamoyl-2-fluorophenyl | benzyl | 5-(C(O)NH₂)thiophen-2-yl |
| 575 | 4-carbamoyl-2-fluorophenyl | benzyl | 3-(2H-tetrazol-5-yl)phenyl |
| 576 | 4-carbamoyl-2-fluorophenyl | benzyl | 1H-indazol-6-yl |
| 577 | 4-carbamoyl-2-fluorophenyl | benzyl | 1H-indazol-5-yl |

TABLE 3-continued (Ie)

| Ex # | A | $R^{11}$ | $R^3$ |
|---|---|---|---|
| 578 | 4-carbamoyl-2-fluorophenyl | benzyl | 3-amino-1H-indazol-6-yl |
| 579 | 4-carbamoyl-2-fluorophenyl | benzyl | 3-amino-1,2-benzisoxazol-6-yl |
| 580 | 4-carbamoyl-2-fluorophenyl | benzyl | 3-hydroxy-1H-indazol-5-yl |

Utility

The compounds of this invention are inhibitors of factor XIa and are useful as anticoagulants for the treatment or prevention of thromboembolic disorders in mammals (i.e., factor XIa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular or cerebrovascular thromboembolic disorders, and thromboembolic disorders in the chambers of the heart. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of serine proteases involved in the coagulation cascade and/or contact activation system, more specifically, inhibition of the coagulation factors: factor XIa, factor VIIa, factor IXa, factor Xa, plasma kallikrein or thrombin.

The compounds of this invention also are inhibitors of plasma kallikrein and are useful as anti-inflammatory agents for the treatment or prevention of diseases associated with an activation of the contact activation system (i.e., plasma kallikrein associated disorders). In general, a contact activation system disorder is a disease caused by activation of blood on artificial surfaces, including prosthetic valves or other implants, indwelling catheters, stents, cardiopulmonary bypass, hemodialysis, microorganism (e.g., bacteria, virus), or other procedures in which blood is exposed to an artificial surface that promotes contact activation, blood clots (i.e., diseases involving fibrin formation, platelet activation, and/or platelet aggregation). It also includes systemic inflammatory response syndrome, sepsis, acute respiratory distress syndrome, hereditary angioedema or other inherited or aquired deficencies of contact activation components or their inhibitors (plasma kallikrein, factor XIIa, high molecular weight kininogen, C1-esterase inhibitor). It may also include acute and chronic inflammations of joints, vessels, or other mammalian organs.

The effectiveness of compounds of the present invention as inhibitors of the coagulation factors XIa, VIIa, IXa, Xa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin, which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 pM (Haematologic Technologies) and the synthetic substrate S-2366 (pyroGlu-Pro-Arg-pNA; Chromogenix) at a concentration of 0.0002-0.00025 M. In general, preferred compounds of the present invention, such as the particular compounds disclosed in the above examples, have been identified to be active and exhibit $K_i$'s of equal to or less than 15 µM in the Factor XIa assay, thereby demonstrating the utility of the compounds of the present invention as especially effective inhibitors of coagulation Factor XIa. More preferred compounds have $K_i$'s of equal to or less than 5 µM, preferably equal to or less than 1 µM, more preferably equal to or less than 0.5 µM.

Factor VIIa determinations were made in 0.005 M calcium chloride, 0.15 M sodium chloride, 0.05 M HEPES buffer containing 0.5% PEG 8000 at a pH of 7.4. Determinations were made using purified human Factor VIIa (Haematologic Technologies) or recombinant human Factor VIIa (Novo Nordisk) at a final assay concentration of 2-5 nM, recombinant soluble tissue factor at a concentration of 18-35 nM and the synthetic substrate H-D-Ile-Pro-Arg-pNA (S-2288; Chromogenix or BMPM-2; AnaSpec) at a concentration of 0.001 M. In general, compounds tested in the Factor VIIa assay are considered to be active if they exhibit a $K_i$ of equal to or less than 15 µM.

Factor IXa determinations were made in 0.005 M calcium chloride, 0.1 M sodium chloride, 0.05 M TRIS base and 0.5% PEG 8000 at a pH of 7.4. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M. In general, compounds tested in the Factor IXa assay are considered to be active if they exhibit a $K_i$ of equal to or less than 15 µM.

Factor Xa determinations were made in 0.1 M sodium phosphate buffer at a pH of 7.4 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; Chromogenix) at a concentration of 0.0002-0.0003 M. In general, compounds tested in the Factor Xa assay are considered to be active if they exhibit a $K_i$ of equal to or less than 15 µM.

Plasma kallikrein determinations were made in 0.1 M sodium phosphate buffer at a pH of 7.4 containing 0.2 M sodium chloride and 0.5% PEG 8000. Determinations were made using purified human kallikrein (Enzyme Research Laboratories) at a final assay concentration of 200 pM and the synthetic substrate S-2302 (H-(D)-Pro-Phe-Arg-pNA; Chromogenix) at a concentration of 0.00008-0.0004 M. The Km value used for calculation of $K_i$ was 0.00005 to 0.00007 M. In general, Compounds tested in the plasma kallikrein assay are considered to be active if they exhibit a $K_i$ of equal to or less than 15 µM.

Thrombin determinations were made in 0.1 M sodium phosphate buffer at a pH of 7.4 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix) at a concentration of 0.0002 M. In general, compounds tested in the thrombin assay are considered to be active if they exhibit a $K_i$ of equal to or less than 15 µM.

In general, preferred compounds of the present invention have demonstrated $K_i$ values of equal to or less than 15 µM in at least one of the above assays, thereby confirming the utility of the compounds of the present invention as effective inhibitors of the coagulation cascade and/or contact activation system, and useful as anticoagulants for the prevention or treatment of thromboembolic disorders in mammals and/or as anti-inflammatory agents for the prevention or treatment of inflammatory disorders in mammals.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$(v_o - v_s)/v_s = I/(K_i(1 + S/K_m))$ for a competitive inhibitor with one binding site; or $v_s/v_o = A + ((B-A)/1 + ((IC_{50}/(I)^n)))$ and $K_i = IC_{50}/(1 + S/K_m)$ for a competitive inhibitor where:

$v_o$ is the velocity of the control in the absence of inhibitor;

$v_s$ is the velocity in the presence of inhibitor;

I is the concentration of inhibitor;

A is the minimum activity remaining (usually locked at zero);

B is the maximum activity remaining (usually locked at 1.0);

n is the Hill coefficient, a measure of the number and cooperativity of potential inhibitor binding sites;

$IC_{50}$ is the concentration of inhibitor that produces 50% inhibition under the assay conditions;

$K_i$ is the dissociation constant of the enzyme:inhibitor complex;

S is the concentration of substrate; and $K_m$ is the Michaelis constant for the substrate.

The effectiveness of compounds of the present invention as inhibitors of the coagulation factors XIa, VIIa, IXa, Xa, or thrombin, can be determined using relevant in vivo thrombosis models, including In Vivo Electrically-induced Carotid Artery Thrombosis Models and In Vivo Rabbit Arterio-venous Shunt Thrombosis Models.

In Vivo Electrically-induced Carotid Artery Thrombosis Model:

The antithrombotic effect of compounds of the present invention can be demonstrated in the electrically-induced carotid artery thrombosis (ECAT) model in rabbits. In this model, rabbits are anesthetized with a mixture of ketamine (50 mg/kg i.m.) and xylazine (10 mg/kg i.m.). A femoral vein and a femoral artery are isolated and catheterized. The carotid artery is also isolated such that its blood flow can be measured with a calibrated flow probe that is linked to a flowmeter. A stainless steel bipolar hook electrode is placed on the carotid artery and positioned caudally in relationship to the flow probe as a means of applying electrical stimulus. In order to protect the surrounding tissue, a piece of Parafilm is placed under the electrode.

Test compounds are considered to be effective as anticoagulants based on their ability to maintain blood flow in the carotid artery following the induction of thrombosis by an electrical stimulus. A test compound or vehicle is given as continuous intravenous infusion via the femoral vein, starting 1 hour before electrical stimulation and continuing to the end of the test. Thrombosis is induced by applying a direct electrical current of 4 mA for 3 min to the external arterial surface, using a constant current unit and a d.c. stimulator. The carotid blood flow is monitored and the time to occlusion (decrease of blood flow to zero following induction of thrombosis) in minutes is noted. The change in observed blood flow is calculated as a percentage of the blood flow prior to induction of thrombosis and provides a measure of the effect of a test compound when compared to the case where no compound is administered. This information is used to estimate the $ED_{50}$ value, the dose that increases blood flow to 50% of the control (blood flow prior to induction of thrombosis) and is accomplished by nonlinear least square regression.

In Vivo Rabbit Arterio-venous Shunt Thrombosis Model:

The antithrombotic effect of compounds of the present invention can be demonstrated in a rabbit arterio-venous (AV) shunt thrombosis model. In this model, rabbits weighing 2-3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The anti-inflammatory effect of these compounds can be demonstrated in an Evans Blue dye extravasation assay using C1-esterase inhibitor deficient mice. In this model, mice are dosed with a compound of the present invention, Evans Blue is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The utility of the compounds of the current invention to reduce or prevent the morbidity and/or mortality of sepsis can be assessed by injecting a mammalian host with bacteria or viruses or extracts there of and compounds of the present invention. Typical read-outs of the efficacy include changes in the LD50 and blood pressure preservation.

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

The compounds of the present invention can be administered alone or in combination with one or more additional therapeutic agents. These include other anti-coagulant or coagulation inhibitory agents, anti-platelet or platelet inhibitory agents, anti-inflammatory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as define below, to a mammal in a therapeutically effective amount. When administered in a combination, the combination of compounds is preferably, but not necessarily, a synergistic combination. Synergy, as described for example by Chou and Talalay, Adv. Enzyme Regul. 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Compounds which can be administered in combination with the compounds of the present invention include, but are not limited to, anticoagulants, anti-thrombin agents, anti-platelet agents, fibrinolytics, hypolipideric agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX™), aprotinin, synthetic pentasaccharide, direct acting thrombin inhibitors including hirudin and argatroban, as well as other factor VIIa, VIIIa, IXa, Xa, XIa, thrombin, TAFI, and fibrinogen inhibitors known in the art.

The term anti-platelet agents (or platelet inhibitory agents), as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the puringergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use. The compounds of the present invention may also be dosed in combination with aprotinin.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin), endothelial cell activation, inflammatory reactions, and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-I inhibitors (i.e., inactivators of tissue plasminogen activator inhibitors), alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); $K^+$ channel openers such as $I_{Ach}$ inhibitors, and $I_{Kur}$ inhibitors (e.g., compounds such as those disclosed in WO01/40231).

The term antihypertensive agents, as used herein, include: alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; angiotensin-converting enzyme (ACE) inhibitors (e.g., captopril, lisinopril, fosinopril, enalapril, ceranopril, cilazopril, delapril, pentopril, quinapril, ramipril, lisinopril); angiotensin-II receptor antagonists (e.g., irbestatin, losartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual ACE/NEP inhibitors, e.g., omapatrilat, gemopatrilat, nitrates); and β-blockers (e.g., propanolol, nadolo, or carvedilol).

Examples of suitable cardiac glycosides for use in combination with the compounds of the present invention include digitalis and ouabain.

Examples of suitable mineralocorticoid receptor antagonists for use in combination with the compounds of the present invention include sprionolactone and eplirinone.

Examples of suitable cholesterol/lipid lowering agents and lipid profile therapies for use in combination with the compounds of the present invention include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/ glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 µM against the target protease and greater than or equal to 0.1 µM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent and selective Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolyic agent when administered alone may be reduced by about 70-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:

1. A compound of Formula (I):

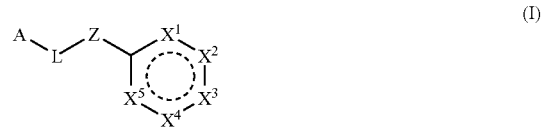

or a stereoisomer or pharmaceutically acceptable salt, or solvate thereof, wherein:

A is $C_{3-7}$ cycloalkyl substituted with 0-1 $R^1$ and 0-2 $R^2$, $C_{3-7}$ cycloalkenyl substituted with 0-1 $R^1$ and 0-2 $R^2$, phenyl substituted with 0-1 $R^1$ and 0-3 $R^2$, naphthyl substituted with 0-1 $R^1$ and 0-3 $R^2$, or a 5- to 12-membered heterocycle comprising: carbon atoms and 1-4 heteroatoms selected from N, O, and $S(O)_p$, wherein said heterocycle is substituted 0-1 $R^1$ and 0-3 $R^2$;

the group

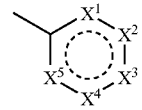

is selected from:

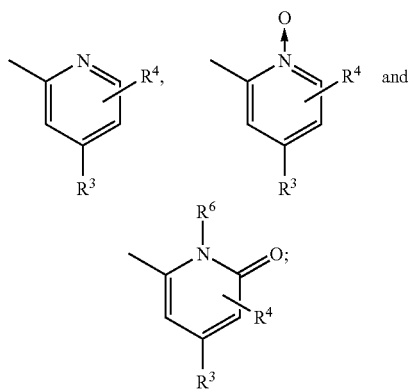

Z is —$CH(R^{11})$;

L is —$C(O)NR^{10}$;

$R^1$ is, independently at each occurrence, —$NH_2$, —$NH(C_{1-3}$ alkyl), —$N(C_{1-3}$ alkyl$)_2$, —$C(=NH)NH_2$, —$C(O)NH_2$, —$CH_2NH_2$, —$(CH_2)_rNR^7R^8$, —$CH_2NH(C_{1-3}$ alkyl), —$CH_2N(C_{1-3}$ alkyl$)_2$, —$CH_2CH_2NH_2$, —$CH_2CH_2NH(C_{1-3}$ alkyl), —$CH_2CH_2N(C_{1-3}$ alkyl$)_2$, —$CH(C_{1-4}$ alkyl)$NH_2$, —$C(C_{1-4}$ alkyl$)_2NH_2$, —$C(=NR^{8a})NR^7R^8$, —$NR^8CR^8(=NR^{8a})$, —$NHC(=NR^{8a})NR^7R^8$, =$NR^8$, —$C(O)NR^8R^9$, —$S(O)_p$ $NR^8R^9$, —$(CH_2)_rNR^7C(O)OR^a$, F, Cl, Br, I, $OCF_3$, $CF_3$, $OR^a$, $SR^a$, CN, 1-$NH_2$-1-cyclopropyl, or $C_{1-6}$ alkyl substituted with 0-1 $R^{1a}$;

$R^{1a}$ is H, —$C(=NR^{8a})NR^7R^8$, —$NHC(=NR^{8a})NR^7R^8$, —$NR^8CR^8(=NR^{8a})$, —$NR^7R^8$, —$C(O)NR^8R^9$, F, $OCF_3$, $CF_3$, $OR^a$, $SR^a$, CN, —$NR^8SO_2NR^8R^9$, —$NR^8SO_2R^c$, —$S(O)_p$—$C_{1-4}$alkyl, —$S(O)_p$-phenyl, or —$(CF_2)_rCF_3$;

$R^2$ is, independently at each occurrence, H, =O, F, Cl, Br, I, $OCF_3$, $CF_3$, $CHF_2$, CN, $NO_2$, $OR^a$, $SR^a$, —$C(O)R^a$, —$C(O)OR^a$, —$OC(O)R^a$, —$NR^7R^8$, —$C(O)NR^7R^8$, —$NR^7C(O)R^b$, —$S(O)_pNR^8R^9$, —$NR^8S(O)_2R^c$, —$S(O)R^c$, —$S(O)_2R^c$, $C_{1-6}$ alkyl substituted with 0-2 $R^{2a}$, $C_{2-6}$ alkenyl substituted with 0-2 $R^{2a}$, $C_{2-6}$ alkynyl substituted with 0-2 $R^{2a}$, —$(CH_2)_r$—$C_{3-10}$ carbocycle substituted with 0-3 $R^{2b}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{2b}$;

$R^{2a}$ is, independently at each occurrence, H, F, Cl, Br, I, =O, =$NR^8$, CN, $OCF_3$, $CF_3$, $OR^a$, $SR^a$, —$NR^7R^8$, —$C(O)NR^8R^9$, —$NR^7C(O)R^b$, —$S(O)_pNR^8R^9$, —$NR^8SO_2R^c$, —$S(O)R^c$, or —$S(O)_2R^c$;

$R^{2b}$ is, independently at each occurrence, H, F, Cl, Br, I, =O, =$NR^8$, CN, $NO_2$, $OR^a$, $SR^a$, —$C(O)R^a$, —$C(O)OR^a$, —$OC(O)R^a$, —$NR^7R^8$, —$C(O)NR^7R^8$, —$NR^7C(O)R^b$, —$S(O)_pNR^8R^9$, —$SO_2R^c$, —$NR^8SO_2NR^8R^9$, —$NR^8SO_2R^c$, —$(CF_2)_rCF_3$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$ haloalkyloxy-;

alternately, when $R^1$ and $R^2$ are substituted on adjacent ring atoms, they can be taken together with the ring atoms to which they are attached to form a 5- to 7-membered carbocycle or heterocycle comprising: carbon atoms and 0-4 heteroatoms selected from N, O, and $S(O)_p$, wherein said carbocycle or heterocycle is substituted with 0-2 $R^{2b}$;

$R^3$ is, independently at each occurrence, —$(CH_2)_rC(O)NR^8R^9$, —$(CH_2)_rC(O)NR^8(CH_2)_sCO_2R^{3b}$, —$(CH_2)_rCO_2R^{3b}$, —$(CH_2)_r$-phenyl substituted with 0-3 $R^{3a}$ and 0-1 $R^{3d}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^{3a}$ is, independently at each occurrence, =O, F, Cl, Br, I, $OCF_3$, $CF_3$, CN, $NO_2$, —$(CH_2)_rOR^{3b}$, —$(CH_2)_rSR^{3b}$, —$(CH_2)_rNR^7R^8$, —$C(=NR^{8a})NR^8R^9$, —$NHC(=NR^{8a})NR^7R^8$, —$NR^8CR^8(=NR^{8a})$, —$(CH_2)_rNR^8C(O)R^{3b}$, =$NR^8$, —$(CH_2)_rNR^8C(O)R^{3b}$, —$(CH_2)_rNR^8C(O)_2R^{3b}$, —$(CH_2)_rS(O)_pNR^8R^9$, —$(CH_2)_rNR^8S(O)_pR^{3c}$, —$S(O)R^{3c}$, —$S(O)_2R^{3c}$, —$C(O)$—$C_{1-4}$ alkyl, —$(CH_2)_rCO_2R^{3b}$, —$(CH_2)_rC(O)NR^8R^9$, —$(CH_2)_rOC(O)NR^8R^9$, —$NHCOCF_3$, —$NHSO_2CF_3$, —$SO_2NHR^{3b}$, —$SO_2NHCOR^{3c}$, —$SO_2NHCO_2R^{3c}$, —$CONHSO_2R^{3c}$, —$NHSO_2R^{3c}$, —$CONHOR^{3b}$, $C_{1-4}$ haloalkyl, $C_{1-4}$ haloalkyloxy-, $C_{1-6}$ alkyl substituted by $R^{3d}$, $C_{2-6}$ alkenyl substituted by $R^{3d}$, $C_{1-6}$ alkynyl substituted by $R^{3d}$, $C_{3-6}$ cycloalkyl substituted by 0-1 $R^{3d}$, —$(CH_2)_r$—$C_{3-10}$ carbocycle substituted with 0-3 $R^{3d}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

alternately, when two $R^{3a}$ groups are substituted on adjacent atoms, they can be taken together with the atoms to which they are attached to form a $C_{3-10}$ carbocycle substituted with 0-2 $R^{3d}$, or a 5- to 10-membered heterocycle comprising: carbon atoms and 1-4 heteroatoms selected from N, O, and $S(O)_p$, wherein said heterocycle is substituted with 0-2 $R^{3d}$;

$R^{3b}$ is, independently at each occurrence, H, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, —$(CH_2)_r$—$C_{3-10}$ carbocycle substituted with 0-3 $R^{3d}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3c}$ is, independently at each occurrence, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, —$(CH_2)_r$—$C_{3-10}$ carbocycle substituted with 0-3 $R^{3d}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3d}$ is, independently at each occurrence, H, =O, —$(CH_2)_rOR^a$, F, Cl, Br, CN, $NO_2$, —$(CH_2)_rNR^7R^8$, —$C(O)R^a$, —$C(O)OR^a$, —$OC(O)R^a$, —$NR^7C(O)R^b$, —$C(O)NR^8R^9$, —$S(O)_2NR^8R^9$, —$NR^8S(O)_2NR^8R^9$, —$NR^8S(O)_2R^c$, —$S(O)_pR^c$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_r$—$C_{3-10}$ carbocycle substituted with 0-3 $R^d$, or —$(CH_2)_r$-5- to 10-membered heterocycle comprising: carbon atoms and 1-4 heteroatoms selected from N, O, and $S(O)_p$, wherein said heterocycle is substituted with 0-3 $R^d$;

$R^4$ is, independently at each occurrence, H, =O, F, Cl, Br, I, $OCF_3$, $CF_3$, CN, $NO_2$, $OR^a$, $SR^a$, —$C(O)R^a$, —$C(O)OR^a$, —$OC(O)R^a$, —$NR^7R^8$, —$C(O)NR^8R^9$, —$NR^7C(O)R^b$, —$S(O)_pNR^8R^9$, —$NR^8S(O)_pR^c$, —$S(O)_2R^c$, $C_{1-6}$ alkyl substituted with 0-2 $R^{4a}$, $C_{2-6}$ alkenyl substituted with 0-2 $R^{4a}$, $C_{2-6}$ alkynyl substituted with 0-2 $R^{4a}$, —$(CH_2)_r$—$C_{3-10}$ carbocycle substituted with 0-3 $R^{4b}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{4b}$;

$R^{4a}$ is, independently at each occurrence, H, F, =O, $C_{1-4}$ alkyl, $OR^a$, $SR^a$, $CF_3$, CN, $NO_2$, —$C(O)R^a$, —$C(O)OR^a$, —$NR^7R^8$, —$C(O)NR^8R^9$, —$NR^7C(O)R^b$, —$S(O)_pNR^8R^9$, —$NR^8S(O)_pR^c$, —$S(O)R^c$, or —$S(O)_2R^c$;

$R^{4b}$ is, independently at each occurrence, H, =O, =$NR^8$, F, Cl, Br, I, $OR^a$, $SR^a$, CN, $NO_2$, —$NR^7R^8$, —$C(O)R^a$, —$C(O)OR^a$, —$NR^7C(O)R^b$, —$C(O)NR^8R^9$, —$SO_2NR^8R^9$, —$S(O)_2R^c$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$ haloalkyloxy-;

alternately, $R^3$ and $R^4$ groups when located on adjacent atoms, can be taken together to form a $C_{3-10}$ carbocycle substituted with 0-2 $R^{3d}$ or a 5- to 10-membered heterocycle comprising: carbon atoms and 1-4 heteroatoms selected from N, O, and $S(O)_p$, wherein said heterocycle is substituted with 0-2 $R^{3d}$;

$R^6$ is, independently at each occurrence, H, $C_{1-6}$ alkyl, $C_{1-4}$ haloalkyl, —$CH_2OR^a$, —$C(O)R^c$, —$C(O)_2R^c$, —$S(O)_2R^c$, or —$(CH_2)_r$-phenyl substituted with 0-3 $R^d$;

$R^7$ is, independently at each occurrence, H, $C_{1-6}$ alkyl, —$(CH_2)_n$—$C_{3-10}$ carbocycle, —$(CH_2)_n$-(5-10 membered heteroaryl), —$C(O)R^c$, —CHO, —$C(O)_2R^c$, —$S(O)_2R^c$, —$CONR^8R^c$, —$OCONHR^c$, —$C(O)O$—$(C_{1-4}$ alkyl)$OC(O)$—$(C_{1-4}$ alkyl), or —$C(O)O$—$(C_{1-4}$ alkyl)$OC(O)$—$(C_{6-10}$ aryl); wherein said alkyl, carbocycle, heteroaryl, and aryl are optionally substituted with 0-2 $R^f$;

R$^8$ is, independently at each occurrence, H, C$_{1-6}$ alkyl, —(CH$_2$)$_n$-phenyl, or —(CH$_2$)$_n$-5-10 membered heterocycle comprising: carbon atoms and 1-4 heteroatoms selected from N, O, and S(O)$_p$; wherein said alkyl, phenyl and heterocycle are optionally substituted with 0-2 R$^f$;

alternatively, R$^7$ and R$^8$, when attached to the same nitrogen, combine to form a 5- to 10-membered heterocycle comprising: carbon atoms and 0-2 additional heteroatoms selected from N, O, and S(O)$_p$, wherein said heterocycle is substituted with 0-2 R$^d$;

R$^{8a}$ is, independently at each occurrence, R$^7$, OH, C$_{1-6}$ alkyl, C$_{1-4}$ alkoxy, (C$_{6-10}$ aryl)-C$_{1-4}$ alkoxy, —(CH$_2$)$_n$-phenyl, —(CH$_2$)$_n$-(5-10 membered heteroaryl); wherein said phenyl, aryl and heteroaryl are optionally substituted with 0-2 R$^f$;

R$^9$ is, independently at each occurrence, H, C$_{1-6}$ alkyl, or —(CH$_2$)$_n$-phenyl; wherein said alkyl and phenyl are optionally substituted with 0-2 R$^f$;

R$^{9a}$ is, independently at each occurrence, H, C$_{1-6}$ alkyl, or —(CH$_2$)$_n$-phenyl;

alternatively, R$^8$ and R$^9$, when attached to the same nitrogen, combine to form a 5- to 10-membered heterocycle comprising: carbon atoms and 0-2 additional heteroatoms selected from N, O, and S(O)$_p$, wherein said heterocycle is substituted with 0-2 R$^d$;

R$^{10}$ is, independently at each occurrence, H, C$_{1-6}$ alkyl substituted with 0-2 R$^{10a}$, C$_{2-6}$ alkenyl substituted with 0-3 R$^{10a}$, C$_{2-6}$ alkynyl substituted with 0-3 R$^{10a}$, —(CH$_2$)$_r$—C$_{3-10}$ carbocycle substituted with 0-3 R$^d$, or —(CH$_2$)$_r$-5- to 10-membered heterocycle comprising carbon atoms and 1-4 heteroatoms selected from N, O, and S(O)$_p$, wherein said heterocycle is substituted with 0-3 R$^d$;

R$^{10a}$ is, independently at each occurrence, H, =O, C$_{1-4}$ alkyl, OR$^a$, SR$^a$, F, CF$_3$, CN, NO$_2$, —C(O)R$^a$, —C(O)OR$^a$, —C(O)NR$^7$R$^8$, —NR$^7$C(O)R$^b$, —S(O)$_p$NR$^8$R$^9$, —NR$^8$S(O)$_p$R$^c$, —S(O)R$^c$, or —S(O)$_2$R$^c$;

R$^{11}$ is C$_{1-4}$ haloalkyl, —(CH$_2$)$_r$—C(O)NR$^8$R$^9$, C$_{1-6}$ alkyl substituted with 0-3 R$^{11a}$, C$_{2-6}$ alkenyl substituted with 0-3 R$^{11a}$, C$_{2-6}$ alkynyl substituted with 0-3 R$^{11a}$, —(CR$^{14}$R$^{15}$)$_r$—C$_{3-10}$ carbocycle substituted with 0-3 R$^{11b}$, or —(CR$^{14}$R$^{15}$)$_r$-5- to 10-membered heterocycle comprising: carbon atoms and 1-4 heteroatoms selected from N, O, and S(O)$_p$, wherein said heterocycle is substituted with 0-3 R$^{11b}$;

R$^{11a}$ is, independently at each occurrence, H, =O, C$_{1-4}$ alkyl, OR$^a$, SR$^a$, F, CF$_3$, CN, NO$_2$, —NR$^7$R$^8$, —C(O)R$^a$, —C(O)OR$^a$, —C(O)NR$^7$R$^8$, —NR$^7$C(O)R$^b$, —S(O)$_p$NR$^8$R$^9$, —NR$^8$S(O)$_p$R$^c$, —S(O)$_p$R$^c$, C$_{3-6}$ cycloalkyl, C$_{1-4}$ haloalkyl, C$_{1-4}$ haloalkyloxy-, —(CH$_2$)$_r$—C$_{3-10}$ carbocycle substituted with 0-3 R$^d$, or —(CH$_2$)$_r$-5- to 10-membered heterocycle comprising carbon atoms and 1-4 heteroatoms selected from N, O, and S(O)$_p$, and substituted with 0-3 R$^d$;

R$^{11b}$ is, independently at each occurrence, H, =O, =NR$^8$, OR$^a$, F, Cl, Br, CN, NO$_2$, CF$_3$, OCF$_3$, OCHF$_2$, —NR$^7$R$^8$, —C(O)R$^a$, —C(O)OR$^a$, —C(O)NR$^7$R$^8$, —NR$^7$C(O)R$^b$, —NR$^8$C(O)$_2$R$^c$, —S(O)$_p$NR$^8$R$^9$, —NR$^8$S(O)$_p$R$^c$, —S(O)$_p$R$^c$, C$_{1-6}$ alkyl, C$_{2-6}$ alkenyl, C$_{2-6}$ alkynyl, C$_{3-6}$ cycloalkyl, C$_{1-4}$ haloalkyl, C$_{1-4}$ haloalkyloxy-, —(CH$_2$)$_r$—C$_{3-10}$ carbocycle substituted with 0-3 R$^d$, or —(CH$_2$)$_r$-5- to 10-membered heterocycle comprising carbon atoms and 1-4 heteroatoms selected from N, O, and S(O)$_p$, and substituted with 0-3 R$^d$;

alternately, when two R$^{11b}$ groups are substituents on adjacent atoms they may be taken together with the atoms to which they are attached to form a 5- to 7-membered heterocycle comprising carbon atoms and 1-4 heteroatoms selected from N, O, and S(O)$_p$ and substituted with 0-2 R$^g$;

R$^{13}$ is H, C$_{1-6}$ alkyl, —C(O)R$^c$, —C(O)OR$^c$, —CONR$^8$R$^c$, —OCONR$^8$R$^c$, —S(O)$_2$R$^c$, —(CH$_2$)$_n$-phenyl, —(CH$_2$)$_n$-(5-10 membered heteroaryl), —C(O)O—(C$_{1-4}$ alkyl)-OC(O)—(C$_{1-4}$ alkyl), or —C(O)O—(C$_{1-4}$ alkyl)-OC(O)—(C$_{6-10}$ aryl);

wherein said alkyl, phenyl, aryl, and heteroaryl are optionally substituted with 0-2 R$^f$;

R$^{14}$ and R$^{15}$ are, independently at each occurrence, H, F, or C$_{1-4}$ alkyl;

alternatively, R$^{14}$ combines with R$^{15}$ to form =O;

R$^a$ is, independently at each occurrence, H, CF$_3$, C$_{1-6}$ alkyl, —(CH$_2$)$_r$—C$_{3-7}$ cycloalkyl, —(CH$_2$)$_r$—C$_{6-10}$ aryl, or —(CH$_2$)$_r$-5- to 10-membered heterocycle comprising: carbon atoms and 1-4 heteroatoms selected from N, O, and S(O)$_p$; wherein said cycloalkyl, aryl and heterocycle groups are optionally substituted with 0-2 R$^f$;

R$^b$ is, independently at each occurrence, CF$_3$, OH, C$_{1-4}$ alkoxy, C$_{1-6}$ alkyl, —(CH$_2$)$_r$—C$_{3-10}$ carbocycle substituted with 0-3 R$^d$, or —(CH$_2$)$_r$-5- to 10-membered heterocycle comprising: carbon atoms and 1-4 heteroatoms selected from N, O, and S(O)$_p$ and substituted with 0-2 R$^d$;

R$^c$ is, independently at each occurrence, CF$_3$, C$_{1-6}$ alkyl substituted with 0-2 R$^f$, C$_{3-6}$ cycloalkyl substituted with 0-2 R$^f$, C$_{6-10}$ aryl, 5- to 10-membered heteroaryl, (C$_{6-10}$ aryl)-C$_{1-4}$ alkyl, or (5- to 10-membered heteroaryl)-C$_{1-4}$ alkyl, wherein said aryl and heteroaryl groups are substituted with 0-3 R$^f$;

R$^d$ is, independently at each occurrence, H, =O, =NR$^8$, OR$^a$, F, Cl, Br, I, CN, NO$_2$, —NR$^7$R$^8$, —C(O)R$^a$, —C(O)OR$^a$, —OC(O)R$^a$, —NR$^8$C(O)R$^a$, —C(O)NR$^7$R$^8$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl substituted with 0-2 R$^e$, C$_{2-6}$ alkenyl substituted with 0-2 R$^e$, or C$_{2-6}$ alkynyl substituted with 0-2 R$^e$;

R$^e$ is, independently at each occurrence, =O, OR$^a$, F, Cl, Br, I, CN, NO$_2$, —NR$^8$R$^9$, —C(O)R$^a$, —C(O)OR$^a$, —NR$^8$C(O)R$^a$, —C(O)NR$^7$R$^8$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

R$^f$ is, independently at each occurrence, H, =O, —(CH$_2$)$_r$OR$^g$, F, Cl, Br, I, CN, NO$_2$, —NR$^{9a}$R$^{9a}$, —C(O)R$^g$, —C(O)OR$^g$, —NR$^{9a}$C(O)R$^g$, —C(O)NR$^{9a}$R$^{9a}$, —SO$_2$NR$^{9a}$R$^{9a}$, —NR$^{9a}$SO$_2$NR$^{9a}$R$^{9a}$, —NR$^{9a}$SO$_2$—C$_{1-4}$ alkyl, —NR$^{9a}$SO$_2$CF$_3$, —NR$^{9a}$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, or —(CH$_2$)$_n$-phenyl;

R$^g$ is, independently at each occurrence, H, C$_{1-6}$ alkyl, or —(CH$_2$)$_n$-phenyl;

n, at each occurrence, is selected from 0, 1, 2, 3, and 4;
p, at each occurrence, is selected from 0, 1, and 2; and
r, at each occurrence, is selected from 0, 1, 2, 3, and 4; and
s, at each occurrence, is selected from 1, 2, 3, and 4.

2. A compound according to claim 1, wherein:
A is substituted with 0-1 R$^1$ and 0-2 R$^2$ and selected from;
C$_{3-7}$ cycloalkyl, phenyl, napthyl, pyridyl, 1,2,3,4-tetrahydronaphthyl, indazolyl, benzimidazolyl, benzisoxazolyl, isoquinolinyl, 5,6,7,8-tetrahydroisoquinolinyl, 1,2,3,4-tetrahydroisoquinolinyl, quinazolinyl, 1,1H-quinazolin-4-onyl, 2H-isoquinolin-1-onyl, 3H-quinazolin-4-onyl, 3,4-dihydro-2H-isoquinolin-1-onyl, 2,3-dihydroisoindolinonyl, and phthalazinyl;

$R^4$ is, independently at each occurrence, H, F, Cl, Br, I, $OCF_3$, $CF_3$, CN, $NO_2$, $OR^a$, $SR^a$, —$C(O)R^a$, —$C(O)OR^a$, —$NR^7R^8$, —$C(O)NR^8R^9$, —$NR^7C(O)R^b$, —$S(O)_pNR^8R^9$, —$NR^8S(O)_pR^c$, —$S(O)R^c$, —$S(O)_2R^c$, $C_{1-6}$ alkyl substituted with 0-2 $R^{4a}$, $C_{2-6}$ alkenyl substituted with 0-2 $R^{4a}$, $C_{2-6}$ alkynyl substituted with 0-2 $R^{4a}$, phenyl substituted with 0-2 $R^{4b}$, or a 5-10 membered heterocycle comprising: carbon atoms and 1-4 heteroatoms selected from N, O, and $S(O)_p$, wherein said heterocycle is substituted with 0-3 $R^{4b}$;

$R^6$ is H, or $C_{1-4}$alkyl;

$R^{10}$ is, independently at each occurrence, H, $C_{1-6}$ alkyl substituted with 0-2 $R^{10a}$, —$(CH_2)_r$-phenyl substituted with 0-2 $R^d$, or —$(CH_2)_r$-5-10 membered heterocycle comprising carbon atoms and 1-4 heteroatoms selected from N, O, and $S(O)_p$, wherein said heterocycle is substituted with 0-2 $R^d$; and $R^{11}$ is $C_{1-4}$ haloalkyl, —$(CH_2)_r$—$CONR^8R^9$, $C_{1-6}$ alkyl substituted with 0-2$R^{11a}$, $C_{2-6}$ alkenyl substituted with 0-2 $R^{11a}$, $C_{2-6}$ alkynyl substituted with 0-2 $R^{11a}$, —$(CH_2)_r$—$C_{3-10}$ carbocycle substituted with 0-3 $R^{11b}$, or —$(CH_2)_r$-5- to 10-membered heterocycle comprising carbon atoms and 1-4 heteroatoms selected from N, O, and $S(O)_p$, wherein said heterocycle is substituted with 0-3 $R^{11b}$.

3. A compound according to claim 2, wherein:

$R^1$ is, independently at each occurrence, F, Cl, Me, Et, —$NH_2$, —$C(=NH)NH_2$, —$C(O)NH_2$, —$CH_2NH_2$, —$CH_2CH_2NH_2$, —$CH_2NHCO_2Bn$, —$CH_2NHCO_2$(t-Bu), —$CH(Me)NH_2$, —$CMe_2NH_2$, —NHEt, —$NHCO_2$(t-Bu), —$NHCO_2Bn$, —$SO_2NH_2$, $OR^a$, or —$CH_2R^{1a}$;

$R^3$ is —$CO_2H$, —$CO_2Me$, —$C(O)NHCH_2CO_2H$, —$C(O)NHCH_2CO_2Et$, —$C(O)NH_2$, —$C(O)NHMe$, —$C(O)NHBn$, —$(CH_2)_r$-phenyl substituted with 0-2 $R^{3a}$ and 0-1 $R^{3d}$, naphthyl substituted with 0-2 $R^{3a}$ and 0-1 $R^{3d}$, indanyl substituted with 0-2 $R^{3a}$ and 0-1 $R^{3d}$, or a 5- to 10-membered heterocycle selected from N, O, and $S(O)_p$, wherein said heterocycle is substituted with 0-2 $R^{3a}$ and 0-1 $R^{3d}$;

$R^4$ is H, F, Cl, Br, OMe, $NH_2$, $CF_3$, $CO_2H$, $CO_2Me$, $CO_2Et$, —$CONR^8R^9$, $C_{1-6}$ alkyl substituted with 0-2 $R^{4a}$, phenyl substituted with 0-2 $R^{4b}$, or a 5-10 membered heterocycle comprising: carbon atoms and 1-4 heteroatoms selected from N, O, and $S(O)_p$, wherein said heterocycle is substituted with 0-3 $R^{4b}$;

$R^6$ is H;

$R^{10}$ is H; and $R^{11}$ is $C_{1-6}$ alkyl, —$(CH_2)_r$—$C(O)NR^8R^9$, —$CH_2OBn$, —$CH_2SBn$, —$(CH_2)_s$-cyclohexyl substituted with 0-2 $R^{11b}$, —$(CH_2)_s$-phenyl substituted with 0-2 $R^{11b}$, —$(CH_2)_s$-naphthyl substituted with 0-2 $R^{11b}$, —$(CH_2)_s$-5- to 10-membered heteroaryl substituted with 0-1 $R^{11b}$; wherein said heteroaryl selected from thiazolyl, imidazolyl, pyridyl, indolyl benzimidazolyl, and benzothiazolyl.

4. A compound according to claim 3, wherein:

L is —C(O)NH—; and $R^{11}$ is phenylmethyl, 4-imidazolylmethyl, 4-thiazolylmethyl, 2-benzthiazolylmethyl, 2-pyridylmethyl, 3-pyridylmethyl, 4-pyridylmethyl, 3-indolylmethyl, 2-benzimidazolylmethyl, 1-naphthylmethyl, 2-naphthylmethyl, cyclohexylmethyl, —$CH_2C(O)NHCH_2$-pyridin-2-yl or —$(CH_2)_2C(O)NHCH_2$-pyridin-2-yl, wherein each phenyl, naphthyl, imidazolyl, thiazolyl, benzthiazolyl, pyridinyl, or cyclohexyl group is substituted with 0-2 $R^{11b}$;

$R^{11b}$ is, independently at each occurrence, H, F, Cl, Br, $CF_3$, OMe, $OCF_3$, $OCHF_2$, OPh, OBn, $NO_2$, —$NH_2$, —C(O)Ph, —NHC(O)Bn, —$NHC(O)CH_2CH_2Ph$, —$NHS(O)_2Ph$, —$C(O)NR^7R^8$, —$NR^7C(O)R^b$, —$S(O)_pNR^8R^9$, —$NR^8S(O)_pR^c$, Ph, or Bn;

alternately, when two $R^{11b}$ groups are substituents on adjacent atoms they may be taken together with the atoms to which they are attached to form a 5- to 7-membered heterocycle comprising carbon atoms and 1-4 heteroatoms selected from N, O, and $S(O)_p$ and substituted with 0-2 $R^g$.

5. A compound according to claim 4, wherein:

$R^3$ is phenyl substituted with 0-2 $R^{3a}$, naphthyl substituted with 0-2 $R^{3a}$, indanone substituted with 0-2 $R^{3a}$, or a 5- to 10-membered heterocycle substituted with 0-2 $R^{3a}$ and selected from: pyridine, pyridinone, pyrimidine, pyrrole, pyrazole, indole, 2-oxoindole, indazole, benzofuran, benzothiophene, benzimidazole, benzisoxazole, benzoxazole, quinazoline, 3H-quinazolin-4-one, phthalazine, 2H-phthalazin-1-one, 1H-quinolin-4-one, isoquinoline, and 2H-3,4-dihydroisoquinolin-1-one.

6. A compound according to claim 5, wherein:

A is 4-aminomethyl-cyclohexyl, 4-carbamoyl-cyclohexyl, 4-amidino-phenyl, 4-benzyloxycarbonylamino-cyclohexyl, phenyl, 1,2,3,4-tetrahydronapht h-2-yl, 4-aminomethyl-phenyl, 4-carbamoyl-phenyl, 4 aminomethyl-2-fluoro-phenyl, 2-F-5-OMe-phenyl, 2-F-4-Me-phenyl, 2-F-4-Cl-phenyl, 2-F-4-carbamoyl-phenyl, 2-OMe-4-carbamoyl-phenyl, 3-OMe-4-carbamoyl-phenyl, 2-Et-4-aminomethyl-phenyl, 2-$NH_2$-pyridin-4-yl, 2-ethylamino-4-aminomethyl-phenyl, 1-aminoisoquinolin-6-yl, 1-$NH_2$-5,6,7,8-tetrahydroisoquinolin-6-yl, 1-$NH_2$-1,2,3,4-tetrahydroisoquinolin-6-yl, 3-$NH_2$-benzisoxazol-5-yl, 3-$NH_2$-benzisoxazol-6-yl, 3-$NH_2$-indazol-6-yl, 3-$NH_2$-indazol-5-yl, 1-Me-3-$NH_2$-indazoly-6-yl, 1,2,3,4-tetrahydroisoquinolin-3-yl, 1,2,3,4-tetrahydroisoquinolin-1-on-6-yl, isoquinolin-6-yl, 1-$NH_2$-isoquinolin-6-yl, 1-$NH_2$-5,6,7,8-tetrahydroisoquinolin-6-yl, 1,2,3,4-tetrahydroisoquinolin-6-yl, 1H-quinazolin-4-onyl, 2H-isoquinolin-1-onyl, 3H-quinazolin-4-onyl, 3,4-dihydro-2H-isoquinolin-1-onyl, 2,3-dihydroisoindolinonyl, or 1-$NH_2$-phthalazin-6-yl; and $R^3$ is phenyl, 3-OH-phenyl, 3,4-methylenedioxyphenyl, 2-naphthyl, 1-naphthyl, 3-$NMe_2$-phenyl, 4-benzyloxyphenyl, 4-t-butoxyphenyl, 4-methylsulfonylphenyl, 4-Cl-phenyl, 2-OMe-phenyl, 3-OMe-phenyl, 4-OMe-phenyl, 2-F-phenyl, 3-F-phenyl, 4-F-phenyl, 4-Br-phenyl, 3-$CF_3$-phenyl, 3-$NH_2$-phenyl, 4-$NH_2$-phenyl, 3-CN-phenyl, 4-CN-phenyl, 3-$CO_2H$-phenyl, 4-$CO_2H$-phenyl, 3-$CO_2Me$-phenyl, 4-$CO_2Me$-phenyl, 3-OH-phenyl, 3-$CH_2CO_2H$-phenyl, 3-$CH_2CO_2Me$-phenyl, 3-$CH_2CO_2Et$-phenyl, 3-$CONH_2$-phenyl, 4-$CONH_2$-phenyl, 4-$CH_2CO_2Et$-phenyl, 3-$CH_2C(O)NH_2$-phenyl, 4-C(O)NHMe-phenyl, 3-NHCOMe-phenyl, 4-$NHCO_2Me$-phenyl, 2,4-diF-phenyl, 3-F-4-CN-phenyl, 3-CN-4-F-phenyl, 3-OMe-4-$CONH_2$-phenyl, 3-OH-4-$CONH_2$-phenyl, 3-$NH_2$-4-$CONH_2$-phenyl, 3-$CO_2Me$-4-$NH_2$-phenyl, 3-$CO_2H$-4-$NH_2$-phenyl, 3-$CONH_2$-4-$NH_2$-phenyl, 3-$CO_2H$-4-F-phenyl, pyrrol-3-yl, pyrazol-3-yl, pyrazol-4-yl, 3-$NH_2$-pyrazol-5-yl, pyridyl-2-yl, pyrid-3-yl, pyrid-4-yl, 2-F-pyrid-4-yl, 2-F-pyrid-5-yl, 2-OMe-pyrid-4-yl, 2-OMe-pyrid-5-yl, 2-NH$_2$-pyrid-3-yl, 2-NH$_2$-pyrid-4-yl, 2-NHH$_2$-pyrid-5-yl, 2-NH$_2$-pyrid-6-yl, 2-NHMe-pyrid-4-yl, 2-NMe$_2$-pyrid-4-yl, 2-CONH$_2$-pyrid-4-yl, 2-CO$_2$H-pyrid-4-yl, 2-CONH$_2$-pyrid-5-yl, 2-OMe-6-NH$_2$-pyridyl-4-yl, 4-NH$_2$-pyrimidin-6-yl, 4-NH$_2$-pyrimidin-2-yl, 2-NH$_2$-pyrimidin-4-yl, 2-NH$_2$-pyrimidin-5-yl, indol-5-yl, indol-6-yl, indazol-5-yl, indazol-6-yl, 3-OH-indazol-5-yl, 3-OH-indazol-6-yl, 3-OMe-indazol-5-yl, 3-OMe-indazol-6-yl, 3-NH$_2$-indazol-5-yl, 3-NH$_2$-indazol-6-yl, benzisoxalol-6-yl, benzisoxazol-5-yl, 3-NH$_2$-benzoisoxazol-5-yl, 3-NH$_2$-benzoisoxazol-6-yl, 4-OMe-quinolin-6-yl, 1-NH$_2$-phthalazin-6-yl, 1-NH$_2$-phthalazin-7-yl, 4-NH$_2$-quinazolin-6-yl, 2-Me-4-aminoquinazolin-6-yl, 4-NH$_2$-quinazolin-7-yl, 2-Me-4-NH$_2$-quinazolin-7-yl, 2,4-di-NH$_2$-quinazolin-7-yl,

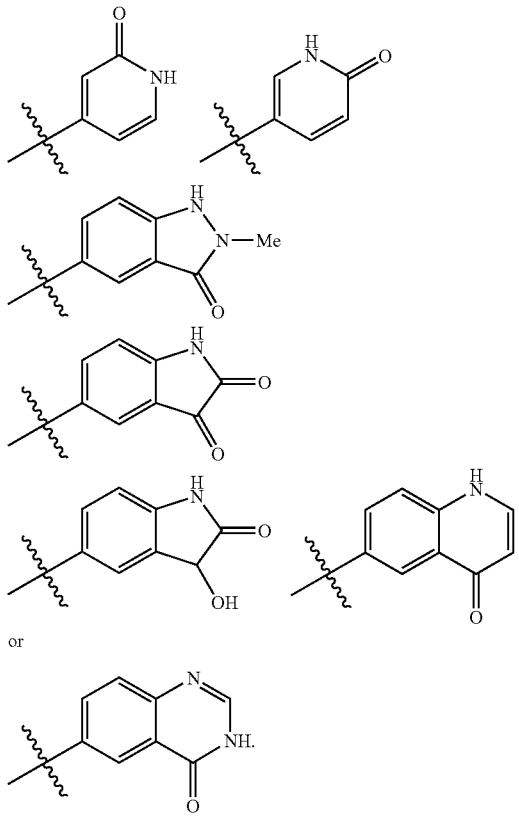

or

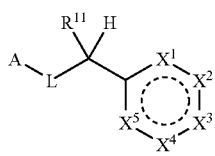

7. A compound of Formula (Ia):

(Ia)

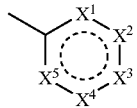

or a stereoisomer or pharmaceutically acceptable salt, or solvate thereof, wherein:

A is C$_{3-7}$ cycloalkyl substituted with 0-1 R$^1$ and 0-2 R$^2$, C$_{3-7}$ cycloalkenyl substituted with 0-1 R$^1$ and 0-2 R$^2$, phenyl substituted with 0-1 R$^1$ and 0-3 R$^2$, naphthyl substituted with 0-1 R$^1$ and 0-3 R$^2$, or a 5- to 10-membered heterocycle comprising: carbon atoms and 1-4 heteroatoms selected from N, O, and S(O)$_p$, wherein said heterocycle is substituted 0-1 R$^1$ and 0-3 R$^2$;

the group

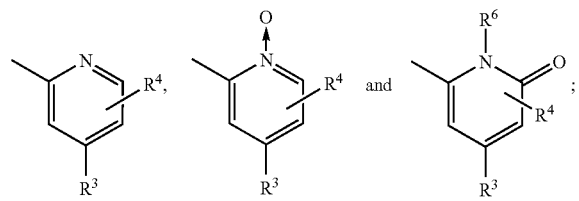

is selected from:

L is —C(O)NR$^{10}$—;

R$^1$ is, independently at each occurrence, —NH$_2$, —NH(C$_{1-3}$ alkyl), —N(C$_{1-3}$ alkyl)$_2$, —C(=NH)NH$_2$, —C(O)NH$_2$, —CH$_2$NH$_2$, —(CH$_2$)$_r$NR$^7$R$^8$, —CH$_2$NH(C$_{1-3}$ alkyl), —CH$_2$N(C$_{1-3}$ alkyl)$_2$, —CH$_2$CH$_2$NH$_2$, —CH$_2$CH$_2$NH(C$_{1-3}$ alkyl), —CH$_2$CH$_2$N(C$_{1-3}$ alkyl)$_2$, —CH(C$_{1-4}$ alkyl)NH$_2$, —C(C$_{1-4}$ alkyl)$_2$NH$_2$, —C(=NR$^{8a}$)NR$^7$R$^8$, —NR$^8$CR$^8$(=NR$^{8a}$), —NHC(=NR$^{8a}$)NR$^7$R$^8$, =NR$^8$, —C(O)NR$^8$R$^9$, —S(O)$_p$NR$^8$R$^9$, —(CH$_2$)$_r$NR$^7$C(O)OR$^a$, F, Cl, Br, I, OCF$_3$, CF$_3$, OR$^a$, SR$^a$, CN, 1-NH$_2$-1-cyclopropyl, or C$_{1-6}$ alkyl substituted with 0-1 R$^{1a}$;

R$^{1a}$ is H, —C(=NR$^{8a}$)NR$^7$R$^8$, —NHC(=NR$^{8a}$)NR$^7$R$^8$, —NR$^8$CR$^8$(=NR$^{8a}$), —NR$^7$R$^8$, —C(O)NR$^8$R$^9$, F, OCF$_3$, CF$_3$, OR$^a$, SR$^a$, CN, —NR$^8$SO$_2$NR$^8$R$^9$, —NR$^8$SO$_2$R$^c$, —S(O)$_p$—C$_{1-4}$ alkyl, —S(O)$_p$-phenyl, or —(CF$_2$)$_r$CF$_3$;

R$^2$ is, independently at each occurrence, H, =O, F, Cl, Br, I, OCF$_3$, CF$_3$, CHF$_2$, CN, NO$_2$, OR$^a$, SR$^a$, —C(O)R$^a$, —C(O)OR$^a$, —OC(O)R$^a$, —NR$^7$R$^8$, —C(O)NR$^7$R$^8$, —NR$^7$C(O)R$^b$, —S(O)$_p$NR$^8$R$^9$, —NR$^8$S(O)$_2$R$^c$, —S(O)R$^c$, —S(O)$_2$R$^c$, C$_{1-6}$ alkyl, C$_{2-6}$ alkenyl, C$_{2-6}$ alkynyl, —(CH$_2$)$_r$-phenyl substituted with 0-2 R$^{2b}$, or —(CH$_2$)$_r$-5- to 6-membered heterocycle comprising: carbon atoms and 1-4 heteroatoms selected from N, O, and S(O)$_p$, wherein said heterocycle is substituted with 0-3 R$^{2b}$;

R$^{2b}$ is, independently at each occurrence, H, F, Cl, Br, I, =O, =NR$^8$, CN, NO$_2$, CF$_3$, OR$^a$, SR$^a$, —C(O)R$^a$, —C(O)OR$^a$, —OC(O)R$^a$, —NR$^7$R$^8$, —C(O)NR$^7$R$^8$, —NR$^7$C(O)R$^b$, —S(O)$_p$NR$^8$R$^9$, —SO$_2$R$^c$, —NR$^8$SO$_2$NR$^8$R$^9$, —NR$^8$SO$_2$R$^c$, —(CF$_2$)$_r$CF$_3$, C$_{1-6}$ alkyl, C$_{2-6}$ alkenyl, C$_{2-6}$ alkynyl, C$_{3-6}$ cycloalkyl, C$_{1-4}$ haloalkyl, or C$_{1-4}$ haloalkyloxy-;

alternately, when R$^1$ and R$^2$ are substituted on adjacent ring atoms, they can be taken together with the ring atoms to which they are attached to form a 5- to 7-membered carbocycle or heterocycle comprising: carbon atoms and 0-4 heteroatoms selected from N, O, and S(O)$_p$, wherein said carbocycle or heterocycle is substituted with 0-2 R$^{2b}$;

R$^3$ is, independently at each occurrence, —(CH$_2$)$_r$C(O)NR$^8$R$^9$, —(CH$_2$)$_r$C(O)NR$^8$(CH$_2$)$_s$CO$_2$R$^{3b}$, —(CH$_2$)$_r$CO$_2$R$^{3b}$, —(CH$_2$)$_r$-phenyl substituted with 0-3 R$^{3a}$ and 0-1 $R^{3d}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^{3a}$ is, independently at each occurrence, =O, F, Cl, Br, I, $OCF_3$, $CF_3$, CN, $NO_2$, —$(CH_2)_rOR^{3b}$, $SR^{3b}$, —$(CH_2)_rNR^7R^8$, —$C(=NR^{8a})NR^8R^9$, —$NHC(=NR^{8a})NR^7R^8$, —$NR^8CR^8(=NR^{8a})$, —$(CH_2)_rNR^8C(O)R^{3b}$, =$NR^8$, —$(CH_2)_rNR^8C(O)R^{3b}$, —$(CH_2)_rNR^8C(O)_2R^{3b}$, —$(CH_2)_rS(O)_pNR^8R^9$, —$(CH_2)_rNR^8S(O)_pR^{3c}$, —$S(O)R^{3c}$, —$S(O)_2R^{3c}$, —C(O)—$C_{1-4}$ alkyl, —$(CH_2)_rCO_2R^{3b}$, —$(CH_2)_rC(O)NR^8R^9$, —$(CH_2)_rOC(O)NR^8R^9$, —$NHCOCF_3$, —$NHSO_2CF_3$, —$SO_2NHR^{3b}$, —$SO_2NHCOR^{3c}$, —$SO_2NHCO_2R^{3c}$, —$CONHSO_2R^{3c}$, —$NHSO_2R^{3c}$, —$CONHOR^{3b}$, $C_{1-4}$ haloalkyl, $C_{1-4}$ haloalkyloxy-, $C_{1-6}$ alkyl substituted by $R^{3d}$, $C_{2-6}$ alkenyl substituted by $R^{3d}$, $C_{1-6}$ alkynyl substituted by $R^{3d}$, $C_{3-6}$ cycloalkyl substituted by 0-1 $R^{3d}$, —$(CH_2)_r$—$C_{3-10}$ carbocycle substituted with 0-3 $R^{3d}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

alternately, when two $R^{3a}$ groups are substituted on adjacent atoms, they can be taken together with the atoms to which they are attached to form a $C_{3-10}$ carbocycle substituted with 0-2 $R^{3d}$, or a 5- to 10-membered heterocycle comprising: carbon atoms and 1-4 heteroatoms selected from N, O, and $S(O)_p$, wherein said heterocycle is substituted with 0-2 $R^{3d}$;

$R^{3b}$ is, independently at each occurrence, H, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, —$(CH_2)_r$—$C_{3-10}$ carbocycle substituted with 0-3 $R^{3d}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3c}$ is, independently at each occurrence, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, —$(CH_2)_r$—$C_{3-10}$ carbocycle substituted with 0-3 $R^{3d}$, or —$(CH_2)_r$-5- to 10-membered heterocycle comprising:

carbon atoms and 1-4 heteroatoms selected from N, O, and $S(O)_p$, wherein said heterocycle is substituted with 0-3 $R^{3d}$;

$R^{3d}$ is, independently at each occurrence, H, =O, —$(CH_2)_rOR^a$, F, Cl, Br, CN, $NO_2$, —$(CH_2)_rNR^7R^8$, —$C(O)R^a$, —$C(O)OR^a$, —$OC(O)R^a$, —$NR^7C(O)R^b$, —$C(O)NR^8R^9$, —$S(O)_2NR^8R^9$, —$NR^8S(O)_2NR^8R^9$, —$NR^8S(O)_2R^c$, —$S(O)_pR^c$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_r$—$C_{3-10}$ carbocycle substituted with 0-3 $R^d$, or —$(CH_2)_r$-5- to 10-membered heterocycle comprising: carbon atoms and 1-4 heteroatoms selected from N, O, and $S(O)_p$, wherein said heterocycle is substituted with 0-3 $R^d$;

$R^4$ is, independently at each occurrence, H, =O, F, Cl, Br, I, $OCF_3$, $CF_3$, CN, $NO_2$, $OR^a$, $SR^a$, —$C(O)R^a$, —$C(O)OR^a$, —$OC(O)R^a$, —$NR^7R^8$, —$C(O)NR^8R^9$, —$NR^7C(O)R^b$, —$S(O)_pNR^8R^9$, —$NR^8S(O)_pR^c$, —$S(O)_2R^c$, $C_{1-6}$ alkyl substituted with 0-2 $R^{4a}$, $C_{2-6}$ alkenyl substituted with 0-2 $R^{4a}$, $C_{2-6}$ alkynyl substituted with 0-2 $R^{4a}$, —$(CH_2)_r$—$C_{3-10}$ carbocycle substituted with 0-3 $R^{4b}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{4b}$;

$R^{4a}$ is, independently at each occurrence, H, F, —O, $C_{1-4}$ alkyl, $OR^a$, $SR^a$, $CF_3$, CN, $NO_2$, —$C(O)R^a$, —$C(O)OR^a$, —$NR^7R^8$, —$C(O)NR^8R^9$, —$NR^7C(O)R^b$, —$S(O)_pNR^8R^9$, —$NR^8S(O)_pR^c$, —$S(O)R^c$, or —$S(O)_2R^c$;

$R^{4b}$ is, independently at each occurrence, H, =O, =$NR^8$, F, Cl, Br, I, $OR^a$, $SR^a$, CN, $NO_2$, —$NR^7R^8$, —$C(O)R^a$, —$C(O)OR^a$, —$NR^7C(O)R^b$, —$C(O)NR^8R^9$, —$SO_2NR^8R^9$, —$S(O)_2R^c$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$ haloalkyloxy-;

alternately, $R^3$ and $R^4$ groups when located on adjacent atoms, can be taken together to form a $C_{3-10}$ carbocycle substituted with 0-2 $R^{3d}$ or a 5- to 10-membered heterocycle comprising: carbon atoms and 1-4 heteroatoms selected from N, O, and $S(O)_p$, wherein said heterocycle is substituted with 0-2 $R^{3d}$;

$R^6$ is, independently at each occurrence, H, $C_{1-6}$ alkyl, $C_{1-4}$ haloalkyl, —$CH_2OR^a$, —$C(O)R^c$, —$C(O)_2R^c$, —$S(O)_2R^c$, or —$(CH_2)_r$-phenyl substituted with 0-3 $R^d$;

$R^7$ is, independently at each occurrence, H, $C_{1-6}$ alkyl, —$(CH_2)_n$—$C_{3-10}$ carbocycle, —$(CH_2)_n$-(5-10 membered heteroaryl), —$C(O)R^c$, —CHO, —$C(O)_2R^c$, —$S(O)_2R^c$, —$CONR^8R^c$, —$OCONHR^c$, —$C(O)O$—$(C_{1-4}$ alkyl)$OC(O)$—$(C_{1-4}$ alkyl), or —$C(O)O$—$(C_{1-4}$ alkyl)$OC(O)$—$(C_{6-10}$ aryl); wherein said alkyl, carbocycle, heteroaryl, and aryl are optionally substituted with 0-2 $R^f$;

$R^8$ is, independently at each occurrence, H, $C_{1-6}$ alkyl, —$(CH_2)_n$-phenyl, or —$(CH_2)_n$-5-10 membered heterocycle comprising: carbon atoms and 1-4 heteroatoms selected from N, O, and $S(O)_p$; wherein said alkyl, phenyl and heterocycle are optionally substituted with 0-2 $R^f$;

alternatively, $R^7$ and $R^8$, when attached to the same nitrogen, combine to form a 5- to 10-membered heterocycle comprising: carbon atoms and 0-2 additional heteroatoms selected from N, O, and $S(O)_p$, wherein said heterocycle is substituted with 0-2 $R^d$;

$R^{8a}$ is, independently at each occurrence, $R^7$, OH, $C_{1-6}$ alkyl, $C_{1-4}$ alkoxy, $(C_{6-10}$ aryl)-$C_{1-4}$ alkoxy; wherein said aryl is optionally substituted with 0-2 $R^f$;

$R^9$ is, independently at each occurrence, H, $C_{1-6}$ alkyl, or —$(CH_2)_n$-phenyl; wherein said alkyl and phenyl are optionally substituted with 0-2 $R^f$;

$R^{9a}$ is, independently at each occurrence, H, $C_{1-6}$ alkyl, or —$(CH_2)_n$-phenyl;

alternatively, $R^8$ and $R^9$, when attached to the same nitrogen, combine to form a 5- to 10-membered heterocycle comprising: carbon atoms and 0-2 additional heteroatoms selected from N, O, and $S(O)_p$, wherein said heterocycle is substituted with 0-2 $R^d$;

$R^{10}$ is, independently at each occurrence, H, $C_{1-6}$ alkyl substituted with 0-2 $R^{10a}$, —$(CH_2)_r$-phenyl substituted with 0-3 $R^d$, or —$(CH_2)_r$-5- to 10-membered heterocycle comprising carbon atoms and 1-4 heteroatoms selected from N, O, and $S(O)_p$, wherein said heterocycle is substituted with 0-3 $R^d$;

$R^{10a}$ is, independently at each occurrence, H, =O, $C_{1-4}$ alkyl, $OR^a$, $SR^a$, F, $CF_3$, CN, $NO_2$, —$C(O)R^a$, —$C(O)OR^a$, —$C(O)NR^7R^8$, —$NR^7C(O)R^b$, —$S(O)_pNR^8R^9$, —$NR^8S(O)_pR^c$, —$S(O)R^c$, or —$S(O)_2R^c$;

$R^{11}$ is $C_{1-4}$ haloalkyl, —$(CH_2)_r$—$C(O)NR^8R^9$, $C_{1-6}$ alkyl substituted with 0-3 $R^{11a}$, $C_{2-4}$ alkenyl substituted with 0-3 $R^{11a}$, $C_{2-4}$ alkynyl substituted with 0-3 $R^{11a}$, —(CH$_2$)$_s$—C$_{3-7}$ cycloalkyl substituted with 0-3 R$^{11b}$, —(CH$_2$)$_s$-phenyl substituted with 0-3 R$^{11b}$, or —(CH$_2$)$_s$-5- to 10-membered heterocycle comprising: carbon atoms and 1-4 heteroatoms selected from N, O, and S(O)$_p$, wherein said heterocycle is substituted with 0-3 R$^{11b}$;

R$^{11a}$ is, independently at each occurrence, H, =O, C$_{1-4}$ alkyl, OR$^a$, SR$^a$, F, CF$_3$, CN, NO$_2$, —NR$^7$R$^8$, —C(O)R$^a$, —C(O)OR$^a$, —C(O)NR$^7$R$^8$, —NR$^7$C(O)R$^b$, —S(O)$_p$NR$^8$R$^9$, —NR$^8$S(O)$_p$R$^c$, or —S(O)$_p$R$^c$, C$_{3-6}$ cycloalkyl, C$_{1-4}$ haloalkyl, C$_{1-4}$ haloalkyloxy-, —(CH$_2$)$_r$—C$_{3-10}$ carbocycle substituted with 0-3 R$^d$, or —(CH$_2$)$_r$-5- to 10-membered heterocycle comprising carbon atoms and 1-4 heteroatoms selected from N, O, and S(O)$_p$, and substituted with 0-3 R$^d$;

R$^{11b}$ is, independently at each occurrence, H, =O, =NR$^8$, OR$^a$, F, Cl, Br, CN, NO$_2$, CF$_3$, OCF$_3$, OCHF$_2$, —NR$^7$R$^8$, —C(O)R$^a$, —C(O)OR$^a$, —C(O)NR$^7$R$^8$, —NR$^7$C(O)R$^b$, —NR$^8$C(O)$_2$R$^c$, —S(O)$_p$NR$^8$R$^9$, —NR$^8$S(O)$_p$R$^c$, —S(O)$_p$R$^c$, C$_{1-6}$ alkyl, C$_{2-6}$ alkenyl, C$_{2-6}$ alkynyl, C$_{3-6}$ cycloalkyl, C$_{1-4}$ haloalkyl, C$_{1-4}$ haloalkyloxy-, —(CH$_2$)$_r$—C$_{3-10}$ carbocycle substituted with 0-3 R$^d$, or —(CH$_2$)$_r$-5- to 10-membered heterocycle comprising carbon atoms and 1-4 heteroatoms selected from N, O, and S(O)$_p$, and substituted with 0-3 R$^d$;

alternately, when two R$^{11b}$ groups are substituents on adjacent atoms they may be taken together with the atoms to which they are attached to form a 5- to 7-membered heterocycle comprising carbon atoms and 1-4 heteroatoms selected from N, O, and S(O)$_p$ and substituted with 0-2 R$^g$;

R$^{13}$ is H, C$_{1-6}$ alkyl, —C(O)R$^c$, —C(O)OR$^c$, —CONR$^8$R$^c$, —OCONR$^8$R$^c$, —S(O)$_2$R$^c$, —(CH$_2$)$_n$-phenyl, —(CH$_2$)$_n$-(5-10 membered heteroaryl), —C(O)O—(C$_{1-4}$ alkyl)-OC(O)—(C$_{1-4}$ alkyl), or —C(O)O—(C$_{1-4}$ alkyl)-OC(O)—(C$_{6-10}$ aryl);

wherein said alkyl, phenyl, aryl, and heteroaryl are optionally substituted with 0-2 R$^f$;

R$^a$ is, independently at each occurrence, H, CF$_3$, C$_{1-6}$ alkyl, —(CH$_2$)$_r$—C$_{3-7}$ cycloalkyl, —(CH$_2$)$_r$—C$_{6-10}$ aryl, or —(CH$_2$)$_r$-5- to 10-membered heterocycle comprising: carbon atoms and 1-4 heteroatoms selected from N, O, and S(O)$_p$; wherein said cycloalkyl, aryl and heterocycle groups are optionally substituted with 0-2 R$^f$;

R$^b$ is, independently at each occurrence, CF$_3$, OH, C$_{1-4}$ alkoxy, C$_{1-6}$ alkyl, —(CH$_2$)$_r$—C$_{3-10}$ carbocycle substituted with 0-3 R$^d$, or —(CH$_2$)$_r$-5- to 10-membered heterocycle comprising: carbon atoms and 1-4 heteroatoms selected from N, O, and S(O)$_p$ and substituted with 0-2 R$^d$;

R$^c$ is, independently at each occurrence, CF$_3$, C$_{1-6}$ alkyl substituted with 0-2 R$^f$, C$_{3-6}$ cycloalkyl substituted with 0-2 R$^f$, C$_{6-10}$ aryl, 5- to 10-membered heteroaryl, (C$_{6-10}$ aryl)-C$_{1-4}$ alkyl, or (5- to 10-membered heteroaryl)-C$_{1-4}$ alkyl, wherein said aryl and heteroaryl groups are substituted with 0-3 R$^f$;

R$^d$ is, independently at each occurrence, H, =O, =NR$^8$, OR$^a$, F, Cl, Br, I, CN, NO$_2$, —NR$^7$R$^8$, —C(O)R$^a$, —C(O)OR$^a$, —OC(O)R$^a$, —NR$^8$C(O)R$^a$, —C(O)NR$^7$R$^8$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl substituted with 0-2 R$^e$, C$_{2-6}$ alkenyl substituted with 0-2 R$^e$, or C$_{2-6}$ alkynyl substituted with 0-2 R$^e$;

R$^e$ is, independently at each occurrence, =O, OR$^a$, F, Cl, Br, I, CN, NO$_2$, —NR$^8$R$^9$, —C(O)R$^a$, —C(O)OR$^a$, —NR$^8$C(O)R$^a$, —C(O)NR$^7$R$^8$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

R$^f$ is, independently at each occurrence, H, =O, —(CH$_2$)$_r$OR$^g$, F, Cl, Br, I, CN, NO$_2$, —NR$^{9a}$R$^{9a}$, —C(O)R$^g$, —C(O)OR$^g$, —NR$^{9a}$C(O)R$^g$, —C(O)NR$^{9a}$R$^{9a}$, —SO$_2$NR$^{9a}$R$^{9a}$, —NR$^{9a}$SO$_2$NR$^{9a}$R$^{9a}$, —NR$^{9a}$SO$_2$—C$_{1-4}$ alkyl, —NR$^{9a}$SO$_2$CF$_3$, —NR$^{9a}$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, or —(CH$_2$)$_n$-phenyl;

R$^g$ is, independently at each occurrence, H, C$_{1-6}$ alkyl, or —(CH$_2$)$_n$-phenyl;

n, at each occurrence, is selected from 0, 1, 2, 3, and 4;
p, at each occurrence, is selected from 0, 1, and 2; and
r, at each occurrence, is selected from 0, 1, 2, 3, and 4; and
s, at each occurrence, is selected from 1, 2, 3, and 4.

8. A compound according to claim 7, wherein:

A is substituted with 0-1 R$^1$ and 0-2 R$^2$ and selected from; C$_{3-7}$ cycloalkyl, phenyl, naphthyl, pyridyl, 1,2,3,4-tetrahydronaphthyl, indazolyl, benzimidazolyl, benzisoxazolyl, isoquinolinyl, 5,6,7,8-tetrahydroisoquinolinyl, 1,2,3,4-tetrahydroisoquinolinyl, quinazolinyl, 1H-quinazolin-4-onyl, 2H-isoquinolin-1-onyl, 3H-quinazolin-4-onyl, 3,4-dihydro-2H-isoquinolin-1-onyl, 2,3-dihydroisoindolinonyl, and phthalazinyl;

R$^4$ is, independently at each occurrence, H, F, Cl, Br, I, CF$_3$, CN, NO$_2$, OR$^a$, SR$^a$, —C(O)R$^a$, —C(O)OR$^a$, —NR$^7$R$^8$, —C(O)NR$^8$R$^9$, —NR$^7$C(O)R$^b$, —S(O)$_p$NR$^8$R$^9$, —NR$^8$S(O)$_p$R$^c$, —S(O)$_2$R$^c$, C$_{1-6}$ alkyl substituted with 0-2 R$^{4a}$, C$_{2-6}$ alkenyl substituted with 0-2 R$^{4a}$, C$_{2-6}$ alkynyl substituted with 0-2 R$^{4a}$; and R$^6$ is H, or C$_{1-4}$ alkyl.

9. A compound according to claim 8, wherein:

R$^1$ is, independently at each occurrence, F, Cl, Me, Et, —NH$_2$, —C(=NH)NH$_2$, —C(O)NH$_2$, —CH$_2$NH$_2$, —CH$_2$NHCO$_2$Bn, —CH$_2$NHCO$_2$(t-Bu), —CH(Me)NH$_2$, —CMe$_2$NH$_2$, —NHEt, —NHCO$_2$(t-Bu), —NHCO$_2$Bn, —SO$_2$NH$_2$, OR$^a$, or —CH$_2$R$^{1a}$;

R$^2$ is, independently at each occurrence, F, Cl, Me, OMe, OEt, Bn, —CH$_2$OMe, —CH$_2$OEt, or —CH$_2$OPh;

R$^3$ is —CO$_2$H, —CO$_2$Me, —C(O)NHCH$_2$CO$_2$H, —C(O)NHCH$_2$CO$_2$Et, —C(O)NH$_2$, —C(O)NHMe, —C(O)NHBn, phenyl substituted with 0-2 R$^{3a}$, naphthyl substituted with 0-2 R$^{3a}$, indane substituted with 0-2 R$^{3a}$, or a 5- to 10-membered heterocycle selected from N, O, and S(O)$_p$, wherein said heterocycle is substituted with 0-2 R$^3$a;

R$^{3a}$ is, independently at each occurrence, =O, F, Cl, Br, Me, CN, OH, NH$_2$, OMe, O(t-Bu), OBn, CF$_3$, CO$_2$H, CO$_2$Me, —CH$_2$CO$_2$H, —CH$_2$CO$_2$Me, —CH$_2$CO$_2$Et, —NHCOMe, —CONH$_2$, —CH$_2$CONH$_2$, —CONHMe, —CONMe$_2$, —C(=NH)NH$_2$, —NR$^7$R$^8$, SO$_2$Me, —SO$_2$NH$_2$, Ph, or 2-oxo-piperidin-1-yl; wherein two of the R$^{3a}$ groups located on adjacent atoms can be taken together to form 5- to 10-membered heterocycle with 0-2 R$^{3d}$;

R$^4$ is H, F, Cl, Br, OMe, or NH$_2$;

R$^6$ is H;

R$^{10}$ is H; and

R$^{11}$ is —(CH$_2$)$_r$—C(O)NR$^8$R$^9$, —CH$_2$OBn, —CH$_2$SBn, —(CH$_2$)$_s$-cyclohexyl substituted with 0-2 R$^{11b}$, —(CH$_2$)$_s$-phenyl substituted with 0-2 R$^{11b}$, —(CH$_2$)$_s$-naphthyl substituted with 0-2 R$^{11b}$, —(CH$_2$)$_s$-5- to 10-membered heteroaryl substituted with 0-1 $R^{11b}$; wherein said heteroaryl selected from thiazolyl, imidazolyl, pyridyl, indolyl benzimidazolyl, and benzothiazolyl.

10. A compound according to claim 9, wherein:

L is —C(O)NH—; and $R^{11}$ is phenylmethyl, 4-imidazolylmethyl, 4-thiazolylmethyl, 2-benzthiazolylmethyl, 2-pyridylmethyl, 3-pyridylmethyl, 4-pyridylmethyl, 3-indolylmethyl, 2-benzimidazolylmethyl, 1-naphthylmethyl, 2-naphthylmethyl, cyclohexylmethyl, —CH$_2$C(O)NHCH$_2$-pyridin-2-yl or —(CH$_2$)$_2$C(O)NHCH$_2$-pyridin-2-yl, wherein each phenyl, naphthyl, imidazolyl, thiazolyl, benzthiazolyl, pyridinyl, or cyclohexyl group is substituted with 0-2 $R^{11b}$;

$R^{11b}$ is, independently at each occurrence, H, F, Cl, Br, CF$_3$, OMe, OCF$_3$, OCHF$_2$, OPh, OBn, NO$_2$, —NH$_2$, —C(O)Ph, —NHC(O)Bn, —NHC(O)CH$_2$CH$_2$Ph, —NHS(O)$_2$Ph, —C(O)NR$^7$R$^8$, —NR$^7$C(O)R$^b$, —S(O)$_p$NR$^8$R$^9$, —NR$^8$S(O)$_p$R$^c$, Ph, or Bn;

alternately, when two $R^{11b}$ groups are substituents on adjacent atoms they may be taken together with the atoms to which they are attached to form a 5- to 7-membered heterocycle comprising carbon atoms and 1-4 heteroatoms selected from N, O, and S(O)$_p$ and substituted with 0-2 $R^g$.

11. A compound according to claim 10, wherein:

$R^3$ is phenyl substituted with 0-2 $R^{3a}$, naphthyl substituted with 0-2 $R^{3a}$, indanone substituted with 0-2 $R^{3a}$, or a 5- to 10-membered heterocycle substituted with 0-2 $R^{3a}$ and selected from: pyridine, pyridinone, pyrimidine, pyrrole, pyrazole, indole, 2-oxoindole, indazole, benzofuran, benzothiophene, benzimidazole, benzisoxazole, benzoxazole, quinazoline, 3H-quinazolin-4-one, phthalazine, 2H-phthalazin-1-one, 1H-quinolin-4-one, isoquinoline, and 2H-3,4-dihydroisoquinolin-1-one.

12. A compound according to claim 11, wherein:

A is 4-aminomethyl-cyclohexyl, 4-carbamoyl-cyclohexyl, 4-amidino-phenyl, 4-benzyloxycarbonylamino-cyclohexyl, phenyl, 1,2,3,4-tetrahydronaphth-2-yl, 4-aminomethyl-phenyl, 4-carbamoyl-phenyl, 4 aminomethyl-2-fluoro-phenyl, 2-F-5-OMe-phenyl, 2-F-4-Me-phenyl, 2-F-4-Cl-phenyl, 2-F-4-carbamoyl-phenyl, 2-OMe-4-carbamoyl-phenyl, 3-OMe-4-carbamoyl-phenyl, 2-Et-4-aminomethyl-phenyl, 2-NH$_2$-pyridin-4-yl, 2-ethylamino-4-aminomethyl-phenyl, 1-aminoisoquinolin-6-yl, 1-NH$_2$-5,6,7,8-tetrahydroisoquinolin-6-yl, 1-NH$_2$-1,2,3,4-tetrahydroisoquinolin-6-yl, 3-NH$_2$-benzisoxazol-5-yl, 3-NH$_2$-berzisoxazol-6-yl, 3-NH$_2$-indazol-6-yl, 3-NH$_2$-indazol-5-yl, 1-Me-3-NH$_2$-indazoly-6-yl, 1,2,3,4-tetrahydroisoquinolin-3-yl, 1,2,3,4-tetrahydroisoquinolin-1-on-6-yl, isoquinolin-6-yl, 1-NH$_2$-isoquinolin-6-yl, 1-NH$_2$-5,6,7,8-tetrahydroisoquinolin-6-yl, 1,2,3,4-tetrahydroisoquinolin-6-yl, 1H-quinazolin-4-onyl, 2H-isoquinolin-1-onyl, 3H-quinazolin-4-onyl, 3,4-dihydro-2H-isoquinolin-1-onyl, 2,3-dihydroisoindolinonyl, or 1-NH$_2$-phthalazin-6-yl; and $R^3$ is phenyl, 3-OH-phenyl, 3,4-methylenedioxyphenyl, 2-naphthyl, 1-naphthyl, 3-NMe$_2$-phenyl, 4-benzyloxyphenyl, 4-t-butoxyphenyl, 4-methylsulfonylphenyl, 4-Cl-phenyl, 2-OMe-phenyl, 3-OMe-phenyl, 4-OMe-phenyl, 2-F-phenyl, 3-F-phenyl, 4-F-phenyl, 4-Br-phenyl, 3-CF$_3$-phenyl, 3-NH$_2$-phenyl, 4-NH$_2$-phenyl, 3-CN-phenyl, 4-CN-phenyl, 3-CO$_2$H-phenyl, 4-CO$_2$H-phenyl, 3-CO$_2$Me-phenyl, 4-CO$_2$Me-phenyl, 3-OH-phenyl, 3-CH$_2$CO$_2$H-phenyl, 3-CH$_2$CO$_2$Me-phenyl, 3-CH$_2$CO$_2$Et-phenyl, 3-CONH$_2$-phenyl, 4-CONH$_2$-phenyl, 4-CH$_2$CO$_2$Et-phenyl, 3-CH$_2$C(O)NH$_2$-phenyl, 4-C(O)NHMe-phenyl, 3-NHCOMe-phenyl, 4-NHCO$_2$Me-phenyl, 2,4-diF-phenyl, 3-F-4-CN-phenyl, 3-CN-4-F-phenyl, 3-OMe-4-CONH$_2$-phenyl, 3-OH-4-CONH$_2$-phenyl, 3-NH$_2$-4-CONH$_2$-phenyl, 3-CO$_2$Me-4-NH$_2$-phenyl, 3-CO$_2$H-4-NH$_2$-phenyl, 3-CONH$_2$-4-NH$_2$-phenyl, 3-CO$_2$H-4-F-phenyl, pyrrol-3-yl, pyrazol-3-yl, pyrazol-4-yl, 3-NH$_2$-pyrazol-5-yl, pyridyl-2-yl, pyrid-3-yl, pyrid-4-yl, 2-F-pyrid-4-yl, 2-F-pyrid-5-yl, 2-OMe-pyrid-4-yl, 2-OMe-pyrid-5-yl, 2-NH$_2$-pyrid-3-yl, 2-NH$_2$-pyrid-4-yl, 2-NH$_2$-pyrid-5-yl, 2-NH$_2$-pyrid-6-yl, 2-NHMe-pyrid-4-yl, 2-NMe$_2$-pyrid-4-yl, 2-CONH$_2$-pyrid-4-yl, 2-CO$_2$H-pyrid-4-yl, 2-CONH$_2$-pyrid-5-yl, 2-OMe-6-NH$_2$-pyridyl-4-yl, 4-NH$_2$-pyrimidin-6-yl, 4-NH$_2$-pyrimidin-2-yl, 2-NH$_2$-pyrimidin-4-yl, 2-NH$_2$-pyrimidin-5-yl, indol-5-yl, indol-6-yl, indazol-5-yl, indazol-6-yl, 3-OH-indazol-5-yl, 3-OH-indazol-6-yl, 3-OMe-indazol-5-yl, 3-OMe-indazol-6-yl, 3-NH$_2$-indazol-5-yl, 3-NH$_2$-indazol-6-yl, benzisoxalol-6-yl, benzisoxazol-5-yl, 3-NH$_2$-benzoisoxazol-5-yl, 3-NH$_2$-benzoisoxazol-6-yl, 4-OMe-quinolin-6-yl, 1-NH$_2$-phthalazin-6-yl, 1-NH$_2$-phthalazin-7-yl, 4-NH$_2$-quinazolin-6-yl, 2-Me-4-aminoquinazolin-6-yl, 4-NH$_2$-quinazolin-7-yl, 2-Me-4-NH$_2$-quinazolin-7-yl, 2,4-di-NH$_2$-quinazolin-7-yl,

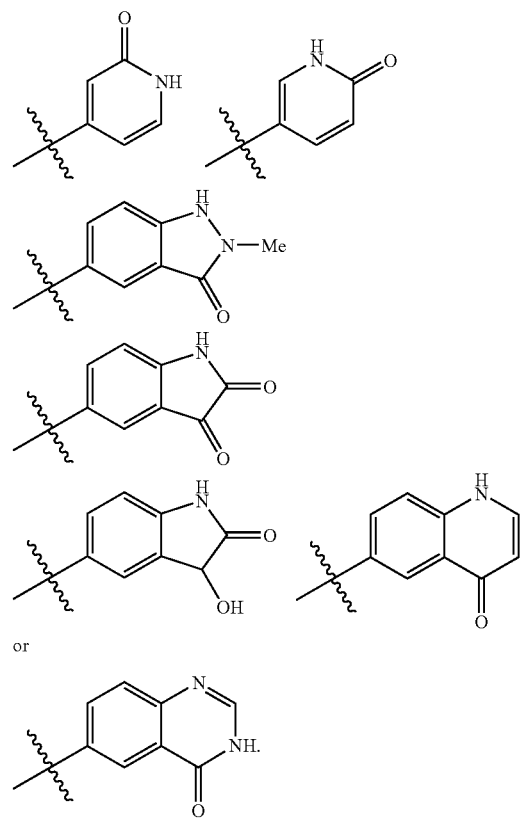

or

13. A compound according to claim 12, wherein:
A is 4-aminomethyl-cyclohexyl; and
the group

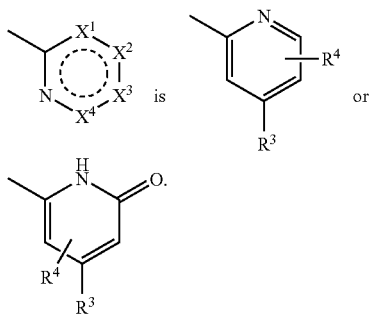

is or

14. A compound according to claim 7, wherein the compound is selected from:
- 4-aminomethyl-[2-phenyl-1-(4-phenyl-pyridin-2-yl)-ethyl]-trans cyclohexanecarboxamide,
- 4-aminomethyl-[1-(1-oxy-4-phenyl-pyridin-2-yl)-2-phenyl-ethyl]-cyclohexanecarboxamide,
- 3-(2-{1-[trans-(4-aminomethyl-cyclohexanecarboxamido]-2-phenyl-ethyl}-pyridin-4-yl)-benzoic acid methyl ester,
- 4-aminomethyl-{1-[4-(3-acetylamino-phenyl)-pyridin-2-yl]-2-phenyl-ethyl}-trans-cyclohexanecarboxamide,
- 4-aminomethyl-{1-[4-(3-hydroxy-phenyl)-pyridin-2-yl]-2-phenyl-ethyl}-trans-cyclohexanecarboxamide,
- 4-aminomethyl-{1-[4-(3-amino-phenyl)-pyridin-2-yl]-2-phenyl-ethyl}-trans-cyclobexanecarboxamide,
- 4-aminomethyl-N-{1-[4-(3-cyano-phenyl)-pyridin-2-yl]-2-phenyl-ethyl}-trans-cyclohexanecarboxamide,
- 3-(2-{1-[trans-(4-aminomethyl-cyclohexanecarboxamido]-2-phenyl-ethyl}-pyridin-4-yl)-benzoic acid,
- 4-aminomethyl-N-{1-[4-(4-methoxy-phenyl)-pyridin-2-yl]-2-phenyl-ethyl}-trans-cyclohexanecarboxamide,
- 4-aminomethyl-N-{1-[4-(3-methoxy-phenyl)-pyridin-2-yl]-2-phenyl-ethyl]-trans-cyclohexanecarboxamide,
- 4-aminomethyl-N-{2-phenyl-1-[4-(1H-pyrrol-3-yl)-pyridin-2-yl]-ethyl}-trans-cyclohexanecarboxamide,
- 4-aminomethyl-N-(1-[3,4']bipyridinyl-2'-yl-2-phenyl-ethyl)-trans-cyclohexanecarboxamide,
- 4-aminomethyl-[1-(2'-amino-[4,4']bipyridinyl-2-yl)-2-phenyl-ethyl]-trans-cyclobexanecarboxamide,
- 4-aminomethyl-N-{1-[4-(2-methoxy-phenyl)-pyridin-2-yl]-2-phenyl-ethyl}-trans-cyclohexanecarboxamide,
- 4-aminomethyl-N-{1-[4-(3-cyano-4-fluoro-phenyl)-pyridin-2-yl]-2-phenyl-ethyl}-trans-cyclohexanecarboxamide,
- 3-(2-{1-[(4-aminomethyl-cyclohexanecarboxamido]-2-phenyl-ethyl}-pyridin-4-yl)-benzamide,
- 4-(2-{1-[(4-aminomethyl-cyclohexanecarboxamido]-2-phenyl-ethyl}-pyridin-4-yl)-benzoic acid,
- 4-aminomethyl-N-{1-[4-(4-cyano-phenyl)-pyridin-2-yl]-2-phenyl-ethyl}-trans-cyclohexanecarboxamide,
- (+)-4-aminomethyl-N-{1-[4-(4-cyano-3-fluoro-phenyl)-pyridin-2-yl]-2-phenyl-ethyl}-trans-cyclohexanecarboxamide,
- (−)-4-aminomethyl-N-{1-[4-(4-cyano-3-fluoro-phenyl)-pyridin-2-yl]-2-phenyl-ethyl}-trans-cyclohexanecarboxamide,
- 4-(2-{1-[(4-aminomethyl-cyclohexanecarboxamido]-2-phenyl-ethyl}-pyridin-4-yl)-benzamide,
- 4-aminomethyl-{1-[4-(3-amino-1H-indazol-6-yl)-pyridin-2-yl]-2-phenyl-ethyl}-trans-cyclohexanecarboxamide,
- (+)-4-aminomethyl-N-{1-[4-(3-amino-1H-indazol-6-yl)-pyridin-2-yl]-2-phenyl-ethyl}-trans-cyclohexanecarboxamide,
- 4-aminomethyl-N-{1-[4-(3-amino-1,2-benzisoxazol-6-yl)-pyridin-2-yl]-2-phenyl-ethyl}-trans-cyclohexanecarboxamide,
- (+)-4-aminomethyl-N-{1-[4-(3-amino-1,2-benzisoxazol-6-yl)-pyridin-2-yl]-2-phenyl-ethyl}-trans-cyclohexanecarboxamide,
- (−)-4-aminomethyl-N'-1-[4-(3-amino-1,2-benzisoxazol-6-yl)-pyridin-2-yl]-2-phenyl-ethyl}-trans-cyclohexanecarboxamide,
- 4-aminomethyl-N-{1-[4-(3-hydroxy-1H-indazol-6-yl)-pyridin-2-yl]-2-phenyl-ethyl}-trans-cyclohexanecarboxamide,
- 4-aminomethyl-N-{1-[4-(3-amino-1H-indazol-5-yl)-pyridin-2-yl]-2-phenyl-ethyl}-trans-cyclohexanecarboxamide,
- 4-aminomethyl-N-{1-[4-(3-amino-1,2-benzisoxazol-5-yl)-pyridin-2-yl]-2-phenyl-ethyl}-trans-cyclohexanecarboxamide,
- 4-aminomethyl-N-{1-[4-(3-hydroxy-1H-indazol-5-yl)-pyridin-2-yl]-2-phenyl-ethyl}-trans-cyclohexanecarboxamide,
- 4-aminomethyl-[1-(6-methoxy-4-phenyl-pyridin-2-yl)-2-phenyl-ethyl]-trans-cyclohexanecarboxamide,
- 4-aminomethyl-[1-(6-oxo-4-phenyl-1,6-dihydro-pyridin-2-yl)-2-phenyl-ethyl]-trans-cyclohexanecarboxamide,
- 4-aminomethyl-[1-(1-methyl-6-oxo-4-phenyl-1,6-dihydro-pyridin-2-yl)-2-phenyl-ethyl]-trans-cyclohexanecarboxamide,
- 4-aminomethyl-[1-(6-amino-4-phenyl-pyridin-2-yl)-2-phenyl-ethyl]-trans-cyclohexanecarboxamide,
- 4-aminomethyl-[1-(6-chloro-4-phenyl-pyridin-2-yl)-2-phenyl-ethyl]-trans-cyclohexanecarboxamide,
- 4-aminomethyl-N-{1-[4-(3-amino-1H-indazol-6-yl)-6-oxo-1,6-dihydro-pyridin-2-yl]-2-phenyl-ethyl}-trans-cyclohexanecarboxamide,
- 4-aminomethyl-N-{1-[4-(3-amino-1,2-benzisoxazol-6-yl)-6-oxo-1,6-dihydro-pyridin-2-yl]-2-phenyl-ethyl}-trans-cyclohexanecarboxamide,
- 4-aminomethyl-N-{1-[4-(1H-indazol-5-yl)-pyridin-2-yl]-2-phenyl-ethyl}-trans-cyclohexanecarboxamide,
- 4-aminomethyl-N-(1-[4,4']bipyridinyl-2-yl-2-phenyl-ethyl)-trans-cyclohexanecarboxamide,
- 4-aminomethyl-N-(1-(2'-fluoro-[4,4']bipyridinyl-2-yl-2-phenyl-ethyl)-trans-cyclohexanecarboxamide,
- 4-aminomethyl-N-[1-(2'-methylamino-[4,4']bipyridinyl-2-yl)-2-phenyl-ethyl]-trans-cyclohexanecarboxamide,
- 4-aminomethyl-N-[1-(2'-dimethylamino-[4,4']bipyridinyl-2-yl)-2-phenyl-ethyl]-trans-cyclohexanecarboxamide,
- 4-aminomethyl-N-[1-(2'-methoxy-[4,4']bipyridinyl-2-yl)-2-phenyl-ethyl]-trans-cyclohexanecarboxamide,
- 4-aminomethyl-N-[1-(2'-oxo-1',2'-dihydro-[4,4']bipyridinyl-2-yl)-2-phenyl-ethyl]-trans-cyclohexanecarboxamide,
- 4-aminomethyl-N-(1-(6-fluoro-[3,4']bipyridinyl-2'-yl-2-phenyl-ethyl)-trans-cyclobexanecarboxamide,
- 4-aminomethyl-N-(1-(6-amino-[3,4']bipyridinyl-2'-yl-2-phenyl-ethyl)-trans-cyclohexanecarboxamide,
- 4-aminomethyl-N-(1-(6-methoxy-[3,4']bipyridinyl-2'-yl-2-phenyl-ethyl)-trans-cyclohexanecarboxamide, 4-aminomethyl-N-[1-(6-oxo-1,6-dihydro-[3,4']bipyridinyl-2'-yl)-2-phenyl-ethyl]-trans-cyclohexanecarboxamide, 5-(2-{1-[(4-aminomethyl-cyclohexanecarboxamido]-2-phenyl-ethyl}-pyridin-4-yl)-2-fluoro-benzoic acid, 4-aminomethyl-N-{2-phenyl-1-[4-(1H-pyrazol-4-yl)-pyridin-2-yl]-ethyl}-trans-cyclohexanecarboxamide, 2-amino-5-(2-{1-[trans-(4-aminomethyl-cyclohexanecarboxamido]-2-phenyl-ethyl}-pyridin-4-yl)-benzoic acid methyl ester, 4-aminomethyl-N-{1-[4-(4-oxo-3,4-dihydro-quinazolin-6-yl)-pyridin-2-yl]-2-phenyl-ethyl}-trans-cyclohexanecarboxamide, 2-amino-5-(2-{1-[trans-4-aminomethyl-cyclohexanecarboxamido]-2-phenyl-ethyl}-pyridin-4-yl)-benzoic acid, 4-aminomethyl-N-{1-[4-(4-methoxy-quinolin-6-yl)-pyridin-2-yl]-2-phenyl-ethyl}-trans-cyclohexanecarboxamide, 4-aminomethyl-N-{1-[4-(4-oxo-1,4-dihydro-quinolin-6-yl)-pyridin-2-yl]-2-phenyl-ethyl}-trans-cyclohexanecarboxamide, 4-aminomethyl-N-{1-[4-(4-amino-phenyl)-pyridin-2-yl]-2-phenyl-ethyl}-trans-cyclohexanecarboxamide, and

[4-(2-{1-[4-aminomethyl-cyclohexanecarboamido]-2-phenyl-ethyl}-pyridin-4-yl)-phenyl]-carbamic acid methyl ester, or a stereoisomer or pharmaceutically acceptable salt, or solvate thereof.

15. A compound according to claim 1, wherein:

$R^{11}$ is —$(CH_2)_r$—$C(O)NR^8R^9$, $C_{1-6}$ alkyl substituted with 0-3 $R^{11a}$, $C_{2-4}$ alkenyl substituted with 0-3 $R^{11a}$, $C_{2-4}$ alkynyl substituted with 0-3 $R^{11a}$, —$(CH_2)_s$—$C_{3-7}$ cycloalkyl substituted with 0-3 $R^{11b}$, —$(CH_2)_s$-phenyl substituted with 0-3 $R^{11b}$, or —$(CH_2)_s$-5- to 10-membered heterocycle comprising: carbon atoms and 1-4 heteroatoms selected from N, O, and $S(O)_p$, wherein said heterocycle is substituted with 0-3 $R^{11b}$;

$R^{11a}$ is, independently at each occurrence, =O, $OR^a$, $SR^a$, CN, $NO_2$, —$NR^7R^8$, —$C(O)R^a$, —$C(O)OR^a$, —$C(O)NR^7R^8$, —$NR^7C(O)R^b$, —$S(O)_pNR^8R^9$, —$NR^8S(O)_pR^c$, —$S(O)_pR^c$, $C_{3-6}$ cycloalkyl, $C_{1-4}$ haloalkyloxy-, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

$R^{11b}$ is, independently at each occurrence, H, =O, =$NR^8$, $OR^a$, F, Cl, Br, CN, $NO_2$, $CF_3$, $OCF_3$, $OCHF_2$, —$NR^7R^8$, —$C(O)R^a$, —$C(O)OR^a$, —$C(O)NR^7R^8$, —$NR^7C(O)R^b$, —$NR^8C(O)_2R^c$, —$S(O)_pNR^8R^9$, —$NR^8S(O)_pR^c$, —$S(O)_pR^c$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

alternately, when two $R^{11b}$ groups are substituents on adjacent atoms they may be taken together with the atoms to which they are attached to form a 5- to 7-membered heterocycle comprising carbon atoms and 1-4 heteroatoms selected from N, O, and $S(O)_p$ and substituted with 0-2 $R^g$.

16. A compound according to claim 7, wherein:

$R^{11}$ is —$(CH_2)_r$—$C(O)NR^8R^9$, $C_{1-6}$ alkyl substituted with 0-3 $R^{11a}$, $C_{2-4}$ alkenyl substituted with 0-3 $R^{11a}$, $C_{2-4}$ alkynyl substituted with 0-3 $R^{11a}$, —$(CH_2)_s C_{3-7}$ cycloalkyl substituted with 0-3 $R^{11b}$, —$(CH_2)_s$-phenyl substituted with 0-3 $R^{11b}$, or —$(CH_2)_s$-5- to 10-membered heterocycle comprising: carbon atoms and 1-4 heteroatoms selected from N, O, and $S(O)_p$, wherein said heterocycle is substituted with 0-3 $R^{11b}$;

$R^{11a}$ is, independently at each occurrence, =O, $OR^a$, $SR^a$, CN, $NO_2$, —$NR^7R^8$, —$C(O)R^a$, —$C(O)OR^a$, —$C(O)NR^7R^8$, —$NR^7C(O)R^b$, —$S(O)_pNR^8R^9$, —$NR^8S(O)_pR^c$, —$S(O)_pR^c$, $C_{3-6}$ cycloalkyl, $C_{1-4}$ haloalkyloxy-, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

$R^{11b}$ is, independently at each occurrence, H, =O, =$NR^8$, $OR^a$, F, Cl, Br, CN, $NO_2$, $CF_3$, $OCF_3$, $OCHF_2$, —$NR^7R^8$, —$C(O)R^a$, —$C(O)OR^a$, —$C(O)NR^7R^8$, —$NR^7C(O)R^b$, —$NR^8C(O)_2R^c$, —$S(O)_pNR^8R^9$, —$NR^8S(O)_pR^c$, —$S(O)_pR^c$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

alternately, when two $R^{11b}$ groups are substituents on adjacent atoms they may be taken together with the atoms to which they are attached to form a 5- to 7-membered heterocycle comprising carbon atoms and 1-4 heteroatoms selected from N, O, and $S(O)_p$ and substituted with 0-2 $R^g$.

17. A pharmaceutical composition, comprising: a pharmaceutically acceptable carrier and a therapeutically effective amount of a compound of claim 1.

18. A pharmaceutical composition, comprising: a pharmaceutically acceptable carrier and a therapeutically effective amount of a compound of claim 14.

19. A method of treating a thromboembolic disorder, comprising: administering to a patient in need thereof a therapeutically effective amount of a compound of claim 1, wherein the thromboembolic disorder is selected from the group consisting of arterial cardiovascular thromboembolic disorders, venous cardiovascular thromboembolic disorders, and thromboembolic disorders in the chambers of the heart.

20. A method of treating a thromboembolic disorder according to claim 19, wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

* * * * *

UNITED STATES PATENT AND TRADEMARK OFFICE
CERTIFICATE OF CORRECTION

PATENT NO. : 7,429,604 B2
APPLICATION NO. : 11/151627
DATED : September 30, 2008
INVENTOR(S) : James R. Corte et al.

It is certified that error appears in the above-identified patent and that said Letters Patent is hereby corrected as shown below:

COLUMN 1:

Line 7, "Jun. 11" should read -- Jun. 15 --.

COLUMN 327:

Line 13, "($C_{6-1\ 10}$ aryl)" should read -- ($C_{6-10}$ aryl) --; and

Line 63, "$C_{3-0}$" should read -- $C_{3-10}$ --.

COLUMN 328:

Line 52, "-$C(O)OR^9$," and insert -- -$C(O)OR^g$, --; and

Line 66, "napthyl" should read -- naphthyl --.

COLUMN 334:

Line 4, "—O," should read -- =O, --.

COLUMN 336:

Line 51, "$R^3a$" should read -- $R^{3a}$ --.

COLUMN 337:

Line 53, "berzisoxazol" should read -- benzisoxazol --.

COLUMN 339:

Line 33, "cyclobexanecarboxamide" should read -- cyclohexanecarboxamide --;

Line 42 (approx.), "ethyl]" should read -- ethyl} --; and

Line 48, "cyclobexanecarboxamide" should read -- cyclohexanecarboxamide --.

UNITED STATES PATENT AND TRADEMARK OFFICE
CERTIFICATE OF CORRECTION

PATENT NO. : 7,429,604 B2
APPLICATION NO. : 11/151627
DATED : September 30, 2008
INVENTOR(S) : James R. Corte et al.

It is certified that error appears in the above-identified patent and that said Letters Patent is hereby corrected as shown below:

COLUMN 340:

Line 13, "N'" should read -- N-{ --; and

Line 63, "cyclobexanecarboxamide" should read -- cyclohexanecarboxamide --.

COLUMN 341:

Line 24, "cyclobexanecarboxamide" should read -- cyclohexanecarboxamide --.

Signed and Sealed this

Fifth Day of May, 2009

JOHN DOLL
*Acting Director of the United States Patent and Trademark Office*